United States Patent
Lander et al.

(10) Patent No.: US 10,562,947 B2
(45) Date of Patent: Feb. 18, 2020

(54) COMPOSITIONS AND METHODS FOR PREVENTING OR TREATING DISEASES, CONDITIONS OR PROCESSES CHARACTERIZED BY ABERRANT FIBROBLAST PROLIFERATION AND EXTRACELLULAR MATRIX DEPOSITION

(71) Applicant: MOERAE MATRIX, INC., Morristown, NJ (US)

(72) Inventors: Cynthia Lander, Mendham, NJ (US); Colleen Brophy, Nashville, TN (US)

(73) Assignee: MOERAE MATRIX, INC., Morristown, NJ (US)

( * ) Notice: Subject to any disclaimer, the term of this patent is extended or adjusted under 35 U.S.C. 154(b) by 0 days.

(21) Appl. No.: 15/855,398

(22) Filed: Dec. 27, 2017

(65) Prior Publication Data

US 2018/0194817 A1 Jul. 12, 2018

Related U.S. Application Data

(60) Division of application No. 14/473,339, filed on Aug. 29, 2014, now Pat. No. 9,890,200, which is a continuation-in-part of application No. 13/445,759, filed on Apr. 12, 2012, now Pat. No. 9,642,888.

(60) Provisional application No. 61/474,370, filed on Apr. 12, 2011.

(51) Int. Cl.
| | | |
|---|---|---|
| A61K 38/16 | (2006.01) | |
| A61K 38/10 | (2006.01) | |
| C07K 14/47 | (2006.01) | |
| C07K 7/06 | (2006.01) | |
| C07K 7/08 | (2006.01) | |
| A61K 45/06 | (2006.01) | |

(52) U.S. Cl.
CPC .............. *C07K 14/47* (2013.01); *A61K 38/10* (2013.01); *A61K 38/16* (2013.01); *A61K 45/06* (2013.01); *C07K 7/06* (2013.01); *C07K 7/08* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 4,105,027 A | 8/1978 | Lundquist | |
| 4,192,309 A | 3/1980 | Poulsen | |
| 4,227,522 A | 10/1980 | Carris | |
| 4,627,432 A | 12/1986 | Newell et al. | |
| 4,778,054 A | 10/1988 | Newell et al. | |
| 4,811,731 A | 3/1989 | Newell et al. | |
| 5,035,237 A | 7/1991 | Newell et al. | |
| 5,352,461 A | 10/1994 | Feldstein et al. | |
| 5,503,852 A | 4/1996 | Steiner et al. | |
| 5,565,350 A | 10/1996 | Kmiec | |
| 6,071,497 A | 6/2000 | Steiner et al. | |
| 6,331,318 B1 | 12/2001 | Milstein | |
| 6,428,771 B1 | 8/2002 | Steiner et al. | |
| 6,440,463 B1 | 8/2002 | Feldstein et al. | |
| 6,444,226 B1 | 9/2002 | Steiner et al. | |
| 6,652,885 B2 | 11/2003 | Steiner et al. | |
| 6,921,527 B2 | 7/2005 | Platz et al. | |
| 7,709,639 B2 | 5/2010 | Stevenson et al. | |
| 7,799,344 B2 | 9/2010 | Oberg | |
| 7,803,404 B2 | 9/2010 | Hokenson et al. | |
| 7,863,241 B2 | 4/2011 | Cochrane | |
| 8,039,431 B2 | 10/2011 | Wilson et al. | |
| 8,536,303 B2 | 9/2013 | Panitch | |
| 9,327,008 B2 * | 5/2016 | Panitch | ................. A61K 38/16 |
| 9,642,888 B2 | 5/2017 | Lander et al. | |
| 9,890,200 B2 | 2/2018 | Lander et al. | |
| 2004/0131614 A1 | 7/2004 | Banerjee et al. | |
| 2006/0040953 A1 | 2/2006 | Leone-Bay et al. | |
| 2006/0074102 A1 | 4/2006 | Cusack et al. | |
| 2006/0099269 A1 | 5/2006 | Cheatham et al. | |

(Continued)

FOREIGN PATENT DOCUMENTS

| | | |
|---|---|---|
| AU | 2013 202 108 | 5/2013 |
| CA | 2118513 | 11/1993 |

(Continued)

OTHER PUBLICATIONS

Gorska M. et al. "MK2 controls the level of negative feedback in the NF-κB pathway and is essential for vascular permeability and airway inflammation", The Journal of Experimental Medicine, 2007, vol. 204, No. 7, p. 1637-1652.

Altschul S.F., et al., "Gapped Blast and PSI-Blast: a new general6ion of protein database search programs", Nucleic Acids Research, 1997, vol. 25, pp. 3389-3402.

(Continued)

*Primary Examiner* — Xiaozhen Xie

(74) *Attorney, Agent, or Firm* — Cooley LLP; Ivor Elrifi

(57) ABSTRACT

The described invention provides compositions and methods for treating asthma, a disease, condition or pathologic process whose progression is characterized by one or more of aberrant fibroblast proliferation and extracellular matrix deposition producing constriction in an airway, airway remodeling, and airway obstruction in lung tissue. The method includes administering a pharmaceutical composition comprising a therapeutic amount of a polypeptide having the amino acid sequence YARAAARQARAKA-LARQLGVAA (SEQ ID NO: 1) or functional equivalent thereof, and a pharmaceutically acceptable carrier, wherein the therapeutic amount of the polypeptide is effective to reduce the constriction of small airway dimensions and airway obstruction, treat airway remodeling, or a combination thereof.

25 Claims, 28 Drawing Sheets

Specification includes a Sequence Listing.

(56) References Cited

U.S. PATENT DOCUMENTS

| | | | |
|---|---|---|---|
| 2008/0057129 A1* | 3/2008 | Lerner | A61K 9/0075 424/489 |
| 2008/0282320 A1 | 11/2008 | DeNovo et al. | |
| 2009/0196927 A1 | 8/2009 | Panitch et al. | |
| 2010/0098760 A1 | 4/2010 | Panitch | |
| 2010/0158968 A1 | 6/2010 | Panitch et al. | |
| 2011/0053955 A1 | 3/2011 | Abeywardane et al. | |
| 2012/0263680 A1 | 10/2012 | Lander et al. | |
| 2013/0101671 A9 | 4/2013 | Panitch | |
| 2018/0194817 A1 | 7/2018 | Lander et al. | |

FOREIGN PATENT DOCUMENTS

| | | | |
|---|---|---|---|
| WO | WO 1991/16038 | | 10/1991 |
| WO | WO 2008/085191 | * | 7/2008 |
| WO | WO 2009/021137 | | 2/2009 |
| WO | WO 2010/068692 | | 6/2010 |
| WO | WO 2011/149964 | | 12/2011 |
| WO | WO 2012/142320 A2 | | 10/2012 |

OTHER PUBLICATIONS

Anonymous: ""Moerae MatrixMoerae Matrix, Inc."", Dec. 5, 2015, XP55455918 Retrieved from the Internet: URL:https://web.archive.org/web/20151205042021/http://moeraematrix.com/moerae-matrix/ [retrieved on Mar. 2, 2018].

Ausubel F. M., et al., "Use of *Arabidopsis thaliana* defense-related mutants to dissect the plant response to pathogens", Proc. Natl. Acad. Sci USA, 1995, vol. 92, pp. 4189-4196.

Bentzen S.M., et al., "Latent-time estimation for late cutaneous and subcutaneous radiation reactions in a single-follow-up clinical study", Radiotherapy and Oncology, 1989, vol. 15, pp. 267-274.

Bonfield T.L., et al., "Inflammatory cytokines in cystic fibrosis lungs", Am J Respir Crit Care Med, 1995, vol. 152, pp. 2111-2118.

Bousse-Kerdiles M. et al., Ann. Hematol., 78: 434-444 (1999).

Braun R. et al., "IL-17 producing gammadelta T cells are required for a controlled inflammatory response after bleomycin-induced lung injury." Inflammation, 2008, vol. 31(3):167-179.

Brizzolara-Gourdie, et al., "Angiotensin II potentiates vasodilation of rat aorta by cAMP elevating agonists." J. Pharmacol Exp Ther. 1997, vol. 281(1): 354-359.

Brugnano JL et al., "Cell-penetrating peptides can confer biological function: Regulation of inflammatory cytokines in human monocytes by MK2 inhibitor peptides." Journal of Controlled Release, vol. 155, Issue 2, pp. 128-133, 2011.

Cardozo B.L., et al., "Lung damage following bone marrow transplantation: I. The contribution of irradiation". Int. J. Radiation Oncology Biol. Phys., 1985, vol. 11, pp. 907-914.

Cargnello M. et al. "Activation and Function of the MAPKs and Their Substrates, the MAPK-Activate Protein Kinases", Microbiology and Melocular Biology Reviews, 2011, vol. 75, No. 1, p. 50-83. (Exhibit B).

Carpino L.A., et al., "The 9-fluorenylmethoxycarbony Amino-Protecting Group", J Org. Chem., 1972, vol. 37, pp. 3404-3409.

Cheek S. et al. "Sequence and Structure Classification of Kinases", J. Mol. Biol., 2002, vol. 320, p. 855-881. (Exhibit A).

Chmiel et al., Clin Rev Allergy Immunol., 3(1): 5-27 (2002).

Chung, Eur Respir J 2001; 18: Suppl. 34, 50s-59s.

Clarkson M.R., et al.,"T-Cell costimulatory pathways in allografl rejection and tolerance", Transplantation, 2006, vol. 80, pp. 555-563.

Coker and Laurent, Eur Respir J 1998; 11: 1218-1221.

Corpet F., "Multiple sequence alignment with hierarchial clustering", Nucleic Acids Research, 1988, vol. 16, pp. 10881-10890.

Cowley S. et al., "MK2 Signaling in Idiopathic Pulmonary Fibrosis." Am. J_ Respir. Crit. Care Med. 2010, vol. 181:A3506.

Damarla et al., PLoS One 4(2): e4600 Feb. 2009.

Datta, et al., "Novel therapeutic approaches for pulmonary fibrosis", 2011, British Journal of Pharmacology, vol. 163, pp. 141-172.

Demko et al., J Am Soc Nephrol 8: 684-688, 1997.

Dreiza, et al., "The small heat shock protein, HSPB6, in muscle function and disease." Cell Stress Chaperones. 2010, vol. 15(1):1-11.

Ebrahimi et al., American Journal of Pathology, vol. 158, No. 6, Jun. 2001, pp. 2117-2125.

El-Sayed A., et al, "Delivery of macromolecules using arginine-rich cell-penetrating peptides: Ways to overcome endosomal entrapment", 2009, The AAPS Journal, vol. 11, pp. 13-22.

Fan et al., JAMA. 2005; 294(22): 2889-2896.

Fields G.B., et al., "Solid phase peptide synthesis utilizing 9-fluorenylmethoxycarbonyl amino acides", Int. J. Peptide Protein Res., 1990, pp. 161-214.

Goldstein R. et al., "Failure of mechanical properties to parallel changes in lung connective tissue composition in bleomycin-induced pulmonary fibrosis in hamsters." Am Rev Respir Dis. 1979, vol. 120(1): 67-73.

Gross N.J., et al., "Replicative activity of lung type 2 cells following lung X irradiation", Radiation Research, 1987, vol. 111, pp. 143-150.

Guerry-Force, M.L. et al.,"Early structural changes in sheep lung following thoracic irradiation", Radiation Research, 1988, vol. 114, pp. 138-153.

Hayess K. et al., "Effect of protein kinase inhibitors on activity of mammalian small heat-shock protein (HSP25) kinase", Biochemical Pharmacology, 1997, vol. 53, pp. 1239-1247.

Hecker L. et al., "NADPH oxidase-4 mediates myofibroblast activation and fibrogenic responses to lung injury." Nat Med. 2009, vol. 15(9):1077-1081.

Hendry J.H., "Biological response modifiers and normal tissue injury after irradiation", Seminars in Radiation Oncology, 1994, vol. 4, pp. 123-132.

Henikoff S, et al., "Amino acid substitution matrices from protein blocks", Proc. Natl. Acad. Sci. USA, 1992, vol. 89, pp. 10915-10919.

Higgins D.G., et al, "Fast and sensitive multiple sequence alignments on a microcomputer", Cabios Communications, 1989, vol. 5, p. 151-153.

Higgins D.G., et al., "Clustal: A package for performing multiple sequence alignment on a microcomputer", Gene, 1988, vol. 73, pp. 237-244.

Horowitz J. and Thannickal V., "Epithelial-mesenchymal interactions in pulmonary fibrosis." Semin Respir Crit Care Med. 2006, vol. 27(6): 600-612.

Horowitz J. and Thannickal V., "Idiopathic pulmonary fibrosis: new concepts in pathogenesis and implications or drug therapy." Treatments in Respiratory Medicine, 2006, vol. 5(5): 325-342.

Horowitz, J. et al., "Activation of the Pro-survival Phosphalidylinosilol 3-Kinase/AKT Pathway by Transforming GHrowth Factor-pi in Mesenchymal Cells is Mediated by p38 MAPK-dependenl Induction of an Autocrine Growth racier," vol. 279 (2): 1359-1367.

Huang X, et al., "Parallelization of a local similarity algorithm", Cabios, 1992, vol. 8, pp. 155-165.

Izbicki G. et al., "Time course of bleomycin-induced lung fibrosis." Int J Exp Pathol. 2002, vol. 83(3): 111-119.

Janick-Buckner D. et al., "Alteration of bronchoalveolar lavage cell populations following bleomycin treatment in mice." Toxicol Appl Pharmacol. 1989, vol. 100(3): 465-473.

Jiang et al., J. Clin. Invest. 2011; 121 (6): 2336-2349.

Johansen C. et al., "Protein expression of TNF-alpha in psoriatic skin is regulated at a posttranscriptional level by MAPK-activated protein kinase 2." J Immunol. 2006, vol. 176(3): 1431-1438.

Johnson, M., Ann. Allergy Asthma Immunol., 1995, vol. 75(2):177-179 (Abstract).

Karlin S., et al., "Applications and statistics for multiple high-scoring segments in molecular sequences", Proc. Natl. Acad. Sci. USA, 1993, vol. 90, pp. 5873-5877.

Keatings V. et al., "Differences in inlerleukin-8 and tumor necrosis factor-alpha in induced sputum from patients with chronic obstructive pulmonary disease or asthma." AM J Respir Cril Care Med, 1996, 153: 530-534.

Kolb et al. J. Clin. Invest. 107: 1529-1536 (2001).

(56) References Cited

OTHER PUBLICATIONS

Komalvilas, et al., "The small heat shock-related protein, HSP20, is a cAMP-dependent protein kinase substrate that is involved in airway smooth muscle relaxation." Am J Physiol Lung Cell Mol Physiol. 2008, vol. 294(1):L69-78.
Kotlyarov A. et al., "Distinct cellular functions of MK2," Mol Cell Biol. 2002, vol. 22(13): 4827-4835.
Lawson W. et al., "Increased and prolonged pulmonary fibrosis in surfactant protein C-deficient mice following intratracheal bleomycin." Am J Pathol., vol. 2005, vol. 167(5): 1267-1277.
Le Bousse-Kerdilesw M.C, et al., "Dual implication of fibrogenic cylokines in the pathogenesis of fibrosis and myeloproliferation in myeloid metaplasma with myelfibrosis", Ann Hemato, 1999, vol. 78, pp. 437-444.
Lee J. et al. "Radiation-induced fibrosis: A rationale for Smad3 inhibition." Otolaryngology—Head and Neck Surgery, 141: p. 57.
Leikauf, G. et al., "Acute Lung Injury: Functional Genomics and Genetic Susceptibility." Chest, 2002, vol. 121: 70-75.
Ley K., et al., "From Lung injry to fibrosis", Nature Medicine, 2008, vol. 14, pp. 20-21.
Liaw et al., J. Clin. Invest. 1998; 101(7): 1468-1478.
Lim et al., Am J Respir Crit Care Med vol. 162. pp. 1355-1360, 2000.
Liu T., et al., "Lack of MK2 inhibits myofibroblast formation and exacerbates pulmonary fibrosis", American Journal of Respiratory Cell and Molecular Biology, 2007, vol. 37, pp. 507-517.
Liu et al. Am J Respir Cell Mol Biol vol. 37. pp. 507-517, 2007.
Lopes B.C., et al., "Lung damage following bone marrow transplantation: I. The contribution of irradiation", 1985, vol. 11, pp. 907-914.
Lopes L. et al., "Inhibition of HSP27 phosphorylation by a cell-permeant MAPKAP Kinase 2 inhibitor." Biochem Biophys Res Commun. 2009, vol. 382(3): 535-539.
Maasilta P., et al., "Procollagen-111 in serum, plasminogen activation and fibronectin in bronhoalveolar lavage fluid during and following irradiation of human lung", Int. J. Radiation Oncology Biol. Phys., 1991, vol. 20, p. 973-980.
MacIntyre N.R., "Current issues in mechanical ventilation for respiratory failure", Chest, 2005, vol. 128, pp. 561-567.
Meltzer, E. et al., "Idiopathic pulmonary fibrosis." Orphanet Journal of Rare Diseases, 2008, vol. 3:8, 1-15.
Merrifield R.B., "Solid phase peptide synthesis" The synthesis of a tetrapeptide, 1963, vol. 85, pp. 2149-2155.
Moeller, A. et al., "The bleomycin animal model: a useful tool to investigate treatment options for idiopathic pulmonary fibrosis?", Int J Biochem Cell Biol., 2008, vol. 40(3): 362-382.
Moodley et al., Am. J. Respir. Cell Mol. Biol. vol. 29, pp. 490-498, 2003.
Muggia F. et al., "Pulmonary toxicity of antitumor agents" Cancer Treat Rev. 1983, vol. 10(4): 221-243.
Moore, B. et al., "Murine models of pulmonary fibrosis." Am J Physiol Lung Cell Mol Physiol, 2008, vol. 294: 152-160.
Myers E.W., et al., "Optimal alignments in linear space", Cabios, 1988, vol. 4, pp. 11-17.
Naldini et al., J Immunol 2006; 177: 4267-4270.
Needlman S.B., et al., "A general method applicable to the search for similarities in the amino acid sequence of two Proteins", J. Mol. Biol., 1970, vol. 48, pp. 443-453.
Neininger A. et al., "MK2 targets AU-rich elements and regulates biosynthesis of tumor necrosis factor and Interleukin-6 independently at different post-transcriptional levels." J Biol Chem. 2002, vol. 277(5): 3065-3068.
Neuman R. and Logan M., "The determination of collagen and elastin in tissues." J Biol Chem. 1950, vol. 186(2):549-556.
Niewoehner et al., N. Engl. J. Med., 1999, vol. 340:1941-1947.
Noble P. and Homer R., Clin Chest Med., 25(4): 749-758 (2004).
Nuckton T.J., "Pulmonary dead-space fraction as a risk factor for death in the acute respiratory distress syndrome", The New England Journal of Medicine, 2002, vol. 346, pp. 1281-1285.
Pearson W.R., "Using the FASTA Program to search protein and DNA sequences Databases", Methods in Molecular Biology, 1994, vol. 24, pp. 307-331.
Pearson W.R., et al., "Improved tools for biological sequence comparison", Proc. Natl. Acad. Sci. USA, 1988, vol. 85, pp. 2444-2448.
Phan S. et al., "A comparative study of pulmonary fibrosis induced by bleomycin and an 02 metabolite producing enzyme system." Chest, 83(5 Suppl): 44S-45S, 1983.
Phan S. et al., "Bleomycin-induced pulmonary fibrosis in rats: biochemical demonstration of inaeased rate of collagen synthesis." Am Rev Respir Dis. 1980, vol. 121(3): 501-506.
Pittet, J. et al., "TGF-beta is a critical mediator of acute lung injury." J. Clin. Invest. 2009, vol. 107:1537-1544.
Pottier N., et al., "Relationship between early inflammatory response to bleomycin and sensitivity to lung fibrosis: A role for dipeptidyl-peptidase I and tissue inhibitor of metalloproteinase-3?", Am J Respir Grit Care Med, 2007, vol. 176, pp. 1098-1107.
Raghu G. et al., "An official ATS/ERS/JRS/ALAT statement: idiopathic pulmonary fibrosis: evidence-based Guidelines for diagnosis and management." Am. J. Respir. Crit. Care Med., 2011, vol. 183(6): 788-824.
Remy J., et al., "Long-term overproduction of collagen in radiation-induced fibrosis", Radiation Research, 1991, vol. 125, pp. 14-19.
Richards et al., Am J Respir Care Med vol. 185 Issue 1, pp. 67-76, 2012.
Richards et al., Am J Respir Care Med vol. 181. A1120, 2010.
Rodemann H.P., et al., "Cellular basis of radiation-induced fibrosis", Radiotherapy and Oncolocy, 1995, vol. 35, pp. 83-90.
Rosenberg H.F., et al., "Inflammation", Fundamental Immunology, 1999, pp. 1051-1053.
Rosiello R.A., et al. "Radiation Pneumonitis: Bronchoalveolar lavage assessment and modulation by a recombinant cytokine" Am Rev Respir Dis, 1993, vol. 148, pp. 1671-1676.
Rousseau S. et al., "Inhibition of SAPK2a/p38 prevents hnRNP A0 phosphorylation by MAPKAP-K2 and its interaction with cytokine mRNAs." EMBO J., 2002, vol. 21(23):6505-6514.
Rubenfeld, G. et al., "Incidence and Outcomes of Acute Lung Injury." N Engl J Med, 2005, vol. 353:1685-1693.
Satoh M., et al., "Expression of cytokine genes and presence of enteroviral genomic RNA in endomyocardial biopsy issues of myocarditis and dilated cardiomyopathy", Virchows Arch, 1996, vol. 427, pp. 503-509.
Saxena S.K. et al., "Nephragenic systemic fibrosis: an emerging entity", Int Ural Nephrol, 2008, vol. 40, pp. 715-724.
Schlesinger C., et al., "Constrictive (obliterative) bronchitis", Current Opinion in Pulmonary Medicine, 1998, vol. 4, pp. 288-293.
Schrier D. et al., "The role of strain variation in murine bleomycin-induced pulmonary fibrosis." Am Rev Respir Dis. 1983, vol. 127(1): 63-66.
Selman M., "Idiopathic pulmonary fibrosis: Prevailing and evolving hypotheses about its pathogenesis and implications or therapy", Ann Inter Med, 2001, vol. 134, pp. 136-151.
Smith T.F., et al., "Comparison of biosequences", Advances in Applied Mathematics, 1981, vol. 2, pp. 482-489.
Snider G. et al., "Chronic interstitial pulmonary fibrosis produced in hamsters by endotracheal bleomycin. Lung volumes, volume-pressure relations, carbon monoxide uptake, and arterial blood gas studied." Am Rev Respir Dis. 1978, vol. 117(2): 289-297.
Sousa A. et al., "Smooth muscle alpha-actin expression and myofibroblast differentiation by TGFbeta are dependent upon MK2." J Cell Biochem. 2007, vol. 100(6): 1581-1592.
Starcher B. et al., "Increased elastin and collagen content in the lungs of hamsters receiving an intratracheal Injection of bleomycin." Am Rev Respir Dis. 1978, vol. 117(2): 299-305.
Steger-Hartmann T., et al., "The involvement of pro-inflammatory cytokines in nephrogenic systemic fibrosis—a mechanisitic hypothesis based on preclinicl results from a rat model treated with gadodiamide", Experimental and Toxicologic Pathology, 2009, vol. 61, pp. 537-552, Elsevier.
Strieter R.M., "Pathogenesis and natural history of usual interstitial pneumonia: The whole story or the last chapter of a long novel", Chest Journal, 2005, vol. 128, pp. 1-8.

(56) References Cited

OTHER PUBLICATIONS

Su X., "Post-transcriptional regulation of TNF-induced expression of ICAM-1 and IL-8 in human lung microvascular endothelial cells: An obligatory role for the p38 MAPK-MK2 pathway dissociated with HSP27." Biochem Biophys Acta, 2008, pp. 1623-1631, vol. 1783.

Tager A.M., "The lysophosphatidic acid receptor LPA links pulmonary fibrosis to lung injury by mediating fibroblast recruitment and vascular leak", Nature Medicine, 2007, vol. 14, pp. 45-54.

Thannickal V. and Horowitz J., "Evolving concepts of apoptosis in idiopathic pulmonary fibrosis." Proc Am Thorac Soc. 2006, vol. 3(4): 350-356.

Thomas T. et al., "MAPKAP kinase 2-deficiency prevents neurons from cell death by reducing neuroinflammationelevance in a mouse model of Parkinson's disease." J Neurochem. 2008, vol. 105(5): 2039-2052.

Thrall R. et al., "Bleomycin-induced pulmonary fibrosis in the rat: inhibition by indomethacin." Am J Pathol. 1979, vol. 95(1): 117-130.

Tomasek, J. et al., "Myofibroblasts and mechano-regulation of connective tissue remodelling." Nature Reviews Molecular Cell Biology, 2002, vol. 3(5): 349-363.

Townsend, et al., "Active components of ginger potentiate J1-agonist-induced relaxation of airway smooth muscle by modulating cytoskeletal regulatory proteins." Am J Respir Cell Mol Biol. 2014, vol. 50(1):115-24.

Trujillo G. et al., "T regulatory cells and attenuated bleomycin-induced fibrosis in lungs of CCR?-/- mice", Fibrogenesis & tissue repair, 2010, vol. 3:18, 1-9.

Umezawa H. et al., "Studies on bleomycin." Cancer. 1967, vol. 20(5): 891-895.

Umezawa H. et al., "Chemistry and mechanism of action of bleomycin." Fed Proc. 1974, vol. 33(11): 2296-2302.

Vergara J, et al., "Changes in lung morphology and cell number in radiation pheumonitis and fibrosis: A quantitative ultrastructural study", Int. J. Radiation Oncoloy Biol. Phys., 1987, vol. 13, pp. 723-772.

Veevers-Lowe J., et al., "Mesenchymal stem cell migration is regulated by fibronectin through 5b1-integrin-mediated activation or PDGFR-B and potentiation of growth factor signals", Journal of Cell Science, 2010, vol. 124, 1288-1300.

Vittal R. et al., "Peptide-mediated inhibition of mitogen-activated protein kinase-activated protein kinase-2 ameliorates bleomycin-induced pulmonary fibrosis." Am J Respir Cell Mol Biol vol. 49, No. 1, pp. 47-57, 2013.

Vitall R. et al., "Inhibition of MK2 activity protects against bleomycin-injured pulmonary fibrosis in mice." The American Review of Respiratory Disease, American Thoracic Society, vol. 185, p. A1947, 2012.

Vittal R. et al., "Effects of the protein kinase inhibitor, imatinib mesylate, on epithelial/mesenchymal phenotypes: implications for treatment of fibrotic diseases." J Pharmacol Exp Ther. 2007, vol. 321 (1): 35-44.

Vittal R. et al., "Modulation of prosurvivai signaling in fibroblasts by a protein kinase inhibitor protects against fibrotic tissue injury." Am J Pathol. 2005, vol. 166(2): 367-375.

Ward B. et al., "Peptide Inhibitors of MK2 Show Promise for Inhibition of Abdominal Adhesions," J Surg Res. 2011, vol. 169(1): 27-36.

Ward B. et al., "Design of a bioactive cell-penetrating peptide: when a transduction domain does more than transduce", Journal of Peptide Science, vol. 15, No. 10, 2009, pp. 668-674.

Ware L.B., et al., "The acute respiratory distress syndrome", The New England Journal of Medicine, 2000, vol. 342, pp. 1334-1349.

Weber G.F., et al., "The immunology of Ela-1/osteopontin", Cytokine & Growth Factor Reviews, 1996, vol. 7, pp. 241-248.

Wender P.A., et al., "The design of guanidium-rich transporters and their internalization mechanisms" Adv Drug Deliv. Rev., 2008, vol. 60, pp. 452-42.

Wilkes, J. Clin. Invest. 2011; 121(6): 2155-2157.

Wilkes D. et al., "Instillation of allogeneic lung macrophages and dendritic cells cause differential effects on local FN-gamma production, lymphocytic bronchitis, and vasculitis in recipient murine lungs." Journal of Leukocyte Biology, 1998, vol. 64(5): 578-586.

Wilson M.S., et al.,"Bleomycin and IL-IB-mediated pulmonary fibrosis is IL-17A dependent" J. Exp. Med., 2010, vol. 207, pp. 535-552, The Rockefeller Univeristy Press.

Wilson and Ta Wynn, Mucosal Immunol. Mar. 2009; 2(2): 103-121.

Xavier, S. et al., "Amelioration of Radiation-induced Fibrosis." J. Biol. Chem. 2004, vol. 279(15): 15167-15176.

Yamashita C. et al., "Matrix metalloproteinase 3 is a mediator of pulmonary fibrosis." The American Journal of Pathology, 2011, vol. 179(4):1733-1745.

Zhang Y. et al., J. Immunol., 150(9): 4188-4196 (1993).

The Acute Respiratory Distress Syndrome Network, N Engl J Med. 342: 1301-1308 (2000).

* cited by examiner

NEAT SPRAY DRIED INSULIN

PARTICLE SIZE DISTRIBUTION- INSULIN
2.4mg DOSE, ACI@28.3L/min
| INSULIN | <3.0 um | <3.3 um | <4.7 um | <5.0 um | <5.8 um |
|---|---|---|---|---|---|
| % OF TOTAL DETECTED: | 52.58 | 61.14 | 84.66 | 85.56 | 87.97 |
| % OF TOTAL EMITTED: | 56.91 | 66.17 | 91.63 | 92.61 | 95.22 |
| % OF TOTAL DOSED: | 51.48 | 59.93 | 82.89 | 83.77 | 96.13 |
| MEAN AMOUNT PER DOSE: | 1114.45 | 1295.90 | 1794.49 | 1813.64 | 1964.72 |
MEAN EMITTED DOSE = 93.76%

FIG. 4

FLOW-RATE INDEPENDENCE

FINE PARTICLE DOSE

☐ FPD < 4.7 μm
▨ FPD < 3.3 μm

FLOW RATE (l/min)

*SPRAY-DRIED NEAT PEPTIDE 250 mcg*

FIGURE 5

Activated MK2 Differentially Expressed in Human IPF vs. Normal Lung

MMI-0100 Dose-Response Data in Idiopathic Pulmonary Fibrosis Prevention Model
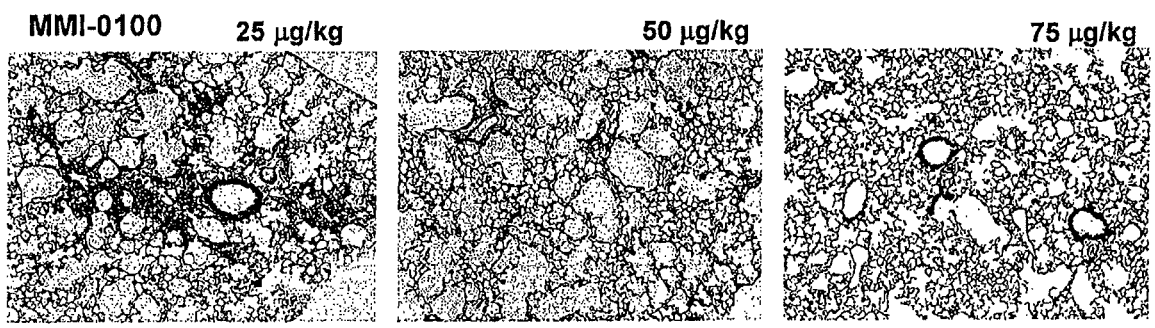
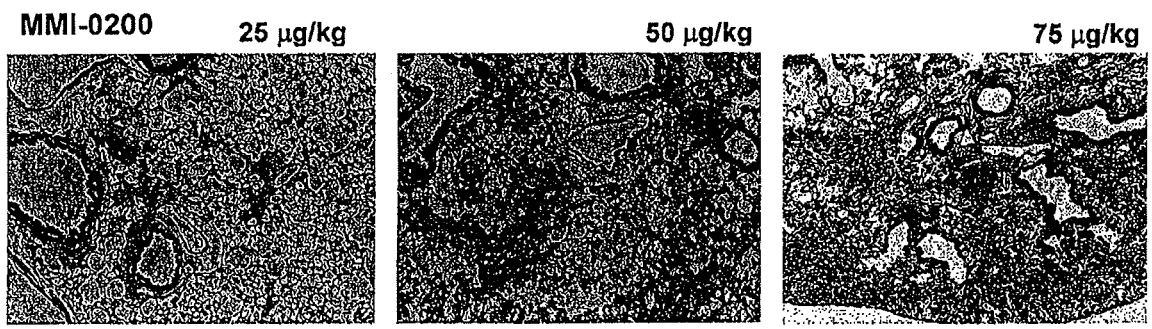
FIGURE 13

Reduced Activated MK2 with MMI-0100 in IPF Treatment Model

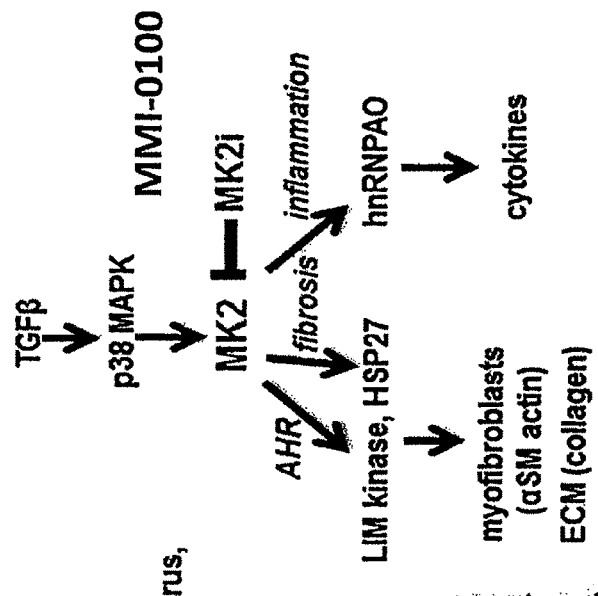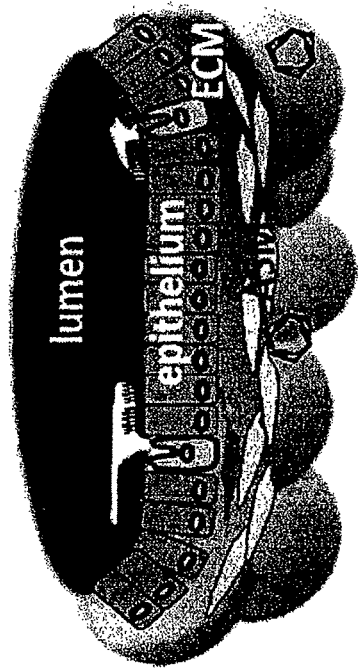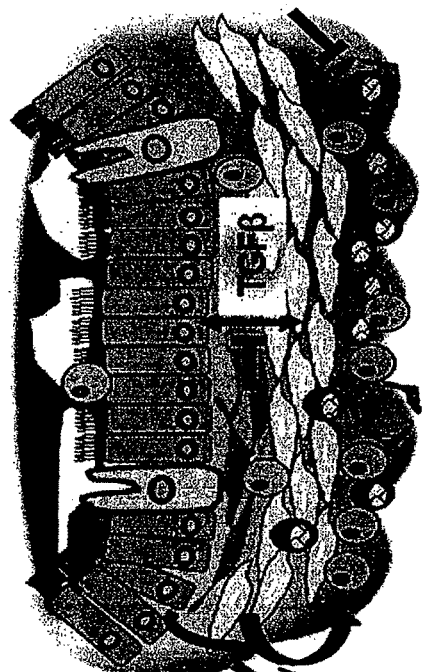
FIGURE 28

SEQUENCE LISTING

```
<160> NUMBER OF SEQ ID NOS: 25

<210> SEQ ID NO 1
<211> LENGTH: 22
<212> TYPE: PRT
<213> ORGANISM: Unknown
<220> FEATURE:
<223> OTHER INFORMATION: Mammalian

<400> SEQUENCE: 1

Tyr Ala Arg Ala Ala Ala Arg Gln Ala Arg Ala Lys Ala Leu Ala Arg
1               5                   10                  15

Gln Leu Gly Val Ala Ala
            20

<210> SEQ ID NO 2
<211> LENGTH: 11
<212> TYPE: PRT
<213> ORGANISM: Unknown
<220> FEATURE:
<223> OTHER INFORMATION: Mammalian

<400> SEQUENCE: 2

Lys Ala Leu Ala Arg Gln Leu Gly Val Ala Ala
1               5                   10

<210> SEQ ID NO 3
<211> LENGTH: 21
<212> TYPE: PRT
<213> ORGANISM: Unknown
<220> FEATURE:
<223> OTHER INFORMATION: Mammalian

<400> SEQUENCE: 3

Phe Ala Lys Leu Ala Ala Arg Leu Tyr Arg Lys Ala Leu Ala Arg Gln
1               5                   10                  15

Leu Gly Val Ala Ala
            20
```

<210> SEQ ID NO 4
<211> LENGTH: 23
<212> TYPE: PRT
<213> ORGANISM: Unknown
<220> FEATURE:
<223> OTHER INFORMATION: Mammalian

<400> SEQUENCE: 4

Lys Ala Phe Ala Lys Leu Ala Ala Arg Leu Tyr Arg Lys Ala Leu Ala
1               5                   10                  15

Arg Gln Leu Gly Val Ala Ala
            20

<210> SEQ ID NO 5
<211> LENGTH: 21
<212> TYPE: PRT
<213> ORGANISM: Unknown
<220> FEATURE:
<223> OTHER INFORMATION: Mammalian

<400> SEQUENCE: 5

Tyr Ala Arg Ala Ala Ala Arg Gln Ala Arg Ala Lys Ala Leu Ala Arg
1               5                   10                  15

Gln Leu Ala Val Ala
            20

<210> SEQ ID NO 6
<211> LENGTH: 21
<212> TYPE: PRT
<213> ORGANISM: Unknown
<220> FEATURE:
<223> OTHER INFORMATION: Mammalian

<400> SEQUENCE: 6

Tyr Ala Arg Ala Ala Ala Arg Gln Ala Arg Ala Lys Ala Leu Ala Arg
1               5                   10                  15

Gln Leu Gly Val Ala
            20

<210> SEQ ID NO 7
<211> LENGTH: 22
<212> TYPE: PRT
<213> ORGANISM: Unknown
<220> FEATURE:
<223> OTHER INFORMATION: Mammalian

<400> SEQUENCE: 7

His Arg Arg Ile Lys Ala Trp Leu Lys Lys Ile Lys Ala Leu Ala Arg
1               5                   10                  15

Gln Leu Gly Val Ala Ala
            20

<210> SEQ ID NO 8
<211> LENGTH: 10
<212> TYPE: PRT
<213> ORGANISM: Unknown
<220> FEATURE:
<223> OTHER INFORMATION: Mammalian

<400> SEQUENCE: 8

Lys Ala Leu Ala Arg Gln Leu Ala Val Ala
1               5                   10

<210> SEQ ID NO 9

```
<211> LENGTH: 10
<212> TYPE: PRT
<213> ORGANISM: Unknown
<220> FEATURE:
<223> OTHER INFORMATION: Mammalian

<400> SEQUENCE: 9

Lys Ala Leu Ala Arg Gln Leu Gly Val Ala
1               5                   10

<210> SEQ ID NO 10
<211> LENGTH: 11
<212> TYPE: PRT
<213> ORGANISM: Unknown
<220> FEATURE:
<223> OTHER INFORMATION: Mammalian

<400> SEQUENCE: 10

Lys Ala Leu Ala Arg Gln Leu Gly Val Ala Ala
1               5                   10

<210> SEQ ID NO 11
<211> LENGTH: 11
<212> TYPE: PRT
<213> ORGANISM: Unknown
<220> FEATURE:
<223> OTHER INFORMATION: Mammalian

<400> SEQUENCE: 11

Tyr Ala Arg Ala Ala Ala Arg Gln Ala Arg Ala
1               5                   10

<210> SEQ ID NO 12
<211> LENGTH: 14
<212> TYPE: PRT
<213> ORGANISM: Unknown
<220> FEATURE:
<223> OTHER INFORMATION: Mammalian

<400> SEQUENCE: 12

Trp Leu Arg Arg Ile Lys Ala Trp Leu Arg Arg Ile Lys Ala
1               5                   10

<210> SEQ ID NO 13
<211> LENGTH: 7
<212> TYPE: PRT
<213> ORGANISM: Unknown
<220> FEATURE:
<223> OTHER INFORMATION: Mammalian

<400> SEQUENCE: 13

Trp Leu Arg Arg Ile Lys Ala
1               5

<210> SEQ ID NO 14
<211> LENGTH: 11
<212> TYPE: PRT
<213> ORGANISM: Unknown
<220> FEATURE:
<223> OTHER INFORMATION: Mammalian

<400> SEQUENCE: 14

Tyr Gly Arg Lys Lys Arg Arg Gln Arg Arg Arg
1               5                   10

<210> SEQ ID NO 15
<211> LENGTH: 12
```

```
<212> TYPE: PRT
<213> ORGANISM: Unknown
<220> FEATURE:
<223> OTHER INFORMATION: Mammalian

<400> SEQUENCE: 15

Trp Leu Arg Arg Ile Lys Ala Trp Leu Arg Arg Ile
1               5                   10

<210> SEQ ID NO 16
<211> LENGTH: 10
<212> TYPE: PRT
<213> ORGANISM: Unknown
<220> FEATURE:
<223> OTHER INFORMATION: Mammalian

<400> SEQUENCE: 16

Phe Ala Lys Leu Ala Ala Arg Leu Tyr Arg
1               5                   10

<210> SEQ ID NO 17
<211> LENGTH: 12
<212> TYPE: PRT
<213> ORGANISM: Unknown
<220> FEATURE:
<223> OTHER INFORMATION: Mammalian

<400> SEQUENCE: 17

Lys Ala Phe Ala Lys Leu Ala Ala Arg Leu Tyr Arg
1               5                   10

<210> SEQ ID NO 18
<211> LENGTH: 11
<212> TYPE: PRT
<213> ORGANISM: Unknown
<220> FEATURE:
<223> OTHER INFORMATION: Mammalian

<400> SEQUENCE: 18

His Arg Arg Ile Lys Ala Trp Leu Lys Lys Ile
1               5                   10

<210> SEQ ID NO 19
<211> LENGTH: 21
<212> TYPE: PRT
<213> ORGANISM: Unknown
<220> FEATURE:
<223> OTHER INFORMATION: Mammalian

<400> SEQUENCE: 19

Tyr Ala Arg Ala Ala Ala Arg Gln Ala Arg Ala Lys Ala Leu Asn Arg
1               5                   10                  15

Gln Leu Gly Val Ala
            20

<210> SEQ ID NO 20
<211> LENGTH: 9
<212> TYPE: PRT
<213> ORGANISM: Unknown
<220> FEATURE:
<223> OTHER INFORMATION: Mammalian

<400> SEQUENCE: 20

Arg Lys Lys Arg Arg Gln Arg Arg Arg
1               5
```

```
<210> SEQ ID NO 21
<211> LENGTH: 10
<212> TYPE: PRT
<213> ORGANISM: Unknown
<220> FEATURE:
<223> OTHER INFORMATION: Mammalian

<400> SEQUENCE: 21

Lys Lys Leu Asn Arg Thr Leu Ser Val Ala
1               5                   10

<210> SEQ ID NO 22
<211> LENGTH: 13
<212> TYPE: PRT
<213> ORGANISM: Unknown
<220> FEATURE:
<223> OTHER INFORMATION: Mammalian

<400> SEQUENCE: 22

Lys Lys Lys Ala Leu Asn Arg Gln Leu Gly Val Ala Ala
1               5                   10

<210> SEQ ID NO 23
<211> LENGTH: 17
<212> TYPE: PRT
<213> ORGANISM: Unknown
<220> FEATURE:
<223> OTHER INFORMATION: Mammalian
<220> FEATURE:
<221> NAME/KEY: MISC_FEATURE
<222> LOCATION: (3)..(12)
<223> OTHER INFORMATION: Wherein the "Xaa's" represent any amino acid
      and a sequence of amino acids with a length of 10 residues.

<400> SEQUENCE: 23

Lys Lys Xaa Xaa Xaa Xaa Xaa Xaa Xaa Xaa Xaa Xaa Lys Arg Arg Lys
1               5                   10                  15

Lys

<210> SEQ ID NO 24
<211> LENGTH: 7
<212> TYPE: PRT
<213> ORGANISM: Unknown
<220> FEATURE:
<223> OTHER INFORMATION: Mammalian

<400> SEQUENCE: 24

Leu Leu Lys Arg Arg Lys Lys
1               5

<210> SEQ ID NO 25
<211> LENGTH: 6
<212> TYPE: PRT
<213> ORGANISM: Unknown
<220> FEATURE:
<223> OTHER INFORMATION: Mammalian
<220> FEATURE:
<221> NAME/KEY: MISC_FEATURE
<222> LOCATION: (1)..(1)
<223> OTHER INFORMATION: Wherein the "Xaa" represents a bulky
      hydrophobic residue selected from the group consisting of Val,
      Ile, Leu, Met, and Phe.
<220> FEATURE:
<221> NAME/KEY: MISC_FEATURE
<222> LOCATION: (2)..(2)
<223> OTHER INFORMATION: Wherein the "Xaa" represents any amino acid
<220> FEATURE:
<221> NAME/KEY: MISC_FEATURE
<222> LOCATION: (4)..(5)
<223> OTHER INFORMATION: Wherein the "Xaa's" represent any amino acid
```

```
        and a sequence of amino acids with a length of 2 residues.
<220> FEATURE:
<221> NAME/KEY: MISC_FEATURE
<222> LOCATION: (6)..(6)
<223> OTHER INFORMATION: Wherein the "Xaa" represents phosphorylated Ser
      or phosphorylated Thr.

<400> SEQUENCE: 25

Xaa Xaa Arg Xaa Xaa Xaa
1               5
```

COMPOSITIONS AND METHODS FOR PREVENTING OR TREATING DISEASES, CONDITIONS OR PROCESSES CHARACTERIZED BY ABERRANT FIBROBLAST PROLIFERATION AND EXTRACELLULAR MATRIX DEPOSITION

CROSS REFERENCE TO RELATED APPLICATIONS

This application is a Divisional of U.S. patent application Ser. No. 14/473,339, (filed Aug. 29, 2014), now U.S. Pat. No. 9,890,200, issued on Feb. 13, 2018, which is a continuation-in-part of U.S. patent application Ser. No. 13/445,759, filed Apr. 12, 2012, now U.S. Pat. No. 9,642,888, issued on May 9, 2017, which claims the benefit of priority to U.S. Provisional Application No. 61/474,370, filed Apr. 12, 2011, entitled "COMPOSITIONS AND METHODS FOR TREATING OR PREVENTING AIRWAY OR LUNG TISSUE DISEASES", the content of each of which is incorporated by reference herein in its entirety.

STATEMENT OF GOVERNMENT FUNDING

The described invention was made with government support from a Small Business Innovation Research (SBIR) grant to Moerae Matrix, LLC. The government has certain rights in the invention.

FIELD OF THE INVENTION

The invention is in the fields of cell and molecular biology, polypeptides, and therapeutic methods of use.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: 128542-00704_SL.txt, date recorded Mar. 26, 2018, file size 7 kilobytes).

BACKGROUND

1. Mechanisms of Wound Healing and Fibrosis

The term "wound healing" refers to the process by which the body repairs trauma to any of its tissues, especially those caused by physical means and with interruption of continuity.

A wound-healing response often is described as having three distinct phases-injury, inflammation and repair. Generally speaking, the body responds to injury with an inflammatory response, which is crucial to maintaining the health and integrity of an organism. If however it goes awry, it can result in tissue destruction.

Phase I: Injury

Injury caused by factors including, but not limited to, autoimmune or allergic reactions, environmental particulates, infection or mechanical damage often results in the disruption of normal tissue architecture, initiating a healing response. Damaged epithelial and endothelial cells must be replaced to maintain barrier function and integrity and prevent blood loss, respectively. Acute damage to endothelial cells leads to the release of inflammatory mediators and initiation of an anti-fibrinolytic coagulation cascade, temporarily plugging the damaged vessel with a platelet and fibrin-rich clot. For example, lung homogenates, epithelial cells or bronchoalveolar lavage fluid from idiopathic pulmonary fibrosis (IPF) patients contain greater levels of the platelet-differentiating factor, X-box-binding protein-1, compared with chronic obstructive pulmonary disease (COPD) and control patients, suggesting that clot-forming responses are continuously activated. In addition, thrombin (a serine protease required to convert fibrinogen into fibrin) is also readily detected within the lung and intra-alveolar spaces of several pulmonary fibrotic conditions, further confirming the activation of the clotting pathway. Thrombin also can directly activate fibroblasts, increasing proliferation and promoting fibroblast differentiation into collagen-producing myofibroblasts. Damage to the airway epithelium, specifically alveolar pneumocytes, can evoke a similar anti-fibrinolytic cascade and lead to interstitial edema, areas of acute inflammation and separation of the epithelium from the basement membrane.

Platelet recruitment, degranulation and clot formation rapidly progress into a phase of vasoconstriction with increased permeability, allowing the extravasation (movement of white blood cells from the capillaries to the tissues surrounding them) and direct recruitment of leukocytes to the injured site. The basement membrane, which forms the extracellular matrix underlying the epithelium and endothelium of parenchymal tissue, precludes direct access to the damaged tissue. To disrupt this physical barrier, zinc-dependent endopeptidases, also called matrix metalloproteinases (MMPs), cleave one or more extracelluar matrix constituents allowing extravasation of cells into, and out of, damaged sites. Specifically, MMP-2 (gelatinase A, Type N collagenase) and MMP-9 (gelatinase B, Type IV collagenase) cleave type N collagens and gelatin, two important constituents of the basement membrane. Recent studies have found that MMP-2 and MMP-9 are upregulated, highlighting that tissue-destructive and regenerative processes are common in fibrotic conditions. The activities of MMPs are controlled by several mechanisms including transcriptional regulation, proenzyme regulation, and specific tissue inhibitors of MMPs. The balance between MMPs and the various inhibitory mechanisms can regulate inflammation and determine the net amount of collagen deposited during the healing response.

Previous studies using a model of allergic airway inflammation and remodeling with MMP-$2^{-/-}$, MMP-$9^{-/-}$ and MMP-$2^{-/-}$ MMP-$9^{-/-}$ double knockout mice showed that MMP-2 and MMP-9 were required for successful egression and clearance of inflammatory cells out of the inflamed tissue and into the airspaces. In the absence of these MMPs, cells were trapped within the parenchyma of the lung and were not able to move into the airspaces, which resulted in fatal asphyxiation.

Phase II: Inflammation

Once access to the site of tissue damage has been achieved, chemokine gradients recruit inflammatory cells. Neutrophils, eosinophils, lymphocytes, and macrophages are observed at sites of acute injury with cell debris and areas of necrosis cleared by phagocytes.

The early recruitment of eosinophils, neutrophils, lymphocytes, and macrophages providing inflammatory cytokines and chemokines can contribute to local TGF-β and IL-13 accumulation. Following the initial insult and wave of inflammatory cells, a late-stage recruitment of inflammatory cells may assist in phagocytosis, in clearing cell debris, and in controlling excessive cellular proliferation, which together may contribute to normal healing. Late-stage inflammation may serve an anti-fibrotic role and may be required for successful resolution of wound-healing responses. For example, a late-phase inflammatory profile rich in phagocytic macrophages, assisting in fibroblast clearance, in addition to IL-10-secreting regulatory T cells, suppressing local chemokine production and TGF-β, may prevent excessive fibroblast activation.

The nature of the insult or causative agent often dictates the character of the ensuing inflammatory response. For example, exogenous stimuli like pathogen-associated molecular patterns (PAMPs) are recognized by pathogen recognition receptors, such as toll-like receptors and NOD-like receptors (cytoplasmic proteins that have a variety of functions in regulation of inflammatory and apoptotic responses), and influence the response of innate cells to invading pathogens. Endogenous danger signals also can influence local innate cells and orchestrate the inflammatory cascade.

The nature of the inflammatory response dramatically influences resident tissue cells and the ensuing inflammatory cells. Inflammatory cells themselves also propagate further inflammation through the secretion of chemokines, cytokines, and growth factors. Many cytokines are involved throughout a wound-healing and fibrotic response, with specific groups of genes activated in various conditions. For example, chronic allergic airway disease in asthmatics is associated commonly with elevated type-2 helper T cell ($Th_2$) related cytokine profiles (including, but not limited to, interleukin-4 (IL-4), interleukin-5 (IL-5), interleukin-6 (IL-6), interleukin-13 (IL-13), and interleukin-9 (IL-9)), whereas chronic obstructive pulmonary disease and fibrotic lung disease (such as idiopathic pulmonary fibrosis) patients more frequently present pro-inflammatory cytokine profiles (including, but not limited to, interleukin-1 alpha (IL-1α), interleukin-1 beta (IL-1β), interleukin-6 (IL-6), tumor necrosis factor alpha (TNF-α), transforming growth factor beta (TGF-β), and platelet-derived growth factors (PDGFs)). Each of these cytokines has been shown to exhibit significant pro-fibrotic activity, acting through the recruitment, activation and proliferation of fibroblasts, macrophages, and myofibroblasts.

Phase III: Tissue Repair and Contraction

The closing phase of wound healing consists of an orchestrated cellular re-organization guided by a fibrin (a fibrous protein that is polymerized to form a "mesh" that forms a clot over a wound site)-rich scaffold formation, wound contraction, closure and re-epithelialization. The vast majority of studies elucidating the processes involved in this phase of wound repair have come from dermal wound studies and in vitro systems.

Myofibroblast-derived collagens and smooth muscle actin (α-SMA) form the provisional extracellular matrix, with macrophage, platelet, and fibroblast-derived fibronectin forming a fibrin scaffold. Collectively, these structures are commonly referred to as granulation tissues. Primary fibroblasts or alveolar macrophages isolated from idiopathic pulmonary fibrosis patients produce significantly more fibronectin and α-SMA than control fibroblasts, indicative of a state of heightened fibroblast activation. It has been reported that IPF patients undergoing steroid treatment had similar elevated levels of macrophage-derived fibronectin as IPF patients without treatment. Thus, similar to steroid resistant IL-13-mediated myofibroblast differentiation, macrophage-derived fibronectin release also appears to be resistant to steroid treatment, providing another reason why steroid treatment may be ineffective. From animal models, fibronectin appears to be required for the development of pulmonary fibrosis, as mice with a specific deletion of an extra type III domain of fibronectin (EDA) developed significantly less fibrosis following bleomycin administration compared with their wild-type counterparts.

In addition to fibronectin, the provisional extracellular matrix consists of glycoproteins (such as PDGF), glycosaminoglycans (such as hyaluronic acid), proteoglycans and elastin. Growth factor and TGF-β-activated fibroblasts migrate along the extracellular matrix network and repair the wound. Within skin wounds, TGF-β also induces a contractile response, regulating the orientation of collagen fibers. Fibroblast to myofibroblast differentiation, as discussed above, also creates stress fibers and the neo-expression of α-SMA, both of which confer the high contractile activity within myofibroblasts. The attachment of myofibroblasts to the extracellular matrix at specialized sites called the "fibronexus" or "super mature focal adhesions" pull the wound together, reducing the size of the lesion during the contraction phase. The extent of extracellular matrix laid down and the quantity of activated myofibroblasts determines the amount of collagen deposition. To this end, the balance of matrix metalloproteinases (MMPs) to tissue inhibitor of metalloproteinases (TIMPs) and collagens to collagenases vary throughout the response, shifting from pro-synthesis and increased collagen deposition towards a controlled balance, with no net increase in collagen. For successful wound healing, this balance often occurs when fibroblasts undergo apoptosis, inflammation begins to subside, and granulation tissue recedes, leaving a collagen-rich lesion. The removal of inflammatory cells, and especially α-SMA-positive myofibroblasts, is essential to terminate collagen deposition. Interestingly, in idiopathic pulmonary fibrosis patients, the removal of fibroblasts can be delayed, with cells resistant to apoptotic signals, despite the observation of elevated levels of pro-apoptotic and FAS-signaling molecules. This relative resistance to apoptosis may potentially underlie this fibrotic disease. However, several studies also have observed increased rates of collagen-secreting fibroblast and epithelial cell apoptosis in idiopathic pulmonary fibrosis, suggesting that yet another balance requires monitoring of fibroblast apoptosis and fibroblast proliferation. From skin studies, re-epithelialization of the wound site re-establishes the barrier function and allows encapsulated cellular re-organization. Several in vitro and in vivo models, using human or rat epithelial cells grown over a collagen matrix, or tracheal wounds in vivo, have been used to identify significant stages of cell migration, proliferation, and cell spreading. Rapid and dynamic motility and proliferation, with epithelial restitution from the edges of the denuded area occur within hours of the initial wound. In addition, sliding sheets of epithelial cells can migrate over the injured area assisting wound coverage. Several factors have been shown to regulate re-epithelialization, including serum-derived transforming growth factor alpha (TGF-α), and matrix metalloproteinase-7 (MMP-7) (which itself is regulated by TIMP-1).

Collectively, the degree of inflammation, angiogenesis, and amount of extracellular matrix deposition all contribute to ultimate development of a fibrotic lesion. Thus, therapeutic intervention that interferes with fibroblast activation, proliferation, or apoptosis requires a thorough understanding and appreciation of all of the phases of wound repair. Although these three phases are often presented sequentially, during chronic or repeated injury these processes function in parallel, placing significant demands on regulatory mechanisms. (Wilson and Wynn, *Mucosal Immunol.*, 2009, 3(2):103-121).

2. Fibrosis as a Pathology

Fibrosis represents the formation or development of excess fibrous connective tissue in an organ or tissue, which is formed as a consequence of the normal or abnormal/reactive wound healing response leading to a scar. Fibrosis is characterized by, for example, without limitation, an aberrant deposition of an extracellular matrix protein, an aberrant promotion of fibroblast proliferation, an aberrant induction of differentiation of a population of fibroblasts into a population of myofibroblasts, an aberrant promotion of attachment of myofibroblasts to an extracellular matrix, or a combination thereof.

Pro-Inflammatory Mediators

Accumulating evidence has suggested that polypeptide mediators known as cytokines, including various lymphokines, interleukins, and chemokines, are important stimuli to collagen deposition in fibrosis. Released by resident tissue cells and recruited inflammatory cells, cytokines are thought to stimulate fibroblast proliferation and increased synthesis of extracellular matrix proteins, including collagen. For example, an early feature in the pathogenesis of idiopathic pulmonary fibrosis is alveolar epithelial and/or capillary cell injury. This promotes recruitment into the lung of circulating immune cells, such as monocytes, neutrophils, lymphocytes and eosinophils. These effector cells, together with resident lung cells, such as macrophages, alveolar epithelial and endothelial cells, then release cytokines, which stimulate target cells, typically fibroblasts, to replicate and synthesize increased amounts of collagen. Breakdown of extracellular matrix protein also may be inhibited, thereby contributing to the fibrotic process. (Coker and Laurent, *Eur Respir J,* 1998; 11:1218-1221)

Numerous cytokines have been implicated in the pathogenesis of fibrosis, including, without limitation, transforming growth factor-β (TGF-β), tumor necrosis factor-α (TNF-α), platelet-derived growth factor (PDGF), insulin-like growth factor-1 (IGF-1), endothelin-1 (ET-1) and the interleukins, interleukin-1 (IL-1), interleukin-6 (IL-6), interleukin-8 (IL-8), and interleukin-17 (IL-17). Chemokine leukocyte chemoattractants, including the factor Regulated upon Activation in Normal T-cells, Expressed and Secreted (RANTES), are also thought to play an important role. Elevated levels of pro-inflammatory cytokines, such as Interleukin 8 (IL-8), as well as related downstream cell adhesion molecules (CAMs) such as intercellular adhesion molecule-1 (ICAM-1) and vascular cell adhesion molecule-1 (VCAM-1), matrix metalloproteinases such as matrix metalloproteinase-7 (MMP-7), and signaling molecules such as S100 calcium-binding protein A12 (S100A12, also known as calgranulin C), in the peripheral blood have been found to be associated with mortality, lung transplant-free survival, and disease progression in patients with idiopathic pulmonary fibrosis (Richards et al, *Am J Respir Crit Care Med,* 2012, 185: 67-76).

The TGF-β family of proteins has a potent stimulatory effect on extracellular matrix deposition, and in fact has been used in constructing induced animal models of fibrosis through gene transfer. In vitro studies show that TGF-β1, secreted as a latent precursor, promotes fibroblast procollagen gene expression and protein synthesis. The data suggest that the other mammalian isoforms, TGF-β2 and TGF-β3, also stimulate human lung fibroblast collagen synthesis and reduce breakdown in vitro. In animal models of pulmonary fibrosis, enhanced TGF-β1 gene expression is temporally and spatially related to increased collagen gene expression and protein deposition. TGF-β1 antibodies reduce collagen deposition in murine bleomycin-induced lung fibrosis, and human fibrotic lung tissue shows enhanced TGF-β1 gene and protein expression.

TNF-α can stimulate fibroblast replication and collagen synthesis in vitro, and pulmonary TNF-α gene expression rises after administration of bleomycin in mice. Soluble TNF-α receptors reduce lung fibrosis in murine models, and pulmonary overexpression of TNF-α in transgenic mice is characterized by lung fibrosis. In patients with IPF or asbestosis (a chronic inflammatory and fibrotic medical condition affecting the parenchymal tissue of the lungs caused by the inhalation and retention of asbestos fibers), bronchoalveolar lavage fluid-derived macrophages release increased amounts of TNF-α compared with controls.

Endothelin (ET-1) also fulfills the criteria for a profibrotic cytokine. This molecule promotes fibroblast proliferation and chemotaxis and stimulates procollagen production. It is present in the lungs of patients with pulmonary fibrosis, and a recent report suggests that the ET-1 receptor antagonist, bosentan, ameliorates lung fibrosis when administered to experimental animals.

Unchecked Myofibroblast Proliferation/Activation and Fibrotic Foci Formation

Differentiation of fibroblasts into myofibroblasts has long been believed to be an important event in many conditions, including wound repair and fibrosis. For example, it has been reported that myofibroblasts occur in areas of active fibrosis and are responsible for production and deposition of extracellular matrix (ECM) proteins in pulmonary fibrosis. (Liu, T. et al., *Am J Respir Cell Mol Biol,* 2007, 37:507-517).

One hypothesis for the causation of idiopathic pulmonary fibrosis suggests that a still-unidentified stimulus produces repeated episodes of acute lung injury. Wound healing at these sites of injury ultimately leads to fibrosis, with loss of lung function. Fibroblast foci, the hallmark lesions of idiopathic pulmonary fibrosis, feature vigorous replication of mesenchymal cells and exuberant deposition of fresh extracellular matrix. Such foci are typical of alveolar epithelial-cell injury, with endoluminal plasma exudation and collapse of the distal air space. Mediators normally associated with wound healing, such as transforming growth factor-β1 (TGF-β1) and connective-tissue growth factor, are expressed also at these sites. The driving force for this focal acute lung injury and wound repair is unknown.

3. Disease or Conditions in which Fibrosis Plays a Role

Fibrosis has been implicated in a number of heterogeneous diseases or conditions, including, but not limited to, interstitial lung disease, such as idiopathic pulmonary fibrosis, acute lung injury (ALI), radiation-induced fibrosis, and transplant rejection.

3.1. Idiopathic Pulmonary Fibrosis (IPF)

Idiopathic Pulmonary fibrosis (IPF, also known as cryptogenic fibrosing alveolitis, CFA, or Idiopathic Fibrosing Interstitial Pneumonia) is defined as a specific form of chronic, progressive fibrosing interstitial pneumonia of uncertain etiology that occurs primarily in older adults, is limited to the lungs, and is associated with the radiologic and histological pattern of usual interstitial pneumonia (UIP) (Raghu G. et al., *Am J Respir Crit Care Med.,* 183(6):788-824, 2011; Thannickal, V. et al., *Proc Am Thorac Soc.,* 3(4):350-356, 2006). It may be characterized by abnormal and excessive deposition of fibrotic tissue in the pulmonary interstitium. On high-resolution computed tomography (HRCT) images, UIP is characterized by the presence of reticular opacities often associated with traction bronchiectasis. As IPF progresses, honeycombing becomes more prominent (Neininger A. et al., *J Biol Chem.,* 277(5):3065-8, 2002). Pulmonary function tests often reveal restrictive impairment and reduced diffusing capacity for carbon monoxide (Thomas, T. et al., *J Neurochem.*, 105(5): 2039-52, 2008). Studies have reported significant increases in TNF-α and IL-6 release in patients with idiopathic pulmonary fibrosis (IPF) (Zhang, Y, et al. *J. Immunol.* 150(9):4188-4196, 1993), which has been attributed to the level of expression of IL-1β (Kolb, M., et al. *J. Clin. Invest,* 107 (12):1529-1536, 2001). The onset of IPF symptoms, shortness of breath and cough, are usually insidious but gradually progress, with death occurring in 70% of patients within five years after diagnosis. This grim prognosis is similar to numbers of annual deaths attributable to breast cancer (Raghu G. et al., *Am J Respir Crit Care Med.*, 183(6):788-824, 2011).

IPF afflicts nearly 130,000 patients in the United States, with approximately 50,000 new patients annually and nearly 40,000 deaths each year worldwide (Raghu G. et al., *Am J Respir Crit Care Med.*, 183(6):788-824, 2011). While these data are notable, a recent study reported that IPF may be 5-10 times more prevalent than previously thought, perhaps due to increasing prevalence or enhanced diagnostic capabilities (Thannickal, V. et al., *Proc Am Thorac Soc.*, 3(4): 350-356, 2006). Lung transplantation is considered a definitive therapy for IPF, but the five year survival post lung transplantation is less than 50%. Accordingly, even lung transplantation cannot be considered a "cure" for IPF. In addition to the physical and emotional toll on the patient, IPF is extremely expensive to treat and care for with national healthcare costs to in the range of $2.8 billion dollars for every 100,000 patients annually.

In addition, previous studies have suggested that superimposed environmental insults may be important in the pathogenesis of idiopathic pulmonary fibrosis. In most reported case series, up to 75 percent of index patients with idiopathic pulmonary fibrosis are current or former smokers. In large epidemiologic studies, cigarette smoking has been strongly associated with idiopathic pulmonary fibrosis. In addition, many of the inflammatory features of idiopathic pulmonary fibrosis are more strongly linked to smoking status than to the underlying lung disease. Thus, cigarette smoking may be an independent risk factor for idiopathic pulmonary fibrosis. Latent viral infections, especially those of the herpes virus family, have also been reported to be associated with idiopathic pulmonary fibrosis.

Since there is no known effective treatment for IPF, including lung transplantation, there remains a critical need for the development of novel therapeutics. There are a variety of therapeutic approaches currently being investigated, including anti-fibrotic therapies that may slow or inhibit the body's ability to produce scar or fibrotic tissue and pulmonary vasodilators to increase the tissue area for gas exchange in the lung. Aside from lung transplantation, potential IPF treatments have included corticosteroids, azathioprine, cyclophosphamide, anticoagulants, and N-acetylcysteine (Raghu G. et al., *Am J Respir Crit Care Med.*, 183(6):788-824, 2011). In addition, supportive therapies such as oxygen therapy and pulmonary rehabilitation are employed routinely. However, none of these have definitely impacted the long term survival of IPF patients, which further highlights the unmet medical need for treatment options in IPF. As an example, despite mixed clinical program results, InterMune's oral small-molecule Esbriet® (pirfenadone) received European and Japanese approvals for patients with IPF. Esbriet® thus became the first medication specifically indicated for the treatment of IPF; due to equivocal trial outcomes and drug side effects, the drug's utility is viewed with skepticism in the United States, and did not receive an FDA approval based on the data submitted at that time. Accordingly, a large phase 3 clinical trial is in progress to determine its efficacy to support a New Drug Application in the United States.

Histopathologically, IPF can be described as accumulation of activated myofibroblasts (or mesenchymal cells) in fibroblastic foci (Thannickal, V. et al., *Proc Am Thorac Soc.*, 3(4):350-356, 2006). Impaired apoptosis of myofibroblasts may result in a persistent and dysregulated repair process that culminates in tissue fibrosis. Arguably, inflammation also plays a critical role in IPF, perhaps through cyclic acute stimulation of fibroblasts. These findings point to potential targets for therapeutic intervention.

3.1.1. Pathogenesis of Idiopathic Pulmonary Fibrosis (IPF)

While pathogenic mechanisms are incompletely understood, the currently accepted paradigm proposes that injury to the alveolar epithelium is followed by a burst of pro-inflammatory and fibroproliferative mediators that invoke responses associated with normal tissue repair. For unclear reasons, these repair processes never resolve and progressive fibrosis ensues. (Selman M, et al., *Ann Intern Med,* 134(2):136-151, 2001; Noble, P. and Homer R., *Clin Chest Med,* 25(4):749-58, 2004; Strieter, R., *Chest,* 128 (5 Suppl 1):526S-532S, 2005).

3.1.2. Bleomycin Mouse Model of Pulmonary Fibrosis

Although a number of animal models exist and can be useful (e.g., the TGF-β adenovirus transduction model or the radiation-induced fibrosis model), the bleomycin model is well-documented and the best characterized murine model in use today to demonstrate efficacy of a particular drug or protein kinase inhibitor in the post-inflammatory/pre-fibrotic/fibro-preventive stages (Vittal, R. et al., *J Pharmacol Exp Ther.*, 321(1):35-44, 2007; Vittal, R. et al., *Am J Pathol.*, 166(2):367-75, 2005; Hecker L. et al., *Nat Med.*, 15(9): 1077-81, 2009).

The antibiotic bleomycin was originally isolated from *Streptomyces verticillatus* (Umezawa, H. et al., *Cancer* 20: 891-895, 1967). This antibiotic was subsequently found to be effective against squamous cell carcinomas and skin tumors (Umezawa, H., *Fed Proc,* 33: 2296-2302, 1974); however, its usefulness as an anti-neoplastic agent was limited by dose-dependent pulmonary toxicity resulting in fibrosis (Muggia, F. et al., *Cancer Treat Rev,* 10: 221-243, 1983). The delivery of bleomycin via the intratracheal route (generally 1.25-4 U/kg, depending on the source) has the advantage that a single injection of the drug produces lung injury and resultant fibrosis in rodents (Phan, S. et al., *Am Rev Respir Dis* 121: 501-506, 1980; Snider, G. et al., *Am Rev Respir Dis.* 117: 289-297, 1978; Thrall, R. et al., *Am J Pathol,* 95: 117-130, 1979). Intratracheal delivery of the drug to rodents results in direct damage initially to alveolar epithelial cells. This event is followed by the development of neutrophilic and lymphocytic pan-alveolitis within the first week (Janick-Buckner, D. et al., *Toxicol Appl Pharmacol.*, 100(3):465-73, 1989). Subsequently, alveolar inflammatory cells are cleared, fibroblast proliferation is noted, and extracellular matrix is synthesized (Schrier D. et al., *Am Rev Respir Dis.*, 127(1):63-6, 1983). The development of fibrosis in this model can be seen biochemically and histologically by day 14 with maximal responses generally noted around days 21-28 (Izbicki G. et al., *Int J Exp Pathol.*, 83(3):111-9, 2002; Phan, S. et al., *Chest.*, 83(5 Suppl):44S-45S, 1983). Beyond 28 days, however, the response to bleomycin is more variable. Original reports suggest that bleomycin delivered intratracheally may induce fibrosis that progresses or persists for 60-90 days (Thrall R. et al., *Am J Pathol.*, 95(1):117-30, 1979; Goldstein R., et al., *Am Rev Respir Dis.*, 120(1):67-73, 1979; Starcher B. et al., *Am Rev Respir Dis.*, 117(2):299-305, 1978); however, other reports demonstrate a self-limiting response that begins to resolve after this period (Thrall R. et al., *Am J Pathol.*, 95(1):117-30, 1979; Phan, S. et al., *Chest,* 83(5 Suppl): 44S-45S, 1983; Lawson W. et al., *Am J Pathol.* 2005; 167(5):1267-1277). While the resolving nature of this model does not mimic human disease, this aspect of the model offers an opportunity for studying fibrotic resolution at these later time points.

3.2. Acute Lung Injury (ALI)

Acute lung injury (ALI) and its more severe form, the acute respiratory distress syndrome (ARDS), are syndromes of acute respiratory failure that result from acute pulmonary edema and inflammation. ALI/ARDS is a cause of acute respiratory failure that develops in patients of all ages from a variety of clinical disorders, including sepsis (pulmonary and nonpulmonary), pneumonia (bacterial, viral, and fungal), aspiration of gastric and oropharyngeal contents, major trauma, and several other clinical disorders, including severe acute pancreatitis, drug over dose, and blood products (Ware, L. and Matthay, M., *N Engl J Med,* 342:1334-1349, 2000). Most patients require assisted ventilation with positive pressure. The primary physiologic abnormalities are severe arterial hypoxemia as well as a marked increase in minute ventilation secondary to a sharp increase in pulmonary dead space fraction. Patients with ALI/ARDS develop protein-rich pulmonary edema resulting from exudation of fluid into the interstitial and airspace compartments of the lung secondary to increased permeability of the barrier. Additional pathologic changes indicate that the mechanisms involved in lung edema are complex and that edema is only one of the pathophysiologic events in ALI/ARDS. One physiologic consequence is a significant decrease in lung compliance that results in an increased work of breathing (Nuckton T. et al., *N Engl J Med,* 346:1281-1286, 2002), one of the reasons why assisted ventilation is required to support most patients.

It was suggested that mechanical ventilation (MV), a mainstay treatment for ALI, potentially contributes to and worsens permeability by exacting mechanical stress on various components of the respiratory system causing ventilator-associated lung injury (VALI) (Fan, E. et al., *JAMA,* 294:2889-2896, 2005; MacIntyre N., *Chest,* 128:561S-567, 2005). A recent trial demonstrated a significant improvement in survival in patients ventilated with low ($LV_T$) compared to high tidal volumes ($HV_T$) (The Acute Respiratory Distress Syndrome N. Ventilation with Lower Tidal Volumes as Compared with Traditional Tidal Volumes for Acute Lung Injury and the Acute Respiratory Distress Syndrome. *N Engl J Med;* 342:1301-1308, 2000). Other than ventilating at lower tidal volumes, which presumably imparts lower mechanical stress, there is little mechanistic understanding of the pathophysiology and no directed therapies for VALI.

It was suggested that the high tidal volumes ($HV_T$) mechanical ventilation (MV) results in phosphorylation of p38 MAP kinase, activation of MK2, and phosphorylation of HSPB1, a process that causes actin to disassociate from HSPB1 and polymerize to form stress fibers, which ultimately leads to paracellular gaps and increased vascular permeability. Furthermore, it was shown that inhibiting p38 MAP kinase or its downstream effector MK2 prevents the phosphorylation of HSPB1 and protects from vascular permeability by abrogating actin stress fiber formation and cytoskeletal rearrangement, suggesting that targeted inhibition of MK2 could be a potential therapeutic strategy for the treatment of acute lung injury (Damarla, M. et al., *PLoS ONE,* 4(2): E4600, 2009).

Moreover, studies have suggested that pulmonary fibrosis can also result from ALI. ALI may completely resolve or proceed to fibrosing alveolitis accompanied by persistent low oxygen in the blood (hypoxemia) and a reduced ability of the lung to expand with every breath (reduced pulmonary compliance). It was suggested that while the etiology of injury-induced lung fibrosis is different from idiopathic pulmonary fibrosis, both diseases share a common pathological mechanism, i.e., infiltration of fibroblasts into the airspaces of lung (Tager et al., *Nat. Med.* 14: 45-54, 2008; Ley, K. and Zarbock, A., *Nat. Med.* 14: 20-21; 2008).

3.3. Radiation-Induced Fibrosis

Fibrosis is a common sequela of both cancer treatment by radiotherapy and accidental irradiation. Fibrotic lesions following radiotherapy have been described in many tissues, including skin (Bentzen, S. et al., *Radiother. Oncol.* 15: 261-214, 1989; Brocheriou, C., et al., *Br. J. Radiol. Suppl.* 19: 101-108, 1986), lung (Lopez Cardozo, B. et al., *Int. J. Radiat. Oncol. Biol. Phys.,* 11: 907-914, 1985), heart (Fajardo, L. and Stewart, J., *Lab. Invest.,* 29: 244-257, 1973), and liver (Ingold, J. et al., *Am. J. Roentgenol.,* 93: 200-208, 1965).

In the lung (late responding tissue), two radiation toxicity syndromes, radiation pneumonitis and pulmonary fibrosis, may occur. Pneumonitis is manifested 2-3 months after radiotherapy is completed. Pathologically, pneumonitis is characterized by interstitial edema, the presence of interstitial and alveolar inflammatory cells, and an increase in the number of type II pneumocytes (Gross, N. et al., *Radiat. Res.,* III: 143-50, 1981; Guerry-Force, M. et al., *Radiat. Res.* 114: 138-53, 1988). In pneumonitis, the primary damage to the tissue is most likely caused by depletion of parenchymal cells (Hendry, J., *Radiat. Oncol. Vol.* 4,2: 123-132, 1994; Rosiello, R. et al., *Am. Rev. Respir. Dis.,* 148: 1671-1676, 1993; Travis, E. and Terry, N., Front. *Radiat. Ther. Oncol.,* 23: 41-59, 1989).

The fibrotic reaction is typified by increased interstitial collagen deposition, thickening of vascular walls and vascular occlusions (Vergava, J. et al., *Int. J. Radiat. Oncol. Biol. Phys.* 2: 723-732, 1987). Histological examinations of fibrotic lesions have revealed that fibrotic tissue contains infiltrating inflammatory cells, fibroblasts, and larger amounts of various extracellular matrix components. In fibrotic tissues, an enhanced synthesis and deposition of the interstitial collagens, fibronectin, and proteoglycans have been described (Maasiha, P. et al., *Int. J. Radiat. Oncol. Biol. Phys.* 20: 973-980, 1991), and this has been interpreted as the result of the radiation-induced modulation of the fibroblast cell system (Remy, J. et al., *Radiat. Res.* 125: 14-19, 1991).

Radiation-induced fibrosis, especially of the lung, was suggested to be due to an interplay of cellular and molecular events between several cell systems engaged in a fibrotic reaction. Irradiation alone is able to induce a premature terminal differentiation process of the fibroblast/fibrocyte cell system resulting in the enhanced accumulation of post-mitotic fibrocytes, which are characterized by a several-fold increase in the synthesis of interstitial collagens. Concomitantly, irradiation of accompanying parenchymal cell types, such as alveolar macrophages and alveolar type II pneumocytes, induces the immediate synthesis of specific cytokines, like TGF-β1, which then alter the interaction of the parenchymal cells with the fibroblast cell system. TGF-β1, as one of the major cytokines responsible for the fibrotic reaction, induces the fibroblast proliferation via an expansion of the progenitor fibroblast cell types as well as a premature terminal differentiation of progenitor fibroblasts into post-mitotic fibrocytes. This leads to an accumulation of post-mitotic fibrocytes due to a disturbance of the well-balanced cell type ratio of progenitor fibroblasts and post-mitotic fibrocytes. It was proposed that the pathophysiological tissue response following irradiation is caused by an altered cytokine- and growth factor-mediated interaction of multicellular cell systems resulting in the disturbance of the well-balanced cell type ratio of the interstitial fibroblast/fibrocyte cell system. (Rodemann, H. and Bamberg, M., *Radiotherapy and Oncology*, 35, 83-90, 1995).

3.4. Transplant Rejection

Transplantation is the act of transferring cells, tissues, or organs from one site to another. The malfunction of an organ system can be corrected with transplantation of an organ (e.g., kidney, liver, heart, lung, or pancreas) from a donor. However, the immune system remains the most formidable barrier to transplantation as a routine medical treatment, and rejection of such organ often corresponds to a fibrotic phenotype in the grafted organ. The immune system has developed elaborate and effective mechanisms to combat foreign agents. These mechanisms are also involved in the rejection of transplanted organs, which are recognized as foreign by the host's immune system.

The degree of immune response to a graft depends partly on the degree of genetic disparity between the grafted organ and the host. Xenografts, which are grafts between members of different species, have the most disparity and elicit the maximal immune response, undergoing rapid rejection. Autografts, which are grafts from one part of the body to another (e.g., skin grafts), are not foreign tissue and, therefore, do not elicit rejection. Isografts, which are grafts between genetically identical individuals (e.g., monozygotic twins), also undergo no rejection.

Allografts are grafts between members of the same species that differ genetically. This is the most common form of transplantation. The degree to which allografts undergo rejection depends partly on the degree of similarity or histocompatibility between the donor and the host.

The degree and type of response also vary with the type of the transplant. Some sites, such as the eye and the brain, are immunologically privileged (i.e., they have minimal or no immune system cells and can tolerate even mismatched grafts). Skin grafts are not initially vascularized and so do not manifest rejection until the blood supply develops. The lungs, heart, kidneys, and liver are highly vascular organs and often lead to a vigorous cell mediated response in the host, requiring immunosuppressive therapies.

Constrictive bronchiolitis (CB), also termed in lung transplant patients obliterative bronchiolitis, is inflammation and fibrosis occurring predominantly in the walls and contiguous tissues of membranous and respiratory bronchioles with resultant narrowing of their lumens. CB is found in a variety of settings, most often as a complication of lung and heart-lung transplantation (affecting 34% to 39% of patients, usually in the first 2 years after transplantation) and bone marrow transplantation, but also in rheumatoid arthritis, after inhalation of toxic agents such as nitrogen dioxide, after ingestion of certain drugs such as penicillamine and ingestion of the East Asian vegetable *Sauropus* androgynous, and as a rare complication of adenovirus, influenza type A, measles, and *Mycoplasma* pneumoniae infections in children. In lung transplants, CB is the single most important factor leading to death thereafter. In one study, the overall mortality rate was 25%. However, at the same time, 87% of patients who were asymptomatic and diagnosed solely by transbronchial biopsy had resolution or stabilization of disease. Decreases in $FEV_1$ from baseline can be used to clinically support CB in transplant patients; the term bronchiolitis obliterans syndrome is used to denote this clinical dysfunction, and a grading system has been established for it that is now widely used in the literature. Significant risk factors for the development of CB in lung transplants include alloantigen-dependent and -independent mechanisms. In the former group are late acute rejection and HLA mismatches at the A loci; in the latter are ischemia/reperfusion injuries to airways that result from the transplantation surgery and cytomegalovirus infection (Schlesinger C. et al, *Curr Opin Pulm. Med.*, 4(5): 288-93, 1998).

Mechanisms of Rejection

The immune response to a transplanted organ consists of both cellular (lymphocyte mediated) and humoral (antibody mediated) mechanisms. Although other cell types are also involved, the T cells are central in the rejection of grafts. The rejection reaction consists of the sensitization stage and the effector stage.

Sensitization Stage

In this stage, the CD4 and CD8 T cells, via their T-cell receptors, recognize the alloantigens expressed on the cells of the foreign graft. Two signals are needed for recognition of an antigen; the first is provided by the interaction of the T cell receptor with the antigen presented by MHC molecules, the second by a co-stimulatory receptor/ligand interaction on the T cell/APC surface. Of the numerous co-stimulatory pathways, the interaction of CD28 on the T cell surface with its APC surface ligands, B7-1 or B7-2 (commonly known as CD80 or CD86, respectively), has been studied the most (Clarkson, M. and Sayegh, M., *Transplantation*; 80(5): 555-563, 2005). In addition, cytotoxic T lymphocyte-associated antigen-4 (CTLA4) also binds to these ligands and provides an inhibitory signal. Other co-stimulatory molecules include CD40 and its ligand CD40L (CD154). Typically, helices of the MHC molecules form the peptide-binding groove and are occupied by peptides derived from normal cellular proteins. Thymic or central tolerance mechanisms (clonal deletion) and peripheral tolerance mechanisms (e.g., anergy) ensure that these self-peptide MHC complexes are not recognized by the T cells, thereby preventing autoimmune responses.

Effector Stage

Alloantigen-dependent and independent factors contribute to the effector mechanisms. Initially, nonimmunologic "injury responses" (ischemia) induce a nonspecific inflammatory response. Because of this, antigen presentation to T cells is increased as the expression of adhesion molecules, class II MHC, chemokines, and cytokines is upregulated. It also promotes the shedding of intact, soluble MHC molecules that may activate the indirect allorecognition pathway. After activation, CD4-positive T cells initiate macrophage-mediated delayed type hypersensitivity (DTH) responses and provide help to B cells for antibody production.

Various T cells and T cell-derived cytokines such as IL-2 and IFN-γ are upregulated early after transplantation. Later, β-chemokines like RANTES (regulated upon activation, normal T cell expressed and secreted), IP-10, and MCP-1 are expressed, and this promotes intense macrophage infiltration of the allograft. IL-6, TNF-α, inducible nitric oxide synthase (iNOS) and growth factors, also play a role in this process. Growth factors, including TGF-β and endothelin, cause smooth muscle proliferation, intimal thickening, interstitial fibrosis, and, in the case of the kidney, glomerulosclerosis.

Endothelial cells activated by T cell-derived cytokines and macrophages express class II MHC, adhesion molecules, and co-stimulatory molecules. These can present antigen and thereby recruit more T cells, amplifying the rejection process. CD8-positive T cells mediate cell-mediated cytotoxicity reactions either by delivering a "lethal hit" or, alternatively, by inducing apoptosis.

In addition, emerging studies have suggested involvement of fibrotic processes in chronic transplant rejection of an organ transplant. For example, it was shown that chronic lung allograft rejection is mediated by a relative deficiency of allograft endothelial cell-derived HIF-1α, leading to fibrotic remodeling of the transplanted organ (Wilkes, D., *J Clin Invest.*, 121(6): 2155-2157, 2011; Jiang, X. et al., *J Clin Invest.*, 121(6): 2336-2349, 2011).

3.5. Chronic Obstructive Pulmonary Disease (COPD)

Chronic obstructive pulmonary disease (COPD) is a collective description for lung diseases represented by chronic and relatively irreversible expiratory airflow dysfunction due to some combination of chronic obstructive bronchitis, emphysema, and/or chronic asthma. COPD is caused by a range of environmental and genetic risk factors, including smoking that contributes to the disease.

The prevalence of COPD is increasing worldwide, and COPD has become the fourth leading cause of death in the United States. In the United States, despite the decrease in cigarette smoking in recent decades, both the prevalence of, and the mortality associated with, COPD have increased and are projected to continue to increase for some years yet. Furthermore, COPD is costly, and acute exacerbations, which occur roughly once a year in patients with COPD of moderate or greater severity, constitute the most expensive component.

In COPD, airflow obstruction can occur on the basis of either of two very different pathophysiological processes in the lung: 1) inflammation of the parenchyma resulting in proteolysis of the lung parenchyma and loss of lung elasticity (emphysema); and 2) inflammation, scarring and narrowing of the small airways ("small airway disease"). In an individual patient, one of these processes, which may be controlled by different genetic factors, may predominate although both usually co-exist. Ultimately, both of these processes produce similar patterns of functional impairment: decreased expiratory flow, hyperinflation and abnormalities of gas exchange.

At an early stage of COPD, the following symptoms are found in the lungs of COPD patients: 1) breach of airway epithelium by damaging aerosols, 2) accumulation of inflammatory mucous exudates, 3) infiltration of the airway wall by inflammatory immune cells, 4) airway remodeling/thickening of the airway wall and encroachment on lumenal space, and 5) increased resistance to airflow. During this early stage, smooth muscle contraction and hyper-responsiveness also increase resistance, but the increased resistance is relieved by bronchodilators.

At an advanced stage, COPD patients characteristically develop deposition of fibrous connective tissue in the sub-epithelial and aventitial compartments surrounding the airway wall. Such peribronchiolar fibrosis contributes to fixed airway obstruction by restricting the enlargement of airway caliber that occurs with lung inflation.

3.5.1. Chronic Bronchitis

Chronic bronchitis is defined as the presence of chronic cough and sputum production for at least three months of two consecutive years in the absence of other diseases recognized to cause sputum production. In chronic bronchitis, epidemiologically the bronchial epithelium becomes chronically inflamed with hypertrophy of the mucus glands and an increased number of goblet cells. The cilia are also destroyed and the efficiency of the mucociliary escalator is greatly impaired. Mucus viscosity and mucus production are increased, leading to difficulty in expectorating. Pooling of the mucus leads to increased susceptibility to infection.

Microscopically there is infiltration of the airway walls with inflammatory cells. Inflammation is followed by scarring and remodeling that thickens the walls and also results in narrowing of the airways. As chronic bronchitis progresses, there is squamous metaplasia (an abnormal change in the tissue lining the inside of the airway) and fibrosis (further thickening and scarring of the airway wall). The consequence of these changes is a limitation of airflow. Repeated infections and inflammation over time leads to irreversible structural damage to the walls of the airways and to scarring, with narrowing and distortion of the smaller peripheral airways.

3.5.2. Emphysema

Emphysema is defined in terms of its pathological features, characterized by abnormal dilatation of the terminal air spaces distal to the terminal bronchioles, with destruction of their wall and loss of lung elasticity. Bullae (blisters larger than 1 cm wide) may develop as a result of overdistention if areas of emphysema are larger than 1 cm in diameter. The distribution of the abnormal air spaces allows for the classification of the two main patterns of emphysema: panacinar (panlobular) emphysema, which results in distension, and destruction of the whole of the acinus, particularly the lower half of the lungs. Centriacinar (centrilobular) emphysema involves damage around the respiratory bronchioles affecting the upper lobes and upper parts of the lower lobes of the lung. Certain forms of emphysema are furthermore known to be associated with fibrosis.

The destructive process of emphysema is predominantly associated with cigarette smoking. Cigarette smoke is an irritant and results in low-grade inflammation of the airways and alveoli. It is known that cigarettes contain over 4,000 toxic chemicals, which affect the balance between the anti-protease and proteases within the lungs, causing permanent damage. Inflammatory cells (macrophages and neutrophils) produce a proteolytic enzyme known as elastase, which destroys elastin, an important component of lung tissue.

The alveoli or air sacs of the lung contain elastic tissue, which supports and maintains the potency of the intrapulmonary airways. The destruction of the alveolar walls allows narrowing in the small airways by loosening the guy ropes that help keep the airways open. During normal inspiration, the diaphragm moves downwards while the rib cage moves outwards, and air is drawn into the lungs by the negative pressure that is created. On expiration, as the rib cage and diaphragm relax, the elastic recoil of the lung parenchyma pushes air upwards and outwards. With destruction of the lung parenchyma, which results in floppy lungs and loss of the alveolar guy ropes, the small airways collapse and air trapping occurs, leading to hyperinflation of the lungs. Hyperinflation flattens the diaphragm, which results in less effective contraction and reduced alveolar efficiency, which in turn leads to further air trapping. Over time the described mechanism leads to severe airflow obstruction, resulting in insufficient expiration to allow the lungs to deflate fully prior to the next inspiration.

3.5.3 Chronic Asthma

Asthma is defined as a chronic inflammatory condition of the airways, leading to widespread and variable airway obstruction that is reversible spontaneously or with treatment. In some patients with chronic asthma, the disease progresses, leading to irreversible airway obstruction, particularly if the asthma is untreated, either because it has not been diagnosed or mismanaged, or if it is particularly severe. Children with asthma have a one in ten chance of developing irreversible asthma, while the risk for adult-onset asthmatics is one in four. Studies also have found that in both children and adults that asthma might lead to irreversible deterioration in lung function if their asthma was not treated appropriately, particularly with corticosteroid therapy.

The airway inflammation in asthma over time can lead to remodeling of the airways through increased smooth muscle, disruption of the surface epithelium, increased collagen deposition and thickening of the basement membrane.

Increased Smooth Muscle

Increased airway smooth muscle (ASM) mass is the most prominent feature of airway remodeling (N. Carroll, J. Elliot, A. Morton, and A. James, "The structure of large and small airways in nonfatal and fatal asthma," American Review of Respiratory Disease, vol. 147, no. 2, pp. 405-410, 1993), with ASM mass increasing disproportionately compared to the increase in total wall thickness (E. Tagaya and J. Tamaoki, "Mechanisms of airway remodeling in asthma," Allergology International, vol. 56, no. 4, pp. 331-340, 2007). Airway remodeling has been documented in both fatal and nonfatal asthma (A. J. James, "Relationship between airway wall thickness and airway hyperresponsiveness," in Airway Wall Remodeling in Asthma, A. G. Stewart, Ed., pp. 1-27, CRC Press, Boca Raton, Fla., USA, 1997), and correlates with both disease severity and duration, being greater in fatal than nonfatal cases (N. Carroll, J. Elliot, A. Morton, and A. James, "The structure of large and small airways in nonfatal and fatal asthma," American Review of Respiratory Disease, vol. 147, no. 2, pp. 405-410, 1993; A. L. James, P. D. Pare, and J. C. Hogg, "The mechanics of airway narrowing in asthma," American Review of Respiratory Disease, vol. 139, no. 1, pp. 242-246, 1989; K. Kuwano, C. H. Bosken, P. D. Pare, T. R. Bai, B. R. Wiggs, and J. C. Hogg, "Small airways dimensions in asthma and in chronic obstructive pulmonary disease," American Review of Respiratory Disease, vol. 148, no. 5, pp. 1220-1225, 1993) and greater in older patients than in younger patients with fatal asthma. The increase in ASM mass may be the coordinated result of increased myocyte size (hypertrophy), increased myocyte number (hyperplasia), and differentiation and migration of mesenchymal cells to ASM bundles (S. Beqaj, S. Jakkaraju, R. R. Mattingly, D. Pan, and L. Schuger, "High RhoA activity maintains the undifferentiated mesenchymal cell phenotype, whereas RhoA down-regulation by laminin-2 induces smooth muscle myogenesis," Journal of Cell Biology, vol. 156, no. 5, pp. 893-903, 2002; S. J. Hirst, J. G. Martin, J. V. Bonacci et al., "Proliferative aspects of airway smooth muscle," Journal of Allergy and Clinical Immunology, vol. 114, no. 2, pp. S2-S17, 2004; M. Schmidt, G. Sun, M. A. Stacey, L. Mori, and S. Mattoli, "Identification of circulating fibrocytes as precursors of bronchial myofibroblasts in asthma," Journal of Immunology, vol. 171, no. 1, pp. 380-389, 2003; C. Bergeron, W. Al-Ramli, and Q. Hamid, "Remodeling in asthma," Proceedings of the American Thoracic Society, vol. 6, no. 3, pp. 301-305, 2009).

Mitogens, chemical compounds that stimulate cell division and trigger mitosis (A. Shifren, C. Witt, C. Christie and M. Castro, "Mechanisms of Remodeling in Asthmatic Airways," Journal of Allergy, vol. 2012, Article ID 316049, pp. 1-12), play an integral role in the development of increased ASM mass typical of asthmatic airways. Mitogens bind receptor tyrosine kinases (RTK), G protein-coupled receptors (GPCR), and cytokine receptors, all of which are capable of producing increases in ASM mass in cell culture models (E. Tagaya and J. Tamaoki, "Mechanisms of airway remodeling in asthma," Allergology International, vol. 56, no. 4, pp. 331-340, 2007). The list of mitogens is extensive, and includes TGF-β, IL-1β, IL-6, thromboxanes, leukotrienes, histamine, tryptase, serotonin, vascular endothelial growth factor (VEGF), and numerous others (S. J. Hirst, J. G. Martin, J. V. Bonacci et al., "Proliferative aspects of airway smooth muscle," Journal of Allergy and Clinical Immunology, vol. 114, no. 2, pp. S2-S17, 2004; A. M. Freyer, S. R. Johnson, and I. P. Hall, "Effects of growth factors and extracellular matrix on survival of human airway smooth muscle cells," American Journal of Respiratory Cell and Molecular Biology, vol. 25, no. 5, pp. 569-576, 2001; P. H. Howarth, A. J. Knox, Y. Amrani, O. Tliba, R. A. Panettieri, and M. Johnson, "Synthetic responses in airway smooth muscle," Journal of Allergy and Clinical Immunology, vol. 114, no. 2, supplement 1, pp. S32-S50, 2004). The receptor systems regulate mitogenesis primarily through the phosphoinositide 3'-kinase (PI3K) and extracellular signal-regulated kinase (ERK) signaling pathways (K. Page, J. Li, Y. Wang, S. Kartha, R. G. Pestell, and M. B. Hershenson, "Regulation of cyclin D(1) expression and DNA synthesis by phosphatidylinositol 3-kinase in airway smooth muscle cells," American Journal of Respiratory Cell and Molecular Biology, vol. 23, no. 4, pp. 436-443, 2000; M. J. Orsini, V. P. Krymskaya, A. J. Eszterhas, J. L. Benovic, R. A. Panettieri, and R. B. Penn, "MAPK superfamily activation in human airway smooth muscle: mitogenesis requires prolonged p42/p44 activation," American Journal of Physiology, vol. 277, no. 3, pp. L479-L488, 1999). The PI3K and ERK pathways activate transcription factors which phosphorylate D-type cyclins facilitating cell cycle progression (E. Tagaya and J. Tamaoki, "Mechanisms of airway remodeling in asthma," Allergology International, vol. 56, no. 4, pp. 331-340, 2007). Almost all of these mitogens have been identified in airway biopsies and bronchoalveolar lavage (BAL) fluid from asthmatic patients or are detected in asthmatic airway cell cultures (R. M. Pascual and S. P. Peters, "Airway remodeling contributes to the progressive loss of lung function in asthma: an overview," Journal of Allergy and Clinical Immunology, vol. 116, no. 3, pp. 477-486, 2005).

ASM cells are often noted in close proximity to the airway epithelium (A. Shifren, C. Witt, C. Christie and M. Castro, "Mechanisms of Remodeling in Asthmatic Airways," Journal of Allergy, vol. 2012, Article ID 316049, pp. 1-12). This epithelial-muscle distance was measured at 67 μm in asthmatics compared to 135 μm in controls (L. Benayoun, A. Druilhe, M. C. Dombret, M. Aubier, and M. Pretolani, "Airway structural alterations selectively associated with severe asthma," American Journal of Respiratory and Critical Care Medicine, vol. 167, no. 10, pp. 1360-1368, 2003). It has been postulated that mesenchymal airway cells differentiate into ASM with subsequent migration of the new ASM cells into muscle bundles (J. M. Madison, "Migration of airway smooth muscle cells," American Journal of Respiratory Cell and Molecular Biology, vol. 29, no. 1, pp. 8-11, 2003). Whether these phenomena occur in vivo is unknown, but reports indicate that cultured human ASM cells migrate in response to mitogenic stimuli (M. Hoshino, M. Takahashi, and N. Aoike, "Expression of vascular endothelial growth factor, basic fibroblast growth factor, and angiogenin immunoreactivity in asthmatic airways and its relationship to angiogenesis," Journal of Allergy and Clinical Immunology, vol. 107, no. 2, pp. 295-301, 2001). Many of the mitogens involved in cell proliferation, including TGF-β, IL-1β, and VEGF, also induce ASM cell migration (R. M. Pascual and S. P. Peters, "Airway remodeling contributes to the progressive loss of lung function in asthma: an overview," Journal of Allergy and Clinical Immunology, vol. 116, no. 3, pp. 477-486, 2005; E. Tagaya and J. Tamaoki, "Mechanisms of airway remodeling in asthma," Allergology International, vol. 56, no. 4, pp. 331-340, 2007).

Disruption of Surface Epithelium

Epithelial cell shedding, ciliated cell loss, and goblet cell hyperplasia have all been described in asthmatic airways (N. Carroll, J. Elliot, A. Morton, and A. James, "The structure of large and small airways in nonfatal and fatal asthma," American Review of Respiratory Disease, vol. 147, no. 2, pp. 405-410, 1993; T. Aikawa, S. Shimura, H. Sasaki, M. Ebina, and T. Takishima, "Marked goblet cell hyperplasia with mucus accumulation in the airways of patients who died of severe acute asthma attack," Chest, vol. 101, no. 4, pp. 916-921, 1992; B. NAYLOR, "The shedding of the mucosa of the bronchial tree in asthma," Thorax, vol. 17, pp. 69-72, 1962). Evidence of increased epithelial cell proliferation contributing to thickening of the epithelium and an increased lamina reticularis (also known as subepithelial fibrosis) has been observed in patients with moderate to severe asthma while being absent in patients with mild persistent asthma, chronic bronchitis, and normal controls (L. Cohen, E. Xueping, J. Tarsi et al., "Epithelial cell proliferation contributes to airway remodeling in severe asthma," American Journal of Respiratory and Critical Care Medicine, vol. 176, no. 2, pp. 138-145, 2007). These studies suggest that thickening of the airway seen in severe asthma may be due, in part, to airway epithelial proliferation.

Goblet cell hyperplasia has been consistently demonstrated in mild, moderate, and severe forms of asthma (H. A. Jenkins, C. Cool, S. J. Szefler et al., "Histopathology of severe childhood asthma: a case series," Chest, vol. 124, no. 1, pp. 32-41, 2003; C. L. Ordoñez, R. Khashayar, H. H. Wong et al., "Mild and moderate asthma is associated with airway goblet cell hyperplasia and abnormalities in mucin gene expression," American Journal of Respiratory and Critical Care Medicine, vol. 163, no. 2, pp. 517-523, 2001) Similarly, an increase in the area of airway wall occupied by submucosal mucus glands is a frequent finding in asthmatic airways, and occurs in both fatal and nonfatal forms of asthma (N. Carroll, J. Elliot, A. Morton, and A. James, "The structure of large and small airways in nonfatal and fatal asthma," American Review of Respiratory Disease, vol. 147, no. 2, pp. 405-410, 1993). Goblet cells produce mucin glycoproteins (MUC), of which thirteen (13) have been identified in human airways (E. Tagaya and J. Tamaoki, "Mechanisms of airway remodeling in asthma," Allergology International, vol. 56, no. 4, pp. 331-340, 2007). The dominant mucin in humans is MUC5AC, which is expressed in the airways of normal subjects and is upregulated in asthmatic subjects (J. V. Fahy, "Remodeling of the airway epithelium in asthma," American Journal of Respiratory and Critical Care Medicine, vol. 164, no. 10, pp. S46-51, 2001). Goblet cell hyperplasia has been demonstrated following adoptive transfer of Th2 cells into ovalbumin-challenged mice and is most likely the result of Th2-driven interleukin expression (L. Cohn, J. S. Tepper, and K. Bottomly, "Cutting edge: IL-4-independent induction of airway hyperresponsiveness by Th2, but not Th1, cells," Journal of Immunology, vol. 161, no. 8, pp. 3813-3816, 1998). IL-13 signals through the STAT-6 signaling pathway (R. J. Homer and J. A. Elias, "Airway remodeling in asthma: therapeutic implications of mechanisms," Physiology, vol. 20, no. 1, pp. 28-35, 2005) and the effects of IL-13 overexpression in mice are almost completely STAT-6 dependent (D. A. Kuperman, X. Huang, L. L. Koth et al., "Direct effects of interleukin-13 on epithelial cells cause airway hyperreactivity and mucus overproduction in asthma," Nature Medicine, vol. 8, no. 8, pp. 885-889, 2002).

Epithelial injury is normally followed by upregulation of proteins responsible for tissue repair. Expression of epithelial growth factor receptor (EGFR) and MUCSAC are both markedly upregulated in the epithelium of asthmatic patients (M. Amishima, M. Munakata, Y. Nasuhara et al., "Expression of epidermal growth factor and epidermal growth factor receptor immunoreactivity in the asthmatic human airway," American Journal of Respiratory and Critical Care Medicine, vol. 157, no. 6, pp. 1907-1912, 1998; S. M. Puddicombe, R. Polosa, A. Richter et al., "Involvement of the epidermal growth factor receptor in epithelial repair in asthma," FASEB Journal, vol. 14, no. 10, pp. 1362-1374, 2000), and have been shown to co-localize in goblet cells (K. Takeyama, J. V. Fahy, and J. A. Nadel, "Relationship of epidermal growth factor receptors to goblet cell production in human bronchi," American Journal of Respiratory and Critical Care Medicine, vol. 163, no. 2, pp. 511-516, 2001). Immunoreactivity to EGFR and the total area of MUCSAC staining show a positive correlation in both asthmatics and control subjects. Furthermore, activation of EGFR has been shown to upregulate both mucin production and goblet cell generation in human epithelial cells in vitro (M. Amishima, M. Munakata, Y. Nasuhara et al., "Expression of epidermal growth factor and epidermal growth factor receptor immunoreactivity in the asthmatic human airway," American Journal of Respiratory and Critical Care Medicine, vol. 157, no. 6, pp. 1907-1912, 1998).

Increased Collagen Deposition and Thickening of the Basement Membrane

The original report of airway remodeling described the phenomenon of basement membrane thickening (H. L. Huber and K. K. Koessler, "The pathology of bronchial asthma," Archives of Internal Medicine, vol. 30, no. 6, pp. 689-760, 1922). Electron microscopy has subsequently shown that thickening occurs just below the true basement membrane in a zone known as the lamina reticularis (W. R. Roche, J. H. Williams, R. Beasley, and S. T. Holgate, "Subepithelial fibrosis in the bronchi of asthmatics," Lancet, vol. 1, no. 8637, pp. 520-524, 1989). The lamina reticularis is a collagenous layer 4-5 μm thick in control subjects. In asthmatics, thickness of the lamina reticularis has been documented at between 7 and 23 μm (R. J. Homer and J. A. Elias, "Consequences of long-term inflammation: airway remodeling," Clinics in Chest Medicine, vol. 21, no. 2, pp. 331-343, 2000). Thickening is the result of extracellular matrix deposition, primarily collagens I, III, and V (R. J. Homer and J. A. Elias, "Airway remodeling in asthma: therapeutic implications of mechanisms," Physiology, vol. 20, no. 1, pp. 28-35, 2005). In addition, abnormalities of noncollagenous matrix, including elastin, fibronectin, tenascin, lumican, and proteoglycans, have also been described (W. R. Roche, J. H. Williams, R. Beasley, and S. T. Holgate, "Subepithelial fibrosis in the bronchi of asthmatics," Lancet, vol. 1, no. 8637, pp. 520-524, 1989; J. Huang, R. Olivenstein, R. Taha, Q. Hamid, and M. Ludwig, "Enhanced proteoglycan deposition in the airway wall of atopic asthmatics," American Journal of Respiratory and Critical Care Medicine, vol. 160, no. 2, pp. 725-729, 1999; A. Laitinen, A. Altraja, M. Kampe, M. Linden, I. Virtanen, and L. A. Laitinen, "Tenascin is increased in airway basement membrane of asthmatics and decreased by an inhaled steroid,"

American Journal of Respiratory and Critical Care Medicine, vol. 156, no. 3, pp. 951-958, 1997).

Myofibroblasts are believed to be key effectors of subepithelial fibrosis. Myofibroblasts are specialized cells with phenotypic characteristics of both fibroblasts and myocytes (E. Tagaya and J. Tamaoki, "Mechanisms of airway remodeling in asthma," Allergology International, vol. 56, no. 4, pp. 331-340, 2007). They express α-smooth muscle actin, produce inflammatory mediators, and are major producers of extracellular matrix proteins necessary for tissue repair and remodeling.

Transforming growth factor- (TGF-) β mediates the effects of IL-13 overexpressing mice (Chun Geun Lee, R. J. Homer, Z. Zhu et al., "Interleukin-13 induces tissue fibrosis by selectively stimulating and activating transforming growth factor β1," Journal of Experimental Medicine, vol. 194, no. 6, pp. 809-821, 2001). TGF-β is a cytokine produced by multiple lung cells including epithelial cells, macrophages, fibroblasts, lymphocytes, and eosinophils (E. Tagaya and J. Tamaoki, "Mechanisms of airway remodeling in asthma," Allergology International, vol. 56, no. 4, pp. 331-340, 2007). TGF-β induces fibroblasts to express α-smooth muscle actin and assume a myofibroblast phenotype (V. Batra, A. I. Musani, A. T. Hastie et al., "Bronchoalveolar lavage fluid concentrations of transforming growth factor (TGF)-β1, TGF-β2, interleukin (IL)-4 and IL-13 after segmental allergen challenge and their effects on α-smooth muscle actin and collagen III synthesis by primary human lung fibroblasts," Clinical and Experimental Allergy, vol. 34, no. 3, pp. 437-444, 2004). As part of normal wound repair, TGF-β induces expression and secretion of multiple extracellular matrix proteins while also inhibiting their degradation. In many diseases, excessive TGF-β results in an excess of pathologic tissue fibrosis leading to compromised organ function (M. H. Branton and J. B. Kopp, "TGF-β and fibrosis," Microbes and Infection, vol. 1, no. 15, pp. 1349-1365, 1999). TGF-β expression is increased in asthmatic airways and BAL fluid, compared to controls. In addition, TGF-β levels correlate with the extent of subepithelial fibrosis, airway fibroblast numbers, and disease severity (E. M. Minshall, D. Y. M. Leung, R. J. Martin et al., "Eosinophil-associated TGF-β1 mRNA expression and airways fibrosis in bronchial asthma," American Journal of Respiratory Cell and Molecular Biology, vol. 17, no. 3, pp. 326-333, 1997; I. Ohno, Y. Nitta, K. Yamauchi et al., "Transforming growth factor β1 (TGFβ1) gene expression by eosinophils in asthmatic airway inflammation," American Journal of Respiratory Cell and Molecular Biology, vol. 15, no. 3, pp. 404-409, 1996; L. P. Boulet, M. Belanger, and G. Carrier, "Airway responsiveness and bronchial-wall thickness in asthma with or without fixed airflow obstruction," American Journal of Respiratory and Critical Care Medicine, vol. 152, no. 3, pp. 865-871, 1995). Thus, excess TGF-β production may be pivotal for the development of subepithelial fibrosis.

Matrix metalloproteinases are zinc-dependent endopeptidases capable of degrading extracellular matrix molecules. The dynamic equilibrium between matrix metalloproteinases and their inhibitors is a critical determinant of matrix remodeling (R. Visse and H. Nagase, "Matrix metalloproteinases and tissue inhibitors of metalloproteinases: structure, function, and biochemistry," Circulation Research, vol. 92, no. 8, pp. 827-839, 2003). The existence of increased subepithelial fibrosis in asthmatic airways suggests that a profibrotic balance exists between the two. In asthma, the most important metalloproteinase molecules are MMP-9 and its inhibitor, tissue inhibitor of metalloproteinase- (TIMP-) 1 (R. J. Homer and J. A. Elias, "Airway remodeling in asthma: therapeutic implications of mechanisms," Physiology, vol. 20, no. 1, pp. 28-35, 2005). Both MMP-9 and TIMP-1 levels are elevated in airway biopsies and BAL fluid of asthmatic patients (A. M. Vignola, L. Riccobono, A. Mirabella et al., "Sputum metalloproteinase-9/tissue inhibitor of metalloproteinase-1 ratio correlates with airflow obstruction in asthma and chronic bronchitis," American Journal of Respiratory and Critical Care Medicine, vol. 158, no. 6, pp. 1945-1950, 1998; M. Hoshino, Y. Nakamura, J. Sim, J. Shimojo, and S. Isogai, "Bronchial subepithelial fibrosis and expression of matrix metalloproteinase-9 in asthmatic airway inflammation," Journal of Allergy and Clinical Immunology, vol. 102, no. 5, pp. 783-788, 1998; G. Mautino, C. Henriquet, C. Gougat et al., "Increased expression of tissue inhibitor of metalloproteinase-1 and loss of correlation with matrix metalloproteinase-9 by macrophages in asthma). However, compared to control subjects, asthmatics have a significantly lower MMP-9 to TIMP-1 ratio, supporting a profibrotic balance (inhibition over degradation). In addition, the lower MMP-9 to TIMP-1 ratios correlate with the degree of airway obstruction (E. A. Kelly and N. N. Jarjour, "Role of matrix metalloproteinases in asthma," Current Opinion in Pulmonary Medicine, vol. 9, no. 1, pp. 28-33, 2003).

TGF-β is secreted from cells as a latent complex and is targeted to the extracellular matrix by latent TGF-β binding proteins for subsequent activation (M. Hyytiainen, C. Penttinen, and J. Keski-Oja, "Latent TGF-β binding proteins: extracellular matrix association and roles in TGF-β activation," Critical Reviews in Clinical Laboratory Sciences, vol. 41, no. 3, pp. 233-264, 2004). MMPs regulate matrix-bound cytokine release (E. A. Kelly and N. N. Jarjour, "Role of matrix metalloproteinases in asthma," Current Opinion in Pulmonary Medicine, vol. 9, no. 1, pp. 28-33, 2003), and activation of TGF-β is MMP-9 dependent (Chun Geun Lee, R. J. Homer, Z. Zhu et al., "Interleukin-13 induces tissue fibrosis by selectively stimulating and activating transforming growth factor β1," Journal of Experimental Medicine, vol. 194, no. 6, pp. 809-821, 2001). Therefore, the role of elevated levels of MMP-9 in asthma may be related to TGF-β activation and its downstream fibrotic sequelae (R. J. Homer and J. A. Elias, "Airway remodeling in asthma: therapeutic implications of mechanisms," Physiology, vol. 20, no. 1, pp. 28-35, 2005).

3.6 Other Types of Fibrosis

Other types of fibrosis include, without limitation, cystic fibrosis of the pancreas and lungs, injection fibrosis, endomyocardial fibrosis, mediastinal fibrosis, myelofibrosis, retroperitoneal fibrosis, and nephrogenic systemic fibrosis.

Cystic fibrosis (CF, mucovidosis, mucovisidosis) is an inherited autosomal recessive disorder. It is one of the most common fatal genetic disorders in the United States, affecting about 30,000 individuals, and is most prevalent in the Caucasian population, occurring in one of every 3,300 live births. The gene involved in cystic fibrosis, which was identified in 1989, codes for a protein called the cystic fibrosis transmembrane conductance regulator (CFTR). CFTR normally is expressed by exocrine epithelia throughout the body and regulates the movement of chloride ions, bicarbonate ions and glutathione into and out of cells. In cystic fibrosis patients, mutations in the CFTR gene lead to alterations or total loss of CFTR protein function, resulting in defects in osmolarity, pH and redox properties of exocrine secretions. In the lungs, CF manifests itself by the presence of a thick mucus secretion which clogs the airways. In other exocrine organs, such as the sweat glands, CF may not manifest itself by an obstructive phenotype, but rather by abnormal salt composition of the secretions (hence the clinical sweat osmolarity test to detect CF patients). The predominant cause of illness and death in cystic fibrosis patients is progressive lung disease. The thickness of CF mucus, which blocks the airway passages, is believed to stem from abnormalities in osmolarity of secretions, as well as from the presence of massive amounts of DNA, actin, proteases and prooxidative enzymes originating from a subset of inflammatory cells, called neutrophils. Indeed, CF lung disease is characterized by early, hyperactive neutrophil-mediated inflammatory reactions to both viral and bacterial pathogens. The hyperinflammatory syndrome of CF lungs has several underpinnings, among which an imbalance between pro-inflammatory chemokines, chiefly IL-8, and anti-inflammatory cytokines, chiefly IL-10, has been reported to play a major role. See Chmiel et al., *Clin Rev Allergy Immunol.* 3(1):5-27 (2002). Studies have reported that levels of TNF-α, IL-6 and IL-1β were higher in the bronchoalveolar lavage fluid of cystic fibrosis patients, than in healthy control bronchoalveolar lavage fluid (Bondfield, T. L., et al. *Am. J. Resp. Crit. Care Med.* 152(1):2111-2118, 1995).

Injection fibrosis (IF) is a complication of intramuscular injection often occurring in the quadriceps, triceps and gluteal muscles of infants and children in which subjects are unable to fully flex the affected muscle. It typically is painless, but progressive. Studies have reported that the glycoprotein osteopontin (OPN) plays a role in tissue remodeling (Liaw, L., et al. *J. Clin. Invest,* 101(7):1469-1478, 1998) and that this proinflammatory mediator induces IL-1β up-regulation in human monocytes and an accompanying enhanced production of TNF-α and IL-6 (Naldini, A., et al. *J. Immunol.* 177:4267-4270, 2006; Weber, G. F., and Cantor, H. *Cytokine Growth Factor Reviews.* 7(3):241-248, 1996).

Endomyocardial disease (hyperosinophilic syndrome (HS)) is a disease process characterized by a persistently elevated eosinophil count (1500 eosinophils/mm$^3$) in the blood. HS simultaneously affects many organs. Studies have reported that IL-1β, IL-6 and TNF-α are expressed at high levels in viral-induced myocarditis patients (Satoh, M., et al. *Virchows Archiv.* 427(5):503-509, 1996). Symptoms may include cardiomyopathy, skin lesions, thromboembolic disease, pulmonary disease, neuropathy, hepatosplenomegaly (coincident enlargement of the liver and spleen), and reduced ventricular size. Treatment may include utilizing corticosteroids to reduce eosinophil levels.

Mediastinal fibrosis (MF) is characterized by invasive, calcified fibrosis centered on lymph nodes that blocks major vessels and airways. MF is a late complication of histoplasmosis. Studies in murine models of fibrosis have reported that IL-10 and TNF-α are elevated significantly (Ebrahimi, B, et al. *Am. J. Pathol.* 158:2117-2125, 2001).

Myelofibrosis (myeloid metaplasia, chronic idiopathic myelofibrosis, primary myelofibrosis) is a disorder of the bone marrow in which the marrow undergoes fibrosis. Myelofibrosis leads to progressive bone marrow failure. The mean survival is five years and causes of death include infection, bleeding, organ failure, portal hypertension, and leukemic transformation. It has been reported that TNF-α and IL-6 levels are elevated in animal models of viral-induced myelofibrosis (Bousse-Kerdiles, M., et al. *Ann. Hematol.* 78:434-444, 1999).

Retroperitoneal fibrosis (Ormond's disease) is a disease featuring the proliferation of fibrous tissue in the retroperitoneum. The retroperitoneum is the body compartment containing the kidneys, aorta, renal tract, and other structures. It has been reported that IL-1, IL-6 and TNF-α have key roles in the pathogenesis of retroperitoneal fibrosis (Demko, T., et al, *J. Am. Soc. Nephrol.* 8:684-688, 1997). Symptoms of retroperitoneal fibrosis may include, but are not limited to, lower back pain, renal failure, hypertension, and deep vein thrombosis.

Nephrogenic systemic fibrosis (NSF, nephrogenic fibrosing dermopathy) involves fibrosis of the skin, joints, eyes and internal organs. NSF may be associated with exposure to gadolinium. Patients develop large areas of hardened skin with fibrotic nodules and plaques. Flexion contractures with an accompanying limitation of range of motion also may occur. NSF shows a proliferation of dermal fibroblasts and dendritic cells, thickened collagen bundles, increased elastic fibers, and deposits of mucin. Some reports have suggested that a proinflammatory state provides a predisposing factor for causing nephrogenic systemic fibrosis (Saxena, S., et al. *Int. Urol. Nephrol.* 40:715-724, 2008), and that the level of TNF-a is elevated in animal models of nephrogenic systemic fibrosis (Steger-Hartmann, T., et al. *Exper. Tox. Pathol.* 61(6): 537-552, 2009).

4. Risk Factors
4.1. Primary Risk Factors
    4.1.1. Cigarette Smoking
    While a number of risk factors for fibrotic airway diseases have been identified (some of which may play a role in their causation), tobacco smoke remains the principal and most important cause of COPD. The greater the number of cigarettes smoked, the greater is the risk of developing fibrotic airway diseases. An overwhelming majority of people who develop fibrotic airway diseases are smokers, and their lung function decreases faster than that of non-smokers.

The most effective intervention is to stop smoking, preferably at an early stage. Smokers who quit will not recover lost lung function, but the rate of decline may revert to that of a non-smoker. Stopping smoking at an early stage improves the prognosis, regardless of how many attempts are needed to quit. Individual susceptibility to developing fibrotic airway diseases. in relation to cigarette smoking varies. Approximately 15% of smokers will develop clinically significant COPD, while approximately 50% will never develop any symptoms. The decrease in lung function is gradual, and the disease is usually diagnosed late because patients may adapt to symptoms of shortness of breath, or may not notice the symptoms. Studies have shown that depending on the number of cigarettes smoked per day, 24-47% of smokers develop airflow obstruction. Exposure to passive smoking increases susceptibility to the disease.

4.1.2. Alpha-1 Antitrypsin Deficiency
    This rare inherited condition results in the complete absence of one of the key antiprotease protection systems in the lung. It is a recessive disorder affecting 1:4000 of the population. Patients with alpha-1 antitrypsin deficiency are at risk of developing emphysema at an early age—between the ages of 20 and 40 years—and often have a strong family history of the disease. Patients with the deficiency and emphysema inherit one abnormal gene from each parent; that is to say, the parents are carriers of the gene. Such parents will have half the normal levels of the antitrypsin in the blood, which may be enough to protect from developing emphysema. Likewise, all the children of an alpha-1 antitrypsin deficient patient will carry one abnormal gene, but will not be affected. The two common forms of alpha-1 antitrypsin deficiency result from point mutations in the gene that codes for alpha-1 antitrypsin.

4.2. Associated Risk Factors

4.2.1. Environmental Pollution

There is strong evidence that fibrotic airway diseases may be aggravated by air pollution, but the role of pollution in the etiology of fibrotic airway diseases is small when compared with that of cigarette smoking. Air pollution with heavy particulate matter, carbon, and sulphur dioxide, which are produced by the burning of coal and petroleum fossil fuels, are important causes or cofactors in the development of fibrotic airway diseases. These originate mainly from vehicle exhaust emissions, and photochemical pollutants such as ozone, in particular, are to be blamed. Indoor air pollution from biomass fuel burned for cooking and heating in poorly ventilated homes may be an important risk factor for fibrotic airway diseases, such as COPD, in developing countries, in particular for women.

4.2.2. Occupational Factors

Some occupations in which workers are exposed to coal, silica and cation, such as miners, textile workers and cement workers, are associated with an increased risk of fibrotic airway diseases. Exposure to cadmium, a heavy metal, and welding fumes has been recognized as a cause of emphysema since the 1950s.

Many dusty occupations are more hazardous than exposure to gas or fumes and are associated with the development of chronic bronchitis and various forms of airway obstructive disease. Shipyard welders and caulkers are also known to have an increased risk of developing fibrotic airway diseases, as well as those working in the construction industries that are exposed to cement dust.

4.2.3. Childhood Respiratory Infections

Chest infections in the first year of life, such as pneumonia and bronchiolitis, may predispose to the development of COPD in later life. This may be as a result or incomplete development of the respiratory system at birth until lung growth ends in early adulthood. If developing lungs are damaged, maximum potential lung function will not be achieved, producing symptoms of COPD at an early age.

4.3. Other Risk Factors

Other risk factors, which may play a role in causation and/or serves as early symptoms of fibrotic airway diseases, such as pulmonary fibroses, include hypersensitivity pneumonitis (most often resulting from inhaling dust contaminated with bacterial, fungal, or animal products), some typical connective tissue diseases (such as rheumatoid arthritis, systemic lupus erythematosus (SLE) and scleroderma), other diseases that involve connective tissue (such as sarcoidosis and Wegener's granulomatosis), infections, certain medications (e.g. amiodarone, bleomycin, busulfan, methotrexate, and nitrofurantoin), and radiation therapy to the chest.

5. Current and Emerging Therapeutic Approaches for Treating Fibrotic Diseases or Conditions Therapeutic agents currently being used to treat fibrotic diseases are disclosed in Datta et al., *British Journal of Pharmacology*, 163: 141-172, 2011; incorporated by reference herein). Non-limiting examples of such therapeutic agents include, but are not limited to, purified bovine Type V collagens (e.g., IW-001; ImmuneWorks; United Therapeutics), IL-13 receptor antagonists (e.g., QAX576; Novartis), protein tyrosine kinase inhibitors (e.g., imatinib (Gleevec®); Craig Daniels/Novartis), endothelial receptor antagonists (e.g., ACT-064992 (macitentan); Actelion), dual endothelin receptor antagonists (e.g., bosentan (Tracleer®); Actelion), prostacyclin analogs (inhaled iloprost (e.g., Ventavis®); Actelion), anti-CTGF monoclonal antibodies (e.g., FG-3019), endothelin receptor antagonists (A-selective) (e.g., ambrisentan (Letairis®), Gilead), AB0024 (Arresto), lysyl oxidase-like 2 (LOXL2) monoclonal antibodies (e.g., GS-6624 (formerly AB0024); Gilead), c-Jun N-terminal kinase (JNK) inhibitors (e.g., CC-930; Celgene), Pirfenidone (e.g., Esbriet® (InterMune), Pirespa® (Shionogi)), IFN-γ1b (e.g., Actimmune®; InterMune), pan-neutralizing IgG4 human antibodies against all three TGF-β isoforms (e.g., GC1008; Genzyme), TGF-β activation inhibitors (e.g., Stromedix (STX-100)) recombinant human Pentraxin-2 protein (rhPTX-2) (e.g., PRM151; Promedior), bispecific IL4/IL13 antibodies (e.g., SAR156597; Sanofi), humanized monoclonal antibodies targeting integrin αvβ6 (BIBF 1120; Boehringer Ingelheim), N-acetylcysteine (Zambon SpA), Sildenafil (Viagra®), TNF antagonists (e.g., etanercept (Enbrel®); Pfizer), glucocorticoids (e.g., prednisone, budesonide, mometasone furoate, fluticasone propionate, and fluticasone furoate), bronchodilators (e.g., leukotriene modifers (e.g., Montelukast (SINGUAIR®)), anticholingertic bronchodilators (e.g., Ipratropium bromide and Tiotropium), short-acting β2-agonists (e.g., isoetharine mesylate (Bronkometer®), adrenalin, salbutanol/albuterol, and terbutaline), long-acting β2-agonists (e.g., salmeterol, formoterol, indecaterol (Onbrez®), and combination bronchodilators including, but not limited to, SYMBICORT® (containing both budesonide and formoterol), corticosteroids (e.g., prednisone, budesonide, mometasone furoate), methylated xanthine and its derivatives (e.g., caffeine, aminophylline, IBMX, paraxanthine, pentoxifylline, theobromine, and theophylline), neutrophil elastase inhibitors (e.g., ONO-5046, MR-889, L-694,458, CE-1037, GW-311616, and TEI-8362, and transition-state inhibitors, such as ONO-6818, AE-3763, FK-706, ICI-200,880, ZD-0892 and ZD-8321), phosphodiesterase inhibitors (e.g., roflumilast (DAXAS®; Daliresp®), and cilomilast (Ariflo®, SB-207499)).

5.1. Kinases and Phosphorylation

Kinases are a ubiquitous group of enzymes that catalyze the phosphoryl transfer reaction from a phosphate donor (usually adenosine-5'-triphosphate (ATP)) to a receptor substrate. Although all kinases catalyze essentially the same phosphoryl transfer reaction, they display remarkable diversity in their substrate specificity, structure, and the pathways in which they participate. A recent classification of all available kinase sequences (approximately 60,000 sequences) indicates kinases can be grouped into 25 families of homologous (meaning derived from a common ancestor) proteins. These kinase families are assembled into 12 fold groups based on similarity of structural fold. Further, 22 of the 25 families (approximately 98.8% of all sequences) belong to 10 fold groups for which the structural fold is known. Of the other 3 families, polyphosphate kinase forms a distinct fold group, and the 2 remaining families are both integral membrane kinases and comprise the final fold group. These fold groups not only include some of the most widely spread protein folds, such as Rossmann-like fold (three or more parallel β strands linked by two a helices in the topological order β-α-β-α-β), ferredoxin-like fold (a common α+β protein fold with a signature βαββαβ secondary structure along its backbone), TIM-barrel fold (meaning a conserved protein fold consisting of eight α-helices and eight parallel β-strands that alternate along the peptide backbone), and antiparallel β-barrel fold (a beta barrel is a large beta-sheet that twists and coils to form a closed structure in which the first strand is hydrogen bonded to the last), but also all major classes (all α, all β, α+β, α/β) of protein structures. Within a fold group, the core of the nucleotide-binding domain of each family has the same architecture, and the topology of the protein core is either identical or related by circular permutation. Homology between the families within a fold group is not implied.

Group I (23,124 sequences) kinases incorporate protein S/T-Y kinase, atypical protein kinase, lipid kinase, and ATP grasp enzymes and further comprise the protein S/T-Y kinase, and atypical protein kinase family (22,074 sequences). These kinases include: choline kinase (EC 2.7.1.32); protein kinase (EC 2.7.137); phosphorylase kinase (EC 2.7.1.38); homoserine kinase (EC 2.7.1.39); I-phosphatidylinositol 4-kinase (EC 2.7.1.67); streptomycin 6-kinase (EC 2.7.1.72); ethanolamine kinase (EC 2.7.1.82); streptomycin 3'-kinase (EC 2.7.1.87); kanamycin kinase (EC 2.7.1.95); 5-methylthioribose kinase (EC 2.7.1.100); viomycin kinase (EC 2.7.1.103); [hydroxymethylglutaryl-CoA reductase (NADPH2)] kinase (EC 2.7.1.109); protein-tyrosine kinase (EC 2.7.1.112); [isocitrate dehydrogenase (NADP+)] kinase (EC 2.7.1.116); [myosin light-chain] kinase (EC 2.7.1.117); hygromycin-B kinase (EC 2.7.1.119); calcium/calmodulin-dependent protein kinase (EC 2.7.1.123); rhodopsin kinase (EC 2.7.1.125); [beta-adrenergic-receptor] kinase (EC 2.7.1.126); [myosin heavy-chain] kinase (EC 2.7.1.129); [Tau protein] kinase (EC 2.7.1.135); macrolide 2'-kinase (EC 2.7.1.136); I-phosphatidylinositol 3-kinase (EC 2.7.1.137); [RNA-polymerase]-subunit kinase (EC 2.7.1.141); phosphatidylinositol-4,5-bisphosphate 3-kinase (EC 2.7.1.153); and phosphatidylinositol-4-phosphate 3-kinase (EC 2.7.1.154). Group I further comprises the lipid kinase family (321 sequences). These kinases include: I-phosphatidylinositol-4-phosphate 5-kinase (EC 2.7.1.68); I D-myo-inositol-triphosphate 3-kinase (EC 2.7.1.127); inositol-tetrakisphosphate 5-kinase (EC 2.7.1.140); I-phosphatidylinositol-5-phosphate 4-kinase (EC 2.7.1.149); I-phosphatidylino sitol-3-phosphate 5-kinase (EC 2.7.1.150); inositol-polyphosphate multikinase (EC 2.7.1.151); and inositol-hexakiphosphate kinase (EC 2.7.4.21). Group I further comprises the ATP-grasp kinases (729 sequences) which include inositol-tetrakisphosphate I-kinase (EC 2.7.1.134); pyruvate, phosphate dikinase (EC 2.7.9.1); and pyruvate, water dikinase (EC 2.7.9.2).

Group II (17,071 sequences) kinases incorporate the Rossman-like kinases. Group II comprises the P-loop kinase family (7,732 sequences). These include gluconokinase (EC 2.7.1.12); phosphoribulokinase (EC 2.7.1.19); thymidine kinase (EC 2.7.1.21); ribosylnicotinamide kinase (EC 2.7.1.22); dephospho-CoA kinase (EC 2.7.1.24); adenylylsulfate kinase (EC 2.7.1.25); pantothenate kinase (EC 2.7.1.33); protein kinase (bacterial) (EC 2.7.1.37); uridine kinase (EC 2.7.1.48); shikimate kinase (EC 2.7.1.71); deoxycytidine kinase (EC 2.7.1.74); deoxyadenosine kinase (EC 2.7.1.76); polynucleotide 5'-hydroxyl-kinase (EC 2.7.1.78); 6-phosphofructo-2-kinase (EC 2.7.1.105); deoxyguanosine kinase (EC 2.7.1.113); tetraacyldisaccharide 4'-kinase (EC 2.7.1.130); deoxynucleoside kinase (EC 2.7.1.145); adenosylcobinamide kinase (EC 2.7.1.156); polyphosphate kinase (EC 2.7.4.1); phosphomevalonate kinase (EC 2.7.4.2); adenylate kinase (EC 2.7.4.3); nucleoside-phosphate kinase (EC 2.7.4.4); guanylate kinase (EC 2.7.4.8); thymidylate kinase (EC 2.7.4.9); nucleoside-triphosphate-adenylate kinase (EC 2.7.4.10); (deoxy) nucleoside-phosphate kinase (EC 2.7.4.13); cytidylate kinase (EC 2.7.4.14); and uridylate kinase (EC 2.7.4.22). Group II further comprises the phosphoenolpyruvate carboxykinase family (815 sequences). These enzymes include protein kinase (HPr kinase/phosphatase) (EC 2.7.1.37); phosphoenolpyruvate carboxykinase (GTP) (EC 4.1.1.32); and phosphoenolpyruvate carboxykinase (ATP) (EC 4.1.1.49). Group II further comprises the phosphoglycerate kinase (1,351 sequences) family. These enzymes include phosphoglycerate kinase (EC 2.7.2.3) and phosphoglycerate kinase (GTP) (EC 2.7.2.10). Group II further comprises the aspartokinase family (2,171 sequences). These enzymes include carbamate kinase (EC 2.7.2.2); aspartate kinase (EC 2.7.2.4); acetylglutamate kinase (EC 2.7.2.8 1); glutamate 5-kinase (EC 2.7.2.1) and uridylate kinase (EC 2.7.4). Group II further comprises the phosphofructokinase-like kinase family (1,998 sequences). These enzymes include 6-phosphofrutokinase (EC 2.7.1.11); NAD (+) kinase (EC 2.7.1.23); I-phosphofructokinase (EC 2.7.1.56); diphosphate-fructose-6-phosphate I-phosphotransferase (EC 2.7.1.90); sphinganine kinase (EC 2.7.1.91); diacylglycerol kinase (EC 2.7.1.107); and ceramide kinase (EC 2.7.1.138). Group II further comprises the ribokinase-like family (2,722 sequences). These enzymes include: glucokinase (EC 2.7.1.2); ketohexokinase (EC 2.7.1.3); fructokinase (EC 2.7.1.4); 6-phosphofructokinase (EC 2.7.1.11); ribokinase (EC 2.7.1.15); adenosine kinase (EC 2.7.1.20); pyridoxal kinase (EC 2.7.1.35); 2-dehydro-3-deoxygluconokinase (EC 2.7.1.45); hydroxymethylpyrimidine kinase (EC 2.7.1.49); hydroxyethylthiazole kinase (EC 2.7.1.50); I-phosphofructokinase (EC 2.7.1.56); inosine kinase (EC 2.7.1.73); 5-dehydro-2-deoxygluconokinase (EC 2.7.1.92); tagatose-6-phosphate kinase (EC 2.7.1.144); ADP-dependent phosphofructokinase (EC 2.7.1.146); ADP-dependent glucokinase (EC 2.7.1.147); and phosphomethylpyrimidine kinase (EC 2.7.4.7). Group II further comprises the thiamin pyrophosphokinase family (175 sequences) which includes thiamin pyrophosphokinase (EC 2.7.6.2). Group II further comprises the glycerate kinase family (107 sequences) which includes glycerate kinase (EC 2.7.1.31).

Group III kinases (10,973 sequences) comprise the ferredoxin-like fold kinases. Group III further comprises the nucleoside-diphosphate kinase family (923 sequences). These enzymes include nucleoside-diphosphate kinase (EC 2.7.4.6). Group III further comprises the HPPK kinase family (609 sequences). These enzymes include 2-amino-4-hydroxy-6-hydroxymethyldihydropteridine pyrophosphokinase (EC 2.7.6.3). Group III further comprises the guanido kinase family (324 sequences). These enzymes include guanidoacetate kinase (EC 2.7.3.1); creatine kinase (EC 2.7.3.2); arginine kinase (EC 2.7.3.3); and lombricine kinase (EC 2.7.3.5). Group III further comprises the histidine kinase family (9,117 sequences). These enzymes include protein kinase (histidine kinase) (EC 2.7.1.37); [pyruvate dehydrogenase (lipoamide)] kinase (EC 2.7.1.99); and [3-methyl-2-oxybutanoate dehydrogenase (lipoamide)] kinase (EC 2.7.1.115).

Group IV kinases (2,768 sequences) incorporate ribonuclease H-like kinases. These enzymes include hexokinase (EC 2.7.1.1); glucokinase (EC 2.7.1.2); fructokinase (EC 2.7.1.4); rhamnulokinase (EC 2.7.1.5); mannokinase (EC 2.7.1.7); gluconokinase (EC 2.7.1.12); L-ribulokinase (EC 2.7.1.16); xylulokinase (EC 2.7.1.17); erythritol kinase (EC 2.7.1.27); glycerol kinase (EC 2.7.1.30); pantothenate kinase (EC 2.7.1.33); D-ribulokinase (EC 2.7.1.47); L-fucolokinase (EC 2.7.1.51); L-xylulokinase (EC 2.7.1.53); allose kinase (EC 2.7.1.55); 2-dehydro-3-deoxygalactonokinase (EC 2.7.1.58); N-acetylglucosamine kinase (EC 2.7.1.59); N-acylmannosamine kinase (EC 2.7.1.60); polyphosphate-glucose phosphotransferase (EC 2.7.1.63); beta-glucoside kinase (EC 2.7.1.85); acetate kinase (EC 2.7.2.1); butyrate kinase (EC 2.7.2.7); branched-chain-fatty-acid kinase (EC 2.7.2.14); and propionate kinase (EC 2.7.2.15).

Group V kinases (1,119 sequences) incorporate TIM β-barrel kinases. These enzymes include pyruvate kinase (EC 2.7.1.40).

Group VI kinases (885 sequences) incorporate GHMP kinases. These enzymes include galactokinase (EC 2.7.1.6); mevalonate kinase (EC 2.7.1.36); homoserine kinase (EC 2.7.1.39); L-arabinokinase (EC 2.7.1.46); fucokinase (EC 2.7.1.52); shikimate kinase (EC 2.7.1.71); 4-(cytidine 5'-diphospho)-2-C-methyl-D-erythriol kinase (EC 2.7.1.148); and phosphomevalonate kinase (EC 2.7.4.2).

Group VII kinases (1,843 sequences) incorporate AIR synthetase-like kinases. These enzymes include thiamine-phosphate kinase (EC 2.7.4.16) and selenide, water dikinase (EC 2.7.9.3).

Group VIII kinases (565 sequences) incorporate riboflavin kinases (565 sequences). These enzymes include riboflavin kinase (EC 2.7.1.26).

Group IX kinases (197 sequences) incorporate dihydroxyacetone kinases. These enzymes include glycerone kinase (EC 2.7.1.29).

Group X kinases (148 sequences) incorporate putative glycerate kinases. These enzymes include glycerate kinase (EC 2.7.1.31).

Group XI kinases (446 sequences) incorporate polyphosphate kinases. These enzymes include polyphosphate kinases (EC 2.7.4.1).

Group XII kinases (263 sequences) incorporate integral membrane kinases. Group XII comprises the dolichol kinase family. These enzymes include dolichol kinases (EC 2.7.1.108). Group XII further comprises the undecaprenol kinase family. These enzymes include undecaprenol kinases (EC 2.7.1.66).

Kinases play indispensable roles in numerous cellular metabolic and signaling pathways, and they are among the best-studied enzymes at the structural level, biochemical level, and cellular level. Despite the fact that all kinases use the same phosphate donor (in most cases, ATP) and catalyze apparently the same phosphoryl transfer reaction, they display remarkable diversity in their structural folds and substrate recognition mechanisms. This probably is due largely to the extraordinary diverse nature of the structures and properties of their substrates.

5.1.1 Mitogen-Activated Protein Kinase-Activated Protein Kinases (MK2 and MK3)

Different groups of MAPK-activated protein kinases (MAP-KAPKs) have been defined downstream of mitogen-activated protein kinases (MAPKs). These enzymes transduce signals to target proteins that are not direct substrates of the MAPKs and, therefore, serve to relay phosphorylation-dependent signaling with MAPK cascades to diverse cellular functions. One of these groups is formed by the three MAPKAPKs: MK2, MK3 (also known as 3pK), and MK5 (also designated PRAK). Mitogen-activated protein kinase-activated protein kinase 2 (also referred to as "MAP-KAPK2", "MAPKAP-K2", or "MK2") is a kinase of the serine/threonine (Ser/Thr) protein kinase family. MK2 is highly homologous to MK3 (approximately 75% amino acid identity). The kinase domains of MK2 and MK3 are most similar (approximately 35% to 40% identity) to calcium/calmodulin-dependent protein kinase (CaMK), phosphorylase b kinase, and the C-terminal kinase domain (CTKD) of the ribosomal S6 kinase (RSK) isoforms. The mk2 gene encodes two alternatively spliced transcripts of 370 amino acids (MK2A) and 400 amino acids (MK2B). The mk3 gene encodes one transcript of 382 amino acids. The MK2- and MK3 proteins are highly homologous, yet MK2A possesses a shorter C-terminal region. The C-terminus of MK2B contains a functional bipartite nuclear localization sequence (NLS) (Lys-Lys-Xaa$_{10}$-Lys-Arg-Arg-Lys-Lys; SEQ ID NO: 23) that is not present in the shorter MK2A isoform, indicating that alternative splicing determines the cellular localization of the MK2 isoforms. MK3 possesses a similar nuclear localization sequence. The nuclear localization sequence found in both MK2B and MK3 encompasses a D domain (Leu-Leu-Lys-Arg-Arg-Lys-Lys; SEQ ID NO: 24) that studies have shown to mediate the specific interaction of MK2B and MK3 with p38α and p38β. MK2B and MK3 also possess a functional nuclear export signal (NES) located N-terminal to the NLS and D domain. The NES in MK2B is sufficient to trigger nuclear export following stimulation, a process which may be inhibited by leptomycin B. The sequence N-terminal to the catalytic domain in MK2 and MK3 is proline rich and contains one (MK3) or two (MK2) putative Src homology 3 (SH3) domain-binding sites, which studies have shown, for MK2, to mediate binding to the SH3 domain of c-Abl in vitro. Recent studies suggest that this domain is involved in MK2-mediated cell migration.

MK2B and MK3 are located predominantly in the nucleus of quiescent cells while MK2A is present in the cytoplasm. Both MK2B and MK3 are rapidly exported to the cytoplasm via a chromosome region maintenance protein (CRM1)-dependent mechanism upon stress stimulation. Nuclear export of MK2B appears to be mediated by kinase activation, as phosphomimetic mutation of Thr334 within the activation loop of the kinase enhances the cytoplasmic localization of MK2B. Without being limited by theory, it is thought that MK2B and MK3 may contain a constitutively active NLS and a phosphorylation-regulated NES.

MK2 and MK3 appear to be expressed ubiquitously, with predominant expression in the heart, in skeletal muscle, and in kidney tissues.

5.1.2. Activation

Various activators of p38α and p38β potently stimulate MK2 and MK3 activity. p38 mediates the in vitro and in vivo phosphorylation of MK2 on four proline-directed sites: Thr25, Thr222, Ser272, and Thr334. Of these sites, only Thr25 is not conserved in MK3. Without being limited by theory, while the function of phosphorylated Thr25 in unknown, its location between the two SH3 domain-binding sites suggests that it may regulate protein-protein interactions. Thr222 in MK2 (Thr201 in MK3) is located in the activation loop of the kinase domain and has been shown to be essential for MK2 and MK3 kinase activity. Thr334 in MK2 (Thr313 in MK3) is located C-terminal to the catalytic domain and is essential for kinase activity. The crystal structure of MK2 has been resolved and, without being limited by theory, suggests that Thr334 phosphorylation may serve as a switch for MK2 nuclear import and export. Phosphorylation of Thr334 also may weaken or interrupt binding of the C terminus of MK2 to the catalytic domain, exposing the NES and promoting nuclear export.

Studies have shown that, while p38 is capable of activating MK2 and MK3 in the nucleus, experimental evidence suggests that activation and nuclear export of MK2 and MK3 are coupled by a phosphorylation-dependent conformational switch that also dictates p38 stabilization and localization, and the cellular location of p38 itself is controlled by MK2 and possibly MK3. Additional studies have shown that nuclear p38 is exported to the cytoplasm in a complex with MK2 following phosphorylation and activation of MK2. The interaction between p38 and MK2 may be important for p38 stabilization since studies indicate that p38 levels are low in MK2-deficient cells and expression of a catalytically inactive MK2 protein restores p38 levels.

5.1.3. Substrates and Functions

Further studies have shown that the small heat shock protein HSPB1 (also known as heat shock protein 27 or Hsp27), lymphocyte-specific protein LSP-1, and vimentin are phosphorylated by MK2. HSPB1 is of particular interest because it forms large oligomers, which may act as molecular chaperones and protect cells from heat shock and oxidative stress. Upon phosphorylation, HSPB1 loses its ability to form large oligomers and is unable to block actin polymerization, suggesting that MK2-mediated phosphorylation of HSPB1 serves a homeostatic function aimed at regulating actin dynamics that otherwise would be destabilized during stress.

MK3 also was shown to phosphorylate HSPB1 in vitro and in vivo, but its role during stressful conditions has not yet been elucidated. MK2 shares many substrates with MK3. Both enzymes have comparable substrate preferences and phosphorylate peptide substrates with similar kinetic constants. The minimum sequence required for efficient phosphorylation by MK2 was found to be Hyd-Xaa-Arg-Xaa-Xaa-pSer/Thr (SEQ ID NO: 25), where Hyd is a bulky hydrophobic residue.

Experimental evidence supports a role for p38 in the regulation of cytokine biosynthesis and cell migration. The targeted deletion of the mk2 gene in mice suggested that although p38 mediates the activation of many similar kinases, MK2 seems to be the key kinase responsible for these p38-dependent biological processes. Loss of MK2 leads (i) to a defect in lipopolysaccharide (LPS)-induced synthesis of cytokines such as tumor necrosis factor alpha (TNF-α), interleukin-6 (IL-6), and gamma interferon (IFN-γ) and (ii) to changes in the migration of mouse embryonic fibroblasts, smooth muscle cells, and neutrophils.

Consistent with a role for MK2 in inflammatory responses, MK2-deficient mice showed increased susceptibility to Listeria monocytogenes infection and reduced inflammation-mediated neuronal death following focal ischemia. Since the levels of p38 protein also are reduced significantly in MK2-deficient cells, it was necessary to distinguish whether these phenotypes were due solely to the loss of MK2. To achieve this, MK2 mutants were expressed in MK2-deficient cells, and the results indicated that the catalytic activity of MK2 was not necessary to restore p38 levels but was required to regulate cytokine biosynthesis.

The knockout or knockdown studies of MK2 provided strong support that activated MK2 enhances stability of IL-6 mRNA through phosphorylation of proteins interacting with the AU-rich 3' untranslated region of IL-6 mRNA. In particular, it has been shown that MK2 is principally responsible for phosphorylation of hnRNPAO, an mRNA-binding protein that stabilizes IL-6 RNA. In addition, several additional studies investigating diverse inflammatory diseases have found that levels of pro-inflammatory cytokines, such as IL-6, IL-1β, TNF-α and IL-8, are increased in induced sputum from patients with stable chronic obstructive pulmonary disease (COPD) or from the alveolar macrophages of cigarette smokers (Keatings V. et al, *Am J Resp Crit Care Med*, 1996, 153:530-534; Lim, S. et al., *J Respir Crit Care Med*, 2000, 162:1355-1360). Elevated levels of pro-inflammatory cytokines, such as interleukin-8 (IL-8) and interleukin-6 (IL-6), as well as related downstream cell adhesion molecules (CAMs) such as intercellular adhesion molecule-1 (ICAM-1) and vascular cell adhesion molecule-1 (VCAM-1), matrix metalloproteinases such as matrix metalloproteinase-7 (MMP-7), and signaling molecules such as S100 calcium-binding protein A12 (S100A12, also known as calgranulin C), in the peripheral blood have been found to be associated with mortality, lung transplant-free survival, and disease progression in patients with idiopathic pulmonary fibrosis (Richards et al., *Am J Respir Crit Care Med*, 2012, 185: 67-76; Richards, T. et al., *Am J Respir Crit Care Med*, 181: A1120, 2010; Moodley, Y. et al., *Am J Respir Cell Mol Biol.*, 29(4): 490-498, 2003). Taken together, these studies implicate that elevated levels of inflammatory cytokines induced by MK2 activation may be involved in the pathogenesis of airway or lung tissue diseases; and suggest a potential for anti-cytokine therapy for treating airway or lung tissue diseases, such as idiopathic pulmonary fibrosis and chronic obstructive pulmonary disease (COPD) (Chung, K., *Eur Respir J*, 2001, 18: Suppl. 34: 50-59).

5.1.4. Regulation of mRNA Translation

Previous studies using MK2 knockout mice or MK2-deficient cells have shown that MK2 increases the production of inflammatory cytokines, including TNF-α, IL-1, and IL-6, by increasing the rate of translation of its mRNA. No significant reductions in the transcription, processing, and shedding of TNF-α could be detected in MK2-deficient mice. The p38 pathway is known to play an important role in regulating mRNA stability, and MK2 represents a likely target by which p38 mediates this function. Studies utilizing MK2-deficient mice indicated that the catalytic activity of MK2 is necessary for its effects on cytokine production and migration, suggesting that, without being limited by theory, MK2 phosphorylates targets involved in mRNA stability. Consistent with this, MK2 has been shown to bind and/or phosphorylate the heterogeneous nuclear ribonucleoprotein (hnRNP) A0, tristetraprolin, the poly (A)-binding protein PABP1, and HuR, a ubiquitously expressed member of the elav (embryonic-lethal abnormal visual in *Drosophila melanogaster*) family of RNA-binding protein. These substrates are known to bind or copurify with mRNAs that contain AU-rich elements in the 3' untranslated region, suggesting that MK2 may regulate the stability of AU-rich mRNAs such as TNF-α. It currently is unknown whether MK3 plays similar functions, but LPS treatment of MK2-deficient fibroblasts completely abolished hnRNP AO phosphorylation, suggesting that MK3 is not able to compensate for the loss of MK2.

MK3 participates with MK2 in phosphorylation of the eukaryotic elongation factor 2 (eEF2) kinase. eEF2 kinase phosphorylates and inactivates eEF2. eEF2 activity is critical for the elongation of mRNA during translation, and phosphorylation of eEF2 on Thr56 results in the termination of mRNA translation. MK2 and MK3 phosphorylation of eEF2 kinase on Ser377 suggests that these enzymes may modulate eEF2 kinase activity and thereby regulate mRNA translation elongation.

5.1.5. Transcriptional Regulation by MK2 and MK3

Nuclear MK2, similar to many MKs, contributes to the phosphorylation of cAMP response element binding (CREB), serum response factor (SRF), and transcription factor ER81. Comparison of wild-type and MK2-deficient cells revealed that MK2 is the major SRF kinase induced by stress, suggesting a role for MK2 in the stress-mediated immediate-early response. Both MK2 and MK3 interact with basic helix-loop-helix transcription factor E47 in vivo and phosphorylate E47 in vitro. MK2-mediated phosphorylation of E47 was found to repress the transcriptional activity of E47 and thereby inhibit E47-dependent gene expression, suggesting that MK2 and MK3 may regulate tissue-specific gene expression and cell differentiation.

5.1.6. Other Targets of MK2 and MK3.

Several other MK2 and MK3 substrates also have been identified, reflective of the diverse functions of MK2 and MK3 in several biological processes. The scaffolding protein 14-3-3ζ is a physiological MK2 substrate. Studies indicate 14-3-3ζ interacts with a number of components of cell signaling pathways, including protein kinases, phosphatases, and transcription factors. Additional studies have shown that MK2-mediated phosphorylation of 14-3-3ζ on Ser58 compromises its binding activity, suggesting that MK2 may affect the regulation of several signaling molecules normally regulated by 14-3-3ζ.

Additional studies have shown that MK2 also interacts with and phosphorylates the p16 subunit of the seven-member Arp2 and Arp3 complex (p16-Arc) on Ser77. p16-Arc has roles in regulating the actin cytoskeleton, suggesting that MK2 may be involved in this process.

MK2 and MK3 also may phosphorylate 5-lipoxygenase. 5-lipoxygenase catalyzes the initial steps in the formation of the inflammatory mediator leukotrienes. Tyrosine hydroxylase, glycogen synthase, and Akt also were shown to be phosphorylated by MK2. Finally, MK2 phosphorylates the tumor suppressor protein tuberin on Ser1210, creating a docking site for 14-3-3ζ. Tuberin and hamartin normally form a functional complex that negatively regulates cell growth by antagonizing mTOR-dependent signaling, suggesting that p38-mediated activation of MK2 may regulate cell growth by increasing 14-3-3ζ binding to tuberin.

5.2. Kinase Inhibition

The eukaryotic protein kinases constitute one of the largest superfamilies of homologous proteins that are related by virtue of their catalytic domains. Most related protein kinases are specific for either serine/threonine or tyrosine phosphorylation. Protein kinases play an integral role in the cellular response to extracellular stimuli. Thus, stimulation of protein kinases is considered to be one of the most common activation mechanisms in signal transduction systems. Many substrates are known to undergo phosphorylation by multiple protein kinases, and a considerable amount of information on primary sequence of the catalytic domains of various protein kinases has been published. These sequences share a large number of residues involved in ATP binding, catalysis, and maintenance of structural integrity. Most protein kinases possess a well conserved 30-32 kDa catalytic domain.

Studies have attempted to identify and utilize regulatory elements of protein kinases. These regulatory elements include inhibitors, antibodies, and blocking peptides.

5.2.1. Inhibitors

Enzyme inhibitors are molecules that bind to enzymes thereby decreasing enzyme activity. The binding of an inhibitor may stop a substrate from entering the active site of the enzyme and/or hinder the enzyme from catalyzing its reaction. Inhibitor binding is either reversible or irreversible. Irreversible inhibitors usually react with the enzyme and change it chemically (e.g., by modifying key amino acid residues needed for enzymatic activity) so that it no longer is capable of catalyzing its reaction. In contrast, reversible inhibitors bind non-covalently and different types of inhibition are produced depending on whether these inhibitors bind the enzyme, the enzyme-substrate complex, or both.

Enzyme inhibitors often are evaluated by their specificity and potency. The term "specificity" as used in this context refers to the selective attachment of an inhibitor or its lack of binding to other proteins. The term "potency" as used herein refers to an inhibitor's dissociation constant, which indicates the concentration of inhibitor needed to inhibit an enzyme.

Inhibitors of protein kinases have been studied for use as a tool in protein kinase activity regulation. Inhibitors have been studied for use with, for example, cyclin-dependent (Cdk) kinase, MAP kinase, serine/threonine kinase, Src Family protein tyrosine kinase, tyrosine kinase, calmodulin (CaM) kinase, casein kinase, checkpoint kinase (Chkl), glycogen synthase kinase 3 (GSK-3), c-Jun N-terminal kinase (JNK), mitogen-activated protein kinase 1 (MEK), myosin light chain kinase (MLCK), protein kinase A, Akt (protein kinase B), protein kinase C, protein kinase G, protein tyrosine kinase, Raf kinase, and Rho kinase.

5.2.2. Blocking Peptides

A peptide is a chemical compound that is composed of a chain of two or more amino acids whereby the carboxyl group of one amino acid in the chain is linked to the amino group of the other via a peptide bond. Peptides have been used inter alia in the study of protein structure and function. Synthetic peptides may be used inter alia as probes to see where protein-peptide interactions occur. Inhibitory peptides may be used inter alia in clinical research to examine the effects of peptides on the inhibition of protein kinases, cancer proteins and other disorders.

The use of several blocking peptides has been studied. For example, extracellular signal-regulated kinase (ERK), a MAPK protein kinase, is essential for cellular proliferation and differentiation. The activation of MAPKs requires a cascade mechanism whereby MAPK is phosphorylated by an upstream MAPKK (MEK) which then, in turn, is phosphorylated by a third kinase MAPKKK (MEKK). The ERK inhibitory peptide functions as a MEK decoy by binding to ERK.

Other blocking peptides include autocamtide-2 related inhibitory peptide (AIP). This synthetic peptide is a highly specific and potent inhibitor of $Ca^{2+}$/calmodulin-dependent protein kinase II (CaMKII). AIP is a non-phosphorylatable analog of autocamtide-2, a highly selective peptide substrate for CaMKII. AIP inhibits CaMKII with an $IC_{50}$ of 100 nM ($IC_{50}$ is the concentration of an inhibitor required to obtain 50% inhibition). The AIP inhibition is non-competitive with respect to syntide-2 (CaMKII peptide substrate) and ATP but competitive with respect to autocamtide-2. The inhibition is unaffected by the presence or absence of $Ca^{2+}$/calmodulin. CaMKII activity is inhibited completely by AIP (1 μM) while PKA, PKC and CaMKIV are not affected.

Other blocking peptides include cell division protein kinase 5 (Cdk5) inhibitory peptide (CIP). Cdk5 phosphorylates the microtubule protein tau at Alzheimer's Disease-specific phospho-epitopes when it associates with p25. p25 is a truncated activator, which is produced from the physiological Cdk5 activator p35 upon exposure to amyloid β peptides. Upon neuronal infections with CIP, CIPs selectively inhibit p25/Cdk5 activity and suppress the aberrant tau phosphorylation in cortical neurons. The reasons for the specificity demonstrated by CIP are not fully understood.

Additional blocking peptides have been studied for extracellular-regulated kinase 2 (ERK2), ERK3, p38/HOG1, protein kinase C, casein kinase II, $Ca^{2+}$/calmodulin kinase IV, casein kinase II, Cdk4, Cdk5, DNA-dependent protein kinase (DNA-PK), serine/threonine-protein kinase PAK3, phosphoinositide (PI)-3 kinase, PI-5 kinase, PSTAIRE (the cdk highly conserved sequence), ribosomal S6 kinase, GSK-4, germinal center kinase (GCK), SAPK (stress-activated protein kinase), SEK1 (stress signaling kinase), and focal adhesion kinase (FAK).

5.3. Cell Penetrating Peptides (CPPs)

Cell penetrating peptides (CPPs) are a class of peptides capable of penetrating the plasma membrane of mammalian cells and of transporting compounds of many types and molecular weights across the membrane. These compounds include effector molecules, such as proteins, DNA, conjugated peptides, oligonucleotides, and small particles such as liposomes. When CPPs are chemically linked or fused to other proteins, the resulting fusion proteins still are able to enter cells. Although the exact mechanism of transduction is unknown, internalization of these proteins is not believed to be receptor-mediated or transporter-mediated. CPPs are generally 10-16 amino acids in length and may be grouped according to their composition, such as, for example, peptides rich in arginine and/or lysine.

The use of CPPs capable of transporting effector molecules into cells has become increasingly attractive in the design of drugs as they promote the cellular uptake of cargo molecules. These cell-penetrating peptides, generally categorized as amphipathic (meaning having both a polar and a nonpolar end) or cationic (meaning of or relating to containing net positively charged atoms) depending on their sequence, provide a non-invasive delivery technology for macromolecules. CPPs often are referred to as "Trojan peptides," "membrane translocating sequences," "protein transduction domains (PTDs)," or "cell permeable proteins (CPPs)." CPPs also may be used to assist novel HSPB1 kinase inhibitors to penetrate cell membranes. (see U.S. application Ser. No. 11/972,459, entitled "Polypeptide Inhibitors of HSPB1 Kinase and Uses Therefor," filed Jan. 10, 2008, and Ser. No. 12/188,109, entitled "Kinase Inhibitors and Uses Thereof," filed Aug. 7, 2008, the contents of each application are incorporated by reference in their entirety herein).

5.3.1. Viral CPP Containing Proteins

The first proteins to be described as having transduction properties were of viral origin. These proteins still are the most commonly accepted models for CPP action. Among the cell-penetrating peptides, the arginine-rich cell-penetrating peptides, including but not limited to TAT peptide, have been the most widely studied (El-Sayed, A. et al., *AAPS J.* 11, 13-22, 2009; Wender, P. et al., *Adv. Drug Deliv. Rev.* 60, 452-472, 2008).

TAT (HIV-1 trans-activator gene product) is an 86-amino acid polypeptide, which acts as a powerful transcription factor of the integrated HIV-1 genome. TAT acts on the viral genome stimulating viral replication in latently infected cells. The translocation properties of the TAT protein enable it to activate quiescent infected cells, and it may be involved in priming of uninfected cells for subsequent infection by regulating many cellular genes, including cytokines. The minimal CPP of TAT is the 9 amino acid protein sequence RKKRRQRRR (TAT49-57; SEQ ID NO: 20). Studies utilizing a longer fragment of TAT demonstrated successful transduction of fusion proteins up to 120 kDa. The addition of multiple TAT-CPP as well as synthetic TAT derivatives has been demonstrated to mediate membrane translocation. TAT CPP containing fusion proteins have been used as therapeutic moieties in experiments involving cancer, transporting a death-protein into cells, and disease models of neurodegenerative disorders.

VP22 is the HSV-1 tegument protein, a structural part of the HSV virion. VP22 is capable of receptor independent translocation and accumulates in the nucleus. This property of VP22 classifies the protein as a CPPs containing peptide. Fusion proteins comprising full length VP22 have been translocated efficiently across the plasma membrane.

5.3.2. Homeoproteins with Intercellular Translocation Properties

Homeoproteins are highly conserved, transactivating transcription factors involved in morphological processes. They bind to DNA through a specific sequence of 60 amino acids. The DNA-binding homeodomain is the most highly conserved sequence of the homeoprotein. Several homeoproteins have been described to exhibit CPP-like activity; they are capable of efficient translocation across cell membranes in an energy-independent and endocytosis-independent manner without cell type specificity.

The Antennapedia protein (Antp) is a trans-activating factor capable of translocation across cell membranes; the minimal sequence capable of translocation is a 16 amino acid peptide corresponding to the third helix of the protein's homeodomain (HD). The internalization of this helix occurs at 4° C., suggesting that this process is not endocytosis dependent. Peptides up to 100 amino acids produced as fusion proteins with AntpHD penetrate cell membranes.

Other homeodomains capable of translocation include Fushi tarazu (Ftz) and Engrailed (En) homeodomain. Many homeodomains share a highly conserved third helix.

5.3.3. Human CPPs

Human CPPs may circumvent potential immunogenicity issues upon introduction into a human patient. Peptides with CPPs sequences include: Hoxa-5, Hox-A4, Hox-B5, Hox-B6, Hox-B7, HOX-D3, GAX, MOX-2, and FtzCPP. These proteins all share the sequence found in AntpCPPs. Other CPPs include Islet-1, interleukin-1, tumor necrosis factor, and the hydrophobic sequence from Kaposi-fibroblast growth factor or FGF-4) signal peptide, which is capable of energy-, receptor-, and endocytosis-independent translocation. Unconfirmed CPPs include members of the Fibroblast Growth Factor (FGF) family.

6. MK2 Inhibitors and Treatment of Fibrotic Diseases or Conditions

Mitogen-activated protein kinase activated protein kinase 2 (MAPKAPK2 or MK2), a serine/threonine kinase substrate downstream of p38MAPK, has been implicated in many inflammatory diseases that are complicated by scarring and fibrosis (Lopes, L. et al., *Biochem Biophys Res Commun.*, 382(3):535-9, 2009). These include, but are not limited to, cancer, intimal hyperplasia, organ fibrosis, abdominal adhesions, inflammatory bowel disease, and rheumatoid arthritis. In addition to idiopathic pulmonary fibrosis (IPF), other disorders that involve inflammation and fibrosis and impact the lung include acute lung injury (ALI), organ transplant rejection (with lung transplant also a later-stage treatment for IPF), organ failure secondary to sepsis, acute lung failture, auto-immune diseases such as scleroderma, and chronic pulmonary obstructive disease (COPD).

The development of fibrosis is known to require inflammation, proliferation and recruitment of fibroblast that results in cells of myofibroblastic phenotype (Horowitz J. et al., *Semin Respir Crit Care Med.*, 27(6):600-612, 2006). MK2 has been shown to control gene expression at transcriptional and post-transcriptional levels (Neininger A. et al., *J Biol Chem.* 2002; 277(5):3065-8, Thomas T. et al., *J Neurochem.*, 105(5): 2039-52, 2008; Johansen C. et al., *J Immunol.*, 176(3):1431-8, 2006; Rousseau S. et al., *EMBO J.* 21(23):6505-14, 2002) as well as cytoskeletal architecture (Lopes, L. et al., *Biochem Biophys Res Commun.*, 382(3): 535-9, 2009). In addition, it was shown that activated MK2 increases translation and stability of inflammatory cytokine mRNAs and causes actin reorganization; and that inhibition of MK2 is associated with reduced inflammation (Ward, B. et al., *J Surg Res.*, 169(1):e27-36, 2011) and myofibroblast differentiation (Lopes, L. et al., *Biochem Biophys Res Commun.*, 382(3):535-9, 2009).

Together, these data suggest that inhibition of MK2 may provide therapeutic benefits to patients with fibrotic disorders or conditions, for example, idiopathic pulmonary fibrosis (IPF), acute lung injury (ALI), and transplant rejection. In this respect, the described invention offers an approach to intervene in the process of inflammation and fibrosis using cell-penetrating, peptide-based inhibitors of MK2.

SUMMARY OF THE INVENTION

According to one aspect, the described invention provides a method for treating asthma comprising: administering to a subject in need thereof a pharmaceutical composition comprising a therapeutic amount of a polypeptide of the amino acid sequence YARAAARQARAKALARQLGVAA (SEQ ID NO: 1) or a functional equivalent thereof made from a fusion between a first polypeptide that is a cell penetrating peptide (CPP) selected from the group consisting of a polypeptide of amino acid sequence WLRRIKAWLRRIKA (SEQ ID NO: 12), WLRRIKA (SEQ ID NO: 13), YGRKKRRQRRR (SEQ ID NO: 14), WLRRIKAWLRRI (SEQ ID NO: 15), FAKLAARLYR (SEQ ID NO: 16), KAFAKLAARLYR (SEQ ID NO: 17) and HRRIKAWLKKI (SEQ ID NO: 18), and a second polypeptide that is a therapeutic domain (TD) selected from the group consisting of a polypeptide of amino acid sequence KALARQLAVA (SEQ ID NO: 8), KALARQLGVA (SEQ ID NO: 9) and KALARQLGVAA (SEQ ID NO: 10), and a pharmaceutically acceptable carrier thereof, the asthma being a disease, condition or pathologic process whose progression is characterized by one or more of aberrant fibroblast proliferation and extracellular matrix deposition producing constriction in an airway, airway remodeling, and airway obstruction in lung tissue, wherein the therapeutic amount of the polypeptide is effective to reduce the constriction of small airway dimensions and airway obstruction, treat airway remodeling, or a combination thereof. According to one embodiment of the method, the therapeutic amount of the polypeptide is effective to enhance isoproterenol-induced relaxation of human airway smooth muscle. According to another embodiment, the asthma is further characterized by an inflammation in the lung tissue. According to another embodiment, the inflammation is an acute or a chronic inflammation. According to another embodiment, the inflammation is mediated by at least one cytokine selected from the group consisting of Tumor Necrosis Factor-alpha (TNF-α), Interleukin-6 (IL-6), and Interleukin-1β (IL-1β). According to another embodiment, the aberrant fibroblast proliferation and extracellular matrix deposition in the lung tissue is characterized by an aberrant activity of Mitogen-Activated Protein Kinase-Activated Protein Kinase 2 (MK2) in the tissue compared to the activity of Mitogen-Activated Protein Kinase-Activated Protein Kinase 2 (MK2) in the tissue of a normal healthy control subject. According to another embodiment, the administering occurs intratracheally, parenterally, intravenously, or intraperitoneally. According to another embodiment, the administering occurs intratracheally. According to another embodiment, the pharmaceutical composition further comprises at least one additional therapeutic agent. According to another embodiment, the additional therapeutic agent is selected from the group consisting of a purified bovine Type V collagen, an IL-13 receptor antagonist, a protein tyrosine kinase inhibitor, an endothelial receptor antagonist, a dual endothelin receptor antagonist, a prostacyclin analog, an anti-CTGF monoclonal antibody, an endothelin receptor antagonist (A-selective), AB0024, a lysyl oxidase-like 2 (LOXL2) monoclonal antibody, a c-Jun N-terminal kinase (JNK) inhibitor, pirfenidone, IFN-γ1b, a pan-neutralizing IgG4 human antibody against all three TGF-β isoforms, a TGF-β activation inhibitor, a recombinant human Pentraxin-2 protein (rhPTX-2), a bispecific IL-4/IL-13 antibody, a humanized monoclonal antibody targeting integrin αvβ6, N-acetylcysteine, sildenafil, a Tumor Necrosis Factor (TNF) antagonist (etanercept), and a combination thereof. According to another embodiment, the additional therapeutic agent is a glucocorticoid selected from the group consisting of prednisone, budesonide, mometasone furoate, fluticasone propionate, fluticasone furoate, and a combination thereof. According to another embodiment, the additional therapeutic agent is a bronchodilator selected from the group consisting of a leukotriene modifer, an anticholingertic bronchodilator, a short-acting β2-agonist, and long-acting β2-agonist, and a combination thereof. According to another embodiment, the additional therapeutic agent is an analgesic agent. According to another embodiment, the additional therapeutic agent is an anti-infective agent. According to another embodiment, the functional equivalent of the polypeptide YARAAARQARAKALARQLGVAA (SEQ ID NO: 1) is of amino acid sequence FAKLAARLYRKALARQLGVAA (SEQ ID NO: 3). According to another embodiment, the functional equivalent of the polypeptide YARAAARQARAKALARQLGVAA (SEQ ID NO: 1) is of amino acid sequence KAFAKLAARLYRKALARQLGVAA (SEQ ID NO: 4). According to another embodiment, the functional equivalent of the polypeptide YARAAARQARAKALARQLGVAA (SEQ ID NO: 1) is of amino acid sequence YARAAARQARAKALARQLAVA (SEQ ID NO: 5). According to another embodiment, the functional equivalent of the polypeptide YARAAARQARAKALARQLGVAA (SEQ ID NO: 1) is of amino acid sequence YARAAARQARAKALARQLGVA (SEQ ID NO: 6). According to another embodiment, the functional equivalent of the polypeptide YARAAARQARAKALARQLGVAA (SEQ ID NO: 1) is of amino acid sequence HRRIKAWLKKIKALARQLGVAA (SEQ ID NO: 7). According to another embodiment, the therapeutic domain (TD) of the functional equivalent of the polypeptide YARAAARQARAKALARQLGVAA (SEQ ID NO: 1) is made from the fusion of the first polypeptide that is the cell penetrating peptide (CPP) operatively linked to the second polypeptide that is the therapeutic domain (TD), is a polypeptide whose sequence has a substantial identity to amino acid sequence KALARQLGVAA (SEQ ID NO: 2). According to another embodiment, the second polypeptide is a polypeptide of amino acid sequence KALARQLAVA (SEQ ID NO: 8). According to another embodiment, the second polypeptide is a polypeptide of amino acid sequence KALARQLGVA (SEQ ID NO: 9). According to another embodiment, the second polypeptide is a polypeptide of amino acid sequence KALARQLGVAA (SEQ ID NO: 10). According to another embodiment, the functional equivalent of the polypeptide YARAAARQARAKALARQLGVAA (SEQ ID NO: 1) is a fusion protein comprising a first polypeptide operatively linked to a second polypeptide, wherein the first polypeptide is a cell penetrating peptide functionally equivalent to YARAAARQARA (SEQ ID NO: 11) selected from the group consisting of a polypeptide of amino acid sequence WLRRIKAWLRRIKA (SEQ ID NO: 12), WLRRIKA (SEQ ID NO: 13), YGRKKRRQRRR (SEQ ID NO: 14), WLRRIKAWLRRI (SEQ ID NO: 15), FAKLAARLYR (SEQ ID NO: 16), KAFAKLAARLYR (SEQ ID NO: 17) and HRRIKAWLKKI (SEQ ID NO: 18), and the second polypeptide is of amino acid sequence KALARQLGVAA (SEQ ID NO: 2). According to another embodiment, the first polypeptide is a polypeptide of amino acid sequence WLRRIKAWLRRIKA (SEQ ID NO: 12). According to another embodiment, the first polypeptide is a polypeptide of amino acid sequence WLRRIKA (SEQ ID NO: 13). According to another embodiment, the first polypeptide is a polypeptide of amino acid sequence YGRKKRRQRRR (SEQ ID NO: 14). According to another embodiment, the first polypeptide is a polypeptide of amino acid sequence WLRRIKAWLRRI (SEQ ID NO: 15). According to another embodiment, the first polypeptide is a polypeptide of amino acid sequence FAKLAARLYR (SEQ ID NO: 16). According to another embodiment, the first polypeptide is a polypeptide of amino acid sequence KAFAKLAARLYR (SEQ ID NO: 17). According to another embodiment, the first polypeptide is a polypeptide of amino acid sequence HRRIKAWLKKI (SEQ ID NO: 18). According to another embodiment, the carrier is selected from the group consisting of a controlled release carrier, a delayed release carrier, a sustained release carrier, and a long-term release carrier. According to another embodiment, the pharmaceutical composition is in a form of a dry powder. According to another embodiment, the dry powder comprises microparticles with Mass Median Aerodynamic Diameter (MMAD) of 1 to 5 microns. According to another embodiment, administering is via an inhalation device. According to another embodiment, the inhalation device is a nebulizer. According to another embodiment, the inhalation device is a metered-dose inhaler (MDI). According to another embodiment, the inhalation device is a dry powder inhaler (DPI). According to another embodiment, the inhalation device is a dry powder nebulizer. According to another embodiment, the asthma is further characterized by at least one pathology selected from the group consisting of an aberrant deposition of an extracellular matrix protein in a pulmonary interstitium, an aberrant induction of myofibroblast differentiation and an aberrant promotion of attachment of myofibroblasts to an extracellular matrix, compared to a normal healthy control subject. According to another embodiment, the asthma is associated with an allergic reaction, inhalation of environmental particulates, smoking, a bacterial infection, a viral infection, mechanical damage to a lung of the subject, an autoimmune disorder, a genetic disorder, or a combination thereof.

BRIEF DESCRIPTION OF THE DRAWINGS

FIG. 4 shows flow-rate independence of spray-dried neat peptide.

Figure 5:
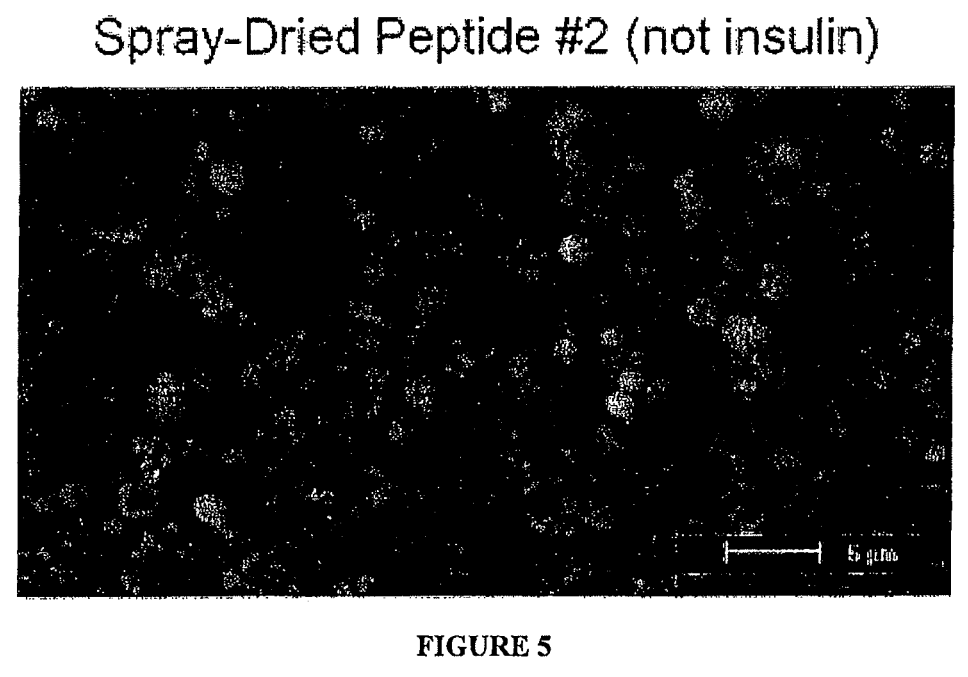

FIG. 5 shows a representative micrograph of a spray-dried peptide (not insulin).

FIG. 13 shows that MMI-0100 (YARAAARQARAKALARQLGVAA; SEQ ID NO: 1) prevents fibrosis due to bleomycin injury in a dose-dependent manner. Masson's blue trichrome staining of lung sections of bleomycin mice. (A) MMI-0100 (YARAAARQARAKALARQLGVAA; SEQ ID NO: 1); (B) MMI-0200 (YARAAARQARAKALNRQLGVA; SEQ ID NO: 19).

BLEO (bleomycin mice treated with PBS); MMI-0100 (NEB) (bleomycin mice treated with nebulized MMI-0100 (YARAAARQARAKALARQLGVAA (SEQ ID NO: 1)); MMI-0100 (IP) (bleomycin mice treated with intraperitoneal MMI-0100 (YARAAARQARAKALARQLGVAA (SEQ ID NO: 1)); NL (normal lung architecture with alveolar sacs); AW (air way); FF (fibroblastic foci from a lung tissue explants with IPF)

Figure 17:
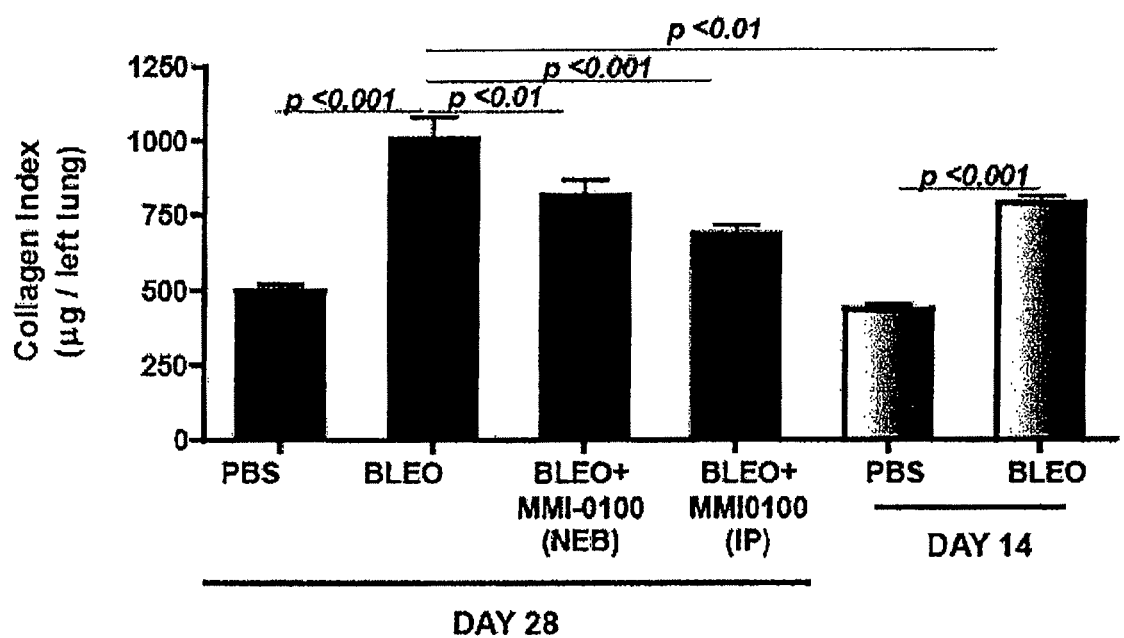

FIG. 17 shows that MMI-0100 (YARAAARQARAKALARQLGVAA (SEQ ID NO: 1)) arrests significant collagen deposition due to bleomycin injury. The abbreviations shown in FIG. 17 are as follows: PBS (wild type mice treated with PBS); BLEO (bleomycin mice treated with PBS); BLEO+MMI-0100 (NEB) (bleomycin mice treated with nebulized MMI-0100 (YARAAARQARAKALARQLGVAA (SEQ ID NO: 1)); BLEO+MMI-0100 (IP) (bleomycin mice treated with intraperitoneal MMI-0100 (YARAAARQARAKALARQLGVAA (SEQ ID NO: 1)). Values represent Means±SEM. n=5 animals per group. Collagen Index=constant factor for collagen 7.5× hydroxyproline concentrations.

Figure 18:
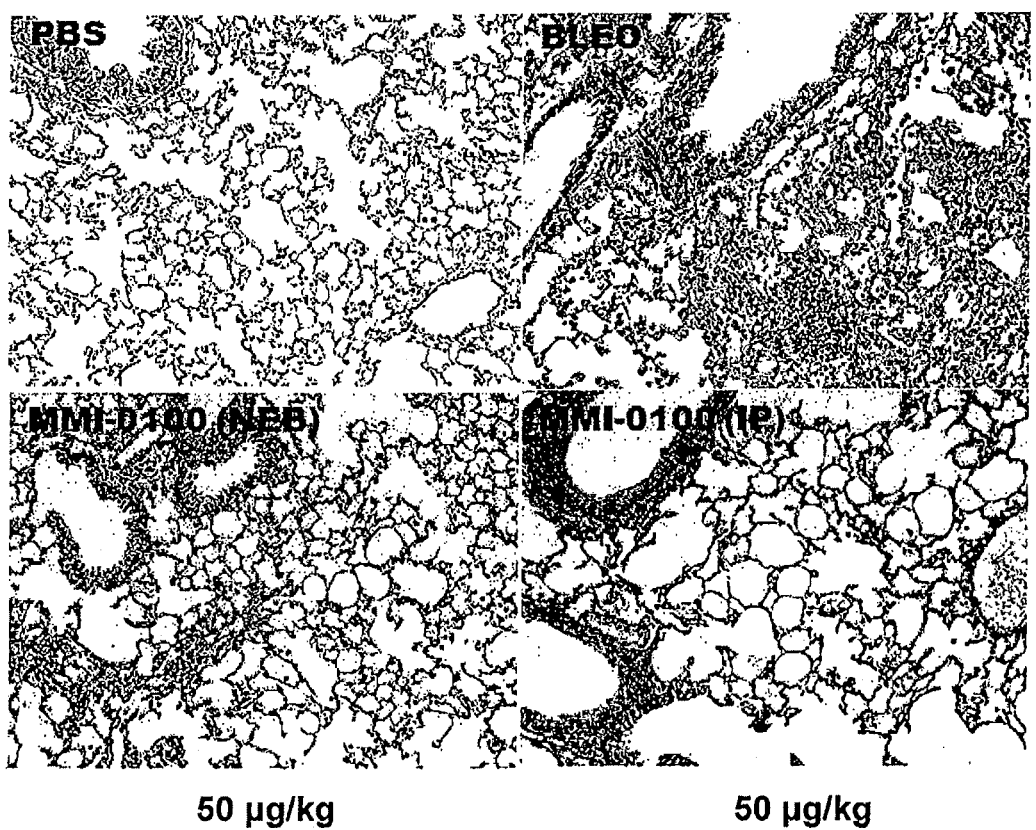

FIG. 18 shows a representative micrographs of anti-phospho-Thr$^{334}$-MAPKAPK2 (an activated form of MK2) staining of lung sections (at day 28 post bleomycin injury) from (i) wild type mice treated with PBS (PBS); (ii) bleomycin mice treated with PBS (BLEO); (iii) bleomycin mice treated with nebulized MMI-0100 (YARAAARQARAKALARQLGVAA (SEQ ID NO: 1)) (BLEO+MMI-0100 (NEB)); and (iv) bleomycin mice treated with intraperitoneal MMI-0100 (YARAAARQARAKALARQLGVAA (SEQ ID NO: 1)) (BLEO+MMI-0100 (IP)). C57-BL/6 mice were subjected to bleomycin injury at day 0. At day 14, the mice were administered 50 μg/kg of MMI-0100 (YARAAARQARAKALARQLGVAA; SEQ ID NO: 1) daily by intraperitoneal (IP) injection or nebulizer (NEB) until day 28 post bleomycin injury. Original magnifications: 20×.

Figure 19:
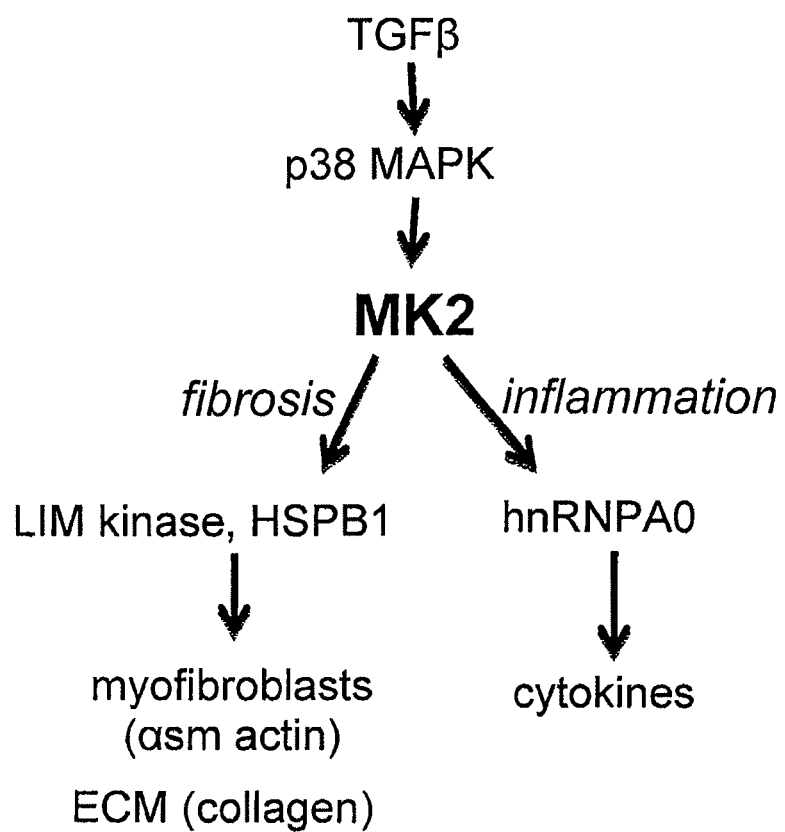

FIG. 19 shows key signaling molecules involved in TGF-β-mediated inflammatory and fibrotic pathways.

Figure 20:
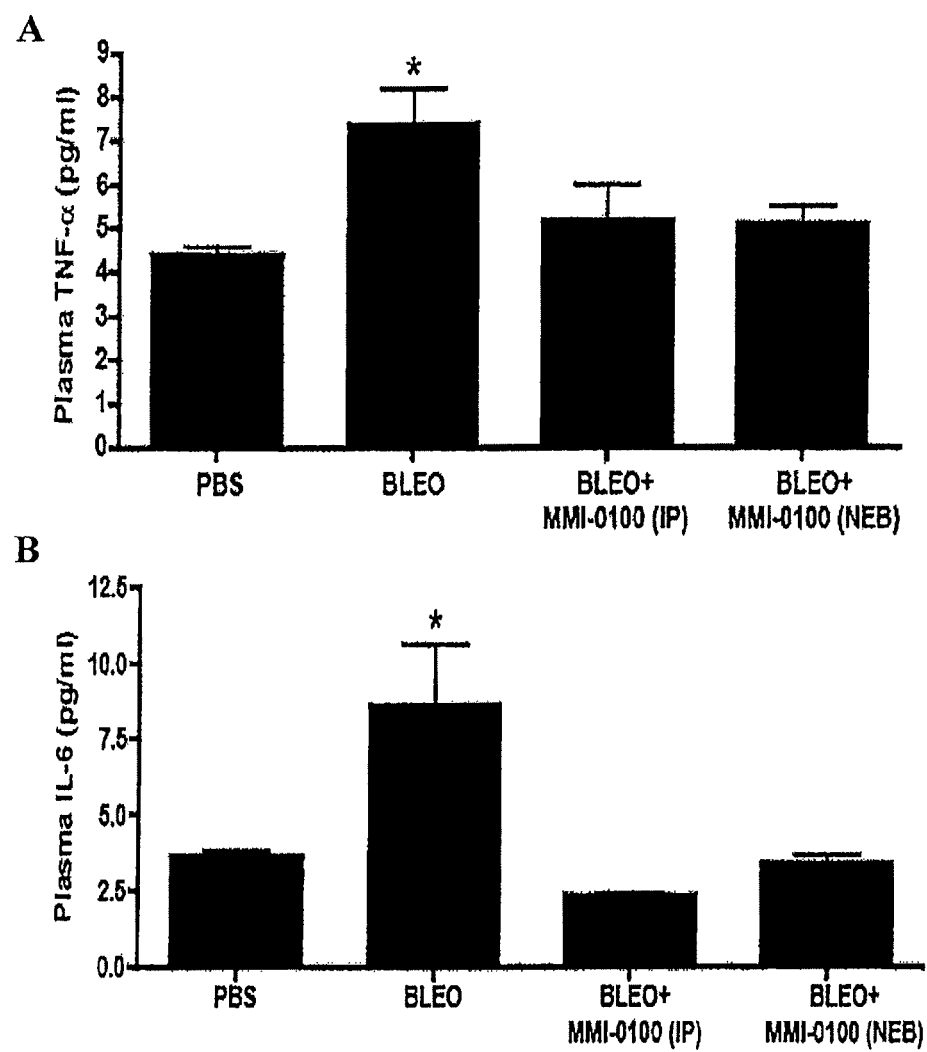

FIG. 20 shows that, 24 hours after final administration, MMI-0100 (YARAAARQARAKALARQLGVAA; SEQ ID NO: 1) downregulates the levels of circulating inflammatory cytokines in the bleomycin mouse model of idiopathic pulmonary fibrosis (treatment model).

Figure 21:
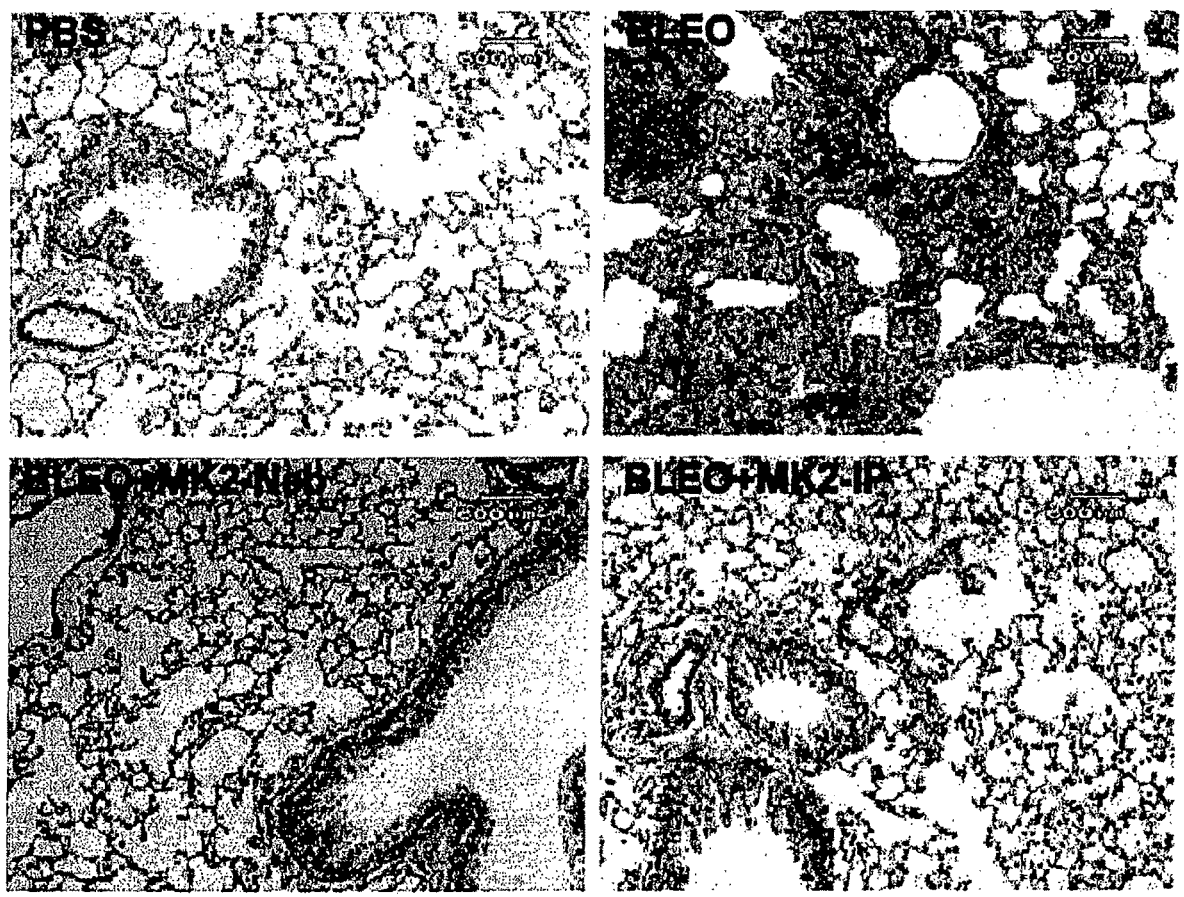

FIG. 21 shows that MMI-0100 (YARAAARQARAKALARQLGVAA; SEQ ID NO: 1) inhibits myofibroblast alpha-smooth muscle actin (α-SMA) activation in the idiopathic pulmonary fibrosis treatment model. C57-BL/6 mice were subjected to bleomycin injury at day 0. At day 14 through day 28, mice were administered 50 μg/kg/day MMI-0100 (YARAAARQARAKALARQLGVAA; SEQ ID NO: 1) by intraperitoneal (IP) injection or nebulizer (NEB). Formalin-fixed lung tissue sections were immunostained against α-SMA. Control staining was with biotinylated secondary IgG antibody. Streptavidin-conjugated horseradish peroxidase was used with 3,3'-diaminobenzidene as substrate and nuclei was counterstained with hematoxylin. Original magnifications: 20×

Figure 22:
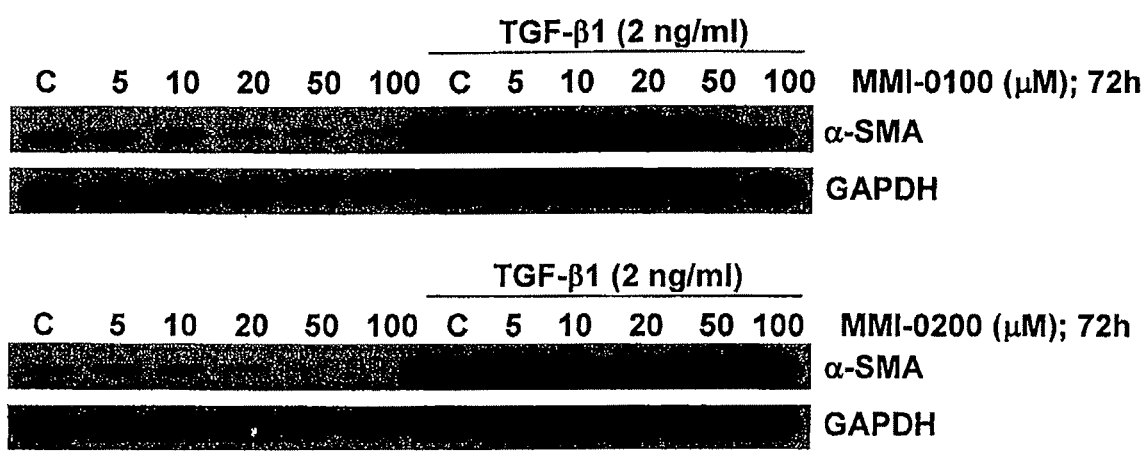

FIG. 22 shows modulation of TGF-β-induced myofibroblast activation by MK2 peptide inhibitors in normal human fetal lung fibroblasts (IMR-90). IMR-90 cells were pre-treated with MMI-0100 (YARAAARQARAKALARQLGVAA; SEQ ID NO: 1) or MMI-0200 (YARAAARQARAKALNRQLGVA; SEQ ID NO: 19) at the indicated doses for 1 h and then cultured in the presence or absence of TGF-β1 (2 ng/ml) for 48 h. Cell lysates were immunoblotted against antibodies for α-SMA (a marker for myofibroblast activation) and GAPDH (loading control).

Figure 23:
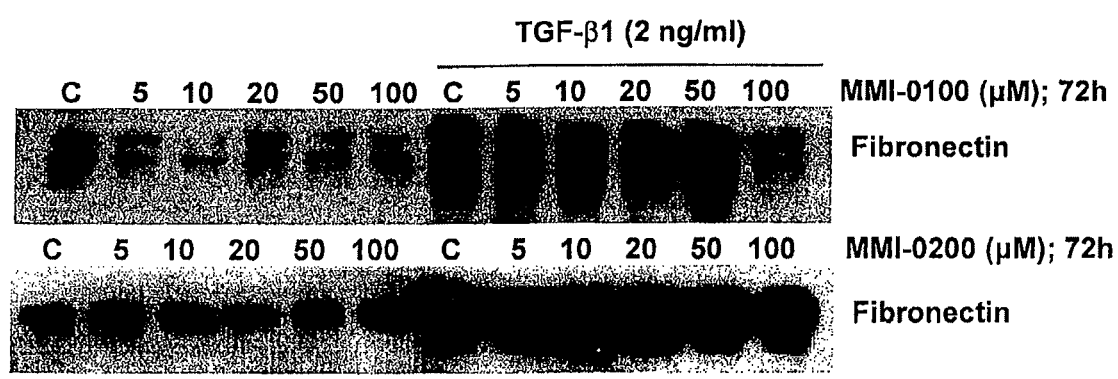

FIG. 23 shows modulation of TGF-β-mediated fibronectin expression in human fetal lung fibroblasts (IMR-90). IMR90 cells were pre-treated with MMI-0100 (YARAAARQARAKALARQLGVAA; SEQ ID NO: 1) or MMI-0200 (YARAAARQARAKALNRQLGVA; SEQ ID NO: 19) at the indicated doses for 1 h, and then cultured in the presence or absence of TGF-β1 (2 ng/ml) for 72 h. Fibronection was measured as secreted fragments in the conditioned media. Equal amounts (14 μg) of total proteins from the conditioned media were loaded in each lane.

Figure 24:
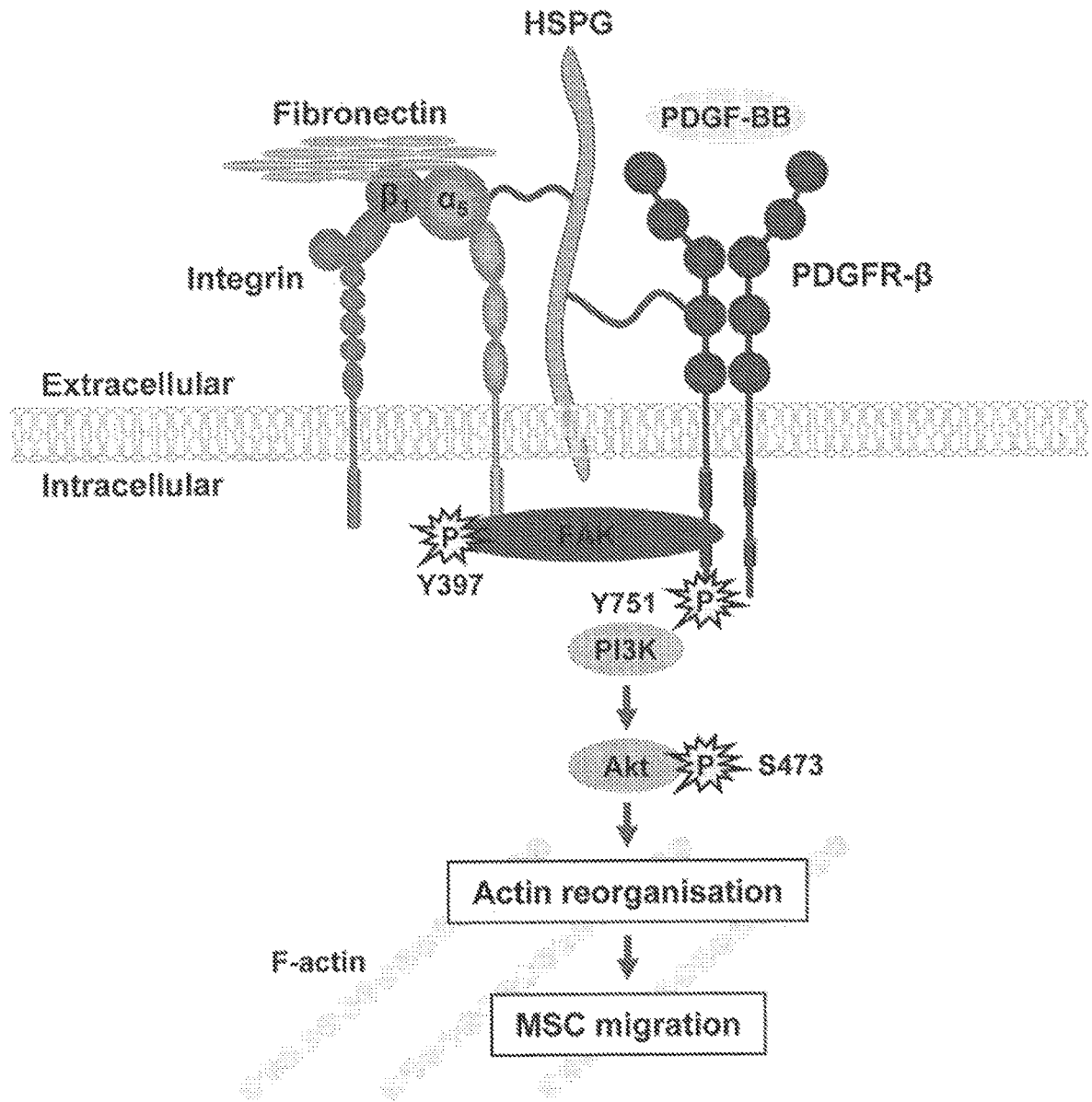

FIG. 24 shows key signaling molecules involved in the regulation of mesenchymal stem cell migration by fibronectin through α5β1-integrin-mediated activation of PDGFR-β (Veevers-Lowe J et al., *J Cell Sci*, 124: 1288-1300, 2011).

Figure 25:
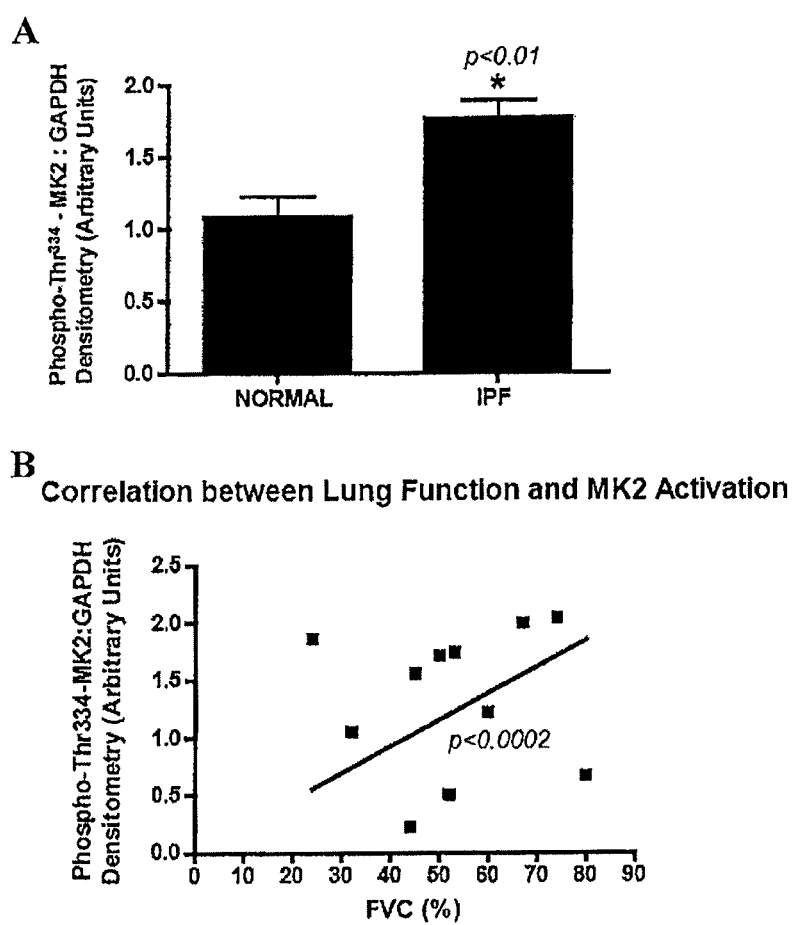

FIG. 25 shows increases in the level of an MK2 kinase activated form in IPF patients. (A) quantitative analysis of phospho-Thr$^{334}$ levels in normal and IPF tissues; (C) correlation between lung function and MK2 activation.

Figure 26:
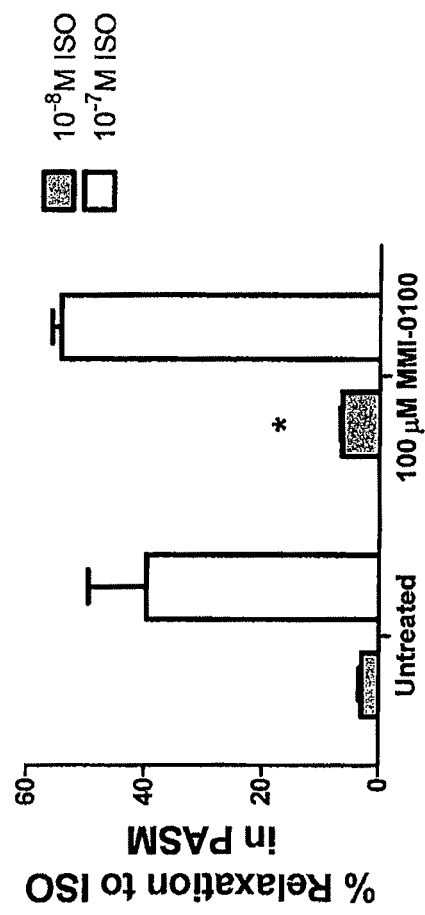

FIG. 26 shows MMI-0100 (YARAAARQARAKALARQLGVAA; SEQ ID NO: 1) enhances isoproterenol (ISO) induced relaxation of porcine airway smooth muscle.

Figure 27:
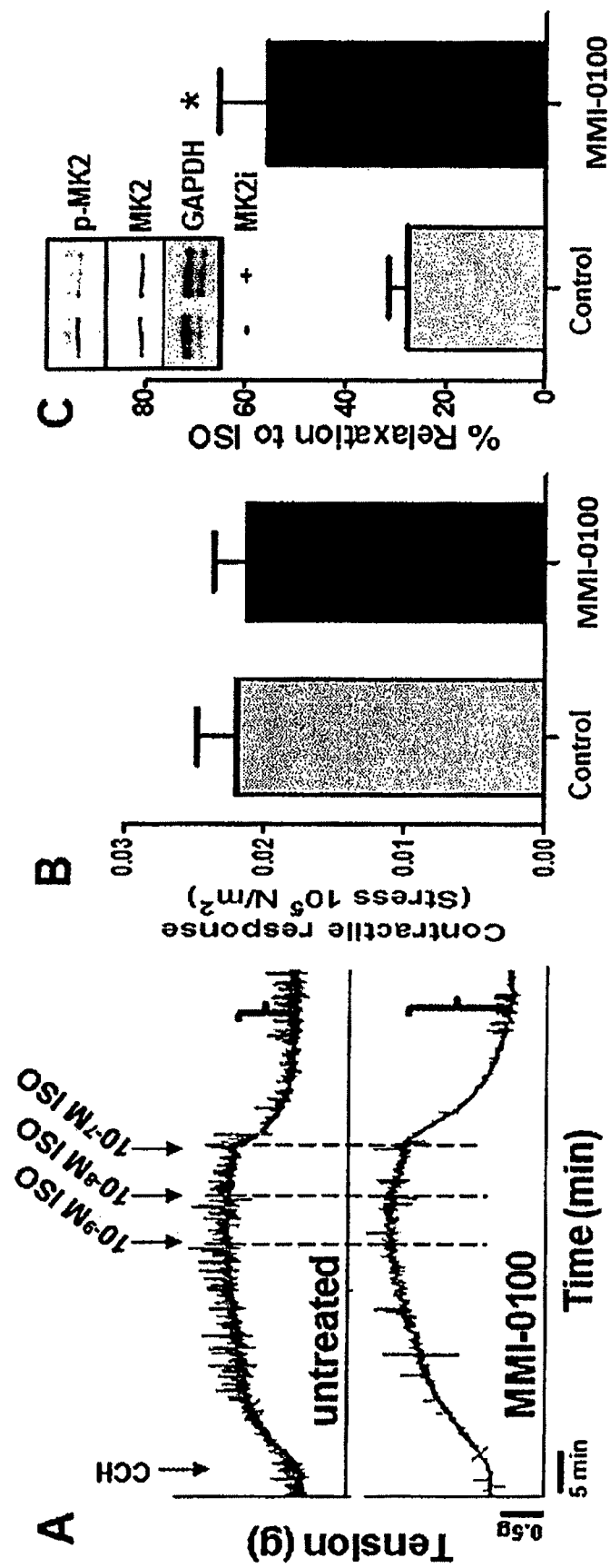

FIG. 27 shows MMI-0100 (YARAAARQARAKALARQLGVAA; SEQ ID NO: 1) enhances isoproterenol (ISO) induced relaxation of human airway smooth muscle. (A) airway smooth muscle tension (g) versus time (min); (B) airway smooth muscle contractile response; (C) percent relaxation of airway smooth muscle in response to isoproterenol (ISO).

FIG. 28 shows a schematic model of MMI-0100 (YARAAARQARAKALARQLGVAA; SEQ ID NO: 1) in asthma.

DETAILED DESCRIPTION OF THE INVENTION

The described invention provides a composition and method for treating a pulmonary fibrosis in a subject in need of thereof, the method comprising administering a therapeutic amount of a composition comprising a polypeptide having the amino acid sequence YARAAARQARAKALARQLGVAA (MMI-0100; SEQ ID NO: 1) or a functional equivalent thereof.

Glossary

The term "airway" as used herein refers to the passages through which air enters and leaves the body. The pulmonary airway comprises those parts of the respiratory tract through which air passes during breathing.

The term "airway obstruction" as used herein refers to any abnormal reduction in airflow. Resistance to airflow can occur anywhere in the airway from the upper airway to the terminal bronchi.

The term "airway disease" as used herein refers to a disease that affects the tubes (airways) that carry oxygen and other gases into and out of the lungs. Airway diseases include, but are not limited to, chronic obstructive pulmonary disease (COPD), including asthma, emphysema, and chronic bronchitis.

The term "lung tissue disease" as used herein refers to a disease that affects the structure of the lung tissue, e.g., pulmonary interstitium. Scarring or inflammation of lung tissue makes the lungs unable to expand fully ("restrictive lung disease"). It also makes the lungs less capable of taking up oxygen (oxygenation) and releasing carbon dioxide. Examples of lung tissue diseases include, but are not limited to, idiopathic pulmonary fibrosis (IPF), acute lung injury (ALI), a radiation-induced fibrosis in the lung, and a fibrotic condition associated with lung transplantation. Sarcoidosis is a disease in which swelling (inflammation) occurs in the lymph nodes, lungs, liver, eyes, skin, or other tissues.

The terms "lung interstitium" or "pulmonary interstitium" are used interchangeably herein to refer to an area located between the airspace epithelium and pleural mesothelium in the lung. Fibers of the matrix proteins, collagen and elastin, are the major components of the pulmonary interstitium. The primary function of these fibers is to form a mechanical scaffold that maintains structural integrity during ventilation.

The term "accessible surface area" or "ASA" as used herein refers to a surface area of a biomolecule that is exposed to solvent. The term "solvent accessible surface" or "SAS" as used herein refers to a percentage of the surface area of a given residue that is accessible to the solvent. It is calculated as a ratio between ASA of a residue in the three dimensional structure and the maximum ASA of its extended peptide confirmation The terms "amino acid residue" or "amino acid" or "residue" are used interchangeably to refer to an amino acid that is incorporated into a protein, a polypeptide, or a peptide, including, but not limited to, a naturally occurring amino acid and known analogs of natural amino acids that can function in a similar manner as naturally occurring amino acids. The amino acids may be L- or D-amino acids. An amino acid may be replaced by a synthetic amino acid, which is altered so as to increase the half-life of the peptide, increase the potency of the peptide, or increase the bioavailability of the peptide.

The single letter designation for amino acids is used predominately herein. As is well known by one of skill in the art, such single letter designations are as follows:

A is alanine; C is cysteine; D is aspartic acid; E is glutamic acid; F is phenylalanine; G is glycine; H is histidine; I is isoleucine; K is lysine; L is leucine; M is methionine; N is asparagine; P is proline; Q is glutamine; R is arginine; S is serine; T is threonine; V is valine; W is tryptophan; and Y is tyrosine.

The following represents groups of amino acids that are conservative substitutions for one another: 1) Alanine (A), Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

As used herein, the singular forms "a", "an" and "the" include plural referents unless the context clearly dictates otherwise. For example, reference to a "polypeptide" means one or more polypeptides.

The term "addition" as used herein refers to the insertion of one or more bases, or of one or more amino acids, into a sequence.

The term "administer" as used herein refers to dispensing, supplying, applying, giving, apportioning or contributing. The terms "administering" or "administration" are used interchangeably and include in vivo administration, as well as administration directly to tissue ex vivo. Generally, compositions may be administered systemically either orally, buccally, parenterally, topically, by inhalation or insufflation (i.e., through the mouth or through the nose), or rectally in dosage unit formulations containing the conventional nontoxic pharmaceutically acceptable carriers, adjuvants, and vehicles as desired, or may be locally administered by means such as, but not limited to, injection, implantation, grafting, topical application, or parenterally. Additional administration may be performed, for example, intravenously, pericardially, orally, via implant, transmucosally, transdermally, topically, intramuscularly, subcutaneously, intraperitoneally, intrathecally, intralymphatically, intralesionally, or epidurally. Administering can be performed, for example, once, a plurality of times, and/or over one or more extended periods.

The term "allergic reaction" as used herein refers to a hypersensitive reaction of the immune system. Allergic reactions occur to normally harmless environmental substances known as allergens; these reactions are acquired, predictable, and rapid. Allergic reaction is characterized by excessive activation of certain white blood cells called mast cells and basophils by a type of antibody known as IgE, resulting in an extreme inflammatory response. Common allergic reactions include eczema, hives, hay fever, asthma attacks, food allergies, and reactions to the venom of stinging insects such as wasps and bees.

The term "α-smooth muscle actin" or "α-SMA" as used herein refers to an actin protein, alpha-actin-2 (ACTA2; also known as actin or aortic smooth muscle actin) first isolated in vascular smooth muscle cells. Actins are highly conserved proteins expressed in all eukaryotic cells. Actin filaments form part of the cytoskeleton and play essential roles in regulating cell shape and movement. Six distinct actin isotypes have been identified in mammalian cells. Each is encoded by a separated gene and is expressed in a developmentally regulated and tissue-specific manner. Alpha and beta cytoplasmic actins are expressed in a wide variety of cells, whereas expression of alpha skeletal, alpha cardiac, alpha vascular, and gamma enteric actins are more restricted to specialized muscle cell type. The gene for alpha-smooth muscle actin is one of a few genes whose expression is relatively restricted to vascular smooth muscle cells, but it is now most commonly used as a marker of myofibroblast formation. Expression of alpha smooth muscle actin is regulated by hormones and cell proliferation, and is altered by pathological conditions, including oncogenic transformation and atherosclerosis.

The term "alveolus" or "alveoli" as used herein refers to an anatomical structure that has the form of a hollow cavity. Found in the lung, the pulmonary alveoli are spherical outcroppings of the respiratory sites of gas exchange with the blood. The alveoli contain some collagen and elastic fibers. Elastic fibers allow the alveoli to stretch as they fill with air when breathing in. They then spring back during breathing out in order to expel the carbon dioxide-rich air.

The term "bleomycin" as used herein refers to a glycopeptide antibiotic produced by the bacterium *Streptomyces verticillus*. It works by inducing DNA strand breaks and inhibiting incorporation of thymidine into DNA strand. The most serious complication of bleomycin is pulmonary fibrosis and impaired lung function.

The term "bronchoalveolar lavage" or "BAL" as used herein refers to a medical procedure in which a bronchoscope is passed through the mouth or nose into the lungs and fluid is squirted into a small part of the lung and then recollected for examination. BAL typically is performed to diagnose lung disease. BAL commonly is used to diagnose infections in people with immune system problems, pneumonia in people on ventilators, some types of lung cancer, and scarring of the lung (interstitial lung disease). BAL is the most common manner to sample the components of the epithelial lining fluid (ELF) and to determine the protein composition of the pulmonary airways, and is often used in immunological research as a means of sampling cells or pathogen levels in the lung.

The terms "carrier" and "pharmaceutical carrier" as used herein refer to a pharmaceutically acceptable inert agent or vehicle for delivering one or more active agents to a subject, and often is referred to as "excipient." The (pharmaceutical) carrier must be of sufficiently high purity and of sufficiently low toxicity to render it suitable for administration to the subject being treated. The (pharmaceutical) carrier further should maintain the stability and bioavailability of an active agent, e.g., a polypeptide of the described invention. The (pharmaceutical) carrier can be liquid or solid and is selected, with the planned manner of administration in mind, to provide for the desired bulk, consistency, etc., when combined with an active agent and other components of a given composition. The (pharmaceutical) carrier may be, without limitation, a binding agent (e.g., pregelatinized maize starch, polyvinylpyrrolidone or hydroxypropyl methylcellulose, etc.), a filler (e.g., lactose and other sugars, microcrystalline cellulose, pectin, gelatin, calcium sulfate, ethyl cellulose, polyacrylates, calcium hydrogen phosphate, etc.), a lubricant (e.g., magnesium stearate, talc, silica, colloidal silicon dioxide, stearic acid, metallic stearates, hydrogenated vegetable oils, corn starch, polyethylene glycols, sodium benzoate, sodium acetate, etc.), a disintegrant (e.g., starch, sodium starch glycolate, etc.), or a wetting agent (e.g., sodium lauryl sulphate, etc.). Other suitable (pharmaceutical) carriers for the compositions of the described invention include, but are not limited to, water, salt solutions, alcohols, polyethylene glycols, gelatins, amyloses, magnesium stearates, talcs, silicic acids, viscous paraffins, hydroxymethylcelluloses, polyvinylpyrrolidones and the like. Compositions that are for parenteral administration of a polypeptide of the described invention may include (pharmaceutical) carriers such as sterile aqueous solutions, non-aqueous solutions in common solvents such as alcohols, or solutions of the polypeptide in a liquid oil base.

The term "collagen" as used herein refers to a group of naturally occurring proteins found in the flesh and in connective tissues of mammals. It is the main component of connective tissue, and is the most abundant protein in mammals, making up about 25% to 35% of the whole-body protein content. Collagen, in the form of elongated fibrils, is mostly found in fibrous tissues, such as tendon, ligament, and skin, and is also abundant in cornea, cartilage, bone, blood vessels, the gut, and intervertebral disc. So far, 29 types of collagen have been identified and over 90% of the collagen in the body is of type I (skin, tendon, vascular, ligature, organs, bone), type II (cartilage), type III (reticulate (main component of reticular fibers), and type IV (which forms the bases of cell base membrane).

The term "condition" as used herein refers to a variety of health states and is meant to include disorders or diseases caused by any underlying mechanism, disorder, or injury.

The term "cytokine," which refers to small soluble protein substances secreted by cells that have a variety of effects on other cells, is generically used to refer to many signaling molecules including, without limitation, lymphokines, interleukins, and chemokines. Cytokines mediate many important physiological functions including growth, development, wound healing, and the immune response. They act by binding to their cell-specific receptors located in the cell membrane that allows a distinct signal transduction cascade to start in the cell, which eventually will lead to biochemical and phenotypic changes in target cells. Generally, cytokines act locally, although some have been found to have systemic immunomodulatory effects, with pleiotropic autocrine, paracrine, and endocrine effects similar to hormones. They include type I cytokines, which encompass many of the interleukins, as well as several hematopoietic growth factors; type II cytokines, including the interferons and interleukin-10; tumor necrosis factor ("TNF")-related molecules, including TNF-α and lymphotoxin; immunoglobulin superfamily members, including interleukin 1 ("IL-1"); and the chemokines, a family of molecules that play a critical role in a wide variety of immune and inflammatory functions. The same cytokine can have different effects on a cell depending on the state of the cell. Cytokines often regulate the expression of, and trigger cascades of, other cytokines.

The terms "disease" or "disorder" as used herein refer to an impairment of health or a condition of abnormal functioning, regardless of cause (whether heritable, environmental, dietary, infectious, due to trauma, or otherwise). Disorders may include, for example, but are not limited to, inflammatory and fibrotic diseases, fibrosis, acute lung injury, radiation-induced fibrosis, transplant rejection, chronic obstructive pulmonary disease (COPD), endotoxic shock, localized inflammatory disease, atherosclerotic cardiovascular disease, Alzheimer's disease, oncological diseases, neural ischemia, connective tissue and systemic autoimmune diseases, rheumatoid arthritis, Crohn's disease, inflammatory bowel disease, systemic lupus erythematosus (SLE), Sjögren's syndrome, scleroderma, vasculitis, intimal hyperplasia, stenosis, restenosis, atherosclerosis, smooth muscle cell tumors and metastasis, smooth muscle spasm, angina, Prinzmetal's angina, ischemia, stroke, bradycardia, hypertension, cardiac hypertrophy, renal failure, stroke, pulmonary hypertension, asthma, toxemia of pregnancy, preterm labor, pre-eclampsia, eclampsia, Raynaud's disease or phenomenon, hemolytic-uremia, anal fissure, achalasia, impotence, migraine, ischemic muscle injury associated with smooth muscle spasm, vasculopathy, bradyarrythmia, congestive heart failure, stunned myocardium, pulmonary hypertension, diastolic dysfunction, gliosis (proliferation of astrocytes, and may include deposition of extracellular matrix (ECM) deposition in damaged areas of the central nervous system), chronic obstructive pulmonary disease (i.e., respiratory tract diseases characterized by airflow obstruction or limitation; includes, but is not limited to, chronic bronchitis, emphysema, and chronic asthma), osteopenia, endothelial dysfunction, inflammation, degenerative arthritis, anklyosing spondylitis, Guillain-Barré disease, infectious disease, sepsis, endotoxemic shock, psoriasis, radiation enteritis, cirrhosis, interstitial fibrosis, pulmonary fibrosis (including idiopathic pulmonary fibrosis), colitis, appendicitis, gastritis, laryngitis, meningitis, pancreatitis, otitis, reperfusion injury, traumatic brain injury, spinal cord injury, peripheral neuropathy, multiple sclerosis, allergy, cardiometabolic diseases, obesity, type II diabetes mellitus, type I diabetes mellitis, and NASH/cirrhosis.

The term "domain" as used herein refers to a region of a protein with a characteristic tertiary structure and function and to any of the three-dimensional subunits of a protein that together makes up its tertiary structure formed by folding its linear peptide chain.

The term "therapeutic domain" (also referred to as "TD") as used herein refers to a peptide, peptide segment or variant, or derivative thereof, with substantial identity to peptide KALARQLGVAA (SEQ ID NO: 2), or segment thereof. Therapeutic domains by themselves generally are not capable of penetrating the plasma membrane of mammalian cells. Once inside the cell, therapeutic domains can inhibit the kinase activity of a specific group of kinases.

The term "cell penetrating peptide" (also referred to as "CPP," "protein transduction domain," "PTD", "Trojan peptide", "membrane translocating sequence", and "cell permeable protein") as used herein refers to a class of peptides generally capable of penetrating the plasma membrane of mammalian cells. It also refers to a peptide, peptide segment, or variant or derivative thereof, with substantial identity to peptide YARAAARQARA (SEQ ID NO: 11), or a functional segment thereof, and to a peptide, peptide segment, or variant or derivative thereof, which is functionally equivalent to SEQ ID NO: 11. CPPs generally are 10-16 amino acids in length and are capable of transporting compounds of many types and molecular weights across mammalian cells. Such compounds include, but are not limited to, effector molecules, such as proteins, DNA, conjugated peptides, oligonucleotides, and small particles such as liposomes. CPPs chemically linked or fused to other proteins ("fusion proteins") still are able to penetrate the plasma membrane and enter cells.

The term "extracellular matrix" as used herein refers to a scaffold in a cell's external environment with which the cell interacts via specific cell surface receptors. The extracellular matrix is composed of an interlocking mesh of fibrous proteins and glycosaminoglycans (GAGs). Examples of fibrous proteins found in the extracellular matrix include, without limitation, collagens, elastin, fibronectin, and laminin. Examples of GAGs found in the extracellular matrix include, without limitation, proteoglycans (e.g., heparin sulfate), chondroitin sulfate, keratin sulfate, and non-proteoglycan polysaccharide (e.g., hyaluronic acid). The term "proteoglycan" refers to a group of glycoproteins that contain a core protein to which is attached one or more glycosaminoglycans. The extracellular matrix serves many functions, including, but not limited to, providing support and anchorage for cells, segregating one tissue from another tissue, and regulating intracellular communication.

The terms "functional equivalent" or "functionally equivalent" are used interchangeably herein to refer to substances, molecules, polynucleotides, proteins, peptides, or polypeptides having similar or identical effects or use. A polypeptide functionally equivalent to polypeptide YARAAARQARAKALARQLGVAA (SEQ ID NO: 1), for example, may have a biologic activity, e.g., an inhibitory activity, kinetic parameters, salt inhibition, a cofactor-dependent activity, and/or a functional unit size that is substantially similar or identical to the expressed polypeptide of SEQ ID NO: 1.

Examples of polypeptides functionally equivalent to YARAAARQARAKALARQLGVAA (SEQ ID NO: 1) include, but are not limited to, a polypeptide of amino acid sequence FAKLAARLYRKALARQLGVAA (SEQ ID NO: 3), a polypeptide of amino acid sequence KAFAKLAARLYRKALARQLGVAA (SEQ ID NO: 4), a polypeptide of amino acid sequence YARAAARQARAKALARQLAVA (SEQ ID NO: 5), a polypeptide of amino acid sequence YARAAARQARAKALARQLGVA (SEQ ID NO: 6), and a polypeptide of amino acid sequence HRRIKAWLKKIKALARQLGVAA (SEQ ID NO: 7).

The MMI-0100 (YARAAARQARAKALARQLGVAA; SEQ ID NO: 1) peptide of amino acid sequence YARAAARQARAKALARQLGVAA (SEQ ID NO: 1) described in the present invention comprises a fusion protein in which a cell penetrating peptide (CPP; YARAAARQARA; SEQ ID NO: 11) is operatively linked to a therapeutic domain (KALARQLGVAA; SEQ ID NO: 2) in order to enhance therapeutic efficacy.

Examples of polypeptides functionally equivalent to the therapeutic domain (TD; KALARQLGVAA; SEQ ID NO: 2) of the polypeptide YARAAARQARAKALARQLGVAA (SEQ ID NO: 1) include, but are not limited to, a polypeptide of amino acid sequence KALARQLAVA (SEQ ID NO: 8), a polypeptide of amino acid sequence KALARQLGVA (SEQ ID NO: 9), and a polypeptide of amino acid sequence KALARQLGVAA (SEQ ID NO: 10).

Examples of polypeptides functionally equivalent to the cell penetrating peptide (CPP; YARAAARQARA; SEQ ID NO: 11) of the polypeptide YARAAARQARAKALARQLGVAA (SEQ ID NO: 1) include, but are not limited to, a polypeptide of amino acid sequence WLRRIKAWLRRIKA (SEQ ID NO: 12), a polypeptide of amino acid sequence WLRRIKA (SEQ ID NO: 13), a polypeptide of amino acid sequence YGRKKRRQRRR (SEQ ID NO: 14), a polypeptide of amino acid sequence WLRRIKAWLRRI (SEQ ID NO: 15), a polypeptide of amino acid sequence FAKLAARLYR (SEQ ID NO: 16), a polypeptide of amino acid sequence KAFAKLAARLYR (SEQ ID NO: 17), and a polypeptide of amino acid sequence HRRIKAWLKKI (SEQ ID NO: 18).

The term "endogenous" as used herein refers to growing or originating from within, or derived internally.

The term "endothelium" as used herein refers to a thin layer of cells that lines the interior surface of blood vessels, forming an interface between circulating blood in the lumen and the rest of the vessel wall. Endothelial cells will line the entire circulatory system, from the heart to the smallest capillary. These cells reduce turbulence of the flow of blood allowing the fluid to be pumped farther.

The term "eosinophils" or "eosinophil granulocytes" as used herein refers to white blood cells responsible for combating multicellular parasites and certain infections in vertebrates. They are granulocytes that develop during hematopoiesis in the bone marrow before migrating into blood. Along with mast cells, they also control mechanisms associated with allergy and asthma. Following activation, eosinophils exert diverse functions, including (1) production of cationic granule proteins and their release by degranulation, (2) production of reactive oxygen species, such as, superoxide, peroxide, and hypobromite (hypobromous acid, which is preferentially produced by eosinophil peroxidase), (3) production of lipid mediators, such as, eicosanoids from leukotriene and prostaglandin families, (4) production of growth factors, such as transforming growth factor (TGF-β), vascular endothelial growth factor (VEGF), and platelet-derived growth factor (PDGF), and (5) production of cytokines such as IL-1, IL-2, IL-4, IL-5, IL-6, IL-8, IL-13, and TNF-α.

The term "epithelium" as used herein refers to a tissue composed of cells that line the cavities and surfaces of structures throughout the body. The basal surface of the epithelium faces underlying connective tissue, and the two layers are separated by a basement membrane.

The term "extravasation" as used herein refers to the movement of blood cell components from the capillaries to the tissues surrounding them (diapedesis). In the case of malignant cancer metastasis, it refers to cancer cells exiting the capillaries and entering organs.

The term "exudation" as used herein refers to a process by which a fluid from the circulatory system passes through the walls of the blood vessels into lesions or areas of inflammation. Blood exudates contain some or all plasma proteins, white blood cells, platelets and red blood cells.

The term "fibrin" as used herein refers to a fibrous protein involved in the clotting of blood. It is a fibrillar protein that is polymerized to form a "mesh" that forms a hemostatic plug or clot (in conjunction with platelets) over a wound site. Fibrin is involved in signal transduction, blood coagulation, platelet activation, and protein polymerization.

The term "fibroblast" as used herein refers to a connective tissue cell that makes and secretes the extracellular matrix proteins, including, but not limited to, collagen. Fibroblasts, the most common cell type found in connective tissues, play an important role in healing wounds. Like other cells of connective tissue, fibroblasts are derived from primitive mesenchyme (a type of loose connective tissue derived from all three germ layers and located in the embryos). In certain situations epithelial cells can give rise to fibroblasts, a process called epithelial-mesenchymal transition. Fibroblasts and fibrocytes are two states of the same cells, the former being the activated state, the latter the less active state, concerned with maintenance and tissue metabolism, with both terms occasionally used interchangeably.

The term "myofibroblasts" as used herein refers to fibroblasts in wound areas that have some characteristics of smooth muscle, such as contractile properties and fibers, and are believed to produce, temporarily, type III collagen. Although there are many possible ways of myofibroblast development, myofibroblasts are cells that are in between fibroblasts and smooth muscle cells in their differentiation. In many organs like liver, lung, and kidney they are primarily involved in fibrosis. In wound tissue, they are implicated in wound strengthening (by extracellular collagen fiber deposition) and then wound contraction (by intracellular contraction and concomitant alignment of the collagen fibers by integrin mediated pulling o to the collagen bundles).

The term "fibronectin" as used herein refers to a high-molecular weight (~440 kDa) extracellular matrix glycoprotein that binds to membrane-spanning cell-surface matrix receptor proteins ("integrins") and to extracellular matrix components such as collagen, fibrin and heparan sulfate proteoglycans (e.g. syndecans). Fibronectin exists as a dimer, consisting of two nearly identical monomers linked by a pair of disulfide bonds. There are multiple isoforms of fibronectin. Plasma fibronectin is soluble and circulates in the blood and other body fluids, where it is thought to enhance blood clotting, wound healing and phagocytosis. The other isoforms assemble on the surface of cells and are deposited in the extracellular matrix as highly insoluble fibronectin fibrils. The fibronectin fibrils that form on or near the surface of fibroblasts usually are aligned with adjacent intracellular actin stress fibers, which promote the assembly of secreted fibronectin molecules into fibrils and influence fibril orientation. Fibronectin plays a major role in cell adhesion, cell growth, cell migration and cell differentiation, and it is important for processes such as wound healing and embryonic development.

The term "fibrosis" as used herein refers to the formation or development of excess fibrous connective tissue in an organ or tissue as a result of injury or inflammation of a part, or of interference with its blood supply. It may be a consequence of the normal healing response leading to a scar, an abnormal, reactive process, or without known or understood causation.

The term "inhalation" as used herein refers to the act of drawing in a medicated vapor with the breath.

The term "insufflation" as used herein refers to the act of delivering air, a gas, or a powder under pressure to a cavity or chamber of the body. For example, nasal insufflation relates to the act of delivering air, a gas, or a powder under pressure through the nose.

The term "inhalation delivery device" as used herein refers to a machine/apparatus or component that produces small droplets or an aerosol from a liquid or dry powder aerosol formulation and is used for administration through the mouth in order to achieve pulmonary administration of a drug, e.g., in solution, powder, and the like. Examples of inhalation delivery device include, but are not limited to, a nebulizer, a metered-dose inhaler, and a dry powder inhaler (DPI).

The term "nebulizer" as used herein refers to a device used to administer liquid medication in the form of a mist inhaled into the lungs.

The term "metered-dose inhaler", "MDI", or "puffer" as used herein refers to a pressurized, hand-held device that uses propellants to deliver a specific amount of medicine ("metered dose") to the lungs of a patient. The term "propellant" as used herein refers to a material that is used to expel a substance usually by gas pressure through a convergent, divergent nozzle. The pressure may be from a compressed gas, or a gas produced by a chemical reaction. The exhaust material may be a gas, liquid, plasma, or, before the chemical reaction, a solid, liquid or gel. Propellants used in pressurized metered dose inhalers are liquefied gases, traditionally chlorofluorocarbons (CFCs) and increasingly hydrofluoroalkanes (HFAs). Suitable propellants include, for example, a chlorofluorocarbon (CFC), such as trichlorofluoromethane (also referred to as propellant 11), dichlorodifluoromethane (also referred to as propellant 12), and 1,2-dichloro-1,1,2,2-tetrafluoroethane (also referred to as propellant 114), a hydrochlorofluorocarbon, a hydrofluorocarbon (HFC), such as 1,1,1,2-tetrafluoroethane (also referred to as propellant 134a, HFC-134a, or HFA-134a) and 1,1,1,2,3,3,3-heptafluoropropane (also referred to as propellant 227, HFC-227, or HFA-227), carbon dioxide, dimethyl ether, butane, propane, or mixtures thereof. In other embodiments, the propellant includes a chlorofluorocarbon, a hydrochlorofluorocarbon, a hydrofluorocarbon, or mixtures thereof. In other embodiments, a hydrofluorocarbon is used as the propellant. In other embodiments, HFC-227 and/or HFC-134a are used as the propellant.

The term "dry powder inhaler" or "DPI" as used herein refers to a device similar to a metered-dose inhaler, but where the drug is in powder form. The patient exhales out a full breath, places the lips around the mouthpiece, and then quickly breathes in the powder. Dry powder inhalers do not require the timing and coordination that are necessary with MDIs.

The term "particles" as used herein refers to refers to an extremely small constituent (e.g., nanoparticles, microparticles, or in some instances larger) in or on which is contained the composition as described herein.

The terms "pulmonary fibrosis", "idiopathic pulmonary fibrosis", and "cryptogenic fibrosing alveolitis" as used herein refer to a major component of interstitial lung disease characterized by abnormal fibroblast proliferation and deposition of extracellular matrix proteins that remodel the normal pulmonary tissue structure and compromise its function. The hallmark lesions of idiopathic pulmonary fibrosis are the fibroblast foci. These sites feature vigorous replication of mesenchymal cells and exuberant deposition of fresh extracellular matrix.

The terms "fibrotic loci" or "fibrotic foci" as used herein interchangeably refer to a specific location in a tissue formed or developed by excessive fibrous tissue.

The term "fusion protein" as used herein refers to a protein or polypeptide constructed by combining multiple protein domains or polypeptides for the purpose of creating a single polypeptide or protein with functional properties derived from each of the original proteins or polypeptides. Creation of a fusion protein may be accomplished by operatively ligating or linking two different nucleotides sequences that encode each protein domain or polypeptide via recombinant DNA technology, thereby creating a new polynucleotide sequences that codes for the desired fusion protein. Alternatively, a fusion protein maybe created by chemically joining the desired protein domains.

The term "idiopathic" as used herein means arising spontaneously or from an obscure or unknown cause.

The term "inflammation" as used herein refers to the physiologic process by which vascularized tissues respond to injury. See, e.g., FUNDAMENTAL IMMUNOLOGY, 4th Ed., William E. Paul, ed. Lippincott-Raven Publishers, Philadelphia (1999) at 1051-1053, incorporated herein by reference. During the inflammatory process, cells involved in detoxification and repair are mobilized to the compromised site by inflammatory mediators. Inflammation is often characterized by a strong infiltration of leukocytes at the site of inflammation, particularly neutrophils (polymorphonuclear cells). These cells promote tissue damage by releasing toxic substances at the vascular wall or in uninjured tissue. Traditionally, inflammation has been divided into acute and chronic responses.

The term "acute inflammation" as used herein refers to the rapid, short-lived (minutes to days), relatively uniform response to acute injury characterized by accumulations of fluid, plasma proteins, and neutrophilic leukocytes. Examples of injurious agents that cause acute inflammation include, but are not limited to, pathogens (e.g., bacteria, viruses, parasites), foreign bodies from exogenous (e.g. asbestos) or endogenous (e.g., urate crystals, immune complexes), sources, and physical (e.g., burns) or chemical (e.g., caustics) agents.

The term "chronic inflammation" as used herein refers to inflammation that is of longer duration and which has a vague and indefinite termination. Chronic inflammation takes over when acute inflammation persists, either through incomplete clearance of the initial inflammatory agent (e.g., cigarette smoking) or as a result of multiple acute events occurring in the same location. Chronic inflammation, which includes the influx of lymphocytes and macrophages and fibroblast growth, may result in tissue scarring at sites of prolonged or repeated inflammatory activity.

The term "inflammatory mediators" as used herein refers to the molecular mediators of the inflammatory and immune processes. These soluble, diffusible molecules act both locally at the site of tissue damage and infection and at more distant sites. Some inflammatory mediators are activated by the inflammatory process, while others are synthesized and/or released from cellular sources in response to acute inflammation or by other soluble inflammatory mediators; still others exhibit anti-inflammatory properties. Examples of inflammatory mediators of the inflammatory response include, but are not limited to, plasma proteases, complement, kinins, clotting and fibrinolytic proteins, lipid mediators, prostaglandins, leukotrienes, platelet-activating factor (PAF), peptides, hormones (including steroid hormones such as glucocorticoids), and amines, including, but not limited to, histamine, serotonin, and neuropeptides, and proinflammatory cytokines, including, but not limited to, interleukin-1-beta (IL-1β), interleukin-4 (IL-4), interleukin-6 (IL-6), interleukin-8 (IL-8), tumor necrosis factor-alpha (TNF-α), interferon-gamma (IF-γ), interleukin-12 (IL-12), and interleukin-17 (IL-17).

Among the pro-inflammatory mediators, IL-1, IL-6, and TNF-α are known to activate hepatocytes in an acute phase response to synthesize acute-phase proteins that activate complement. Complement is a system of plasma proteins that interact with pathogens to mark them for destruction by phagocytes. Complement proteins can be activated directly by pathogens or indirectly by pathogen-bound antibody, leading to a cascade of reactions that occurs on the surface of pathogens and generates active components with various effector functions. IL-1, IL-6, and TNF-α also activate bone marrow endothelium to mobilize neutrophils, and function as endogenous pyrogens, raising body temperature, which helps eliminating infections from the body. A major effect of the cytokines is to act on the hypothalamus, altering the body's temperature regulation, and on muscle and fat cells, stimulating the catabolism of the muscle and fat cells to elevate body temperature. At elevated temperatures, bacterial and viral replications are decreased, while the adaptive immune system operates more efficiently.

The term "tumor necrosis factor" as used herein refers to a cytokine made by white blood cells in response to an antigen or infection, which induce necrosis (death) of tumor cells and possesses a wide range of pro-inflammatory actions. Tumor necrosis factor also is a multifunctional cytokine with effects on lipid metabolism, coagulation, insulin resistance, and the function of endothelial cells lining blood vessels.

The term "interleukin (IL)" as used herein refers to a cytokine from a class of homologously related proteins that were first observed to be secreted by, and acting on, leukocytes. It has since been found that interleukins are produced by a wide variety of body cells. Interleukins regulate cell growth, differentiation, and motility, and stimulates immune responses, such as inflammation. Examples of interleukins include, interleukin-1 (IL-1), interleukin-1β (IL-1β, interleukin-6 (IL-6), interleukin-8 (IL-8), interleukin-12 (IL-12), and interleukin-17 (IL-17).

The terms "inhibiting", "inhibit" or "inhibition" are used herein to refer to reducing the amount or rate of a process, to stopping the process entirely, or to decreasing, limiting, or blocking the action or function thereof. Inhibition may include a reduction or decrease of the amount, rate, action function, or process of a substance by at least 5%, at least 10%, at least 15%, at least 20%, at least 25%, at least 30%, at least 40%, at least 45%, at least 50%, at least 55%, at least 60%, at least 65%, at least 70%, at least 75%, at least 80%, at least 85%, at least 90%, at least 95%, at least 98%, or at least 99%.

The term "inhibitor" as used herein refers to a second molecule that binds to a first molecule thereby decreasing the first molecule's activity. Enzyme inhibitors are molecules that bind to enzymes thereby decreasing enzyme activity. The binding of an inhibitor may stop a substrate from entering the active site of the enzyme and/or hinder the enzyme from catalyzing its reaction. Inhibitor binding is either reversible or irreversible. Irreversible inhibitors usually react with the enzyme and change it chemically, for example, by modifying key amino acid residues needed for enzymatic activity. In contrast, reversible inhibitors bind non-covalently and produce different types of inhibition depending on whether these inhibitors bind the enzyme, the enzyme-substrate complex, or both. Enzyme inhibitors often are evaluated by their specificity and potency.

The term "injury" as used herein refers to damage or harm to a structure or function of the body caused by an outside agent or force, which may be physical or chemical.

The term "isolated" is used herein to refer to material, such as, but not limited to, a nucleic acid, peptide, polypeptide, or protein, which is: (1) substantially or essentially free from components that normally accompany or interact with it as found in its naturally occurring environment. The terms "substantially free" or "essentially free" are used herein to refer to considerably or significantly free of, or more than about 95% free of, or more than about 99% free of such components. The isolated material optionally comprises material not found with the material in its natural environment; or (2) if the material is in its natural environment, the material has been synthetically (non-naturally) altered by deliberate human intervention to a composition and/or placed at a location in the cell (e.g., genome or subcellular organelle) not native to a material found in that environment. The alteration to yield the synthetic material may be performed on the material within, or removed, from its natural state. For example, a naturally occurring nucleic acid becomes an isolated nucleic acid if it is altered, or if it is transcribed from DNA that has been altered, by means of human intervention performed within the cell from which it originates. See, for example, Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868, each incorporated herein by reference in its entirety. Likewise, a naturally occurring nucleic acid (for example, a promoter) becomes isolated if it is introduced by non-naturally occurring means to a locus of the genome not native to that nucleic acid. Nucleic acids that are "isolated" as defined herein also are referred to as "heterologous" nucleic acids.

The term "kinase" as used herein refers to a type of enzyme that transfers phosphate groups from high-energy donor molecules to specific target molecules or substrates. High-energy donor groups may include, but are not limited, to ATP.

The term "leukocyte" or "white blood cell (WBC)" as used herein refers to a type of immune cell. Most leukocytes are made in the bone marrow and are found in the blood and lymph tissue. Leukocytes help the body fight infections and other diseases. Granulocytes, monocytes, and lymphocytes are leukocytes.

The term "lymphocytes" as used herein refers to a small white blood cell (leukocyte) that plays a large role in defending the body against disease. There are two main types of lymphocytes: B cells and T cells. The B cells make antibodies that attack bacteria and toxins while the T cells themselves attack body cells when they have been taken over by viruses or have become cancerous. Lymphocytes secrete products (lymphokines) that modulate the functional activities of many other types of cells and are often present at sites of chronic inflammation.

The term "macrophage" as used herein refers to a type of white blood cell that surrounds and kills microorganisms, removes dead cells, and stimulates the action of other immune system cells. After digesting a pathogen, a macrophage presents an antigen (a molecule, most often a protein found on the surface of the pathogen, used by the immune system for identification) of the pathogen to the corresponding helper T cell. The presentation is done by integrating it into the cell membrane and displaying it attached to an MHC class II molecule, indicating to other white blood cells that the macrophage is not a pathogen, despite having antigens on its surface. Eventually, the antigen presentation results in the production of antibodies that attach to the antigens of pathogens, making them easier for macrophages to adhere to with their cell membrane and phagocytose.

The term "mesenchymal cell" or "mesenchyme" as used herein refers to a cell derived from all three germ layers, which can develop into connective tissue, bone, cartilage, the lymphatic system, and the circulatory system.

The term "MK2 kinase" or "MK2" as used herein refers to mitogen-activated protein kinase-activated protein kinase 2 (also referred to as "MAPKAPK2", "MAPKAP-K2", "MK2"), which is a member of the serine/threonine (Ser/Thr) protein kinase family.

The term "mass median aerodynamic diameter" or "MMAD" as used herein refers to median of the distribution of airborne particle mass with respect to the aerodynamic diameter. MMADs are usually accompanied by the geometric standard deviation (g or sigma g), which characterizes the variability of the particle size distribution.

The term "modulate" as used herein means to regulate, alter, adapt, or adjust to a certain measure or proportion.

The term "monocyte" as used herein refers to a type of immune cell that is made in the bone marrow and travels through the blood to tissues in the body where it becomes a macrophage. A monocyte is a type of white blood cell and a type of phagocyte.

The term "neutrophils" or "polymorphonuclear neutrophils (PMNs)" as used herein refers to the most abundant type of white blood cells in mammals, which form an essential part of the innate immune system. They form part of the polymorphonuclear cell family (PMNs) together with basophils and eosinophils. Neutrophils are normally found in the blood stream. During the beginning (acute) phase of inflammation, particularly as a result of bacterial infection and some cancers, neutrophils are one of the first-responders of inflammatory cells to migrate toward the site of inflammation. They migrate through the blood vessels, then through interstitial tissue, following chemical signals such as interleukin-8 (IL-8) and C5a in a process called chemotaxis, the directed motion of a motile cell or part along a chemical concentration gradient toward environmental conditions it deems attractive and/or away from surroundings it finds repellent.

The term "normal healthy control subject" as used herein refers to a subject having no symptoms or other clinical evidence of airway or lung tissue disease.

The term "nucleic acid" is used herein to refer to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

The term "nucleotide" is used herein to refer to a chemical compound that consists of a heterocyclic base, a sugar, and one or more phosphate groups. In the most common nucleotides, the base is a derivative of purine or pyrimidine, and the sugar is the pentose deoxyribose or ribose. Nucleotides are the monomers of nucleic acids, with three or more bonding together in order to form a nucleic acid. Nucleotides are the structural units of RNA, DNA, and several cofactors, including, but not limited to, CoA, FAD, DMN, NAD, and NADP. Purines include adenine (A), and guanine (G); pyrimidines include cytosine (C), thymine (T), and uracil (U).

The following terms are used herein to describe the sequence relationships between two or more nucleic acids or polynucleotides: (a) "reference sequence", (b) "comparison window", (c) "sequence identity", (d) "percentage of sequence identity", and (e) "substantial identity."

(a) The term "reference sequence" refers to a sequence used as a basis for sequence comparison. A reference sequence may be a subset or the entirety of a specified sequence; for example, as a segment of a full-length cDNA or gene sequence, or the complete cDNA or gene sequence.

(b) The term "comparison window" refers to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be at least 30 contiguous nucleotides in length, at least 40 contiguous nucleotides in length, at least 50 contiguous nucleotides in length, at least 100 contiguous nucleotides in length, or longer. Those of skill in the art understand that to avoid a high similarity to a reference sequence due to inclusion of gaps in the polynucleotide sequence, a gap penalty typically is introduced and is subtracted from the number of matches.

Methods of alignment of sequences for comparison are well-known in the art. Optimal alignment of sequences for comparison may be conducted by the local homology algorithm of Smith and Waterman, *Adv. Appl. Math.* 2:482 (1981); by the homology alignment algorithm of Needleman and Wunsch, *J. Mol. Biol.* 48:443 (1970); by the search for similarity method of Pearson and Lipman, *Proc. Natl. Acad. Sci.* 85:2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73:237-244 (1988); Higgins and Sharp, *CABIOS* 5:151-153 (1989); Corpet, et al., Nucleic Acids Research 16:10881-90 (1988); Huang, et al., Computer Applications in the *Biosciences,* 8:155-65 (1992), and Pearson, et al., *Methods in Molecular Biology,* 24:307-331 (1994). The BLAST family of programs, which can be used for database similarity searches, includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology, Chapter* 19, Ausubel, et al., Eds., Greene Publishing and Wiley-Interscience, New York (1995).

Unless otherwise stated, sequence identity/similarity values provided herein refer to the value obtained using the BLAST 2.0 suite of programs using default parameters. Altschul et al., *Nucleic Acids Res.* 25:3389-3402 (1997). Software for performing BLAST analyses is publicly available, e.g., through the National Center for Biotechnology-Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits then are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, a cutoff of 100, M=5, N=−4, and a comparison of both strands. For amino acid sequences, the BLASTP program uses as defaults a word length (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul, *Proc. Natl. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. BLAST searches assume that proteins may be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar A number of low-complexity filter programs may be employed to reduce such low-complexity alignments. For example, the SEG (Wooten and Federhen, *Comput. Chem.,* 17:149-163 (1993)) and XNU (Claverie and States, *Comput. Chem.,* 17:191-201 (1993)) low-complexity filters may be employed alone or in combination.

(c) The term "sequence identity" or "identity" in the context of two nucleic acid or polypeptide sequences is used herein to refer to the residues in the two sequences that are the same when aligned for maximum correspondence over a specified comparison window. When percentage of sequence identity is used in reference to proteins it is recognized that residue positions that are not identical often differ by conservative amino acid substitutions, i.e., where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.,* 4:11-17 (1988) e.g., as implemented in the program PC/GENE (Intelligenetics, Mountain View, Calif., USA).

(d) The term "percentage of sequence identity" is used herein mean the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e) The term "substantial identity" of polynucleotide sequences means that a polynucleotide comprises a sequence that has at least 70% sequence identity, at least 80% sequence identity, at least 90% sequence identity and at least 95% sequence identity, compared to a reference sequence using one of the alignment programs described using standard parameters. One of skill will recognize that these values may be adjusted appropriately to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, or at least 70%, at least 80%, at least 90%, or at least 95%. Another indication that nucleotide sequences are substantially identical is if two molecules hybridize to each other under stringent conditions. However, nucleic acids that do not hybridize to each other under stringent conditions are still substantially identical if the polypeptides that they encode are substantially identical. This may occur, e.g., when a copy of a nucleic acid is created using the maximum codon degeneracy permitted by the genetic code. One indication that two nucleic acid sequences are substantially identical is that the polypeptide that the first nucleic acid encodes is immunologically cross reactive with the polypeptide encoded by the second nucleic acid.

The phrase "operatively linked" as used herein refers to a linkage in which two or more protein domains or polypeptides are ligated or combined via recombinant DNA technology or chemical reaction such that each protein domain or polypeptide of the resulting fusion protein retains its original function. For example, SEQ ID NO: 1 is constructed by operatively linking a cell penetrating peptide (SEQ ID NO: 11) with a therapeutic domain (SEQ ID NO: 2), thereby creating a fusion peptide that possesses both the cell penetrating function of SEQ ID NO: 11 and the kinase inhibitor function of SEQ ID NO: 2.

The term "parenchyma" as used herein refers to an animal tissue that constitutes the essential part of an organ as contrasted with connective tissue or blood vessels. The term "parenchymal" means pertaining to the parenchyma of an organ.

The term "parenteral" as used herein refers to introduction into the body by way of an injection (i.e., administration by injection), including, for example, subcutaneously (i.e., an injection beneath the skin), intramuscularly (i.e., an injection into a muscle), intravenously (i.e., an injection into a vein), intrathecally (i.e., an injection into the space around the spinal cord or under the arachnoid membrane of the brain), intrasternal injection or infusion techniques, and including intraperitoneal injection or infusion into the body cavity (e.g. peritoneum). A parenterally administered composition is delivered using a needle, e.g., a surgical needle, or other corporal access device. The term "surgical needle" as used herein, refers to any access device adapted for delivery of fluid (i.e., capable of flow) compositions into a selected anatomical structure. Injectable preparations, such as sterile injectable aqueous or oleaginous suspensions, may be formulated according to the known art using suitable dispersing or wetting agents and suspending agents.

The term "particulate" as used herein refers to fine particles of solid or liquid matter suspended in a gas or liquid.

As used herein the term "pharmaceutically acceptable carrier" refers to any substantially non-toxic carrier conventionally useable for administration of pharmaceuticals in which the isolated polypeptide of the present invention will remain stable and bioavailable. The pharmaceutically acceptable carrier must be of sufficiently high purity and of sufficiently low toxicity to render it suitable for administration to the mammal being treated. It further should maintain the stability and bioavailability of an active agent. The pharmaceutically acceptable carrier can be liquid or solid and is selected, with the planned manner of administration in mind, to provide for the desired bulk, consistency, etc., when combined with an active agent and other components of a given composition.

The term "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids.

The terms "polypeptide" and "protein" also are used herein in their broadest sense to refer to a sequence of subunit amino acids, amino acid analogs, or peptidomimetics. The subunits are linked by peptide bonds, except where noted. The polypeptides described herein may be chemically synthesized or recombinantly expressed. Polypeptides of the described invention also can be synthesized chemically. Synthetic polypeptides, prepared using the well known techniques of solid phase, liquid phase, or peptide condensation techniques, or any combination thereof, can include natural and unnatural amino acids. Amino acids used for peptide synthesis may be standard Boc (N-α-amino protected N-α-t-butyloxycarbonyl) amino acid resin with the standard deprotecting, neutralization, coupling and wash protocols of the original solid phase procedure of Merrifield (1963, *J. Am. Chem. Soc.* 85:2149-2154), or the base-labile N-α-amino protected 9-fluorenylmethoxycarbonyl (Fmoc) amino acids first described by Carpino and Han (1972, *J. Org. Chem.* 37:3403-3409). Both Fmoc and Boc N-α-amino protected amino acids can be obtained from Sigma, Cambridge Research Biochemical, or other chemical companies familiar to those skilled in the art. In addition, the polypeptides can be synthesized with other N-α-protecting groups that are familiar to those skilled in this art. Solid phase peptide synthesis may be accomplished by techniques familiar to those in the art and provided, for example, in Stewart and Young, 1984, *Solid Phase Synthesis*, Second Edition, Pierce Chemical Co., Rockford, Ill.; Fields and Noble, 1990, *Int. J. Pept. Protein Res.* 35:161-214, or using automated synthesizers. The polypeptides of the invention may comprise D-amino acids (which are resistant to L-amino acid-specific proteases in vivo), a combination of D- and L-amino acids, and various "designer" amino acids (e.g., β-methyl amino acids, C-α-methyl amino acids, and N-α-methyl amino acids, etc.) to convey special properties. Synthetic amino acids include ornithine for lysine, and norleucine for leucine or isoleucine. In addition, the polypeptides can have peptidomimetic bonds, such as ester bonds, to prepare peptides with novel properties. For example, a peptide may be generated that incorporates a reduced peptide bond, i.e., R1-CH$_2$—NH—R2, where R1 and R2 are amino acid residues or sequences. A reduced peptide bond may be introduced as a dipeptide subunit. Such a polypeptide would be resistant to protease activity, and would possess an extended half-live in vivo. Accordingly, these terms also apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, the protein is specifically reactive to antibodies elicited to the same protein but consisting entirely of naturally occurring amino acids.

The terms "polypeptide", "peptide" and "protein" also are inclusive of modifications including, but not limited to, glycosylation, lipid attachment, sulfation, gamma-carboxylation of glutamic acid residues, hydroxylation, and ADP-ribosylation. It will be appreciated, as is well known and as noted above, that polypeptides may not be entirely linear. For instance, polypeptides may be branched as a result of ubiquitination, and they may be circular, with or without branching, generally as a result of posttranslational events, including natural processing event and events brought about by human manipulation which do not occur naturally. Circular, branched and branched circular polypeptides may be synthesized by non-translation natural process and by entirely synthetic methods, as well. In some embodiments, the peptide is of any length or size.

The term "proenzyme" or "zymogen" as used herein refers to an inactive enzyme precursor. A zymogen requires a biochemical change (such as a hydrolysis reaction revealing the active site, or changing the configuration to reveal the active site) for it to become an active enzyme. The biochemical change usually occurs in a lysosome where a specific part of the precursor enzyme is cleaved in order to activate it. The amino acid chain that is released upon activation is called the activation peptide.

The term "proliferation" as used herein refers to expansion of a population of cells by the continuous division of single cells into identical daughter cells.

The term "pulmonary interstitium" as used herein refers to the tissue and space around the air sacs of the lungs.

The term "pulmonary alveolus" as used herein refers to an anatomical structure that has the form of a hollow cavity. The alveoli are located in the respiratory zone of the lungs, at the distal termination of the alveolar ducts and atria, forming the termination point of the respiratory tract. The pulmonary alveoli are spherical outcroppings of the respiratory sites of gas exchange with the blood and only found in the mammalian lungs. The alveolar membrane is the gas-exchange surface. The blood brings carbon dioxide from the rest of the body for release into the alveoli, and the oxygen in the alveoli is taken up by the blood in the alveolar blood vessels, to be transported to all the cells in the body. The alveoli contain some collagen and elastic fibers. The elastic fibers allow the alveoli to stretch as they fill with air when breathing in. They then spring back during breathing out in order to expel the carbon dioxide-rich air. There are three major alveolar cell types in the alveolar wall, (1) sequamous alveolar cells that form the structure of an alveolar wall, (2) great alveolar cells that secrete pulmonary surfactant to lower the surface tension of water and allows the membrane to separate, thereby increasing the capability to exchange gasses, (3) macrophages that destroy foreign pathogens, such as bacteria.

The term "similar" is used interchangeably with the terms analogous, comparable, or resembling, meaning having traits or characteristics in common.

The term "solution" as used herein refers to a homogeneous mixture of two or more substances. It is frequently, though not necessarily, a liquid. In a solution, the molecules of the solute (or dissolved substance) are uniformly distributed among those of the solvent.

The terms "soluble" and "solubility" refer to the property of being susceptible to being dissolved in a specified fluid (solvent). The term "insoluble" refers to the property of a material that has minimal or limited solubility in a specified solvent. In a solution, the molecules of the solute (or dissolved substance) are uniformly distributed among those of the solvent.

The term "stress fiber" as used herein refers to high order structures in cells consisting of actin filaments, crosslinking proteins (proteins that bind two or more filaments together), and myosin II motors. Actin is a globular protein (~43 kDa), which polymerizes and forms into an ordered filament structure which has two protofilaments wrapping around each other, to form a single "actin filament" also known as a "microfilament." The myosin motors in the stress fibers move, sliding actin filaments past one another, so the fiber can contract. In order for contraction to generate forces, the fibers must be anchored to something. Stress fibers can anchor to the cell membrane, and frequently the sites where this anchoring occurs are also connected to structures outside the cell (the matrix or some other substrate). These connection sites are called focal adhesions. Many proteins are required for proper focal adhesion production and maintenance. Contraction against these fixed external substrates is what allows the force generated by myosin motors and filament growth and rearrangement to move and reshape the cell.

The term "suspension" as used herein refers to a dispersion (mixture) in which a finely-divided species is combined with another species, with the former being so finely divided and mixed that it doesn't rapidly settle out. In everyday life, the most common suspensions are those of solids in liquid.

The terms "subject" or "individual" or "patient" are used interchangeably to refer to a member of an animal species of mammalian origin, including but not limited to, a mouse, a rat, a cat, a goat, sheep, horse, hamster, ferret, platypus, pig, a dog, a guinea pig, a rabbit and a primate, such as, for example, a monkey, ape, or human.

The phrase "subject in need of such treatment" as used herein refers to a patient who suffers from a disease, disorder, condition, or pathological process. In some embodiments, the term "subject in need of such treatment" also is used to refer to a patient who (i) will be administered at least one polypeptide of the invention; (ii) is receiving at least one polypeptide of the invention; or (iii) has received at least one polypeptide of the invention, unless the context and usage of the phrase indicates otherwise.

The term "substitution" is used herein to refer to a situation in which a base or bases are exchanged for another base or bases in a DNA sequence. Substitutions may be synonymous substitutions or nonsynonymous substitutions. As used herein, "synonymous substitutions" refer to substitutions of one base for another in an exon of a gene coding for a protein, such that the amino acid sequence produced is not modified. The term "nonsynonymous substitutions" as used herein refer to substitutions of one base for another in an exon of a gene coding for a protein, such that the amino acid sequence produced is modified.

The terms "therapeutic amount," an "amount effective," or "pharmaceutically effective amount" of an active agent are used interchangeably to refer to an amount that is sufficient to provide the intended benefit of treatment. For example, the "therapeutic amount" of a kinase inhibiting composition of the described invention includes, but is not limited to, an amount sufficient: (1) to remove, or decrease the size of, at least one fibrotic locus or (2) to reduce the rate of extracellular matrix, including collagen and fibronectin, deposition in the interstitia in the lungs of a pulmonary fibrosis patient. The term also encompasses an amount sufficient to suppress or alleviate at least one symptom of a pulmonary fibrosis patient, wherein the symptom includes, but is not limited to, oxygen saturation, dyspnea (difficulty breathing), nonproductive cough (meaning a sudden, noisy expulsion of air from the lungs that may be caused by irritation or inflammation and does not remove sputum from the respiratory tract), clubbing (a disfigurement of the fingers into a bulbous appearance), and crackles (crackling sound in lungs during inhalation, occasionally referred to as rales or crepitations).

An effective amount of an active agent that can be employed according to the described invention generally ranges from generally about 0.001 mg/kg body weight to about 10 g/kg body weight. However, dosage levels are based on a variety of factors, including the type of injury, the age, weight, sex, medical condition of the patient, the severity of the condition, the route and frequency of administration, and the particular active agent employed. Thus the dosage regimen may vary widely, but can be determined routinely by a physician using standard methods.

The term "treat" or "treating" includes abrogating, substantially inhibiting, slowing or reversing the progression of a disease, condition or disorder, substantially ameliorating clinical or esthetical symptoms of a condition, substantially preventing the appearance of clinical or esthetical symptoms of a disease, condition, or disorder, and protecting from harmful or annoying symptoms. Treating further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and (e) limiting recurrence of symptoms in patients that were previously asymptomatic for the disorder(s).

The terms "variants", "mutants", and "derivatives" are used herein to refer to nucleotide or polypeptide sequences with substantial identity to a reference nucleotide or polypeptide sequence. The differences in the sequences may be the result of changes, either naturally or by design, in sequence or structure. Natural changes may arise during the course of normal replication or duplication in nature of the particular nucleic acid sequence. Designed changes may be specifically designed and introduced into the sequence for specific purposes. Such specific changes may be made in vitro using a variety of mutagenesis techniques. Such sequence variants generated specifically may be referred to as "mutants" or "derivatives" of the original sequence.

A skilled artisan likewise can produce polypeptide variants of polypeptide YARAAARQARAKALARQLGVAA (SEQ ID NO: 1) having single or multiple amino acid substitutions, deletions, additions or replacements, but functionally equivalent to SEQ ID NO: 1. These variants may include inter alia: (a) variants in which one or more amino acid residues are substituted with conservative or non-conservative amino acids; (b) variants in which one or more amino acids are added; (c) variants in which at least one amino acid includes a substituent group; (d) variants in which amino acid residues from one species are substituted for the corresponding residue in another species, either at conserved or non-conserved positions; and (d) variants in which a target protein is fused with another peptide or polypeptide such as a fusion partner, a protein tag or other chemical moiety, that may confer useful properties to the target protein, for example, an epitope for an antibody. The techniques for obtaining such variants, including, but not limited to, genetic (suppressions, deletions, mutations, etc.), chemical, and enzymatic techniques, are known to the skilled artisan. As used herein, the term "mutation" refers to a change of the DNA sequence within a gene or chromosome of an organism resulting in the creation of a new character or trait not found in the parental type, or the process by which such a change occurs in a chromosome, either through an alteration in the nucleotide sequence of the DNA coding for a gene or through a change in the physical arrangement of a chromosome. Three mechanisms of mutation include substitution (exchange of one base pair for another), addition (the insertion of one or more bases into a sequence), and deletion (loss of one or more base pairs).

The term "vehicle" as used herein refers to a substance that facilitates the use of a drug or other material that is mixed with it.

The term "wound healing" or "wound repair" as used herein refers generally to the body's natural process of repairing tissue after trauma. When an individual is wounded, a set of complex biochemical events takes place to repair the damage including, hemostasis, inflammation, proliferation, and remodeling.

I. Compositions: Therapeutic Peptides for Preventing or Treating Diseases Characterized by Aberrant Fibroblast Proliferation and Collagen Deposition According to one aspect, the described invention provides a pharmaceutical composition for use in the treatment of a disease, condition, or process characterized by aberrant fibroblast proliferation and extracellular matrix deposition in a tissue of a subject, wherein the pharmaceutical composition comprises a therapeutic amount of a polypeptide of the amino acid sequence YARAAARQARAKALARQLGVAA (SEQ ID NO: 1) or a functional equivalent thereof, and a pharmaceutically acceptable carrier thereof, and wherein the therapeutic amount is effective to reduce the fibroblast proliferation and extracellular matrix deposition in the tissue of the subject.

According to one embodiment, the disease or the condition is Acute Lung Injury (ALI) or acute respiratory distress syndrome (ARDS).

According to another embodiment, the disease or the condition is radiation-induced fibrosis.

According to another embodiment, the disease or the condition is transplant rejection.

According to another embodiment, the tissue is a lung tissue.

According to another embodiment, the disease or the condition is an interstitial lung disease.

According to another embodiment, wherein the disease or the condition is pulmonary fibrosis.

According to another embodiment, wherein the pulmonary fibrosis is idiopathic pulmonary fibrosis.

According to another embodiment, the pulmonary fibrosis results from administration of bleomycin.

According to another embodiment, the pulmonary fibrosis results from an allergic reaction, inhalation of environmental particulates, smoking, a bacterial infection, a viral infection, mechanical damage to a lung of the subject, lung transplantation rejection, an autoimmune disorder, a genetic disorder, or a combination thereof.

According to another embodiment, the disease or the condition is further characterized by an inflammation in the tissue.

According to another embodiment, the inflammation is an acute or a chronic inflammation.

According to another embodiment, the inflammation is mediated by at least one cytokine selected from the group consisting of Tumor Necrosis Factor-alpha (TNF-α), Interleukin-6 (IL-6), and Interleukin-1β (IL-1β).

According to another embodiment, the pulmonary fibrosis is characterized by at least one pathology selected from the group consisting of an aberrant deposition of an extracellular matrix protein in a pulmonary interstitium, an aberrant promotion of fibroblast proliferation in the lung, an aberrant induction of myofibroblast differentiation in the lung, and an aberrant promotion of attachment of myofibroblasts to an extracellular matrix compared to a normal healthy control subject.

According to another embodiment, the aberrant fibroblast proliferation and extracellular matrix deposition in the tissue is characterized by an aberrant activity of Mitogen-Activated Protein Kinase-Activated Protein Kinase 2 (MK2) in the tissue compared to the activity of Mitogen-Activated Protein Kinase-Activated Protein Kinase 2 (MK2) in the tissue of a normal healthy control subject.

According to another embodiment, the aberrant fibroblast proliferation and extracellular matrix deposition in the tissue is evidenced by an aberrant amount or distribution of activated (phosphorylated) Mitogen-Activated Protein Kinase-Activated Protein Kinase 2 (MK2) in the tissue compared to the amount or distribution of activated Mitogen-Activated Protein Kinase-Activated Protein Kinase 2 (MK2) in the tissue of a normal healthy control subject.

According to another embodiment, the pharmaceutical composition inhibits a kinase activity of a kinase selected from the group listed in Table 1 herein.

According to another embodiment, this inhibition may, for example, be effective to reduce fibroblast prolfieration, extracellular matrix deposition, or a combination thereof in the tissue of the subject.

According to another embodiment, this inhibition may, for example, be effective to reduce at least one pathology selected from the group consisting of an aberrant deposition of an extracellular matrix protein in a pulmonary interstitium, an aberrant promotion of fibroblast proliferation in the lung, an aberrant induction of myofibroblast differentiation, and an aberrant promotion of attachment of myofibroblasts to an extracellular matrix, compared to a normal healthy control subject.

According to some embodiments, inhibitory profiles of MMI inhibitors in vivo depend on dosages, routes of administration, and cell types responding to the inhibitors.

According to another embodiment, the pharmaceutical composition inhibits at least 50% of the kinase activity of the kinase. According to another embodiment, the pharmaceutical composition inhibits at least 65% of the kinase activity of the kinase. According to another embodiment, the pharmaceutical composition inhibits at least 75% of the kinase activity of that kinase. According to another embodiment, the pharmaceutical composition inhibits at least 80% of the kinase activity of that kinase. According to another embodiment, the pharmaceutical composition inhibits at least 85% of the kinase activity of that kinase. According to another embodiment, the pharmaceutical composition inhibits at least 90% of the kinase activity of that kinase. According to another embodiment, the pharmaceutical composition inhibits at least 95% of the kinase activity of that kinase.

According to some embodiments, the pharmaceutical composition inhibits a kinase activity of Mitogen-Activated Protein Kinase-Activated Protein Kinase 2 (MK2 kinase). According to some other embodiments, the pharmaceutical composition inhibits at least 50% of the kinase activity of MK2 kinase. According to some other embodiments, the pharmaceutical composition inhibits at least 65% of the kinase activity of MK2 kinase. According to another embodiment, the pharmaceutical composition inhibits at least 75% of the kinase activity of MK2 kinase. According to another embodiment, the pharmaceutical composition inhibits at least 80% of the kinase activity of MK2 kinase. According to another embodiment, the pharmaceutical composition inhibits at least 85% of the kinase activity of MK2 kinase. According to another embodiment, the pharmaceutical composition inhibits at least 90% of the kinase activity of MK2 kinase. According to another embodiment, the pharmaceutical composition inhibits at least 95% of the kinase activity of MK2 kinase.

According to another embodiment, the pharmaceutical composition inhibits a kinase activity of Mitogen-Activated Protein Kinase-Activated Protein Kinase 3 (MK3 kinase). According to another embodiment, the pharmaceutical composition inhibits at least 50% of the kinase activity of MK3 kinase. According to another embodiment, the pharmaceutical composition inhibits at least 65% of the kinase activity of MK3 kinase. According to another embodiment, the pharmaceutical composition inhibits at least 70% of the kinase activity of MK3 kinase. According to another embodiment, the pharmaceutical composition inhibits at least 75% of the kinase activity of MK3 kinase. According to another embodiment, the pharmaceutical composition inhibits at least 80% of the kinase activity of MK3 kinase. According to another embodiment, the pharmaceutical composition inhibits at least 85% of the kinase activity of MK3 kinase. According to another embodiment, the pharmaceutical composition inhibits at least 90% of the kinase activity of MK3 kinase. According to another embodiment, the pharmaceutical composition inhibits at least 95% of the kinase activity of MK3 kinase.

According to another embodiment, the pharmaceutical composition inhibits a kinase activity of calcium/calmodulin-dependent protein kinase I (CaMKI). According to another embodiment, the pharmaceutical composition further inhibits at least 50% of the kinase activity of $Ca^{2+}$/calmodulin-dependent protein kinase I (CaMKI). According to another embodiment, the pharmaceutical composition further inhibits at least 65% of the kinase activity of $Ca^{2+}$/calmodulin-dependent protein kinase I (CaMKI). According to another embodiment, the pharmaceutical composition further inhibits at least 70% of the kinase activity of $Ca^{2+}$/calmodulin-dependent protein kinase I (CaMKI). According to another embodiment, the pharmaceutical composition further inhibits at least 75% of the kinase activity of $Ca^{2+}$/calmodulin-dependent protein kinase I (CaMKI). According to another embodiment, the pharmaceutical composition further inhibits at least 80% of the kinase activity of $Ca^{2+}$/ calmodulin-dependent protein kinase I (CaMKI). According to another embodiment, the pharmaceutical composition further inhibits at least 85% of the kinase activity of $Ca^{2+}$/calmodulin-dependent protein kinase I (CaMKI). According to another embodiment, the pharmaceutical composition further inhibits at least 90% of the kinase activity of $Ca^{2+}$/calmodulin-dependent protein kinase I (CaMKI). According to another embodiment, the pharmaceutical composition further inhibits at least 95% of the kinase activity of $Ca^{2+}$/calmodulin-dependent protein kinase I (CaMKI).

According to another embodiment, the pharmaceutical composition inhibits a kinase activity of BDNF/NT-3 growth factors receptor (TrkB). According to another embodiment, the pharmaceutical further inhibits at least 50% of the kinase activity of BDNF/NT-3 growth factors receptor (TrkB). According to another embodiment, the pharmaceutical further inhibits at least 65% of the kinase activity of BDNF/NT-3 growth factors receptor (TrkB). According to another embodiment, the pharmaceutical further inhibits at least 70% of the kinase activity of BDNF/NT-3 growth factors receptor (TrkB). According to another embodiment, the pharmaceutical further inhibits at least 75% of the kinase activity of BDNF/NT-3 growth factors receptor (TrkB).

According to another embodiment, the pharmaceutical composition inhibits a kinase activity of Mitogen-Activated Protein Kinase-Activated Protein Kinase 2 (MK2) and a kinase activity of Mitogen-Activated Protein Kinase-Activated Protein Kinase 3 (MK3).

According to another embodiment, the pharmaceutical composition inhibits a kinase activity of Mitogen-Activated Protein Kinase-Activated Protein Kinase 2 (MK2) and a kinase activity of calcium/calmodulin-dependent protein kinase I (CaMKI).

According to another embodiment, the pharmaceutical composition inhibits a kinase activity of Mitogen-Activated Protein Kinase-Activated Protein Kinase 2 (MK2) and a kinase activity of BDNF/NT-3 growth factors receptor (TrkB).

According to another embodiment, the pharmaceutical composition inhibits a kinase activity of Mitogen-Activated Protein Kinase-Activated Protein Kinase 2 (MK2), a kinase activity of Mitogen-Activated Protein Kinase-Activated Protein Kinase 3 (MK3), a kinase activity of calcium/calmodulin-dependent protein kinase I (CaMKI), and a kinase activity of BDNF/NT-3 growth factors receptor (TrkB).

According to another embodiment, the pharmaceutical composition inhibits a kinase activity of Mitogen-Activated Protein Kinase-Activated Protein Kinase 2 (MK2), a kinase activity of calcium/calmodulin-dependent protein kinase I (CaMKI), and a kinase activity of BDNF/NT-3 growth factors receptor (TrkB).

According to another embodiment, the pharmaceutical composition inhibits at least 65% of the kinase activity of Mitogen-Activated Protein Kinase-Activated Protein Kinase 2 (MK2).

According to another embodiment, the pharmaceutical composition inhibits at least 65% of the kinase activity of Mitogen-Activated Protein Kinase-Activated Protein Kinase 3 (MK3).

According to another embodiment, the pharmaceutical composition inhibits at least 65% of the kinase activity of calcium/calmodulin-dependent protein kinase I (CaMKI).

According to another embodiment, the pharmaceutical composition inhibits at least 65% of the kinase activity of BDNF/NT-3 growth factors receptor (TrkB).

According to another embodiment, the pharmaceutical composition inhibits at least 65% of the kinase activity of Mitogen-Activated Protein Kinase-Activated Protein Kinase 2 (MK2) and at least 65% of the kinase activity of Mitogen-Activated Protein Kinase-Activated Protein Kinase 3 (MK3).

According to another embodiment, the pharmaceutical composition inhibits at least 65% of the kinase activity of Mitogen-Activated Protein Kinase-Activated Protein Kinase 2 (MK2) and at least 65% of the kinase activity of calcium/calmodulin-dependent protein kinase I (CaMKI).

According to another embodiment, the pharmaceutical composition inhibits at least 65% of the kinase activity of Mitogen-Activated Protein Kinase-Activated Protein Kinase 2 (MK2) and at least 65% of the kinase activity of BDNF/NT-3 growth factors receptor (TrkB).

According to another embodiment, the pharmaceutical composition inhibits at least 65% of the kinase activity of Mitogen-Activated Protein Kinase-Activated Protein Kinase 2 (MK2), at least 65% of the kinase activity of Mitogen-Activated Protein Kinase-Activated Protein Kinase 3 (MK3), at least 65% of the kinase activity of calcium/calmodulin-dependent protein kinase I (CaMKI), and at least 65% of the kinase activity of BDNF/NT-3 growth factors receptor (TrkB).

According to another embodiment, the pharmaceutical composition inhibits the kinase activity of at least one kinase selected from the group of MK2, MK3, CaMKI, TrkB, without substantially inhibiting the activity of one or more other selected kinases from the remaining group listed in Table 1 herein.

According to some embodiments, inhibitory profiles of MMI inhibitors in vivo depend on dosages, routes of administration, and cell types responding to the inhibitors.

According to such embodiment, the pharmaceutical composition inhibits less than 50% of the kinase activity of the other selected kinase(s). According to such embodiment, the pharmaceutical composition inhibits less than 65% of the kinase activity of the other selected kinase(s). According to another embodiment, the pharmaceutical composition inhibits less than 50% of the kinase activity of the other selected kinase(s). According to another embodiment, the pharmaceutical composition inhibits less than 40% of the kinase activity of the other selected kinase(s). According to another embodiment, the pharmaceutical composition inhibits less than 20% of the kinase activity of the other selected kinase(s). According to another embodiment, the pharmaceutical composition inhibits less than 15% of the kinase activity of the other selected kinase(s). According to another embodiment, the pharmaceutical composition inhibits less than 10% of the kinase activity of the other selected kinase(s). According to another embodiment, the pharmaceutical composition inhibits less than 5% of the kinase activity of the other selected kinase(s). According to another embodiment, the pharmaceutical composition increases the kinase activity of the other selected kinases.

According to the embodiments of the immediately preceding paragraph, the one or more other selected kinase that is not substantially inhibited is selected from the group of $Ca^{2+}$/calmodulin-dependent protein kinase II (CaMKII, including its subunit CaMKIIδ), Proto-oncogene serine/threonine-protein kinase (PIM-1), cellular-Sarcoma (c-SRC), Spleen Tyrosine Kinase (SYK), C-src Tyrosine Kinase (CSK), and Insulin-like Growth Factor 1 Receptor (IGF-1R).

According to some embodiments, the pharmaceutical composition further comprises at least one additional therapeutic agent.

According to some such embodiments, the additional therapeutic agent is selected from the group consisting of purified bovine Type V collagens (e.g., IW-001; ImmuneWorks; United Therapeutics), IL-13 receptor antagonists (e.g., QAX576; Novartis), protein tyrosine kinase inhibitors (e.g., imatinib (Gleevec®); Craig Daniels/Novartis), endothelial receptor antagonists (e.g., ACT-064992 (macitentan); Actelion), dual endothelin receptor antagonists (e.g., bosentan (Tracleer®); Actelion), prostacyclin analogs (inhaled iloprost (e.g., Ventavis®); Actelion), anti-CTGF monoclonal antibodies (e.g., FG-3019), endothelin receptor antagonists (A-selective) (e.g., ambrisentan (Letairis®), Gilead), AB0024 (Arresto), lysyl oxidase-like 2 (LOXL2) monoclonal antibodies (e.g., GS-6624 (formerly AB0024); Gilead), c-Jun N-terminal kinase (JNK) inhibitors (e.g., CC-930; Celgene), Pirfenidone (e.g., Esbriet® (InterMune), Pirespa® (Shionogi)), IFN-γ1b (e.g., Actimmune®; InterMune), pan-neutralizing IgG4 human antibodies against all three TGF-β isoforms (e.g., GC1008; Genzyme), TGF-β activation inhibitors (e.g., Stromedix (STX-100)), recombinant human Pentraxin-2 protein (rhPTX-2) (e.g., PRM151; Promedior), bispecific IL4/IL13 antibodies (e.g., SAR156597; Sanofi), humanized monoclonal antibodies targeting integrin αvβ6 (BIBF 1120; Boehringer Ingelheim), N-acetylcysteine (Zambon SpA), Sildenafil (Viagra®), TNF antagonists (e.g., etanercept (Enbrel®); Pfizer), glucocorticoids (e.g., prednisone, budesonide, mometasone furoate, fluticasone propionate, and fluticasone furoate), bronchodilators (e.g., leukotriene modifers (e.g., Montelukast (SINGUAIR®)), anticholingertic bronchodilators (e.g., Ipratropium bromide and Tiotropium), short-acting β2-agonists (e.g., isoetharine mesylate (Bronkometer®), adrenalin, salbutanol/albuterol, and terbutaline), long-acting β2-agonists (e.g., salmeterol, formoterol, indecaterol (Onbrez®), and a combination thereof.

According to some other embodiments, the additional therapeutic agent comprises a bronchodilator including, but not limited to, a leukotriene modifier, an anticholinergic bronchodilator, a β2-agonist, or a combination thereof.

According to another embodiment, the additional therapeutic agent comprises a corticosteroid including, but not limited to, prednisone, budesonide, mometasone, beclemethasone, or a combination thereof.

According to some other embodiments, the additional therapeutic agent is an anti-inflammatory agent.

According to some such embodiments, the anti-inflammatory agent is a nonsteroidal anti-inflammatory agent. The term "non-steroidal anti-inflammatory agent" as used herein refers to a large group of agents that are aspirin-like in their action, including, but not limited to, ibuprofen (Advil®), naproxen sodium (Aleve®), and acetaminophen (Tylenol®). Additional examples of non-steroidal anti-inflammatory agents that are usable in the context of the described invention include, without limitation, oxicams, such as piroxicam, isoxicam, tenoxicam, sudoxicam, and CP-14,304; disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents also may be employed, as well as the dermatologically acceptable salts and esters of these agents. For example, etofenamate, a flufenamic acid derivative, is particularly useful for topical application.

According to another embodiment, the nonsteroidal anti-inflammatory agent comprises Transforming Growth Factor-β3 (TGF-β3), an anti-Tumor Necrosis Factor-alpha (TNF-α) agent, or a combination thereof.

According to another embodiment, the anti-inflammatory agent is a steroidal anti-inflammatory agent. The term "steroidal anti-inflammatory agent", as used herein, refer to any one of numerous compounds containing a 17-carbon 4-ring system and includes the sterols, various hormones (as anabolic steroids), and glycosides. Representative examples of steroidal anti-inflammatory drugs include, without limitation, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflucortolone valerate, fluadrenolone, fluclorolone acetonide, flumethasone pivalate, fluosinolone acetonide, fluocinonide, fluocortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflorosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

According to another embodiment, the steroidal anti-inflammatory agent comprises at least one corticosteroid selected from the group consisting of prednisone, budesonide, mometasone, beclemethasone, and a combination thereof.

According to another embodiment, the additional therapeutic agent comprises a xanthine or xanthine derivative, such as methylxanthine.

According to another embodiment, the additional therapeutic agent comprises a neutrophil elastase inhibitor.

According to another embodiment, the additional therapeutic agent is at least one neutrophil elastase inhibitor, including, but not limited to, ICI 200355, ONO-5046, MR-889, L-694,458, CE-1037, GW-311616, TEI-8362, ONO-6818, AE-3763, FK-706, ICI-200,880, ZD-0892, ZD-8321, and a combination thereof.

According to another embodiment, the additional therapeutic agent comprises at least one phosphodiesterase inhibitor, including, but not limited to, phosphodiesterase 4 inhibitor. Examples of phosphodiesterase 4 inhibitors include, but are not limited to, roflumilast, cilomilast or a combination thereof.

According to another embodiment, the additional therapeutic agent is an analgesic agent. According to some embodiments, the analgesic agent relieves pain by elevating the pain threshold without disturbing consciousness or altering other sensory modalities. According to some such embodiments, the analgesic agent is a non-opioid analgesic. "Non-opioid analgesics" are natural or synthetic substances that reduce pain but are not opioid analgesics. Examples of non-opioid analgesics include, but are not limited to, etodolac, indomethacin, sulindac, tolmetin, nabumetone, piroxicam, acetaminophen, fenoprofen, flurbiprofen, ibuprofen, ketoprofen, naproxen, naproxen sodium, oxaprozin, aspirin, choline magnesium trisalicylate, diflunisal, meclofenamic acid, mefenamic acid, and phenylbutazone. According to some other embodiments, the analgesic is an opioid analgesic. "Opioid analgesics", "opioid", or "narcotic analgesics" are natural or synthetic substances that bind to opioid receptors in the central nervous system, producing an agonist action. Examples of opioid analgesics include, but are not limited to, codeine, fentanyl, hydromorphone, levorphanol, meperidine, methadone, morphine, oxycodone, oxymorphone, propoxyphene, buprenorphine, butorphanol, dezocine, nalbuphine, and pentazocine.

According to another embodiment, the additional therapeutic agent is an anti-infective agent. According to another embodiment, the anti-infective agent is an antibiotic agent. The term "antibiotic agent" as used herein means any of a group of chemical substances having the capacity to inhibit the growth of, or to destroy bacteria and other microorganisms, used chiefly in the treatment of infectious diseases. Examples of antibiotic agents include, but are not limited to, Penicillin G; Methicillin; Nafcillin; Oxacillin; Cloxacillin; Dicloxacillin; Ampicillin; Amoxicillin; Ticarcillin; Carbenicillin; Mezlocillin; Azlocillin; Piperacillin; Imipenem; Aztreonam; Cephalothin; Cefaclor; Cefoxitin; Cefuroxime; Cefonicid; Cefmetazole; Cefotetan; Cefprozil; Loracarbef; Cefetamet; Cefoperazone; Cefotaxime; Ceftizoxime; Ceftriaxone; Ceftazidime; Cefepime; Cefixime; Cefpodoxime; Cefsulodin; Fleroxacin; Nalidixic acid; Norfloxacin; Ciprofloxacin; Ofloxacin; Enoxacin; Lomefloxacin; Cinoxacin; Doxycycline; Minocycline; Tetracycline; Amikacin; Gentamicin; Kanamycin; Netilmicin; Tobramycin; Streptomycin; Azithromycin; Clarithromycin; Erythromycin; Erythromycin estolate; Erythromycin ethyl succinate; Erythromycin glucoheptonate; Erythromycin lactobionate; Erythromycin stearate; Vancomycin; Teicoplanin; Chloramphenicol; Clindamycin; Trimethoprim; Sulfamethoxazole; Nitrofurantoin; Rifampin; Mupirocin; Metronidazole; Cephalexin; Roxithromycin; Co-amoxiclavuanate; combinations of Piperacillin and Tazobactam; and their various salts, acids, bases, and other derivatives. Anti-bacterial antibiotic agents include, but are not limited to, penicillins, cephalosporins, carbacephems, cephamycins, carbapenems, monobactams, aminoglycosides, glycopeptides, quinolones, tetracyclines, macrolides, and fluoroquinolones.

According to another embodiment, the pharmaceutical composition inhibits inflammation occurring in a lung of the subject. According to another embodiment, the inflammation is an acute inflammation. According to another embodiment, the inflammation is a chronic inflammation. According to another embodiment, the inflammation is mediated by Tumor Necrosis Factor-alpha (TNF-α). According to another embodiment, the inflammation is mediated by Interleukin-6 (IL-6). According to another embodiment, the inflammation is mediated by Interleukin-1β (IL-1β).

According to another embodiment, the pharmaceutical composition modulates an amount of Tumor Necrosis Factor-alpha (TNF-α) in the lung, compared to a control. According to another embodiment, the pharmaceutical composition modulates the amount of Interleukin-6 (IL-6) in the lung, compared to a control. According to another embodiment, the pharmaceutical composition modulates the amount of Interleukin-1β (IL-1β) in the lung, compared to a control.

According to another embodiment, the pharmaceutical composition inhibits an activity of Heat Shock 27 kDa protein 1 (HSPB1). According to another embodiment, the activity of HSPB1 inhibited by the pharmaceutical composition is an aberrant induction of fibroblast proliferation. According to another embodiment, the activity of HSPB1 inhibited by the pharmaceutical composition is an aberrant induction of myofibroblast differentiation. According to another embodiment, the activity of HSPB1 inhibited by the pharmaceutical composition is a deposition of an extracellular matrix protein into a pulmonary interstitium. According to another embodiment, the extracelluar matrix protein is collagen. According to another embodiment, the activity of HSPB1 inhibited by the pharmaceutical composition is a promotion of fibrotic loci formation. According to another embodiment, the activity of HSPB1 inhibited by the pharmaceutical composition is an increase of a myofibroblast contractile activity. According to another embodiment, the activity of HSPB1 inhibited by the pharmaceutical composition is a promotion of myofibroblast attachment to extracellular matrix.

According to some embodiments, the functional equivalent of the polypeptide YARAAARQARAKALARQLGVAA (SEQ ID NO: 1) has a substantial sequence identity to amino acid sequence YARAAARQARAKALARQLGVAA (SEQ ID NO: 1).

According to another embodiment, the functional equivalent of the polypeptide YARAAARQARAKALARQLGVAA (SEQ ID NO: 1) has at least 70 percent sequence identity to amino acid sequence YARAAARQARAKALARQLGVAA (SEQ ID NO: 1). According to another embodiment, the functional equivalent of the polypeptide YARAAARQARAKALARQLGVAA (SEQ ID NO: 1) has at least 80 percent sequence identity to amino acid sequence YARAAARQARAKALARQLGVAA (SEQ ID NO: 1). According to another embodiment, the functional equivalent of the polypeptide YARAAARQARAKALARQLGVAA (SEQ ID NO: 1) has at least 90 percent sequence identity to amino acid sequence YARAAARQARAKALARQLGVAA (SEQ ID NO: 1). According to another embodiment, the functional equivalent of the polypeptide YARAAARQARAKALARQLGVAA (SEQ ID NO: 1) has at least 95 percent sequence identity to amino acid sequence YARAAARQARAKALARQLGVAA (SEQ ID NO: 1).

According to another embodiment, the functional equivalent of the polypeptide YARAAARQARAKALARQLGVAA (SEQ ID NO: 1) is of amino acid sequence FAKLAARLYRKALARQLGVAA (SEQ ID NO: 3).

According to another embodiment, the functional equivalent of the polypeptide YARAAARQARAKALARQLGVAA (SEQ ID NO: 1) is of amino acid sequence KAFAKLAARLYRKALARQLGVAA (SEQ ID NO: 4).

According to another embodiment, the functional equivalent of the polypeptide YARAAARQARAKALARQLGVAA (SEQ ID NO: 1) is of amino acid sequence YARAAARQARAKALARQLAVA (SEQ ID NO: 5).

According to another embodiment, the functional equivalent of the polypeptide YARAAARQARAKALARQLGVAA (SEQ ID NO: 1) is of amino acid sequence YARAAARQARAKALARQLGVA (SEQ ID NO: 6).

According to another embodiment, the functional equivalent of the polypeptide YARAAARQARAKALARQLGVAA (SEQ ID NO: 1) is of amino acid sequence HRRIKAWLKKIKALARQLGVAA (SEQ ID NO: 7).

According to some other embodiments, the functional equivalent of the polypeptide YARAAARQARAKALARQLGVAA (SEQ ID NO: 1) is a fusion protein comprising a first polypeptide operatively linked to a second polypeptide, wherein the first polypeptide is of amino acid sequence YARAAARQARA (SEQ ID NO: 11), and the second polypeptide comprises a therapeutic domain whose sequence has substantial identity to amino acid sequence KALARQLGVAA (SEQ ID NO: 2).

According to some such embodiments, the second polypeptide has at least 70 percent sequence identity to amino acid sequence KALARQLGVAA (SEQ ID NO: 2). According some other embodiments, the second polypeptide has at least 80 percent sequence identity to amino acid sequence KALARQLGVAA (SEQ ID NO: 2). According to some other embodiments, the second polypeptide has at least 90 percent sequence identity to amino acid sequence KALARQLGVAA (SEQ ID NO: 2). According to some other embodiments, the second polypeptide has at least 95 percent sequence identity to amino acid sequence KALARQLGVAA (SEQ ID NO: 2).

According to some embodiments, the second polypeptide is a polypeptide of amino acid sequence KALARQLAVA (SEQ ID NO: 8).

According to another embodiment, the second polypeptide is a polypeptide of amino acid sequence KALARQLGVA (SEQ ID NO: 9).

According to another embodiment, the second polypeptide is a polypeptide of amino acid sequence KALARQLGVAA (SEQ ID NO: 10).

According to some other embodiments, the functional equivalent of the polypeptide YARAAARQARAKALARQLGVAA (SEQ ID NO: 1) is a fusion protein comprising a first polypeptide operatively linked to a second polypeptide, wherein the first polypeptide comprises a cell penetrating peptide functionally equivalent to YARAAARQARA (SEQ ID NO: 11), and the second polypeptide is of amino acid sequence KALARQLGVAA (SEQ ID NO: 2).

According to another embodiment, the first polypeptide is a polypeptide of amino acid sequence WLRRIKAWLRRIKA (SEQ ID NO: 12). According to another embodiment, the first polypeptide is a polypeptide of amino acid sequence WLRRIKA (SEQ ID NO: 13). According to another embodiment, the first polypeptide is a polypeptide of amino acid sequence YGRKKRRQRRR (SEQ ID NO: 14). According to another embodiment, the first polypeptide is a polypeptide of amino acid sequence WLRRIKAWLRRI (SEQ ID NO: 15). According to another embodiment, the first polypeptide is a polypeptide of amino acid sequence FAKLAARLYR (SEQ ID NO: 16). According to another embodiment, the first polypeptide is a polypeptide of amino acid sequence KAFAKLAARLYR (SEQ ID NO: 17). According to another embodiment, the first polypeptide is a polypeptide of amino acid sequence HRRIKAWLKKI (SEQ ID NO: 18).

According to another aspect, the described invention also provides an isolated nucleic acid that encodes a protein sequence with at least 70% amino acid sequence identity to amino acid sequence YARAAARQARAKALARQLGVAA (SEQ ID NO: 1). According to some embodiments, the isolated nucleic acid encodes a protein sequence with at least 80% amino acid sequence identity to amino acid sequence YARAAARQARAKALARQLGVAA (SEQ ID NO: 1). According to some other embodiments, the isolated nucleic acid encodes a protein sequence with at least 90% amino acid sequence identity to amino acid sequence YARAAARQARAKALARQLGVAA (SEQ ID NO: 1). According to some other embodiments, the isolated nucleic acid encodes a protein sequence with at least 95% amino acid sequence identity to amino acid sequence YARAAARQARAKALARQLGVAA (SEQ ID NO: 1).

According to some other embodiments, the therapeutic amount of the therapeutic inhibitor peptide of the pharmaceutical composition is of an amount from about 0.000001 mg/kg body weight to about 100 mg/kg body weight. According to another embodiment, the therapeutic amount of the therapeutic inhibitory peptide of the pharmaceutical composition is of an amount from about 0.00001 mg/kg body weight to about 100 mg/kg body weight. According to another embodiment, the therapeutic amount of the therapeutic inhibitory peptide of the pharmaceutical composition is of an amount from about 0.0001 mg/kg body weight to about 100 mg/kg body weight. According to another embodiment, the therapeutic amount of the therapeutic inhibitory peptide of the pharmaceutical composition is of an amount from about 0.001 mg/kg body weight to about 10 mg/kg body weight. According to another embodiment, the therapeutic amount of the therapeutic inhibitory peptide of the pharmaceutical composition is of an amount from about 0.01 mg/kg body weight to about 10 mg/kg body weight. According to another embodiment, the therapeutic amount of the therapeutic inhibitory peptide of the pharmaceutical composition is of an amount from about 0.1 mg/kg (or 100 µg/kg) body weight to about 10 mg/kg body weight. According to another embodiment, the therapeutic amount of the therapeutic inhibitory peptide of the pharmaceutical composition is of an amount from about 1 mg/kg body weight to about 10 mg/kg body weight. According to another embodiment, the therapeutic amount of the therapeutic inhibitory peptide of the pharmaceutical composition is of an amount from about 10 mg/kg body weight to about 100 mg/kg body weight. According to another embodiment, the therapeutic amount of the therapeutic inhibitory peptide of the pharmaceutical composition is of an amount from about 2 mg/kg body weight to about 10 mg/kg body weight. According to another embodiment, the therapeutic amount of the therapeutic inhibitory peptide of the pharmaceutical composition is of an amount from about 3 mg/kg body weight to about 10 mg/kg body weight. According to another embodiment, the therapeutic amount of the therapeutic inhibitory peptide of the pharmaceutical composition is of an amount from about 4 mg/kg body weight to about 10 mg/kg body weight. According to another embodiment, the therapeutic amount of the therapeutic inhibitory peptide of the pharmaceutical composition is of an amount from about 5 mg/kg body weight to about 10 mg/kg body weight. According to another embodiment, the therapeutic amount of the therapeutic inhibitory peptide of the pharmaceutical composition is of an amount from about 60 mg/kg body weight to about 100 mg/kg body weight. According to another embodiment, the therapeutic amount of the therapeutic inhibitory peptide of the pharmaceutical composition is of an amount from about 70 mg/kg body weight to about 100 mg/kg body weight. According to another embodiment, the therapeutic amount of the therapeutic inhibitory peptide of the pharmaceutical composition is of an amount from about 80 mg/kg body weight to about 100 mg/kg body weight. According to another embodiment, the therapeutic amount of the therapeutic inhibitory peptide of the pharmaceutical composition is of an amount from about 90 mg/kg body weight to about 100 mg/kg body weight. According to another embodiment, the therapeutic amount of the therapeutic inhibitor peptide of the pharmaceutical composition is of an amount from about 0.000001 mg/kg body weight to about 90 mg/kg body weight. According to another embodiment, the therapeutic amount of the therapeutic inhibitor peptide of the pharmaceutical composition is of an amount from about 0.000001 mg/kg body weight to about 80 mg/kg body weight. According to another embodiment, the therapeutic amount of the therapeutic inhibitor peptide of the pharmaceutical composition is of an amount from about 0.000001 mg/kg body weight to about 70 mg/kg body weight. According to another embodiment, the therapeutic amount of the therapeutic inhibitor peptide of the pharmaceutical composition is of an amount from about 0.000001 mg/kg body weight to about 60 mg/kg body weight. According to another embodiment, the therapeutic amount of the therapeutic inhibitor peptide of the pharmaceutical composition is of an amount from about 0.000001 mg/kg body weight to about 50 mg/kg body weight. According to another embodiment, the therapeutic amount of the therapeutic inhibitor peptide of the pharmaceutical composition is of an amount from about 0.000001 mg/kg body weight to about 40 mg/kg body weight. According to another embodiment, the therapeutic amount of the therapeutic inhibitor peptide is of an amount from about 0.000001 mg/kg body weight to about 30 mg/kg body weight. According to another embodiment, the therapeutic amount of the therapeutic inhibitor peptide of the pharmaceutical composition is of an amount from about 0.000001 mg/kg body weight to about 20 mg/kg body weight. According to another embodiment, the therapeutic amount of the therapeutic inhibitor peptide of the pharmaceutical composition is of an amount from about 0.000001 mg/kg body weight to about 10 mg/kg body weight. According to another embodiment, the therapeutic amount of the therapeutic inhibitor peptide of the pharmaceutical composition is of an amount from about 0.000001 mg/kg body weight to about 1 mg/kg body weight. According to another embodiment, the therapeutic amount of the therapeutic inhibitor peptide of the pharmaceutical composition is of an amount from about 0.000001 mg/kg body weight to about 0.1 mg/kg body weight. According to another embodiment, the therapeutic amount of the therapeutic inhibitor peptide of the pharmaceutical composition is of an amount from about 0.000001 mg/kg body weight to about 0.1 mg/kg body weight. According to another embodiment, the therapeutic amount of the therapeutic inhibitor peptide of the pharmaceutical composition is of an amount from about 0.000001 mg/kg body weight to about 0.01 mg/kg body weight. According to another embodiment, the therapeutic amount of the therapeutic inhibitor peptide of the pharmaceutical composition is of an amount from about 0.000001 mg/kg body weight to about 0.001 mg/kg body weight. According to another embodiment, the therapeutic amount of the therapeutic inhibitor peptide of the pharmaceutical composition is of an amount from about 0.000001 mg/kg body weight to about 0.0001 mg/kg body weight. According to another embodiment, the therapeutic amount of the therapeutic inhibitor peptide of the pharmaceutical composition is of an amount from about 0.000001 mg/kg body weight to about 0.00001 mg/kg body weight.

According to some other embodiments, the therapeutic dose of the therapeutic inhibitor peptide of the pharmaceutical composition ranges from 1 µg/kg/day to 25 µg/kg/day. According to some other embodiments, the therapeutic dose of the therapeutic inhibitor peptide of the pharmaceutical composition ranges from 1 µg/kg/day to 2 µg/kg/day. According to some other embodiments, the therapeutic dose of the therapeutic inhibitor peptide of the pharmaceutical composition ranges from 2 µg/kg/day to 3 µg/kg/day. According to some other embodiments, the therapeutic dose of the therapeutic inhibitor peptide of the pharmaceutical composition ranges from 3 µg/kg/day to 4 µg/kg/day. According to some other embodiments, the therapeutic dose of the therapeutic inhibitor peptide of the pharmaceutical ranges from 4 µg/kg/day to 5 µg/kg/day. According to some other embodiments, the therapeutic dose of the therapeutic inhibitor peptide of the pharmaceutical composition ranges from 5 µg/kg/day to 6 µg/kg/day. According to some other embodiments, the therapeutic dose of the therapeutic inhibitor peptide of the pharmaceutical composition ranges from 6 µg/kg/day to 7 µg/kg/day. According to some other embodiments, the therapeutic dose of the therapeutic inhibitor peptide of the pharmaceutical composition ranges from 7 µg/kg/day to 8 µg/kg/day. According to some other embodiments, the therapeutic dose of the therapeutic inhibitor peptide of the pharmaceutical composition ranges from 8 µg/kg/day to 9 µg/kg/day. According to some other embodiments, the therapeutic dose of the therapeutic inhibitor peptide of the pharmaceutical composition ranges from 9 µg/kg/day to 10 mg/kg/day. According to some other embodiments, the therapeutic dose of the therapeutic inhibitor peptide of the pharmaceutical composition ranges from 1 µg/kg/day to 5 µg/kg/day. According to some other embodiments, the therapeutic dose of the therapeutic inhibitor peptide of the pharmaceutical composition ranges from 5 µg/kg/day to 10 mg/kg/day. According to some other embodiments, the therapeutic dose of the therapeutic inhibitor peptide of the pharmaceutical composition ranges from 10 mg/kg/day to 15 µg/kg/day. According to some other embodiments, the therapeutic dose of the therapeutic inhibitor peptide of the pharmaceutical composition ranges from 15 µg/kg/day to 20 mg/kg/day. According to some other embodiments, the therapeutic dose of the therapeutic inhibitor peptide of the pharmaceutical composition ranges from 25 µg/kg/day to 30 mg/kg/day. According to some other embodiments, the therapeutic dose of the therapeutic inhibitor peptide of the pharmaceutical composition ranges from 30 µg/kg/day to 35 µg/kg/day. According to some other embodiments, the therapeutic dose of the therapeutic inhibitor peptide of the pharmaceutical composition ranges from 35 µg/kg/day to 40 µg/kg/day. According to some other embodiments, the therapeutic dose of the therapeutic inhibitor peptide of the pharmaceutical composition ranges from 40 µg/kg/day to 45 µg/kg/day. According to some other embodiments, the therapeutic dose of the therapeutic inhibitor peptide of the pharmaceutical composition ranges from 45 µg/kg/day to 50 µg/kg/day. According to some other embodiments, the therapeutic dose of the therapeutic inhibitor peptide of the pharmaceutical composition ranges from 50 µg/kg/day to 55 µg/kg/day. According to some other embodiments, the therapeutic dose of the therapeutic inhibitor peptide of the pharmaceutical composition ranges from 55 µg/kg/day to 60 µg/kg/day. According to some other embodiments, the therapeutic dose of the therapeutic inhibitor peptide of the pharmaceutical composition ranges from 60 µg/kg/day to 65 µg/kg/day. According to some other embodiments, the therapeutic dose of the therapeutic inhibitor peptide of the pharmaceutical composition ranges from 65 µg/kg/day to 70 µg/kg/day. According to some other embodiments, the therapeutic dose of the therapeutic inhibitor peptide of the pharmaceutical composition ranges from 70 µg/kg/day to 75 µg/kg/day. According to some other embodiments, the therapeutic dose of the therapeutic inhibitor peptide of the pharmaceutical composition ranges from 80 µg/kg/day to 85 µg/kg/day. According to some other embodiments, the therapeutic dose of the therapeutic inhibitor peptide of the pharmaceutical composition ranges from 85 µg/kg/day to 90 µg/kg/day. According to some other embodiments, the therapeutic dose of the therapeutic inhibitor peptide of the pharmaceutical composition ranges from 90 µg/kg/day to 95 µg/kg/day. According to some other embodiments, the therapeutic dose of the therapeutic inhibitor peptide of the pharmaceutical composition ranges from 95 µg/kg/day to 100 µg/kg/day.

According to another embodiment, the therapeutic dose of the therapeutic inhibitor peptide of the pharmaceutical composition is 1 µg/kg/day.

According to another embodiment, the therapeutic dose of the therapeutic inhibitor peptide of the pharmaceutical composition is 2 µg/kg/day.

According to another embodiment, the therapeutic dose of the therapeutic inhibitor peptide of the pharmaceutical composition is 5 µg/kg/day.

According to another embodiment, the therapeutic dose of the therapeutic inhibitor peptide of the pharmaceutical composition is 10 µg/kg/day.

According to some embodiments, the polypeptide of the invention comprises D-amino acids (which are resistant to L-amino acid-specific proteases in vivo), a combination of D- and L-amino acids, and various "designer" amino acids (e.g., β-methyl amino acids, C-α-methyl amino acids, and N-α-methyl amino acids, etc.) to convey special properties. Examples of synthetic amino acid substitutions include ornithine for lysine, and norleucine for leucine or isoleucine.

According to some embodiments, the polypeptide may be linked to other compounds to promote an increased half-life in vivo, such as polyethylene glycol or dextran. Such linkage can be covalent or non-covalent as is understood by those of skill in the art. According to some other embodiments, the polypeptide may be encapsulated in a micelle such as a micelle made of poly(ethyleneglycol)-block-poly(polypropylenglycol) or poly(ethyleneglycol)-block-polylactide. According to some other embodiments, the polypeptide may be encapsulated in degradable nano- or micro-particles composed of degradable polyesters including, but not limited to, polylactic acid, polyglycolide, and polycaprolactone.

According to another embodiment, the polypeptide may be prepared in a solid form (including granules, powders or suppositories) or in a liquid form (e.g., solutions, suspensions, or emulsions).

According to another embodiment, the compositions of the described invention may be in the form of a dispersible dry powder for delivery by inhalation or insufflation (either through the mouth or through the nose, respectively). Dry powder compositions may be prepared by processes known in the art, such as lyophilization and jet milling, as disclosed in International Patent Publication No. WO 91/16038 and as disclosed in U.S. Pat. No. 6,921,527, the disclosures of which are incorporated by reference. The composition of the described invention is placed within a suitable dosage receptacle in an amount sufficient to provide a subject with a unit dosage treatment. The dosage receptacle is one that fits within a suitable inhalation device to allow for the aerosolization of the dry powder composition by dispersion into a gas stream to form an aerosol and then capturing the aerosol so produced in a chamber having a mouthpiece attached for subsequent inhalation by a subject in need of treatment. Such a dosage receptacle includes any container enclosing the composition known in the art such as gelatin or plastic capsules with a removable portion that allows a stream of gas (e.g., air) to be directed into the container to disperse the dry powder composition. Such containers are exemplified by those shown in U.S. Pat. Nos. 4,227,522; 4,192,309; and 4,105,027. Suitable containers also include those used in conjunction with Glaxo's Ventolin® Rotohaler brand powder inhaler or Fison's Spinhaler® brand powder inhaler. Another suitable unit-dose container which provides a superior moisture barrier is formed from an aluminum foil plastic laminate. The pharmaceutical-based powders is filled by weight or by volume into the depression in the formable foil and hermetically sealed with a covering foil-plastic laminate. Such a container for use with a powder inhalation device is described in U.S. Pat. No. 4,778,054 and is used with Glaxo's Diskhaler® (U.S. Pat. Nos. 4,627,432; 4,811,731; and 5,035,237). All of these references are incorporated herein by reference in their entireties.

According to another embodiment, the carrier of the composition of the described invention includes a release agent, such as a sustained release or delayed release carrier. In such embodiments, the carrier can be any material capable of sustained or delayed release of the polypeptide to provide a more efficient administration, e.g., resulting in less frequent and/or decreased dosage of the polypeptide, improving ease of handling, and extending or delaying effects on diseases, disorders, conditions, syndromes, and the like, being treated, prevented or promoted. Non-limiting examples of such carriers include liposomes, microsponges, microspheres, or microcapsules of natural and synthetic polymers and the like. Liposomes may be formed from a variety of phospholipids, including, but not limited to, cholesterol, stearylamines or phosphatidylcholines.

Methods for synthesis and preparation of small peptides are well known in the art and are disclosed, for example, in U.S. Pat. Nos. 5,352,461; 5,503,852; 6,071,497; 6,331,318; 6,428,771 and U.S. Publication No. 20060040953. U.S. Pat. Nos. 6,444,226 and 6,652,885 describe preparing and providing microparticles of diketopiperazines in aqueous suspension to which a solution of active agent is added in order to bind the active agent to the particle. These patents further describe a method of removing a liquid medium by lyophilization to yield microparticles comprising an active agent. Altering the solvent conditions of such suspension to promote binding of the active agent to the particle is disclosed in U.S. Application Nos. 60/717,524; Ser. No. 11/532,063; and Ser. No. 11/532,065; U.S. Pat. No. 6,440,463; and U.S. application Ser. No. 11/210,709 and Ser. No. 11/208,087. Each of these patents and patent applications is incorporated by reference herein.

In some embodiments, MMI-0100 (YARAAARQARAKALARQLGVAA; SEQ ID NO: 1) and its functional equivalents of the present invention can be dried by a method of spraying drying as disclosed in, for example, U.S. application Ser. No. 11/678,046 (incorporated by reference herein).

In yet another embodiment, the polypeptide of the invention may be applied in a variety of solutions. A suitable formulation is sterile, dissolves sufficient amounts of the polypeptides, and is not harmful for the proposed application. For example, the compositions of the described invention may be formulated as aqueous suspensions wherein the active ingredient(s) is (are) in admixture with excipients suitable for the manufacture of aqueous suspensions.

Such excipients include, without limitation, suspending agents (e.g., sodium carboxymethylcellulose, methylcellulose, hydroxy-propylmethylcellulose, sodium alginate, polyvinylpyrrolidone, gum tragacanth, and gum acacia), dispersing or wetting agents including, a naturally-occurring phosphatide (e.g., lecithin), or condensation products of an alkylene oxide with fatty acids (e.g., polyoxyethylene stearate), or condensation products of ethylene oxide with long chain aliphatic alcohols (e.g., heptadecaethyl-eneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate).

Compositions of the described invention also may be formulated as oily suspensions by suspending the active ingredient in a vegetable oil (e.g., arachis oil, olive oil, sesame oil or coconut oil) or in a mineral oil (e.g., liquid paraffin). The oily suspensions may contain a thickening agent (e.g., beeswax, hard paraffin or cetyl alcohol).

Compositions of the described invention also may be formulated in the form of dispersible powders and granules suitable for preparation of an aqueous suspension by the addition of water. The active ingredient in such powders and granules is provided in admixture with a dispersing or wetting agent, suspending agent, and one or more preservatives. Suitable dispersing or wetting agents and suspending agents are exemplified by those already mentioned above. Additional excipients also may be present.

According to some embodiments, the dry powder is produced by a spray drying process.

According to some other embodiments, the dry powder is produced by micronization According to another embodiment, the dry powder comprises microparticles with Mass Median Aerodynamic Diameter (MMAD) of 1 to 5 microns.

According to another embodiment, the dry powder comprises microparticles with Mass Median Aerodynamic Diameter (MMAD) of about 2 micron.

According to another embodiment, the pharmaceutical composition is packaged in an inhalation device, including, for example, but not limited to a nebulizer, a metered-dose inhaler (MDI), and a dry powder inhaler (DPI).

According to some other embodiments, the pharmaceutical composition is a liquid for aerosolized delivery using a nebulizer. According to some such embodiments, the flowrate of the pharmaceutical composition is at least 0.3 ml/min, and the pharmaceutical composition is delivered as 2 mm particles, with distribution into deepest alveoli.

Compositions of the described invention also may be in the form of an emulsion. An emulsion is a two-phase system prepared by combining two immiscible liquid carriers, one of which is disbursed uniformly throughout the other and consists of globules that have diameters equal to or greater than those of the largest colloidal particles. The globule size is critical and must be such that the system achieves maximum stability. Usually, separation of the two phases will not occur unless a third substance, an emulsifying agent, is incorporated. Thus, a basic emulsion contains at least three components, the two immiscible liquid carriers and the emulsifying agent, as well as the active ingredient. Most emulsions incorporate an aqueous phase into a non-aqueous phase (or vice versa). However, it is possible to prepare emulsions that are basically non-aqueous, for example, anionic and cationic surfactants of the non-aqueous immiscible system glycerin and olive oil. Thus, the compositions of the invention may be in the form of an oil-in-water emulsion. The oily phase may be a vegetable oil, for example, olive oil or arachis oil, or a mineral oil, for example a liquid paraffin, or a mixture thereof. Suitable emulsifying agents may be naturally-occurring gums, for example, gum acacia or gum tragacanth, naturally-occurring phosphatides, for example soy bean, lecithin, and esters or partial esters derived from fatty acids and hexitol anhydrides, for example sorbitan monooleate, and condensation products of the partial esters with ethylene oxide, for example, polyoxyethylene sorbitan monooleate.

According to some embodiments, the polypeptide of the described invention is chemically synthesized. Such a synthetic polypeptide, prepared using the well known techniques of solid phase, liquid phase, or peptide condensation techniques, or any combination thereof, may include natural and unnatural amino acids. Amino acids used for peptide synthesis may be standard Boc (N-α-amino protected N-α-t-butyloxycarbonyl) amino acid resin with the standard deprotecting, neutralization, coupling and wash protocols of the original solid phase procedure of Merrifield (1963, *J. Am. Chem. Soc.* 85:2149-2154), or the base-labile N-α-amino protected 9-fluorenylmethoxycarbonyl (Fmoc) amino acids first described by Carpino and Han (1972, *J. Org. Chem.* 37:3403-3409). Both Fmoc and Boc N-α-amino protected amino acids can be obtained from Sigma, Cambridge Research Biochemical, or other chemical companies familiar to those skilled in the art. In addition, the polypeptide may be synthesized with other N-α-protecting groups that are familiar to those skilled in this art. Solid phase peptide synthesis may be accomplished by techniques familiar to those in the art and provided, for example, in Stewart and Young, 1984, *Solid Phase Synthesis*, Second Edition, Pierce Chemical Co., Rockford, Ill.; Fields and Noble, 1990, *Int. J. Pept. Protein Res.* 35:161-214, or using automated synthesizers, each incorporated by reference herein in its entirety.

II. Methods for Preventing or Treating Diseases Characterized by Aberrant Fibroblast Proliferation and Collagen Deposition According to another aspect, the described invention provides a method for treating a disease, condition, or process characterized by aberrant fibroblast proliferation and extracellular matrix deposition in a tissue of a subject, the method comprising:

administering to the subject a pharmaceutical composition comprising a therapeutic amount of a polypeptide of the amino acid sequence YARAAARQARAKALARQLGVAA (SEQ ID NO: 1) or a functional equivalent thereof, and a pharmaceutically acceptable carrier thereof, wherein the therapeutic amount is effective to reduce the fibroblast proliferation and extracellular matrix deposition in the tissue of the subject.

According to one embodiment of the method, the disease or the condition is Acute Lung Injury (ALI) or acute respiratory distress syndrome (ARDS).

According to another embodiment, the disease or the condition is radiation-induced fibrosis.

According to another embodiment, the disease or the condition is transplant rejection.

According to another embodiment, the tissue is a lung tissue.

According to another embodiment, the disease or the condition is an interstitial lung disease.

According to another embodiment, the disease or the condition is pulmonary fibrosis.

According to another embodiment, the pulmonary fibrosis is idiopathic pulmonary fibrosis.

According to another embodiment, the pulmonary fibrosis is caused by administration of bleomycin.

According to another embodiment, the pulmonary fibrosis results from an allergic reaction, inhalation of environmental particulates, smoking, a bacterial infection, a viral infection, mechanical damage to a lung of the subject, lung transplantation rejection, an autoimmune disorder, a genetic disorder, or a combination thereof.

According to another embodiment, the disease or the condition is further characterized by an inflammation in the tissue.

According to another embodiment, the inflammation is an acute or a chronic inflammation.

According to another embodiment, the inflammation is mediated by at least one cytokine selected from the group consisting of Tumor Necrosis Factor-alpha (TNF-α), Interleukin-6 (IL-6), and Interleukin-1β (IL-1β).

According to another embodiment, the pulmonary fibrosis is characterized by at least one pathology selected from the group consisting of an aberrant deposition of an extracellular matrix protein in a pulmonary interstitium, an aberrant promotion of fibroblast proliferation in the lung, an aberrant induction of myofibroblast differentiation in the lung, and an aberrant promotion of attachment of myofibroblasts to an extracellular matrix compared to a normal healthy control subject.

According to another embodiment, the aberrant fibroblast proliferation and extracellular matrix deposition in the tissue is characterized by an aberrant activity of Mitogen-Activated Protein Kinase-Activated Protein Kinase 2 (MK2) in the tissue compared to the activity of Mitogen-Activated Protein Kinase-Activated Protein Kinase 2 (MK2) in the tissue of a normal healthy control subject.

According to another embodiment, the aberrant fibroblast proliferation and extracellular matrix deposition in the tissue is evidenced by an aberrant amount or distribution of activated (phosphorylated) Mitogen-Activated Protein Kinase-Activated Protein Kinase 2 (MK2) in the tissue compared to the amount or distribution of activated Mitogen-Activated Protein Kinase-Activated Protein Kinase 2 (MK2) in the tissue of a normal healthy control subject.

According to another embodiment, the pulmonary fibrosis is characterized by at least one pathology selected from the group consisting of an aberrant deposition of an extracellular matrix protein in a pulmonary interstitium, an aberrant promotion of fibroblast proliferation in the lung, an aberrant induction of differentiation of a population of fibroblasts into a population of myofibroblasts in the lung, and an aberrant promotion of attachment of myofibroblasts to an extracellular matrix compared to a normal healthy control subject.

According to another embodiment, the disease or condition is a chronic obstructive pulmonary disease (COPD). According to another embodiment, the chronic obstructive pulmonary disease (COPD) is caused by smoking. According to another embodiment, the chronic obstructive pulmonary disease (COPD) is caused by environmental particulates. According to another embodiment, the chronic obstructive pulmonary disease (COPD) is caused by alpha-1 antitrypsin deficiency. According to another embodiment, the chronic obstructive pulmonary disease (COPD) is caused by a childhood respiratory infection.

According to another embodiment, the pulmonary fibrosis is characterized by an abnormal activity of Heat Shock 27 kDa protein 1 (HSPB1) in a lung of the subject compared to a normal healthy control subject. According to another embodiment, the abnormal activity of HSPB1 is an aberrant deposition of an extracellular matrix protein in a pulmonary interstitium of the subject compared to a normal healthy control subject. According to another embodiment, the extracellular matrix protein is collagen. According to another embodiment, the abnormal activity of HSPB1 is an aberrant promotion of fibroblast proliferation in the lung compared to a normal healthy control subject. According to another embodiment, the abnormal activity of HSPB1 is aberrant induction of myofibroblast differentiation in the lung compared to a normal healthy control subject. According to another embodiment, the abnormal activity of HSPB1 is a promotion of fibrotic loci formation in the lung compared to a normal healthy control subject. According to another embodiment, the abnormal activity of HSPB1 is an increase of myofibroblast contractile activity in the lung compared to a normal healthy control subject. According to another embodiment, the abnormal activity of HSPB1 is an aberrant promotion of myofibroblast attachment to an extracellular matrix in the lung compared to a normal healthy control subject.

According to another embodiment, the pharmaceutical composition inhibits inflammation occurring in a lung of the subject. According to another embodiment, the inflammation is an acute inflammation. According to another embodiment, the inflammation is a chronic inflammation. According to another embodiment, the inflammation is mediated by Tumor Necrosis Factor-alpha (TNF-α). According to another embodiment, the inflammation is mediated by interleukin-1β (IL-1β). According to another embodiment, the inflammation is mediated by interleukin-6 (IL-6).

According to another embodiment, the pharmaceutical composition modulates an amount of Tumor Necrosis Factor-alpha (TNF-α) in the lung of the subject, compared to an untreated control. According to another embodiment, the pharmaceutical composition modulates an amount of interleukin-1β (IL-1β) in the lung of the subject, compared to a control. According to another embodiment, the pharmaceutical composition modulates an amount of interleukin-6 (IL-6) in the lung of the subject, compared to a control.

According to another embodiment, the pharmaceutical composition inhibits an abnormal activity of HSPB1 compared to a normal healthy control subject in a lung of the subject. According to another embodiment, the abnormal activity of HSPB1 is an aberrant deposition of an extracellular matrix protein in a pulmonary interstitium compared to a normal healthy control subject. According to another embodiment, the extracellular matrix protein is collagen. According to another embodiment, the abnormal activity of HSPB1 is an aberrant promotion of fibroblast proliferation in the lung compared to a normal healthy control subject. According to another embodiment, the abnormal activity of HSPB1 is an aberrant induction of fibroblast differentiation into myofibroblasts in the lung compared to a normal healthy control subject. According to another embodiment, the abnormal activity of HSPB1 is an aberrant promotion of fibrotic loci formation compared to a normal healthy control subject. According to another embodiment, the abnormal activity of HSPB1 is an aberrant increase in contractile activity of myofibroblasts compared to a normal healthy control subject. According to another embodiment, the myofibroblast contractile activity is characterized by an elevated level of alpha smooth muscle actin (α-SMA) compared to a normal healthy control subject. According to another embodiment, the myofibroblasts contractile activity is characterized by increases in stress-fiber formation compared to a normal healthy control subject. According to another embodiment, the abnormal activity of HSPB1 is aberrant promotion of myofibroblasts attachment to an extracellular matrix compared to a normal healthy control subject.

According to one embodiment, the pharmaceutical composition inhibits a kinase activity of Mitogen-Activated Protein Kinase-Activated Protein Kinase 2 (MK2 kinase). According to another embodiment, the pharmaceutical composition inhibits at least 50% of the kinase activity of MK2 kinase. According to another embodiment, the pharmaceutical composition inhibits at least 65% of the kinase activity of MK2 kinase. According to another embodiment, the pharmaceutical composition inhibits at least 75% of the kinase activity of MK2 kinase. According to another embodiment, the pharmaceutical composition inhibits at least 80% of the kinase activity of MK2 kinase. According to another embodiment, the pharmaceutical composition inhibits at least 85% of the kinase activity of MK2 kinase. According to another embodiment, the pharmaceutical composition inhibits at least 90% of the kinase activity of MK2 kinase. According to another embodiment, the pharmaceutical composition inhibits at least 95% of the kinase activity of MK2 kinase.

According to another embodiment, the pharmaceutical composition inhibits a kinase activity of Mitogen-Activated Protein Kinase-Activated Protein Kinase 3 (MK3 kinase). According to another embodiment, the pharmaceutical composition further inhibits at least 50% of the kinase activity of MK3 kinase. According to another embodiment, the pharmaceutical composition further inhibits at least 65% of the kinase activity of MK3 kinase. According to another embodiment, the pharmaceutical composition further inhibits at least 70% of the kinase activity of MK3 kinase. According to another embodiment, the pharmaceutical composition further inhibits at least 75% of the kinase activity of MK3 kinase. According to another embodiment, the pharmaceutical composition further inhibits at least 80% of the kinase activity of MK3 kinase. According to another embodiment, the pharmaceutical composition further inhibits at least 85% of the kinase activity of MK3 kinase. According to another embodiment, the pharmaceutical composition further inhibits at least 90% of the kinase activity of MK3 kinase. According to another embodiment, the pharmaceutical composition further inhibits at least 95% of the kinase activity of MK3 kinase.

According to another embodiment, the pharmaceutical composition inhibits a kinase activity of calcium/calmodulin-dependent protein kinase I (CaMKI). According to another embodiment, the pharmaceutical composition further inhibits at least 50% of the kinase activity of $Ca^{2+}$/calmodulin-dependent protein kinase I (CaMKI). According to another embodiment, the pharmaceutical composition further inhibits at least 65% of the kinase activity of $Ca^{2+}$/calmodulin-dependent protein kinase I (CaMKI). According to another embodiment, the pharmaceutical composition further inhibits at least 70% of the kinase activity of $Ca^{2+}$/calmodulin-dependent protein kinase I (CaMKI). According to another embodiment, the pharmaceutical composition further inhibits at least 75% of the kinase activity of $Ca^{2+}$/calmodulin-dependent protein kinase I (CaMKI). According to another embodiment, the pharmaceutical composition further inhibits at least 80% of the kinase activity of $Ca^{2+}$/calmodulin-dependent protein kinase I (CaMKI). According to another embodiment, the pharmaceutical composition further inhibits at least 85% of the kinase activity of $Ca^{2+}$/calmodulin-dependent protein kinase I (CaMKI). According to another embodiment, the pharmaceutical composition further inhibits at least 90% of the kinase activity of $Ca^{2+}$/calmodulin-dependent protein kinase I (CaMKI). According to another embodiment, the pharmaceutical composition further inhibits at least 95% of the kinase activity of $Ca^{2+}$/calmodulin-dependent protein kinase I (CaMKI).

According to another embodiment, the pharmaceutical composition inhibits a kinase activity of BDNF/NT-3 growth factors receptor (TrkB). According to another embodiment, the pharmaceutical further inhibits at least 50% of the kinase activity of BDNF/NT-3 growth factors receptor (TrkB). According to another embodiment, the pharmaceutical further inhibits at least 65% of the kinase activity of BDNF/NT-3 growth factors receptor (TrkB). According to another embodiment, the pharmaceutical further inhibits at least 70% of the kinase activity of BDNF/NT-3 growth factors receptor (TrkB). According to another embodiment, the pharmaceutical further inhibits at least 75% of the kinase activity of BDNF/NT-3 growth factors receptor (TrkB).

According to another embodiment, the pharmaceutical composition inhibits a kinase activity of Mitogen-Activated Protein Kinase-Activated Protein Kinase 2 (MK2) and a kinase activity of Mitogen-Activated Protein Kinase-Activated Protein Kinase 3 (MK3).

According to another embodiment, the pharmaceutical composition inhibits a kinase activity of Mitogen-Activated Protein Kinase-Activated Protein Kinase 2 (MK2) and a kinase activity of calcium/calmodulin-dependent protein kinase I (CaMKI).

According to another embodiment, the pharmaceutical composition inhibits a kinase activity of Mitogen-Activated Protein Kinase-Activated Protein Kinase 2 (MK2) and a kinase activity of BDNF/NT-3 growth factors receptor (TrkB).

According to another embodiment, the pharmaceutical composition inhibits a kinase activity of Mitogen-Activated Protein Kinase-Activated Protein Kinase 2 (MK2), a kinase activity of Mitogen-Activated Protein Kinase-Activated Protein Kinase 3 (MK3), a kinase activity of calcium/calmodulin-dependent protein kinase I (CaMKI), and a kinase activity of BDNF/NT-3 growth factors receptor (TrkB).

According to another embodiment, the pharmaceutical composition inhibits a kinase activity of Mitogen-Activated Protein Kinase-Activated Protein Kinase 2 (MK2), a kinase activity of calcium/calmodulin-dependent protein kinase I (CaMKI), and a kinase activity of BDNF/NT-3 growth factors receptor (TrkB).

According to another embodiment, the pharmaceutical composition inhibits at least 65% of the kinase activity of Mitogen-Activated Protein Kinase-Activated Protein Kinase 2 (MK2).

According to another embodiment, the pharmaceutical composition inhibits at least 65% of the kinase activity of Mitogen-Activated Protein Kinase-Activated Protein Kinase 3 (MK3).

According to another embodiment, the pharmaceutical composition inhibits at least 65% of the kinase activity of calcium/calmodulin-dependent protein kinase I (CaMKI).

According to another embodiment, the pharmaceutical composition inhibits at least 65% of the kinase activity of BDNF/NT-3 growth factors receptor (TrkB).

According to another embodiment, the pharmaceutical composition inhibits at least 65% of the kinase activity of Mitogen-Activated Protein Kinase-Activated Protein Kinase 2 (MK2) and at least 65% of the kinase activity of Mitogen-Activated Protein Kinase-Activated Protein Kinase 3 (MK3).

According to another embodiment, the pharmaceutical composition inhibits at least 65% of the kinase activity of Mitogen-Activated Protein Kinase-Activated Protein Kinase 2 (MK2) and at least 65% of the kinase activity of calcium/calmodulin-dependent protein kinase I (CaMKI).

According to another embodiment, the pharmaceutical composition inhibits at least 65% of the kinase activity of Mitogen-Activated Protein Kinase-Activated Protein Kinase 2 (MK2) and at least 65% of the kinase activity of BDNF/NT-3 growth factors receptor (TrkB).

According to another embodiment, the pharmaceutical composition inhibits at least 65% of the kinase activity of Mitogen-Activated Protein Kinase-Activated Protein Kinase 2 (MK2), at least 65% of the kinase activity of Mitogen-Activated Protein Kinase-Activated Protein Kinase 3 (MK3), at least 65% of the kinase activity of calcium/calmodulin-dependent protein kinase I (CaMKI), and at least 65% of the kinase activity of BDNF/NT-3 growth factors receptor (TrkB).

According to another embodiment, the pharmaceutical composition inhibits the kinase activity of at least one kinase selected from the group of MK2, MK3, CaMKT, TrkB, without substantially inhibiting the activity of one or more other selected kinases from the remaining group listed in Table 1 herein.

According to another embodiment, the pharmaceutical composition inhibits a kinase activity of a kinase selected from the group listed in Table 1 herein.

According to another embodiment, this inhibition may, for example, be effective to reduce fibroblast prolfieration, extracellular matrix deposition, or a combination thereof in the tissue of the subject.

According to another embodiment, this inhibition may, for example, be effective to reduce at least one pathology selected from the group consisting of an aberrant deposition of an extracellular matrix protein in a pulmonary interstitium, an aberrant promotion of fibroblast proliferation in the lung, an aberrant induction of myofibroblast differentiation, and an aberrant promotion of attachment of myofibroblasts to an extracellular matrix, compared to a normal healthy control subject.

According to some embodiments, inhibitory profiles of MMI inhibitors in vivo depend on dosages, routes of administration, and cell types responding to the inhibitors.

According to such embodiment, the pharmaceutical composition inhibits less than 50% of the kinase activity of the other selected kinase(s). According to such embodiment, the pharmaceutical composition inhibits less than 65% of the kinase activity of the other selected kinase(s). According to another embodiment, the pharmaceutical composition inhibits less than 50% of the kinase activity of the other selected kinase(s). According to another embodiment, the pharmaceutical composition inhibits less than 40% of the kinase activity of the other selected kinase(s). According to another embodiment, the pharmaceutical composition inhibits inhibits less than 20% of the kinase activity of the other selected kinase(s). According to another embodiment, the pharmaceutical composition inhibits less than 15% of the kinase activity of the other selected kinase(s). According to another embodiment, the pharmaceutical composition inhibits less than 10% of the kinase activity of the other selected kinase(s). According to another embodiment, the pharmaceutical composition inhibits less than 5% of the kinase activity of the other selected kinase(s). According to another embodiment, the pharmaceutical composition increases the kinase activity of the other selected kinases.

According to the embodiments of the immediately preceding paragraph, the one or more other selected kinase that is not substantially inhibited is selected from the group of $Ca^{2+}$/calmodulin-dependent protein kinase II (CaMKII, including its subunit CaMKIIδ), Proto-oncogene serine/threonine-protein kinase (PIM-1), cellular-Sarcoma (c-SRC), Spleen Tyrosine Kinase (SYK), C-src Tyrosine Kinase (CSK), and Insulin-like Growth Factor 1 Receptor (IGF-1R).

According to some embodiments, the pharmaceutical composition further comprises an additional therapeutic agent.

According to some such embodiments, the additional therapeutic agent is selected from the group consisting of purified bovine Type V collagens (e.g., IW-001; ImmuneWorks; United Therapeutics), IL-13 receptor antagonists (e.g., QAX576; Novartis), protein tyrosine kinase inhibitors (e.g., imatinib (Gleevec®); Craig Daniels/Novartis), endothelial receptor antagonists (e.g., ACT-064992 (macitentan); Actelion), dual endothelin receptor antagonists (e.g., bosentan (Tracleer®); Actelion), prostacyclin analogs (inhaled iloprost (e.g., Ventavis®); Actelion), anti-CTGF monoclonal antibodies (e.g., FG-3019), endothelin receptor antagonists (A-selective) (e.g., ambrisentan (Letairis®), Gilead), AB0024 (Arresto), lysyl oxidase-like 2 (LOXL2) monoclonal antibodies (e.g., GS-6624 (formerly AB0024); Gilead), c-Jun N-terminal kinase (JNK) inhibitors (e.g., CC-930; Celgene), Pirfenidone (e.g., Esbriet® (InterMune), Pirespa® (Shionogi)), IFN-γ1b (e.g., Actimmune®; InterMune), pan-neutralizing IgG4 human antibodies against all three TGF-β isoforms (e.g., GC1008; Genzyme), TGF-β activation inhibitors (e.g., Stromedix (STX-100)), recombinant human Pentraxin-2 protein (rhPTX-2) (e.g., PRM151; Promedior), bispecific IL4/IL13 antibodies (e.g., SAR156597; Sanofi), humanized monoclonal antibodies targeting integrin αvβ6 (BIBF 1120; Boehringer Ingelheim), N-acetylcysteine (Zambon SpA), Sildenafil (Viagra®), TNF antagonists (e.g., etanercept (Enbrel®); Pfizer), glucocorticoids (e.g., prednisone, budesonide, mometasone furoate, fluticasone propionate, and fluticasone furoate), bronchodilators (e.g., leukotriene modifers (e.g., Montelukast (SINGUAIR®)), anticholingertic bronchodilators (e.g., Ipratropium bromide and Tiotropium), short-acting β2-agonists (e.g., isoetharine mesylate (Bronkometer®), adrenalin, salbutanol/albuterol, and terbutaline), long-acting β2-agonists (e.g., salmeterol, formoterol, indecaterol (Onbrez®), and a combination thereof.

According to some other embodiments, the additional therapeutic agent comprises a bronchodilator including, but not limited to, a leukotriene modifier, an anticholinergic bronchodilator, a β2-agonist, or a combination thereof.

According to another embodiment, the additional therapeutic agent comprises a corticosteroid including, but not limited to, prednisone, budesonide, mometasone, beclemethasone, or a combination thereof.

According to some other embodiments, the additional therapeutic agent comprises a bronchodilator including, but not limited to, a leukotriene modifier, an anticholinergic bronchodilator, a β2-agonist, or a combination thereof.

According to another embodiment, the additional therapeutic agent comprises a corticosteroid including, but not limited to, prednisone, budesonide, mometasone, beclemethasone, or a combination thereof.

According to another embodiment, the additional therapeutic agent is an anti-inflammatory agent.

According to another embodiment, the anti-inflammatory agent is a nonsteroidal anti-inflammatory agent. Mixtures of non-steroidal anti-inflammatory agents also may be employed, as well as the dermatologically acceptable salts and esters of these agents. For example, etofenamate, a flufenamic acid derivative, is particularly useful for topical application.

According to another embodiment, wherein the nonsteroidal anti-inflammatory agent comprises Transforming Growth Factor-β3 (TGF-β3), an anti-Tumor Necrosis Factor-alpha (TNF-α) agent, or a combination thereof.

According to another embodiment, the anti-inflammatory agent is a steroidal anti-inflammatory agent. According to another embodiment, the steroidal anti-inflammatory agent comprises at least one corticosteroid selected from the group consisting of prednisone, budesonide, mometasone, beclemethasone, and a combination thereof.

According to another embodiment, the additional therapeutic agent comprises a methylxanthine.

According to another embodiment, the additional therapeutic agent comprises a neutrophil elastase inhibitor.

According to another embodiment, the additional therapeutic agent is at least one neutrophil elastase inhibitor, including, but not limited to, ICI 200355, ONO-5046, MR-889, L-694,458, CE-1037, GW-311616, TEI-8362, ONO-6818, AE-3763, FK-706, ICI-200,880, ZD-0892, ZD-8321, and a combination thereof.

According to another embodiment, the additional therapeutic agent comprises at least one phosphodiesterase inhibitor, including, but not limited to, phosphodiesterase 4 inhibitor. Examples of phosphodiesterase 4 inhibitors include, but are not limited to, roflumilast, cilomilast or a combination thereof.

According to another embodiment, the additional therapeutic agent is an analgesic agent. According to some such embodiments, the analgesic agent is a non-opioid analgesic. According to some other embodiments, the analgesic is an opioid analgesic.

According to another embodiment, the additional therapeutic agent is an anti-infective agent. According to another embodiment, the anti-infective agent is an antibiotic agent.

According to some embodiments, the functional equivalent of the polypeptide YARAAARQARAKALARQLGVAA (SEQ ID NO: 1) has a substantial sequence identity to amino acid sequence YARAAARQARAKALARQLGVAA (SEQ ID NO: 1).

According to some such embodiments, the functional equivalent of the polypeptide YARAAARQARAKALARQLGVAA (SEQ ID NO: 1) has at least 70 percent sequence identity to amino acid sequence YARAAARQARAKALARQLGVAA (SEQ ID NO: 1). According to another embodiment, the functional equivalent of the polypeptide YARAAARQARAKALARQLGVAA (SEQ ID NO: 1) has at least 80 percent sequence identity to amino acid sequence YARAAARQARAKALARQLGVAA (SEQ ID NO: 1). According to another embodiment, the functional equivalent of the polypeptide YARAAARQARAKALARQLGVAA (SEQ ID NO: 1) has at least 90 percent sequence identity to amino acid sequence YARAAARQARAKALARQLGVAA (SEQ ID NO: 1). According to another embodiment, the functional equivalent of the polypeptide YARAAARQARAKALARQLGVAA (SEQ ID NO: 1) has at least 95 percent sequence identity to amino acid sequence YARAAARQARAKALARQLGVAA (SEQ ID NO: 1).

According to another embodiment, the functional equivalent of the polypeptide YARAAARQARAKALARQLGVAA (SEQ ID NO: 1) is of amino acid sequence FAKLAARLYRKALARQLGVAA (SEQ ID NO: 3).

According to another embodiment, the functional equivalent of the polypeptide YARAAARQARAKALARQLGVAA (SEQ ID NO: 1) is of amino acid sequence KAFAKLAARLYRKALARQLGVAA (SEQ ID NO: 4).

According to another embodiment, the functional equivalent of the polypeptide YARAAARQARAKALARQLGVAA (SEQ ID NO: 1) is of amino acid sequence YARAAARQARAKALARQLAVA (SEQ ID NO: 5).

According to another embodiment, the functional equivalent of the polypeptide YARAAARQARAKALARQLGVAA (SEQ ID NO: 1) is of amino acid sequence YARAAARQARAKALARQLGVA (SEQ ID NO: 6).

According to another embodiment, the functional equivalent of the polypeptide YARAAARQARAKALARQLGVAA (SEQ ID NO: 1) is of amino acid sequence HRRIKAWLKKIKALARQLGVAA (SEQ ID NO: 7).

According to some other embodiments, the functional equivalent of the polypeptide YARAAARQARAKALARQLGVAA (SEQ ID NO: 1) is a fusion protein comprising a first polypeptide operatively linked to a second polypeptide, wherein the first polypeptide is of amino acid sequence YARAAARQARA (SEQ ID NO: 11), and the second polypeptide comprises a therapeutic domain whose sequence has a substantial identity to amino acid sequence KALARQLGVAA (SEQ ID NO: 2).

According to another embodiment, the second polypeptide has at least 70 percent sequence identity to amino acid sequence KALARQLGVAA (SEQ ID NO: 2). According to some other embodiments, the second polypeptide has at least 80 percent sequence identity to amino acid sequence KALARQLGVAA (SEQ ID NO: 2). According to some other embodiments, the second polypeptide has at least 90 percent sequence identity to amino acid sequence KALARQLGVAA (SEQ ID NO: 2). According to some other embodiments, the second polypeptide has at least 95 percent sequence identity to amino acid sequence KALARQLGVAA (SEQ ID NO: 2).

According to another embodiment, the second polypeptide is a polypeptide of amino acid sequence KALARQLAVA (SEQ ID NO: 8).

According to another embodiment, the second polypeptide is a polypeptide of amino acid sequence KALARQLGVA (SEQ ID NO: 9).

According to another embodiment, the second polypeptide is a polypeptide of amino acid sequence KALARQLGVAA (SEQ ID NO: 10).

According to some embodiments, the functional equivalent of the polypeptide YARAAARQARAKALARQLGVAA (SEQ ID NO: 1) is a fusion protein comprising a first polypeptide operatively linked to a second polypeptide, wherein the first polypeptide comprises a cell penetrating peptide functionally equivalent to YARAAARQARA (SEQ ID NO: 11), and the second polypeptide is of amino acid sequence KALARQLGVAA (SEQ ID NO: 2), and the pharmaceutical composition inhibits both the kinase activity of Mitogen-Activated Protein Kinase-Activated Protein Kinase 2 (MK2).

According to another embodiment, the first polypeptide is a polypeptide of amino acid sequence WLRRIKAWLRRIKA (SEQ ID NO: 12).

According to another embodiment, the first polypeptide is a polypeptide of amino acid sequence WLRRIKA (SEQ ID NO: 13).

According to another embodiment, the first polypeptide is a polypeptide of amino acid sequence YGRKKRRQRRR (SEQ ID NO: 14).

According to another embodiment, the first polypeptide is a polypeptide of amino acid sequence WLRRIKAWLRRI (SEQ ID NO: 15).

According to another embodiment, the first polypeptide is a polypeptide of amino acid sequence FAKLAARLYR (SEQ ID NO: 16). According to some such embodiments, the first polypeptide is a polypeptide of amino acid sequence KAFAKLAARLYR (SEQ ID NO: 17). According to some such embodiments, the first polypeptide is a polypeptide of amino acid sequence HRRIKAWLKKI (SEQ ID NO: 18).

According to another aspect, the described invention also provides an isolated nucleic acid that encodes a protein sequence with at least 70% amino acid sequence identity to amino acid sequence YARAAARQARAKALARQLGVAA (SEQ ID NO: 1).

According to some such embodiments, the isolated nucleic acid encodes a protein sequence with at least 80% amino acid sequence identity to amino acid sequence YARAAARQARAKALARQLGVAA (SEQ ID NO: 1). According to some other embodiments, the isolated nucleic acid encodes a protein sequence with at least 90% amino acid sequence identity to amino acid sequence YARAAARQARAKALARQLGVAA (SEQ ID NO: 1). According to some other embodiments, the isolated nucleic acid encodes a protein sequence with at least 95% amino acid sequence identity to amino acid sequence YARAAARQARAKALARQLGVAA (SEQ ID NO: 1).

According to another embodiment, the step of administering may occur systemically either orally, buccally, parenterally, topically, by inhalation, by insufflation, or rectally, or may occur locally by means such as, but not limited to, injection, implantation, grafting, topical application, or parenterally. Additional administration may be performed, for example, intravenously, transmucosally, transdermally, intramuscularly, subcutaneously, intratracheally (including by pulmonary inhalation), intraperitoneally, intrathecally, intralymphatically, intralesionally, or epidurally. Administering can be performed, for example, once, a plurality of times, and/or over one or more extended periods either as individual unit doses or in the form of a treatment regimen comprising multiple unit doses of multiple drugs and/or substances.

According to some other embodiments, the step of administering occurs at one time as a single dose. According to some other embodiments, the step of administering is performed as a plurality of doses over a period of time. According to some such embodiments, the period of time is a day, a week, a month, a month, a year, or multiples thereof. According to some embodiments, the step of administering is performed daily for a period of at least one week. According to some embodiments, the step of administering is performed weekly for a period of at least one month. According to some embodiments, the step of administering is performed monthly for a period of at least two months. According to another embodiment, the step of administering is performed repeatedly over a period of at least one year. According to another embodiment, the step of administering is performed at least once monthly. According to another embodiment, the step of administering is performed at least once weekly. According to another embodiment, the step of administering is performed at least once daily.

According to some other embodiments, the therapeutic amount of the pharmaceutical composition is administered via an inhalation device. Examples of the inhalation device that can be used for administering the pharmaceutical composition include, but are not limited to, a nebulizer, a metered-dose inhaler (MDI), a dry powder inhaler (DPI), and a dry powder nebulizer.

According to another embodiment, the dry powder comprises microparticles with Mass Median Aerodynamic Diameter (MMAD) of 1 to 5 microns. According to another embodiment, the dry powder comprises microparticles with Mass Median Aerodynamic Diameter (MMAD) of about 2 micron.

According to some other embodiments, the therapeutic amount of the therapeutic inhibitor peptide of the pharmaceutical composition is of an amount from about 0.000001 mg/kg body weight to about 100 mg/kg body weight. According to another embodiment, the therapeutic amount of the therapeutic inhibitory peptide of the pharmaceutical composition is of an amount from about 0.00001 mg/kg body weight to about 100 mg/kg body weight. According to another embodiment, the therapeutic amount of the therapeutic inhibitory peptide of the pharmaceutical composition is of an amount from about 0.0001 mg/kg body weight to about 100 mg/kg body weight. According to another embodiment, the therapeutic amount of the therapeutic inhibitory peptide of the pharmaceutical composition is of an amount from about 0.001 mg/kg body weight to about 10 mg/kg body weight. According to another embodiment, the therapeutic amount of the therapeutic inhibitory peptide of the pharmaceutical composition is of an amount from about 0.01 mg/kg body weight to about 10 mg/kg body weight. According to another embodiment, the therapeutic amount of the therapeutic inhibitory peptide of the pharmaceutical composition is of an amount from about 0.1 mg/kg (or 100 μg/kg) body weight to about 10 mg/kg body weight. According to another embodiment, the therapeutic amount of the therapeutic inhibitory peptide of the pharmaceutical composition is of an amount from about 1 mg/kg body weight to about 10 mg/kg body weight. According to another embodiment, the therapeutic amount of the therapeutic inhibitory peptide of the pharmaceutical composition is of an amount from about 10 mg/kg body weight to about 100 mg/kg body weight. According to another embodiment, the therapeutic amount of the therapeutic inhibitory peptide of the pharmaceutical composition is of an amount from about 2 mg/kg body weight to about 10 mg/kg body weight. According to another embodiment, the therapeutic amount of the therapeutic inhibitory peptide of the pharmaceutical composition is of an amount from about 3 mg/kg body weight to about 10 mg/kg body weight. According to another embodiment, the therapeutic amount of the therapeutic inhibitory peptide of the pharmaceutical composition is of an amount from about 4 mg/kg body weight to about 10 mg/kg body weight. According to another embodiment, the therapeutic amount of the therapeutic inhibitory peptide of the pharmaceutical composition is of an amount from about 5 mg/kg body weight to about 10 mg/kg body weight. According to another embodiment, the therapeutic amount of the therapeutic inhibitory peptide of the pharmaceutical composition is of an amount from about 60 mg/kg body weight to about 100 mg/kg body weight. According to another embodiment, the therapeutic amount of the therapeutic inhibitory peptide of the pharmaceutical composition is of an amount from about 70 mg/kg body weight to about 100 mg/kg body weight. According to another embodiment, the therapeutic amount of the therapeutic inhibitory peptide of the pharmaceutical composition is of an amount from about 80 mg/kg body weight to about 100 mg/kg body weight. According to another embodiment, the therapeutic amount of the therapeutic inhibitory peptide of the pharmaceutical composition is of an amount from about 90 mg/kg body weight to about 100 mg/kg body weight. According to another embodiment, the therapeutic amount of the therapeutic inhibitor peptide of the pharmaceutical composition is of an amount from about 0.000001 mg/kg body weight to about 90 mg/kg body weight. According to another embodiment, the therapeutic amount of the therapeutic inhibitor peptide of the pharmaceutical composition is of an amount from about 0.000001 mg/kg body weight to about 80 mg/kg body weight. According to another embodiment, the therapeutic amount of the therapeutic inhibitor peptide of the pharmaceutical composition is of an amount from about 0.000001 mg/kg body weight to about 70 mg/kg body weight. According to another embodiment, the therapeutic amount of the therapeutic inhibitor peptide of the pharmaceutical composition is of an amount from about 0.000001 mg/kg body weight to about 60 mg/kg body weight. According to another embodiment, the therapeutic amount of the therapeutic inhibitor peptide of the pharmaceutical composition is of an amount from about 0.000001 mg/kg body weight to about 50 mg/kg body weight. According to another embodiment, the therapeutic amount of the therapeutic inhibitor peptide of the pharmaceutical composition is of an amount from about 0.000001 mg/kg body weight to about 40 mg/kg body weight. According to another embodiment, the therapeutic amount of the therapeutic inhibitor peptide is of an amount from about 0.000001 mg/kg body weight to about 30 mg/kg body weight. According to another embodiment, the therapeutic amount of the therapeutic inhibitor peptide of the pharmaceutical composition is of an amount from about 0.000001 mg/kg body weight to about 20 mg/kg body weight. According to another embodiment, the therapeutic amount of the therapeutic inhibitor peptide of the pharmaceutical composition is of an amount from about 0.000001 mg/kg body weight to about 10 mg/kg body weight. According to another embodiment, the therapeutic amount of the therapeutic inhibitor peptide of the pharmaceutical composition is of an amount from about 0.000001 mg/kg body weight to about 1 mg/kg body weight. According to another embodiment, the therapeutic amount of the therapeutic inhibitor peptide of the pharmaceutical composition is of an amount from about 0.000001 mg/kg body weight to about 0.1 mg/kg body weight. According to another embodiment, the therapeutic amount of the therapeutic inhibitor peptide of the pharmaceutical composition is of an amount from about 0.000001 mg/kg body weight to about 0.1 mg/kg body weight. According to another embodiment, the therapeutic amount of the therapeutic inhibitor peptide of the pharmaceutical composition is of an amount from about 0.000001 mg/kg body weight to about 0.01 mg/kg body weight. According to another embodiment, the therapeutic amount of the therapeutic inhibitor peptide of the pharmaceutical composition is of an amount from about 0.000001 mg/kg body weight to about 0.001 mg/kg body weight. According to another embodiment, the therapeutic amount of the therapeutic inhibitor peptide of the pharmaceutical composition is of an amount from about 0.000001 mg/kg body weight to about 0.0001 mg/kg body weight. According to another embodiment, the therapeutic amount of the therapeutic inhibitor peptide of the pharmaceutical composition is of an amount from about 0.000001 mg/kg body weight to about 0.00001 mg/kg body weight.

According to some other embodiments, the therapeutic dose of the therapeutic inhibitor peptide of the pharmaceutical composition ranges from 1 µg/kg/day to 25 µg/kg/day. According to some other embodiments, the therapeutic dose of the therapeutic inhibitor peptide of the pharmaceutical composition ranges from 1 µg/kg/day to 2 µg/kg/day. According to some other embodiments, the therapeutic dose of the therapeutic inhibitor peptide of the pharmaceutical composition ranges from 2 µg/kg/day to 3 µg/kg/day. According to some other embodiments, the therapeutic dose of the therapeutic inhibitor peptide of the pharmaceutical composition ranges from 3 µg/kg/day to 4 µg/kg/day. According to some other embodiments, the therapeutic dose of the therapeutic inhibitor peptide of the pharmaceutical ranges from 4 µg/kg/day to 5 µg/kg/day. According to some other embodiments, the therapeutic dose of the therapeutic inhibitor peptide of the pharmaceutical composition ranges from 5 µg/kg/day to 6 µg/kg/day. According to some other embodiments, the therapeutic dose of the therapeutic inhibitor peptide of the pharmaceutical composition ranges from 6 µg/kg/day to 7 µg/kg/day. According to some other embodiments, the therapeutic dose of the therapeutic inhibitor peptide of the pharmaceutical composition ranges from 7 µg/kg/day to 8 µg/kg/day. According to some other embodiments, the therapeutic dose of the therapeutic inhibitor peptide of the pharmaceutical composition ranges from 8 µg/kg/day to 9 µg/kg/day. According to some other embodiments, the therapeutic dose of the therapeutic inhibitor peptide of the pharmaceutical composition ranges from 9 µg/kg/day to 10 µg/kg/day. According to some other embodiments, the therapeutic dose of the therapeutic inhibitor peptide of the pharmaceutical composition ranges from 1 µg/kg/day to 5 µg/kg/day. According to some other embodiments, the therapeutic dose of the therapeutic inhibitor peptide of the pharmaceutical composition ranges from 5 µg/kg/day to 10 µg/kg/day. According to some other embodiments, the therapeutic dose of the therapeutic inhibitor peptide of the pharmaceutical composition ranges from 10 µg/kg/day to 15 µg/kg/day. According to some other embodiments, the therapeutic dose of the therapeutic inhibitor peptide of the pharmaceutical composition ranges from 15 µg/kg/day to 20 µg/kg/day. According to some other embodiments, the therapeutic dose of the therapeutic inhibitor peptide of the pharmaceutical composition ranges from 25 µg/kg/day to 30 µg/kg/day. According to some other embodiments, the therapeutic dose of the therapeutic inhibitor peptide of the pharmaceutical composition ranges from 30 µg/kg/day to 35 µg/kg/day. According to some other embodiments, the therapeutic dose of the therapeutic inhibitor peptide of the pharmaceutical composition ranges from 35 µg/kg/day to 40 µg/kg/day. According to some other embodiments, the therapeutic dose of the therapeutic inhibitor peptide of the pharmaceutical composition ranges from 40 µg/kg/day to 45 µg/kg/day. According to some other embodiments, the therapeutic dose of the therapeutic inhibitor peptide of the pharmaceutical composition ranges from 45 µg/kg/day to 50 µg/kg/day. According to some other embodiments, the therapeutic dose of the therapeutic inhibitor peptide of the pharmaceutical composition ranges from 50 µg/kg/day to 55 µg/kg/day. According to some other embodiments, the therapeutic dose of the therapeutic inhibitor peptide of the pharmaceutical composition ranges from 55 µg/kg/day to 60 µg/kg/day. According to some other embodiments, the therapeutic dose of the therapeutic inhibitor peptide of the pharmaceutical composition ranges from 60 µg/kg/day to 65 µg/kg/day. According to some other embodiments, the therapeutic dose of the therapeutic inhibitor peptide of the pharmaceutical composition ranges from 65 µg/kg/day to 70 µg/kg/day. According to some other embodiments, the therapeutic dose of the therapeutic inhibitor peptide of the pharmaceutical composition ranges from 70 µg/kg/day to 75 µg/kg/day. According to some other embodiments, the therapeutic dose of the therapeutic inhibitor peptide of the pharmaceutical composition ranges from 80 µg/kg/day to 85 µg/kg/day. According to some other embodiments, the therapeutic dose of the therapeutic inhibitor peptide of the pharmaceutical composition ranges from 85 µg/kg/day to 90 µg/kg/day. According to some other embodiments, the therapeutic dose of the therapeutic inhibitor peptide of the pharmaceutical composition ranges from 90 µg/kg/day to 95 µg/kg/day. According to some other embodiments, the therapeutic dose of the therapeutic inhibitor peptide of the pharmaceutical composition ranges from 95 µg/kg/day to 100 µg/kg/day.

According to another embodiment, the therapeutic dose of the therapeutic inhibitor peptide of the pharmaceutical composition is 1 µg/kg/day.

According to another embodiment, the therapeutic dose of the therapeutic inhibitor peptide of the pharmaceutical composition is 2 µg/kg/day.

According to another embodiment, the therapeutic dose of the therapeutic inhibitor peptide of the pharmaceutical composition is 5 µg/kg/day.

According to another embodiment, the therapeutic dose of the therapeutic inhibitor peptide of the pharmaceutical composition is 10 µg/kg/day.

III. Systems for Preventing or Treating Diseases Characterized by Aberrant Fibroblast Proliferation and Collagen Deposition According to another aspect, the described invention provides a system for the treatment of a disease, condition, or process characterized by aberrant fibroblast proliferation and extracellular matrix deposition in a tissue of a subject, wherein the pharmaceutical composition comprises a therapeutic amount of a polypeptide of the amino acid sequence YARAAARQARAKALARQLGVAA (SEQ ID NO: 1) or a functional equivalent thereof, and a pharmaceutically acceptable carrier thereof, and wherein the therapeutic amount is effective to reduce the fibroblast proliferation and extracellular matrix deposition in the tissue of the subject.

According to one embodiment of the method, the disease or the condition is Acute Lung Injury (ALI) or acute respiratory distress syndrome (ARDS).

According to another embodiment, the disease or the condition is radiation-induced fibrosis.

According to another embodiment, the disease or the condition is transplant rejection.

According to another embodiment, the tissue is a lung tissue.

According to another embodiment, the disease or the condition is an interstitial lung disease.

According to another embodiment, the disease or the condition is pulmonary fibrosis.

According to another embodiment, the pulmonary fibrosis is idiopathic pulmonary fibrosis.

According to another embodiment, the pulmonary fibrosis results from administration of bleomycin.

According to another embodiment, the pulmonary fibrosis results from an allergic reaction, inhalation of environmental particulates, a bacterial infection, a viral infection, mechanical damage to a lung of the subject, lung transplantation rejection, an autoimmune disorder, a genetic disorder, or a combination thereof.

According to another embodiment, the disease or the condition is further characterized by an inflammation in the tissue.

According to another embodiment, the inflammation is an acute or a chronic inflammation.

According to another embodiment, the inflammation is mediated by at least one cytokine selected from the group consisting of Tumor Necrosis Factor-alpha (TNF-α), Interleukin-6 (IL-6), and Interleukin-1β (IL-1β).

According to another embodiment, the aberrant fibroblast proliferation and extracellular matrix deposition in the tissue is characterized by an aberrant activity of Mitogen-Activated Protein Kinase-Activated Protein Kinase 2 (MK2) in the tissue compared to the activity of Mitogen-Activated Protein Kinase-Activated Protein Kinase 2 (MK2) in the tissue of a normal healthy control subject.

According to another embodiment, the aberrant fibroblast proliferation and extracellular matrix deposition in the tissue is evidenced by an aberrant amount or distribution of activated (phosphorylated) Mitogen-Activated Protein Kinase-Activated Protein Kinase 2 (MK2) in the tissue compared to the amount or distribution of activated Mitogen-Activated Protein Kinase-Activated Protein Kinase 2 (MK2) in the tissue of a normal healthy control subject.

According to another embodiment, the pulmonary fibrosis is characterized by at least one pathology selected from the group consisting of an aberrant deposition of an extracellular matrix protein in a pulmonary interstitium, an aberrant promotion of fibroblast proliferation in the lung, an aberrant induction of differentiation of a population of fibroblasts into a population of myofibroblasts in the lung, and an aberrant promotion of attachment of myofibroblasts to an extracellular matrix compared to a normal healthy control subject.

According to another embodiment, the pharmaceutically acceptable carrier includes, but is not limited to, a controlled release carrier, a delayed release carrier, a sustained release carrier, and a long-term release carrier.

According to another embodiment, the inhalation device is a nebulizer.

According to another embodiment, the inhalation device is a metered-dose inhaler (MDI).

According to another embodiment, the inhalation device is a dry powder inhaler (DPI).

According to another embodiment, the inhalation device is a dry powder nebulizer.

According to another embodiment, the pharmaceutical composition is in a form of a dry powder.

According to another embodiment, the dry powder comprises microparticles with Mass Median Aerodynamic Diameter (MMAD) of 1 to 5 microns.

According to another embodiment, the dry powder comprises microparticles with Mass Median Aerodynamic Diameter (MMAD) of about 2 micron.

According to some embodiments, the pharmaceutical composition further comprises an additional therapeutic agent.

According to some such embodiments, the additional therapeutic agent is selected from the group consisting of purified bovine Type V collagens (e.g., IW-001; ImmuneWorks; United Therapeutics), IL-13 receptor antagonists (e.g., QAX576; Novartis), protein tyrosine kinase inhibitors (e.g., imatinib (Gleevec®); Craig Daniels/Novartis), endothelial receptor antagonists (e.g., ACT-064992 (macitentan); Actelion), dual endothelin receptor antagonists (e.g., bosentan (Tracleer®); Actelion), prostacyclin analogs (inhaled iloprost (e.g., Ventavis®); Actelion), anti-CTGF monoclonal antibodies (e.g., FG-3019), endothelin receptor antagonists (A-selective) (e.g., ambrisentan (Letairis®), Gilead), AB0024 (Arresto), lysyl oxidase-like 2 (LOXL2) monoclonal antibodies (e.g., GS-6624 (formerly AB0024); Gilead), c-Jun N-terminal kinase (JNK) inhibitors (e.g., CC-930; Celgene), Pirfenidone (e.g., Esbriet® (InterMune), Pirespa® (Shionogi)), IFN-γ1b (e.g., Actimmune®; InterMune), pan-neutralizing IgG4 human antibodies against all three TGF-β isoforms (e.g., GC1008; Genzyme), TGF-β activation inhibitors (e.g., Stromedix (STX-100)), recombinant human Pentraxin-2 protein (rhPTX-2) (e.g., PRM151; Promedior), bispecific IL4/IL13 antibodies (e.g., SAR156597; Sanofi), humanized monoclonal antibodies targeting integrin αvβ6 (BIBF 1120; Boehringer Ingelheim), N-acetylcysteine (Zambon SpA), Sildenafil (Viagra®), TNF antagonists (e.g., etanercept (Enbrel®); Pfizer), glucocorticoids (e.g., prednisone, budesonide, mometasone furoate, fluticasone propionate, and fluticasone furoate), bronchodilators (e.g., leukotriene modifers (e.g., Montelukast (SINGUAIR®)), anticholingertic bronchodilators (e.g., Ipratropium bromide and Tiotropium), short-acting β2-agonists (e.g., isoetharine mesylate (Bronkometer®), adrenalin, salbutanol/albuterol, and terbutaline), long-acting β2-agonists (e.g., salmeterol, formoterol, indecaterol (Onbrez®), and a combination thereof.

According to some other embodiments, the additional therapeutic agent comprises a bronchodilator including, but not limited to, a leukotriene modifier, an anticholinergic bronchodilator, a β2-agonist, or a combination thereof.

According to another embodiment, the additional therapeutic agent comprises a corticosteroid including, but not limited to, prednisone, budesonide, mometasone, beclemethasone, or a combination thereof.

According to some such embodiments, the additional therapeutic agent comprises a bronchodilator including, but not limited to, a leukotriene modifier, an anticholinergic bronchodilator, a β2-agonist, or a combination thereof.

According to another embodiment, the additional therapeutic agent comprises a corticosteroid including, but not limited to, prednisone, budesonide, mometasone, beclemethasone, or a combination thereof.

According to another embodiment, the additional therapeutic agent is an anti-inflammatory agent.

According to another embodiment, the anti-inflammatory agent is a nonsteroidal anti-inflammatory agent. Mixtures of non-steroidal anti-inflammatory agents also may be employed, as well as the dermatologically acceptable salts and esters of these agents. For example, etofenamate, a flufenamic acid derivative, is particularly useful for topical application.

According to another embodiment, wherein the nonsteroidal anti-inflammatory agent comprises Transforming Growth Factor-β3 (TGF-β3), an anti-Tumor Necrosis Factor-alpha (TNF-α) agent, or a combination thereof.

According to another embodiment, the anti-inflammatory agent is a steroidal anti-inflammatory agent. According to another embodiment, the steroidal anti-inflammatory agent comprises at least one corticosteroid selected from the group consisting of prednisone, budesonide, mometasone, beclemethasone, and a combination thereof.

According to another embodiment, the additional therapeutic agent comprises a methylxanthine.

According to another embodiment, the additional therapeutic agent comprises a neutrophil elastase inhibitor.

According to another embodiment, the additional therapeutic agent is at least one neutrophil elastase inhibitor, including, but not limited to, ICI 200355, ONO-5046, MR-889, L-694,458, CE-1037, GW-311616, TEI-8362, ONO-6818, AE-3763, FK-706, ICI-200,880, ZD-0892, ZD-8321, and a combination thereof.

According to another embodiment, the additional therapeutic agent comprises at least one phosphodiesterase inhibitor, including, but not limited to, phosphodiesterase 4 inhibitor. Examples of phosphodiesterase 4 inhibitors include, but are not limited to, roflumilast, cilomilast or a combination thereof.

According to another embodiment, the additional therapeutic agent is an analgesic agent. According to some such embodiments, the analgesic agent is a non-opioid analgesic. According to some other embodiments, the analgesic is an opioid analgesic.

According to another embodiment, the additional therapeutic agent is an anti-infective agent. According to another embodiment, the anti-infective agent is an antibiotic agent.

According to another embodiment, the pharmaceutical composition inhibits inflammation occurring in a lung of the subject. According to another embodiment, the inflammation is an acute inflammation. According to another embodiment, the inflammation is a chronic inflammation. According to another embodiment, the inflammation is mediated by an elevated level of Tumor Necrosis Factor-alpha (TNF-α). According to another embodiment, the inflammation is mediated by an elevated level of Interleukin-6 (IL-6). According to another embodiment, the inflammation is mediated by an elevated level of Interleukin-1β (IL-1β).

According to another embodiment, the pharmaceutical composition modulates an amount of Tumor Necrosis Factor-alpha (TNF-α) in the lung, compared to a control. According to another embodiment, the pharmaceutical composition modulates an amount of Interleukin-6 (IL-6) in the lung, compared to a control. According to another embodiment, the pharmaceutical composition modulates an amount of Interleukin-1β (IL-1β) in the lung, compared to a control.

According to another embodiment, the pharmaceutical composition inhibits an activity of HSPB1. According to another embodiment, the activity of HSPB1 inhibited by the pharmaceutical composition is an aberrant induction of fibroblast proliferation. According to another embodiment, the activity of HSPB1 inhibited by the pharmaceutical composition is an aberrant induction of differentiation of a population of fibroblasts into a population of myofibroblasts. According to another embodiment, the activity of HSPB1 inhibited by the pharmaceutical composition is a deposition of an extracellular matrix protein into a pulmonary interstitium. According to another embodiment, the extracellular matrix protein is collagen. According to another embodiment, the activity of HSPB1 inhibited by the pharmaceutical composition is a promotion of fibrotic loci formation. According to another embodiment, the activity of HSPB1 inhibited by the pharmaceutical composition is an increase of myofibroblast contractile activity. According to another embodiment, the activity of HSPB1 inhibited by the pharmaceutical composition is a promotion of myofibroblast attachment to extracellular matrix.

According to another embodiment, the aberrant fibroblast proliferation and extracellular matrix deposition in the tissue is evidenced by an aberrant amount or distribution of activated (phosphorylated) Mitogen-Activated Protein Kinase-Activated Protein Kinase 2 (MK2) in the tissue compared to the amount or distribution of activated Mitogen-Activated Protein Kinase-Activated Protein Kinase 2 (MK2) in the tissue of a normal healthy control subject.

According to another embodiment, the pharmaceutical composition inhibits a kinase activity of a kinase selected from the group listed in Table 1 herein.

According to another embodiment, the pharmaceutical composition inhibits at least 50% of the kinase activity of the kinase. According to another embodiment, the pharmaceutical composition inhibits at least 65% of the kinase activity of the kinase. According to another embodiment, the pharmaceutical composition inhibits at least 75% of the kinase activity of that kinase. According to another embodiment, the pharmaceutical composition inhibits at least 80% of the kinase activity of that kinase. According to another embodiment, the pharmaceutical composition inhibits at least 85% of the kinase activity of that kinase. According to another embodiment, the pharmaceutical composition inhibits at least 90% of the kinase activity of that kinase. According to another embodiment, the pharmaceutical composition inhibits at least 95% of the kinase activity of that kinase.

According to some embodiments, inhibitory profiles of MMI inhibitors in vivo depend on dosages, routes of administration, and cell types responding to the inhibitors.

According to another embodiment, the pharmaceutical composition inhibits at least 50% of the kinase activity of the kinase. According to another embodiment, the pharmaceutical composition inhibits at least 65% of the kinase activity of the kinase. According to another embodiment, the pharmaceutical composition inhibits at least 75% of the kinase activity of that kinase. According to another embodiment, the pharmaceutical composition inhibits at least 80% of the kinase activity of that kinase. According to another embodiment, the pharmaceutical composition inhibits at least 85% of the kinase activity of that kinase. According to another embodiment, the pharmaceutical composition inhibits at least 90% of the kinase activity of that kinase. According to another embodiment, the pharmaceutical composition inhibits at least 95% of the kinase activity of that kinase.

According to another embodiment, the pharmaceutical composition inhibits a kinase activity of Mitogen-Activated Protein Kinase-Activated Protein Kinase 2 (MK2 kinase). According to another embodiment, the pharmaceutical composition inhibits at least 50% of the kinase activity of MK2 kinase. According to another embodiment, the pharmaceutical composition inhibits at least 65% of the kinase activity of MK2 kinase. According to another embodiment, the pharmaceutical composition inhibits at least 75% of the kinase activity of MK2 kinase. According to another embodiment, the pharmaceutical composition inhibits at least 80% of the kinase activity of MK2 kinase. According to another embodiment, the pharmaceutical composition inhibits at least 85% of the kinase activity of MK2 kinase. According to another embodiment, the pharmaceutical composition inhibits at least 90% of the kinase activity of MK2 kinase. According to another embodiment, the pharmaceutical composition inhibits at least 95% of the kinase activity of MK2 kinase.

According to another embodiment, the pharmaceutical composition inhibits a kinase activity of Mitogen-Activated Protein Kinase-Activated Protein Kinase 3 (MK3 kinase). According to another embodiment, the pharmaceutical composition further inhibits at least 50% of the kinase activity of MK3 kinase. According to another embodiment, the pharmaceutical composition further inhibits at least 65% of the kinase activity of MK3 kinase. According to another embodiment, the pharmaceutical composition further inhibits at least 70% of the kinase activity of MK3 kinase. According to another embodiment, the pharmaceutical composition further inhibits at least 75% of the kinase activity of MK3 kinase. According to another embodiment, the pharmaceutical composition further inhibits at least 80% of the kinase activity of MK3 kinase. According to another embodiment, the pharmaceutical composition further inhibits at least 85% of the kinase activity of MK3 kinase. According to another embodiment, the pharmaceutical composition further inhibits at least 90% of the kinase activity of MK3 kinase. According to another embodiment, the pharmaceutical composition further inhibits at least 95% of the kinase activity of MK3 kinase.

According to another embodiment, the pharmaceutical composition inhibits a kinase activity of calcium/calmodulin-dependent protein kinase I (CaMKI). According to another embodiment, the pharmaceutical composition further inhibits at least 50% of the kinase activity of $Ca^{2+}$/calmodulin-dependent protein kinase I (CaMKI). According to another embodiment, the pharmaceutical composition further inhibits at least 65% of the kinase activity of $Ca^{2+}$/calmodulin-dependent protein kinase I (CaMKI). According to another embodiment, the pharmaceutical composition further inhibits at least 70% of the kinase activity of $Ca^{2+}$/calmodulin-dependent protein kinase I (CaMKI). According to another embodiment, the pharmaceutical composition further inhibits at least 75% of the kinase activity of $Ca^{2+}$/calmodulin-dependent protein kinase I (CaMKI). According to another embodiment, the pharmaceutical composition further inhibits at least 80% of the kinase activity of $Ca^{2+}$/calmodulin-dependent protein kinase I (CaMKI). According to another embodiment, the pharmaceutical composition further inhibits at least 85% of the kinase activity of $Ca^{2+}$/calmodulin-dependent protein kinase I (CaMKI). According to another embodiment, the pharmaceutical composition further inhibits at least 90% of the kinase activity of $Ca^{2+}$/calmodulin-dependent protein kinase I (CaMKI). According to another embodiment, the pharmaceutical composition further inhibits at least 95% of the kinase activity of $Ca^{2+}$/calmodulin-dependent protein kinase I (CaMKI).

According to another embodiment, the pharmaceutical composition inhibits a kinase activity of BDNF/NT-3 growth factors receptor (TrkB). According to another embodiment, the pharmaceutical further inhibits at least 50% of the kinase activity of BDNF/NT-3 growth factors receptor (TrkB). According to another embodiment, the pharmaceutical further inhibits at least 65% of the kinase activity of BDNF/NT-3 growth factors receptor (TrkB). According to another embodiment, the pharmaceutical further inhibits at least 70% of the kinase activity of BDNF/NT-3 growth factors receptor (TrkB). According to another embodiment, the pharmaceutical further inhibits at least 75% of the kinase activity of BDNF/NT-3 growth factors receptor (TrkB).

According to another embodiment, the pharmaceutical composition inhibits a kinase activity of Mitogen-Activated Protein Kinase-Activated Protein Kinase 2 (MK2) and a kinase activity of Mitogen-Activated Protein Kinase-Activated Protein Kinase 3 (MK3).

According to another embodiment, the pharmaceutical composition inhibits a kinase activity of Mitogen-Activated Protein Kinase-Activated Protein Kinase 2 (MK2) and a kinase activity of calcium/calmodulin-dependent protein kinase I (CaMKI).

According to another embodiment, the pharmaceutical composition inhibits a kinase activity of Mitogen-Activated Protein Kinase-Activated Protein Kinase 2 (MK2) and a kinase activity of BDNF/NT-3 growth factors receptor (TrkB).

According to another embodiment, the pharmaceutical composition inhibits a kinase activity of Mitogen-Activated Protein Kinase-Activated Protein Kinase 2 (MK2), a kinase activity of Mitogen-Activated Protein Kinase-Activated Protein Kinase 3 (MK3), a kinase activity of calcium/calmodulin-dependent protein kinase I (CaMKI), and a kinase activity of BDNF/NT-3 growth factors receptor (TrkB).

According to another embodiment, the pharmaceutical composition inhibits a kinase activity of Mitogen-Activated Protein Kinase-Activated Protein Kinase 2 (MK2), a kinase activity of calcium/calmodulin-dependent protein kinase I (CaMKI), and a kinase activity of BDNF/NT-3 growth factors receptor (TrkB).

According to another embodiment, the pharmaceutical composition inhibits at least 65% of the kinase activity of Mitogen-Activated Protein Kinase-Activated Protein Kinase 2 (MK2).

According to another embodiment, the pharmaceutical composition inhibits at least 65% of the kinase activity of Mitogen-Activated Protein Kinase-Activated Protein Kinase 3 (MK3).

According to another embodiment, the pharmaceutical composition inhibits at least 65% of the kinase activity of calcium/calmodulin-dependent protein kinase I (CaMKI).

According to another embodiment, the pharmaceutical composition inhibits at least 65% of the kinase activity of BDNF/NT-3 growth factors receptor (TrkB).

According to another embodiment, the pharmaceutical composition inhibits at least 65% of the kinase activity of Mitogen-Activated Protein Kinase-Activated Protein Kinase 2 (MK2) and at least 65% of the kinase activity of Mitogen-Activated Protein Kinase-Activated Protein Kinase 3 (MK3).

According to another embodiment, the pharmaceutical composition inhibits at least 65% of the kinase activity of Mitogen-Activated Protein Kinase-Activated Protein Kinase 2 (MK2) and at least 65% of the kinase activity of calcium/calmodulin-dependent protein kinase I (CaMKI).

According to another embodiment, the pharmaceutical composition inhibits at least 65% of the kinase activity of Mitogen-Activated Protein Kinase-Activated Protein Kinase 2 (MK2) and at least 65% of the kinase activity of BDNF/NT-3 growth factors receptor (TrkB).

According to another embodiment, the pharmaceutical composition inhibits at least 65% of the kinase activity of Mitogen-Activated Protein Kinase-Activated Protein Kinase 2 (MK2), at least 65% of the kinase activity of Mitogen-Activated Protein Kinase-Activated Protein Kinase 3 (MK3), at least 65% of the kinase activity of calcium/calmodulin-dependent protein kinase I (CaMKI), and at least 65% of the kinase activity of BDNF/NT-3 growth factors receptor (TrkB).

According to another embodiment, the pharmaceutical composition inhibits the kinase activity of at least one kinase selected from the group of MK2, MK3, CaMKI, TrkB, without substantially inhibiting the activity of one or more other selected kinases from the remaining group listed in Table 1 herein.

According to another embodiment, the pharmaceutical composition inhibits a kinase activity of a kinase selected from the group listed in Table 1 herein.

According to another embodiment, this inhibition may, for example, be effective to reduce fibroblast prolfieration, extracellular matrix deposition, or a combination thereof in the tissue of the subject.

According to another embodiment, this inhibition may, for example, be effective to reduce at least one pathology selected from the group consisting of an aberrant deposition of an extracellular matrix protein in a pulmonary interstitium, an aberrant promotion of fibroblast proliferation in the lung, an aberrant induction of myofibroblast differentiation, and an aberrant promotion of attachment of myofibroblasts to an extracellular matrix, compared to a normal healthy control subject.

According to some embodiments, inhibitory profiles of MMI inhibitors in vivo depend on dosages, routes of administration, and cell types responding to the inhibitors.

According to such embodiment, the pharmaceutical composition inhibits less than 50% of the kinase activity of the other selected kinase(s). According to such embodiment, the pharmaceutical composition inhibits less than 65% of the kinase activity of the other selected kinase(s). According to such embodiment, the pharmaceutical composition inhibits less than 50% of the kinase activity of the other selected kinase(s). According to another embodiment, the pharmaceutical composition inhibits less than 40% of the kinase activity of the other selected kinase(s). According to another embodiment, the pharmaceutical composition inhibits less than 20% of the kinase activity of the other selected kinase(s). According to another embodiment, the pharmaceutical composition inhibits less than 15% of the kinase activity of the other selected kinase(s). According to another embodiment, the pharmaceutical composition inhibits less than 10% of the kinase activity of the other selected kinase(s). According to another embodiment, the pharmaceutical composition inhibits less than 5% of the kinase activity of the other selected kinase(s). According to another embodiment, the pharmaceutical composition increases the kinase activity of the other selected kinases.

According to the embodiments of the immediately preceding paragraph, the one or more other selected kinase that is not substantially inhibited is selected from the group of $Ca^{2+}$/calmodulin-dependent protein kinase II (CaMKII, including its subunit CaMKIIδ), Proto-oncogene serine/threonine-protein kinase (PIM-1), cellular-Sarcoma (c-SRC), Spleen Tyrosine Kinase (SYK), C-src Tyrosine Kinase (CSK), and Insulin-like Growth Factor 1 Receptor (IGF-1R).

According to some embodiments, the functional equivalent of the polypeptide YARAAARQARAKALARQLGVAA (SEQ ID NO: 1) has a substantial sequence identity to amino acid sequence YARAAARQARAKALARQLGVAA (SEQ ID NO: 1).

According to another embodiments, the functional equivalent of the polypeptide YARAAARQARAKALARQLGVAA (SEQ ID NO: 1) has at least 70 percent sequence identity to amino acid sequence YARAAARQARAKALARQLGVAA (SEQ ID NO: 1). According to another embodiment, the functional equivalent of the polypeptide YARAAARQARAKALARQLGVAA (SEQ ID NO: 1) has at least 80 percent sequence identity to amino acid sequence YARAAARQARAKALARQLGVAA (SEQ ID NO: 1). According to another embodiment, the functional equivalent of the polypeptide YARAAARQARAKALARQLGVAA (SEQ ID NO: 1) has at least 90 percent sequence identity to amino acid sequence YARAAARQARAKALARQLGVAA (SEQ ID NO: 1). According to another embodiment, the functional equivalent of the polypeptide YARAAARQARAKALARQLGVAA (SEQ ID NO: 1) has at least 95 percent sequence identity to amino acid sequence YARAAARQARAKALARQLGVAA (SEQ ID NO: 1).

According to another embodiment, the functional equivalent of the polypeptide YARAAARQARAKALARQLGVAA (SEQ ID NO: 1) is of amino acid sequence FAKLAARLYRKALARQLGVAA (SEQ ID NO: 3).

According to another embodiment, the functional equivalent of the polypeptide YARAAARQARAKALARQLGVAA (SEQ ID NO: 1) is of amino acid sequence KAFAKLAARLYRKALARQLGVAA (SEQ ID NO: 4).

According to another embodiment, the functional equivalent of the polypeptide YARAAARQARAKALARQLGVAA (SEQ ID NO: 1) is of amino acid sequence YARAAARQARAKALARQLAVA (SEQ ID NO: 5).

According to another embodiment, the functional equivalent of the polypeptide YARAAARQARAKALARQLGVAA (SEQ ID NO: 1) is of amino acid sequence YARAAARQARAKALARQLGVA (SEQ ID NO: 6).

According to another embodiment, the functional equivalent of the polypeptide YARAAARQARAKALARQLGVAA (SEQ ID NO: 1) is of amino acid sequence HRRIKAWLKKIKALARQLGVAA (SEQ ID NO: 7).

According to some other embodiments, the functional equivalent of the polypeptide YARAAARQARAKALARQLGVAA (SEQ ID NO: 1) is a fusion protein comprising a first polypeptide operatively linked to a second polypeptide, wherein the first polypeptide is of amino acid sequence YARAAARQARA (SEQ ID NO: 11), and the second polypeptide comprises a therapeutic domain whose sequence has a substantial identity to amino acid sequence KALARQLGVAA (SEQ ID NO: 2).

According to another embodiment, the second polypeptide has at least 70 percent sequence identity to amino acid sequence KALARQLGVAA (SEQ ID NO: 2). According to some other embodiments, the second polypeptide has at least 80 percent sequence identity to amino acid sequence KALARQLGVAA (SEQ ID NO: 2). According to some other embodiments, the second polypeptide has at least 90 percent sequence identity to amino acid sequence KALARQLGVAA (SEQ ID NO: 2). According to some other embodiments, the second polypeptide has at least 95 percent sequence identity to amino acid sequence KALARQLGVAA (SEQ ID NO: 2).

According to another embodiment, the second polypeptide is a polypeptide of amino acid sequence KALARQLAVA (SEQ ID NO: 8).

According to another embodiment, the second polypeptide is a polypeptide of amino acid sequence KALARQLGVA (SEQ ID NO: 9).

According to another embodiment, the second polypeptide is a polypeptide of amino acid sequence KALARQLGVAA (SEQ ID NO: 10).

According to some other embodiments, the functional equivalent of the polypeptide YARAAARQARAKALARQLGVAA (SEQ ID NO: 1) is a fusion protein comprising a first polypeptide operatively linked to a second polypeptide, wherein the first polypeptide comprises a cell penetrating peptide functionally equivalent to YARAAARQARA (SEQ ID NO: 11), and the second polypeptide is of amino acid sequence KALARQLGVAA (SEQ ID NO: 2).

According to a further embodiment, the first polypeptide is a polypeptide of amino acid sequence WLRRIKAWLRRIKA (SEQ ID NO: 12).

According to another embodiment, the first polypeptide is a polypeptide of amino acid sequence WLRRIKA (SEQ ID NO: 13).

According to another embodiment, the first polypeptide is a polypeptide of amino acid sequence YGRKKRRQRRR (SEQ ID NO: 14).

According to another embodiment, the first polypeptide is a polypeptide of amino acid sequence WLRRIKAWLRRI (SEQ ID NO: 15).

According to another embodiment, the first polypeptide is a polypeptide of amino acid sequence FAKLAARLYR (SEQ ID NO: 16).

According to another embodiment, the first polypeptide is a polypeptide of amino acid sequence KAFAKLAARLYR (SEQ ID NO: 17).

According to another embodiment, the first polypeptide is a polypeptide of amino acid sequence HRRIKAWLKKI (SEQ ID NO: 18).

According to another aspect, the described invention also provides an isolated nucleic acid that encodes a protein sequence with at least 70% amino acid sequence identity to amino acid sequence YARAAARQARAKALARQLGVAA (SEQ ID NO: 1). According to some such embodiments, the isolated nucleic acid encodes a protein sequence with at least 80% amino acid sequence identity to amino acid sequence YARAAARQARAKALARQLGVAA (SEQ ID NO: 1). According to some such embodiments, the isolated nucleic acid encodes a protein sequence with at least 90% amino acid sequence identity to amino acid sequence YARAAARQARAKALARQLGVAA (SEQ ID NO: 1). According to some such embodiments, the isolated nucleic acid encodes a protein sequence with at least 95% amino acid sequence identity to amino acid sequence YARAAARQARAKALARQLGVAA (SEQ ID NO: 1).

According to some other embodiments, the therapeutic amount of the therapeutic inhibitor peptide of the pharmaceutical composition is of an amount from about 0.000001 mg/kg body weight to about 100 mg/kg body weight. According to another embodiment, the therapeutic amount of the therapeutic inhibitory peptide of the pharmaceutical composition is of an amount from about 0.00001 mg/kg body weight to about 100 mg/kg body weight. According to another embodiment, the therapeutic amount of the therapeutic inhibitory peptide of the pharmaceutical composition is of an amount from about 0.0001 mg/kg body weight to about 100 mg/kg body weight. According to another embodiment, the therapeutic amount of the therapeutic inhibitory peptide of the pharmaceutical composition is of an amount from about 0.001 mg/kg body weight to about 10 mg/kg body weight. According to another embodiment, the therapeutic amount of the therapeutic inhibitory peptide of the pharmaceutical composition is of an amount from about 0.01 mg/kg body weight to about 10 mg/kg body weight. According to another embodiment, the therapeutic amount of the therapeutic inhibitory peptide of the pharmaceutical composition is of an amount from about 0.1 mg/kg (100 µg/kg) body weight to about 10 mg/kg body weight. According to another embodiment, the therapeutic amount of the therapeutic inhibitory peptide of the pharmaceutical composition is of an amount from about 1 mg/kg body weight to about 10 mg/kg body weight. According to another embodiment, the therapeutic amount of the therapeutic inhibitory peptide of the pharmaceutical composition is of an amount from about 10 mg/kg body weight to about 100 mg/kg body weight. According to another embodiment, the therapeutic amount of the therapeutic inhibitory peptide of the pharmaceutical composition is of an amount from about 2 mg/kg body weight to about 10 mg/kg body weight. According to another embodiment, the therapeutic amount of the therapeutic inhibitory peptide of the pharmaceutical composition is of an amount from about 3 mg/kg body weight to about 10 mg/kg body weight. According to another embodiment, the therapeutic amount of the therapeutic inhibitory peptide of the pharmaceutical composition is of an amount from about 4 mg/kg body weight to about 10 mg/kg body weight. According to another embodiment, the therapeutic amount of the therapeutic inhibitory peptide of the pharmaceutical composition is of an amount from about 5 mg/kg body weight to about 10 mg/kg body weight. According to another embodiment, the therapeutic amount of the therapeutic inhibitory peptide of the pharmaceutical composition is of an amount from about 60 mg/kg body weight to about 100 mg/kg body weight. According to another embodiment, the therapeutic amount of the therapeutic inhibitory peptide of the pharmaceutical composition is of an amount from about 70 mg/kg body weight to about 100 mg/kg body weight. According to another embodiment, the therapeutic amount of the therapeutic inhibitory peptide of the pharmaceutical composition is of an amount from about 80 mg/kg body weight to about 100 mg/kg body weight. According to another embodiment, the therapeutic amount of the therapeutic inhibitory peptide of the pharmaceutical composition is of an amount from about 90 mg/kg body weight to about 100 mg/kg body weight. According to another embodiment, the therapeutic amount of the therapeutic inhibitor peptide of the pharmaceutical composition is of an amount from about 0.000001 mg/kg body weight to about 90 mg/kg body weight. According to another embodiment, the therapeutic amount of the therapeutic inhibitor peptide of the pharmaceutical composition is of an amount from about 0.000001 mg/kg body weight to about 80 mg/kg body weight. According to another embodiment, the therapeutic amount of the therapeutic inhibitor peptide of the pharmaceutical composition is of an amount from about 0.000001 mg/kg body weight to about 70 mg/kg body weight. According to another embodiment, the therapeutic amount of the therapeutic inhibitor peptide of the pharmaceutical composition is of an amount from about 0.000001 mg/kg body weight to about 60 mg/kg body weight. According to another embodiment, the therapeutic amount of the therapeutic inhibitor peptide of the pharmaceutical composition is of an amount from about 0.000001 mg/kg body weight to about 50 mg/kg body weight. According to another embodiment, the therapeutic amount of the therapeutic inhibitor peptide of the pharmaceutical composition is of an amount from about 0.000001 mg/kg body weight to about 40 mg/kg body weight. According to another embodiment, the therapeutic amount of the therapeutic inhibitor peptide is of an amount from about 0.000001 mg/kg body weight to about 30 mg/kg body weight. According to another embodiment, the therapeutic amount of the therapeutic inhibitor peptide of the pharmaceutical composition is of an amount from about 0.000001 mg/kg body weight to about 20 mg/kg body weight. According to another embodiment, the therapeutic amount of the therapeutic inhibitor peptide of the pharmaceutical composition is of an amount from about 0.000001 mg/kg body weight to about 10 mg/kg body weight. According to another embodiment, the therapeutic amount of the therapeutic inhibitor peptide of the pharmaceutical composition is of an amount from about 0.000001 mg/kg body weight to about 1 mg/kg body weight. According to another embodiment, the therapeutic amount of the therapeutic inhibitor peptide of the pharmaceutical composition is of an amount from about 0.000001 mg/kg body weight to about 0.1 mg/kg body weight. According to another embodiment, the therapeutic amount of the therapeutic inhibitor peptide of the pharmaceutical composition is of an amount from about 0.000001 mg/kg body weight to about 0.1 mg/kg body weight. According to another embodiment, the therapeutic amount of the therapeutic inhibitor peptide of the pharmaceutical composition is of an amount from about 0.000001 mg/kg body weight to about 0.01 mg/kg body weight. According to another embodiment, the therapeutic amount of the therapeutic inhibitor peptide of the pharmaceutical composition is of an amount from about 0.000001 mg/kg body weight to about 0.001 mg/kg body weight. According to another embodiment, the therapeutic amount of the therapeutic inhibitor peptide of the pharmaceutical composition is of an amount from about 0.000001 mg/kg body weight to about 0.0001 mg/kg body weight. According to another embodiment, the therapeutic amount of the therapeutic inhibitor peptide of the pharmaceutical composition is of an amount from about 0.000001 mg/kg body weight to about 0.00001 mg/kg body weight.

According to some other embodiments, the therapeutic dose of the therapeutic inhibitor peptide of the pharmaceutical composition ranges from 1 µg/kg/day to 25 µg/kg/day. According to some other embodiments, the therapeutic dose of the therapeutic inhibitor peptide of the pharmaceutical composition ranges from 1 µg/kg/day to 2 µg/kg/day. According to some other embodiments, the therapeutic dose of the therapeutic inhibitor peptide of the pharmaceutical composition ranges from 2 µg/kg/day to 3 µg/kg/day. According to some other embodiments, the therapeutic dose of the therapeutic inhibitor peptide of the pharmaceutical composition ranges from 3 µg/kg/day to 4 µg/kg/day. According to some other embodiments, the therapeutic dose of the therapeutic inhibitor peptide of the pharmaceutical ranges from 4 µg/kg/day to 5 µg/kg/day. According to some other embodiments, the therapeutic dose of the therapeutic inhibitor peptide of the pharmaceutical composition ranges from 5 µg/kg/day to 6 µg/kg/day. According to some other embodiments, the therapeutic dose of the therapeutic inhibitor peptide of the pharmaceutical composition ranges from 6 µg/kg/day to 7 µg/kg/day. According to some other embodiments, the therapeutic dose of the therapeutic inhibitor peptide of the pharmaceutical composition ranges from 7 µg/kg/day to 8 µg/kg/day. According to some other embodiments, the therapeutic dose of the therapeutic inhibitor peptide of the pharmaceutical composition ranges from 8 µg/kg/day to 9 µg/kg/day. According to some other embodiments, the therapeutic dose of the therapeutic inhibitor peptide of the pharmaceutical composition ranges from 9 µg/kg/day to 10 µg/kg/day. According to some other embodiments, the therapeutic dose of the therapeutic inhibitor peptide of the pharmaceutical composition ranges from 1 µg/kg/day to 5 µg/kg/day. According to some other embodiments, the therapeutic dose of the therapeutic inhibitor peptide of the pharmaceutical composition ranges from 5 µg/kg/day to 10 µg/kg/day. According to some other embodiments, the therapeutic dose of the therapeutic inhibitor peptide of the pharmaceutical composition ranges from 10 µg/kg/day to 15 µg/kg/day. According to some other embodiments, the therapeutic dose of the therapeutic inhibitor peptide of the pharmaceutical composition ranges from 15 µg/kg/day to 20 µg/kg/day. According to some other embodiments, the therapeutic dose of the therapeutic inhibitor peptide of the pharmaceutical composition ranges from 25 µg/kg/day to 30 µg/kg/day. According to some other embodiments, the therapeutic dose of the therapeutic inhibitor peptide of the pharmaceutical composition ranges from 30 µg/kg/day to 35 µg/kg/day. According to some other embodiments, the therapeutic dose of the therapeutic inhibitor peptide of the pharmaceutical composition ranges from 35 µg/kg/day to 40 µg/kg/day. According to some other embodiments, the therapeutic dose of the therapeutic inhibitor peptide of the pharmaceutical composition ranges from 40 µg/kg/day to 45 µg/kg/day. According to some other embodiments, the therapeutic dose of the therapeutic inhibitor peptide of the pharmaceutical composition ranges from 45 µg/kg/day to 50 µg/kg/day. According to some other embodiments, the therapeutic dose of the therapeutic inhibitor peptide of the pharmaceutical composition ranges from 50 µg/kg/day to 55 µg/kg/day. According to some other embodiments, the therapeutic dose of the therapeutic inhibitor peptide of the pharmaceutical composition ranges from 55 µg/kg/day to 60 µg/kg/day. According to some other embodiments, the therapeutic dose of the therapeutic inhibitor peptide of the pharmaceutical composition ranges from 60 µg/kg/day to 65 µg/kg/day. According to some other embodiments, the therapeutic dose of the therapeutic inhibitor peptide of the pharmaceutical composition ranges from 65 µg/kg/day to 70 µg/kg/day. According to some other embodiments, the therapeutic dose of the therapeutic inhibitor peptide of the pharmaceutical composition ranges from 70 µg/kg/day to 75 µg/kg/day. According to some other embodiments, the therapeutic dose of the therapeutic inhibitor peptide of the pharmaceutical composition ranges from 80 µg/kg/day to 85 µg/kg/day. According to some other embodiments, the therapeutic dose of the therapeutic inhibitor peptide of the pharmaceutical composition ranges from 85 µg/kg/day to 90 µg/kg/day. According to some other embodiments, the therapeutic dose of the therapeutic inhibitor peptide of the pharmaceutical composition ranges from 90 µg/kg/day to 95 µg/kg/day. According to some other embodiments, the therapeutic dose of the therapeutic inhibitor peptide of the pharmaceutical composition ranges from 95 µg/kg/day to 100 µg/kg/day.

According to another embodiment, the therapeutic dose of the therapeutic inhibitor peptide of the pharmaceutical composition is 1 µg/kg/day.

According to another embodiment, the therapeutic dose of the therapeutic inhibitor peptide of the pharmaceutical composition is 2 µg/kg/day.

According to another embodiment, the therapeutic dose of the therapeutic inhibitor peptide of the pharmaceutical composition is 5 µg/kg/day.

According to another embodiment, the therapeutic dose of the therapeutic inhibitor peptide of the pharmaceutical composition is 10 µg/kg/day.

Within this application, unless otherwise stated, the techniques utilized may be found in any of several well-known references such as: Molecular Cloning: A Laboratory Manual (Sambrook, et al., 1989, Cold Spring Harbor Laboratory Press), Gene Expression Technology (Methods in Enzymology, Vol. 185, edited by D. Goeddel, 1991. Academic Press, San Diego, Calif.), "Guide to Protein Purification" in Methods in Enzymology (M. P. Deutshcer, ed., (1990) Academic Press, Inc.); PCR Protocols: A Guide to Methods and Applications (Innis, et al. 1990. Academic Press, San Diego, Calif.), Culture of Animal Cells: A Manual of Basic Technique, 2nd Ed. (R. I. Freshney. 1987. Liss, Inc. New York, N.Y.), and Gene Transfer and Expression Protocols, pp. 109-128, ed. E. J. Murray, The Humana Press Inc., Clifton, N.J.), all of which are incorporated herein by reference.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the described invention, the preferred methods and materials are now described. All publications mentioned herein are incorporated herein by reference to disclose and describe the methods and/or materials in connection with the publications are cited.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges also is encompassed within the invention, subject to any specifically excluded limit in the stated range. Where the stated range includes one or both of the limits, ranges excluding either both of those included limits also are included in the invention.

It must also be noted that as used herein and in the appended claims, the singular forms "a," "and" and "the" include plural referents unless the context clearly dictates otherwise. All technical and scientific terms used herein have the same meaning.

The publications discussed herein are incorporated herein by reference in their entirety and are provided solely for their disclosure prior to the filing date of the present application. Nothing herein is to be construed as an admission that the described invention is not entitled to antedate such publication by virtue of prior invention. Further, the dates of publication provided may be different from the actual publication dates which may need to be independently confirmed.

It should be understood by those skilled in the art that various changes may be made and equivalents may be substituted without departing from the true spirit and scope of the Invention. In addition, many modifications may be made to adapt a particular situation, material, composition of matter, process, process step or steps, to the objective, spirit and scope of the described invention. All such modifications are intended to be within the scope of the claims appended hereto.

EXAMPLES

The following examples are put forth so as to provide those of ordinary skill in the art with a complete disclosure and description of how to make and use the described invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

I. Materials and Methods

MMI-0100 Drug Development

For good manufacturing practice (GMP) production of MMI-0100 (YARAAARQARAKALARQLGVAA; SEQ ID NO: 1), approximately 1 kg of Fmoc-Ala-Wang Resin is transferred into a 50 L glass solid phase synthesis reaction vessel equipped with a mechanical stirrer. The resin is allowed to swell in dimethylformide (DMF) for no less than (NLT) 2 hours before draining the DMF. The resin beads then are washed with consecutive rinses of DMF. The N-terminal protecting group (i.e. Fmoc) is removed (deblocking step) by treatment with 20% piperidine in DMF and the resin is washed with DMF. The next amino acid in the sequence is coupled in the presence of 1-hydroxybenzotriazole (HOBt) and diisopropylcarbodiimide (DIC). Generally, 2.5-3.5 molar equivalents of Fmoc-amino acid (Fmoc-AA) to the synthesis scale are used for coupling. The Fmoc-AA is dissolved in DMF and activated by the addition of HOBt and DIC. The completion of each coupling is monitored by the Ninhydrin test. If a coupling is incomplete, a second coupling with the same amino acid is performed by using the symmetrical anhydride method. Generally, 3.0-6.0 molar equivalents of Fmoc-AA to the synthesis scale are used for coupling. The Fmoc-AA is dissolved in dichloromethane (DCM) and a minimal volume of DMF and activated through the addition of DIC in a molar ratio of Fmoc-AA/DIC=1.0/0.5. When the full peptide sequence is completed, the peptide resin is rinsed thoroughly with successive washes of DMF and MeOH. The resin then is dried under vacuum for NLT 3 hours. Typical recovery of the total dried peptide resin is approximately 2800 grams, representing a peptide resin yield of ~65%.

Approximately 370-500 grams of peptide resin then are transferred into a suitably sized glass bottle equipped with a magnetic stir bar. The flask containing the peptide resin is cooled in an ice/water bath or in a refrigerator for no later than 30 minutes. The trifluoroacetic acid (TFA) cocktail (a mixture of TFA, TIS, and water in the ratio of 95 mL:2.5 mL: 2.5 mL) is pre-chilled in an ice/water bath for no later than 30 minutes. Approximately 8-12 mL of TFA cleavage cocktail per gram of resin is added to this vessel. As soon as the peptide resin and TFA cocktail are combined, the ice/water bath is removed and the reaction mixture is stirred at room temperature for 2-3 hours. The reaction mixture then is filtered through a coarse glass filter and the resin is washed two times with 0.5-1.0 mL of TFA per gram of resin per wash. The combined filtrate is collected and the resin is discarded. The filtrate is then added to ether that is pre-chilled in a refrigerator for less than 30 minutes, in a ratio of 1 mL of filtrate per 10 mL ether, to precipitate the cleaved peptide. The peptide-ether mixture is equilibrated to room temperature for no later than 30 minutes. The precipitated peptide is collected on a medium glass filter. The precipitate is washed thoroughly with cold ether three times, using enough ether to at least cover all the precipitate on the filter. The ether then is eluted through the same medium glass filter. The crude peptide is transferred into a plastic bottle and is placed in a desiccator connected to a mechanical vacuum pump to dry for no later than 12 hours. After drying, the crude peptide is stored at 5±3° C. The cleavage procedure is repeated multiple times until all the peptide resin is cleaved. A typical batch recovery of total dried crude peptide is approximately 1250 grams, representing a cleavage yield of approximately 110%.

The crude peptide from cleavage is prepared for high-performance liquid chromatography (HPLC) purification by dissolving the peptide in HPLC buffer at a final crude peptide concentration of 20 mg/mL. The peptide solution is filtered through a 1 µm glass filter membrane and loaded onto a C18 reverse phase column, which is operated by a preparative HPLC system. The column is washed and equilibrated. A linear gradient is used to elute the crude peptide from the column. Following each crude purification, the fractions are analyzed by an analytical HPLC system using a Kromasil C18, 5 µm, 100 Å 4.6×250 mm column. Fractions generated from the initial purification are pooled based on the HPLC purity and impurity profile of each fraction. Peptide pools are stored at 2-8° C. until further processing. This process is repeated until all of the crude peptide was purified through the HPLC column and meet the Main Pool purity criteria. A salt exchange to acetate salt is performed by HPLC. The final peptide solution is filtered through a 0.22 µm filter and loaded onto a tray lyophilizer. The peptide is pre-frozen at 40° C. for no later than 720 minutes before starting the lyophilization cycle. The lyophilization takes approximately 5 days. Approximately 50-55% final yield results from the purification and lyophilization steps.

Radiometric $IC_{50}$ Determination

The $IC_{50}$ value was estimated from a 10-point curve of one-half log dilutions. Peptide was supplied in dimethyl sulfoxide (DMSO). Specifically, human recombinant MK2 (h) (5-10 mU) was incubated with 50 mM sodium 3-glycerophosphate (pH=7.5), 0.1 mM EGTA, 30 µM of substrate peptide (KKLNRTLSVA; SEQ ID NO: 21), 10 mM magnesium acetate, and 90 uM γ-$^{33}$P-ATP (final volume of 25 µL) for 40 minutes at room temperature. Then, the reaction was stopped with 3% phosphoric acid. 10 µL of this mixture was spotted onto a P30 filtermat and washed three times for five minutes with 75 mM phosphoric acid and once with methanol. Finally, the membrane was dried and a scintillation counter was used. An ATP concentration within 15 µM of the apparent Km for ATP was chosen, because Hayess and Benndorf (Biochem Pharmacol, 1997, 53(9): 1239-47) showed that the mechanism of their original inhibitor peptide (i.e., the peptide KKKALNRQLGVAA; SEQ ID NO: 22) was not competitive with ATP binding.

In addition to determining the $IC_{50}$ value for MMI-0100 (YARAAARQARAKALARQLGVAA; SEQ ID NO: 1), inhibitory activity against 266 human kinases was tested using Millipore's $IC_{50}$ Profiler Express service (Millipore, Billerica, Mass.).

For specificity analysis, 100 µM of each MMI-0100 (YARAAARQARAKALARQLGVAA; SEQ ID NO: 1), MMI-0200 (YARAAARQARAKALNRQLGVA; SEQ ID NO: 19), MMI-0300 (FAKLAARLYRKALARQLGVAA; SEQ ID NO: 3), MMI-0400 (KAFAKLAARLYRKALARQLGVAA; SEQ ID NO: 4), and MMI-0500 (HRRIKAWLKKIKALARQLGVAA; SEQ ID NO: 7), dissolved in dimethyl sulfoxide (DMSO) was used. The 100 µM concentration was chosen because this concentration inhibited adhesion formation in an in vivo study (as disclosed in U.S. application Ser. No. 12/582,516 filed Oct. 20, 2009, the content of which is incorporated herein by reference in its entirety). Every kinase activity measurement was conducted in duplicate.

Histochemistry and Immunohistochemistry

A mouse model of pulmonary fibrosis was generated by administering 0.025 U of bleomycin/PBS intratracheally to C57BL/6 mice. MMI-0100 (YARAAARQARAKALARQLGVAA; SEQ ID NO: 1) or MMI-0200 (YARAAARQARAKALNRQLGVA; SEQ ID NO: 19) (at dosages of 50 µg/kg, 75 µg/kg, and 100 mg/kg per day) was administered daily starting at day 7 post bleomycin injury (for analysis of post-inflammatory/pre-fibrotic phase; a prevention model) or at day 14 post bleomycin injury (for analysis of post-fibrotic phase; treatment model), either intraperitoneally or via nebulization, through day 21 or 28 post bleomycin delivery. At 21 day post bleomycin delivery (for prevention model) or 28 post bleomycin delivery (for treatment model), groups of mice were sacrificed with a sodium pentobarbital injection (120 mg/kg) and the chest cavity was opened. The right mainstem bronchus was ligated and the right lung was removed. The trachea was cannulated and the left lung was perfused with 4% formaldehyde at 21 cm $H_2O$ pressure. The tissue blocks then were embedded in paraffin, and 4-mm sections were prepared for staining. Sections from each animal were stained with hematoxylin and eosin (H&E) to visualize cells or with Masson's Trichrome staining to highlight collagen deposition. After incubation, sections were washed with 0.2% acetic acid, dehydrated by immersing into 95% alcohol, and cleared with xylene (3-4 times) in a staining dish. Stained sections were mounted onto a labeled glass slide with organic mounting medium.

II. Results

Example 1. $IC_{50}$ and Specificity of MMI-0100 (YARAAARQARAKALARQLGVAA; SEQ ID NO: 1)

$IC_{50}$ (half maximal inhibitory concentrations) value for the MK2 inhibitor peptide (MMI-0100; YARAAARQARAKALARQLGVAA (SEQ ID NO: 1)) was determined using Millipore's $IC_{50}$ Profiler Express service. This quantitative assay measures how much of an inhibitor is needed to inhibit 50% of a given biological process or component of a process (i.e., an enzyme, cell, or cell receptor) [$IC_{50}$].

Specifically, in these assays, a positively charged substrate is phosphorylated with a radiolabeled phosphate group from an ATP if the kinase is not inhibited by an inhibitor peptide. The positively charged substrate then is attracted to a negatively charged filter membrane, quantified with a scintillation counter, and compared to a 100% activity control.

ATP concentrations within 15 µM of the apparent Km for ATP were chosen since an ATP concentration near the Km may allow for the kinases to have the same relative amount of phosphorylation activity. The $IC_{50}$ of the MMI-0100 (YARAAARQARAKALARQLGVAA; SEQ ID NO: 1) was determined to be 22 µM.

In addition to determining the $IC_{50}$ of the compound, the specificity of MK2 inhibitory peptides was assessed by examining activities of all 266 human kinases available for testing in the Millipore kinase profiling service (Table 1). For analysis, the kinases that were inhibited more than 65% by MMI-0100 (YARAAARQARAKALARQLGVAA; SEQ ID NO: 1); MMI-0200 (YARAAARQARAKALNRQLGVA; SEQ ID NO: 19); MMI-0300 (FAKLAARLYRKALARQLGVAA; SEQ ID NO: 3); MMI-0400 (KAFAKLAARLYRKALARQLGVAA; SEQ ID NO: 4); and MMI-0500 (HRRIKAWLKKIKALARQLGVAA; SEQ ID NO: 7) were determined.

As shown in Table 1, at 100 µM, MK2 inhibitory peptides MMI-0100 (SEQ ID NO: 1), MMI-0200 (SEQ ID NO: 19), MMI-0300 (SEQ ID NO: 3), MMI-0400 (SEQ ID NO: 4); and MMI-0500 (SEQ ID NO: 5) inhibited a specific group of kinases and showed very limited off-target kinase inhibition. More specifically, MK2 inhibitory peptides MMI-0100 (SEQ ID NO: 1), MMI-0200 (SEQ ID NO: 19), MMI-0300 (SEQ ID NO: 3); MMI-0400 (SEQ ID NO: 4); and MMI-0500 (SEQ ID NO: 5) inhibited in vitro more than 65% of the kinase activities of Mitogen-Activated Protein Kinase-Activated Protein Kinase 2 (MK2), Mitogen-Activated Protein Kinase-Activated Protein Kinase 3 (MK3), Calcium/Calmodulin-Dependent Protein Kinase I (CaMKI, serine/threonine-specific protein kinase), and BDNF/NT-3 growth factors receptor (TrkB, tyrosine kinase).

TABLE 1

Kinase Profiling Assay

| | MMI-0100 (SEQ ID NO: 1) (100 µM) | MMI-0200 (SEQ ID NO: 19) (100 µM) | MMI-0300 (SEQ ID NO: 3) (100 µM) | MMI-0400 (SEQ ID NO: 4) (100 µM) | MMI-0500 (SEQ ID NO: 7) (100 µM) |
|---|---|---|---|---|---|
| Abl(h) | 136 | 107 | 69 | 84 | 16 |
| Abl(H396P)(h) | 130 | 121 | 101 | 105 | 51 |
| Abl(M351T)(h) | 128 | 119 | 90 | 121 | 61 |
| Abl(Q252H)(h) | 105 | 107 | 82 | 98 | 40 |
| Abl(T315I)(h) | 98 | 108 | 97 | 105 | 16 |
| Abl(Y253F)(h) | 104 | 102 | 86 | 78 | 29 |
| ACK1(h) | 106 | 97 | 104 | 95 | 64 |
| ALK(h) | 118 | 95 | 19 | 16 | 12 |
| ALK4(h) | 124 | 152 | 140 | 130 | 81 |
| Arg(h) | 89 | 82 | 72 | 84 | 22 |
| AMPKα1(h) | 107 | 108 | 71 | 87 | 35 |
| AMPKα2(h) | 121 | 88 | 54 | 58 | 9 |
| ARK5(h) | 108 | 93 | 78 | 69 | 20 |
| ASK1(h) | 100 | 101 | 80 | 69 | −4 |
| Aurora-A(h) | 120 | 107 | 92 | 119 | 110 |
| Aurora-B(h) | 94 | 166 | 128 | 150 | 5 |
| Axl(h) | 81 | 99 | 52 | 41 | 12 |
| Bmx(h) | 62 | 76 | N/D | 26 | 45 |
| BRK(h) | 70 | 127 | 35 | 18 | 41 |
| BrSK1(h) | 100 | 93 | 67 | 76 | 72 |
| BrSK2(h) | 129 | 102 | 83 | 86 | 84 |
| BTK(h) | 112 | 100 | 102 | 94 | 18 |
| BTK(R28H)(h) | 91 | 104 | 74 | 24 | 10 |
| CaMKI(h) | 13 | 21 | 1 | 0 | −1 |
| CaMKIIβ(h) | 58 | 53 | 2 | 11 | 3 |
| CaMKIIγ(h) | 106 | 94 | 5 | 3 | 3 |
| CaMKIδ(h) | 59 | 47 | 10 | 17 | 0 |
| CaMKIIδ(h) | 89 | 2 | 1 | 2 | 1 |
| CaMKIV(h) | 87 | 71 | 17 | 18 | −1 |
| CDK1/cyclinB(h) | 96 | 115 | 73 | 74 | 57 |
| CDK2/cyclinA(h) | 97 | 114 | 86 | 92 | 87 |
| CDK2/cyclinE(h) | 106 | 112 | 94 | 83 | 19 |
| CDK3/cyclinE(h) | 106 | 104 | 94 | 92 | 8 |
| CDK5/p25(h) | 114 | 97 | 89 | 92 | 66 |
| CDK5/p35(h) | 94 | 92 | 79 | 76 | 59 |
| CDK6/cyclinD3(h) | 103 | 100 | 86 | 85 | 23 |
| CDK7/cyclinH/MAT1(h) | 89 | 67 | 65 | 47 | 15 |
| CDK9/cyclin T1(h) | 228 | 103 | 91 | 235 | 6 |
| CHK1(h) | 97 | 115 | 91 | 87 | 65 |

TABLE 1-continued

Kinase Profiling Assay

| | MMI-0100 (SEQ ID NO: 1) (100 μM) | MMI-0200 (SEQ ID NO: 19) (100 μM) | MMI-0300 (SEQ ID NO: 3) (100 μM) | MMI-0400 (SEQ ID NO: 4) (100 μM) | MMI-0500 (SEQ ID NO: 7) (100 μM) |
|---|---|---|---|---|---|
| CHK2(h) | 104 | 105 | 66 | 54 | 13 |
| CHK2(I157T)(h) | 97 | 85 | 43 | 41 | 3 |
| CHK2(R145W)(h) | 97 | 81 | 33 | 31 | 3 |
| CK1γ1(h) | 110 | 98 | 111 | 116 | 109 |
| CK1γ2(h) | 119 | 104 | 123 | 114 | 119 |
| CK1γ3(h) | 105 | 96 | 125 | 115 | 114 |
| CK1δ(h) | 115 | 92 | 92 | 93 | 78 |
| CK2(h) | 90 | 83 | 90 | 101 | 93 |
| CK2α2(h) | 104 | 88 | 105 | 96 | 103 |
| CLK2(h) | 88 | 97 | 103 | 116 | 116 |
| CLK3(h) | 108 | 76 | 61 | 84 | 76 |
| cKit(h) | 95 | 110 | 53 | 43 | 45 |
| cKit(D816V)(h) | 117 | 118 | 60 | 35 | 30 |
| cKit(D816H)(h) | 79 | 106 | 126 | 143 | 194 |
| cKit(V560G)(h) | 94 | 115 | 102 | 124 | 198 |
| cKit(V654A)(h) | 69 | 113 | 134 | 150 | 223 |
| CSK(h) | 70 | 33 | 49 | 16 | 2 |
| c-RAF(h) | 97 | 115 | 107 | 102 | 19 |
| cSRC(h) | 70 | 32 | 26 | 14 | 30 |
| DAPK1(h) | 97 | 113 | 46 | 36 | 0 |
| DAPK2(h) | 41 | 92 | 32 | 16 | 3 |
| DCAMKL2(h) | 146 | 131 | 81 | 70 | 56 |
| DDR2(h) | 105 | 104 | 94 | 95 | 79 |
| DMPK(h) | 60 | 66 | 59 | 54 | 12 |
| DRAK1(h) | 47 | 34 | 14 | 14 | 8 |
| DYRK2(h) | 99 | 142 | 155 | 195 | 127 |
| eEF-2K(h) | 113 | 136 | 91 | 43 | 43 |
| EGFR(h) | 95 | 83 | 21 | 16 | -1 |
| EGFR(L858R)(h) | 76 | 120 | N/D | 52 | 26 |
| EGFR(L861Q)(h) | 53 | 74 | 25 | 22 | 15 |
| EGFR(T790M)(h) | 106 | 113 | 100 | 106 | 70 |
| EGFR(T790M, L858R)(h) | 93 | 108 | 85 | 78 | 53 |
| EphA1(h) | 114 | 136 | 73 | 61 | 40 |
| EphA2(h) | 58 | 95 | 31 | 17 | N/D |
| EphA3(h) | 107 | 117 | 6 | 12 | 33 |
| EphA4(h) | 110 | 127 | 88 | 65 | 48 |
| EphA5(h) | 110 | 123 | 18 | 24 | 42 |
| EphA7(h) | 193 | 220 | 159 | 222 | 189 |
| EphA8(h) | 181 | 133 | 93 | 146 | 337 |
| EphB2(h) | 68 | 128 | 18 | 22 | 70 |
| EphB1(h) | 99 | 95 | 44 | 58 | 37 |
| EphB3(h) | 109 | 128 | 62 | 47 | 79 |
| EphB4(h) | 62 | 131 | 44 | 28 | 38 |
| ErbB4(h) | 73 | 82 | 40 | 0 | 2 |
| FAK(h) | 98 | 110 | 111 | 96 | 94 |
| Fer(h) | 117 | 101 | 130 | 108 | 196 |
| Fes(h) | 44 | 74 | 20 | 16 | 23 |
| FGFR1(h) | 120 | 97 | 55 | 59 | 18 |
| FGFR1(V561M)(h) | 108 | 72 | 74 | 74 | 113 |
| FGFR2(h) | 49 | 73 | 14 | 18 | 12 |
| FGFR2(N549H)(h) | 95 | 104 | 116 | 112 | 105 |
| FGFR3(h) | 73 | 208 | 102 | 0 | 10 |
| FGFR4(h) | 67 | 75 | 28 | 19 | 3 |
| Fgr(h) | 54 | 71 | 60 | 47 | 109 |
| Flt1(h) | 109 | 96 | 69 | 48 | 27 |
| Flt3(D835Y)(h) | 120 | 115 | 80 | 71 | 65 |
| Flt3(h) | 104 | 99 | 84 | 18 | 17 |
| Flt4(h) | 135 | 105 | 83 | 89 | 73 |
| Fms(h) | 89 | 92 | 45 | 37 | 14 |
| Fms(Y969C)(h) | 126 | 88 | 72 | 91 | N/D |
| Fyn(h) | 71 | 75 | 74 | 54 | 83 |
| GCK(h) | 98 | 99 | 70 | 66 | 30 |

TABLE 1-continued

Kinase Profiling Assay

| | MMI-0100 (SEQ ID NO: 1) (100 µM) | MMI-0200 (SEQ ID NO: 19) (100 µM) | MMI-0300 (SEQ ID NO: 3) (100 µM) | MMI-0400 (SEQ ID NO: 4) (100 µM) | MMI-0500 (SEQ ID NO: 7) (100 µM) |
|---|---|---|---|---|---|
| GRK5(h) | 117 | 135 | 136 | 131 | 116 |
| GRK6(h) | 131 | 132 | 147 | 141 | 174 |
| GRK7(h) | 111 | 124 | 122 | 100 | 93 |
| GSK3α(h) | 183 | 119 | 157 | 164 | 175 |
| GSK3β(h) | 113 | 132 | 205 | 202 | 238 |
| Haspin(h) | 127 | 71 | 48 | 36 | 25 |
| Hck(h) | 354 | 107 | 72 | 72 | 78 |
| Hck(h) activated | 58 | 100 | 82 | 81 | 67 |
| HIPK1(h) | 94 | 115 | 74 | 91 | 47 |
| HIPK2(h) | 98 | 102 | 73 | 90 | 38 |
| HIPK3(h) | 105 | 105 | 93 | 105 | 85 |
| IGF-1R(h) | 102 | 49 | 119 | 90 | 117 |
| IGF-1R(h), activated | 126 | 94 | 80 | 77 | 45 |
| IKKα(h) | 108 | 104 | 93 | 87 | 50 |
| IKKβ(h) | 105 | 109 | 84 | 84 | 71 |
| IR(h) | 112 | 90 | 96 | 85 | 95 |
| IR(h), activated | 127 | 105 | 79 | 59 | 90 |
| IRR(h) | 85 | 69 | 8 | 8 | 10 |
| IRAK1(h) | 97 | 101 | 95 | 93 | 5 |
| IRAK4(h) | 100 | 110 | 59 | 59 | 3 |
| Itk(h) | 99 | 98 | 77 | 63 | 7 |
| JAK2(h) | 89 | 131 | 133 | 119 | 49 |
| JAK3(h) | 150 | 117 | 121 | 122 | 95 |
| JNK1α1(h) | 91 | 106 | 97 | 98 | 109 |
| JNK2α2(h) | 114 | 109 | 98 | 96 | 81 |
| JNK3(h) | 104 | 90 | 89 | 70 | 171 |
| KDR(h) | 100 | 110 | 101 | 94 | 15 |
| Lck(h) | 346 | 113 | −2 | 228 | 359 |
| Lck(h) activated | 106 | 90 | 243 | 216 | 76 |
| LIMK1(h) | 103 | 109 | 88 | 92 | 87 |
| LKB1(h) | 111 | 99 | 101 | 89 | 51 |
| LOK(h) | 37 | 67 | 37 | 18 | 7 |
| Lyn(h) | 113 | 98 | 69 | 3 | 31 |
| MAPK1(h) | 108 | 97 | 107 | 100 | 102 |
| MAPK2(h) | 98 | 105 | 98 | 93 | 60 |
| MAPKAP-K2(h) | 19 | 35 | 5 | 5 | 9 |
| MAPKAP-K3(h) | 27 | 39 | 3 | 7 | 9 |
| MEK1(h) | 86 | 116 | 77 | 77 | 21 |
| MARK1(h) | 109 | 102 | 132 | 120 | 110 |
| MELK(h) | 74 | 59 | 16 | 17 | 0 |
| Mer(h) | 47 | 90 | 52 | 50 | 17 |
| Met(h) | 104 | 71 | 65 | 62 | 27 |
| Met(D1246H)(h) | 99 | 139 | 125 | 68 | 150 |
| Met(D1246N)(h) | 114 | 149 | 82 | 31 | 90 |
| Met(M1268T)(h) | 114 | 143 | 255 | 265 | 239 |
| Met(Y1248C)(h) | 77 | 141 | 84 | 36 | 73 |
| Met(Y1248D)(h) | 87 | 118 | 102 | 31 | 218 |
| Met(Y1248H)(h) | 88 | 153 | 117 | 63 | 126 |
| MINK(h) | 96 | 103 | 48 | 52 | 5 |
| MKK6(h) | 74 | 98 | 48 | 44 | 18 |
| MKK7β(h) | 137 | 117 | 100 | 94 | 102 |
| MLCK(h) | 85 | 103 | 2 | 1 | 0 |
| MLK1(h) | 77 | 84 | 40 | 33 | 43 |
| Mnk2(h) | 94 | 106 | 89 | 86 | 6 |
| MRCKα(h) | 98 | 103 | 104 | 97 | 5 |
| MRCKβ(h) | 103 | 102 | 83 | 71 | −10 |
| MSK1(h) | 52 | 50 | 32 | 28 | 8 |
| MSK2(h) | 105 | 88 | 56 | 52 | 14 |
| MSSK1(h) | 82 | 100 | 77 | 75 | 22 |
| MST1(h) | 85 | 72 | 14 | 6 | 3 |
| MST2(h) | 98 | 104 | 19 | 11 | 2 |
| MST3(h) | 104 | 95 | 45 | 36 | 4 |
| mTOR(h) | 102 | 110 | 91 | 93 | 135 |
| mTOR/FKBP12(h) | 117 | 118 | 145 | 125 | 140 |

TABLE 1-continued

Kinase Profiling Assay

| | MMI-0100 (SEQ ID NO: 1) (100 µM) | MMI-0200 (SEQ ID NO: 19) (100 µM) | MMI-0300 (SEQ ID NO: 3) (100 µM) | MMI-0400 (SEQ ID NO: 4) (100 µM) | MMI-0500 (SEQ ID NO: 7) (100 µM) |
|---|---|---|---|---|---|
| MuSK(h) | 85 | 106 | 93 | 93 | 27 |
| NEK2(h) | 102 | 97 | 78 | 61 | 0 |
| NEK3(h) | 100 | 100 | 92 | 85 | 20 |
| NEK6(h) | 109 | 98 | 82 | 85 | 49 |
| NEK7(h) | 97 | 96 | 84 | 87 | 89 |
| NEK11(h) | 102 | 95 | 53 | 33 | 2 |
| NLK(h) | 100 | 106 | 87 | 90 | 19 |
| p70S6K(h) | 89 | 84 | 35 | 33 | 3 |
| PAK2(h) | 71 | 69 | 65 | 59 | 44 |
| PAK4(h) | 92 | 98 | 94 | 89 | 86 |
| PAK3(h) | N/D | 50 | 140 | 121 | 102 |
| PAK5(h) | 97 | 100 | 110 | 117 | 125 |
| PAK6(h) | 121 | 105 | 104 | 100 | 107 |
| PAR-1Bα(h) | 62 | 110 | 113 | 109 | 97 |
| PASK(h) | 81 | 60 | 29 | 28 | 9 |
| PDGFRα(h) | 104 | 108 | 65 | 40 | 40 |
| PDGFRα (D842V)(h) | 103 | 107 | 114 | 118 | 170 |
| PDGFRα (V561D)(h) | 58 | 106 | 82 | 100 | 146 |
| PDGFRβ(h) | 116 | 137 | 81 | 53 | 40 |
| PDK1(h) | 144 | 143 | 135 | 159 | 178 |
| PhKγ2(h) | 62 | 86 | 46 | 38 | 16 |
| Pim-1(h) | 44 | 18 | 8 | 7 | 0 |
| Pim-2(h) | 117 | 74 | 76 | 92 | 46 |
| Pim-3(h) | 98 | 94 | 80 | 80 | 37 |
| PKA(h) | 138 | 110 | 119 | 119 | 118 |
| PKBα(h) | 140 | 110 | 57 | 67 | 30 |
| PKBβ(h) | 284 | 250 | 84 | 98 | 21 |
| PKBγ(h) | 105 | 103 | 20 | 41 | 20 |
| PKCα(h) | 94 | 100 | 89 | 86 | 3 |
| PKCβI(h) | 88 | 98 | 78 | 78 | 1 |
| PKCβII(h) | 102 | 100 | 82 | 75 | 3 |
| PKCγ(h) | 94 | 101 | 89 | 79 | 6 |
| PKCδ(h) | 100 | 101 | 101 | 90 | 61 |
| PKCε(h) | 102 | 98 | 79 | 59 | 23 |
| PKCη(h) | 105 | 101 | 103 | 98 | 45 |
| PKCι(h) | 110 | 97 | 68 | 46 | 7 |
| PKCμ(h) | 79 | 73 | 22 | 14 | 10 |
| PKCθ(h) | 102 | 101 | 88 | 76 | 62 |
| PKCζ(h) | 82 | 98 | 81 | 75 | 7 |
| PKD2(h) | 84 | 78 | 33 | 25 | 10 |
| PKG1α(h) | 82 | 70 | 64 | 58 | 25 |
| PKG1β(h) | 71 | 57 | 50 | 53 | 24 |
| Plk1(h) | 109 | 128 | 115 | 119 | 104 |
| Plk3(h) | 107 | 107 | 127 | 129 | 122 |
| PRAK(h) | 159 | 115 | 128 | 118 | 95 |
| PRK2(h) | 72 | 74 | 33 | 27 | 7 |
| PrKX(h) | 84 | 112 | 61 | 76 | 57 |
| PTK5(h) | 135 | 108 | 132 | 129 | 96 |
| Pyk2(h) | 113 | 127 | 47 | 34 | 46 |
| Ret(h) | 108 | 96 | 140 | 145 | 174 |
| Ret(V804L)(h) | 113 | 100 | 79 | 73 | 20 |
| Ret(V804M)(h) | 92 | 105 | 95 | 87 | 36 |
| RIPK2(h) | 92 | 98 | 97 | 98 | 30 |
| ROCK-I(h) | 99 | 117 | 79 | 73 | 17 |
| ROCK-II(h) | 102 | 85 | 74 | 77 | 2 |
| Ron(h) | 117 | 120 | 93 | 79 | 46 |
| Ros(h) | 107 | 86 | 95 | 99 | 150 |
| Rse(h) | 109 | 88 | 88 | 89 | 63 |
| Rsk1(h) | 86 | 102 | 46 | 54 | 34 |
| Rsk2(h) | 65 | 101 | 51 | 38 | 14 |
| Rsk3(h) | 76 | 109 | 76 | 71 | 23 |
| Rsk4(h) | 99 | 125 | 90 | 91 | 29 |
| SAPK2a(h) | 110 | 107 | 90 | 85 | 52 |
| SAPK2a (T106M)(h) | 101 | 100 | 97 | 99 | 32 |
| SAPK2b(h) | 99 | 95 | 81 | 82 | 42 |
| SAPK3(h) | 106 | 97 | 84 | 79 | 24 |
| SAPK4(h) | 98 | 106 | 96 | 91 | 48 |
| SGK(h) | 128 | 115 | 48 | 54 | 2 |

TABLE 1-continued

Kinase Profiling Assay

| | MMI-0100 (SEQ ID NO: 1) (100 µM) | MMI-0200 (SEQ ID NO: 19) (100 µM) | MMI-0300 (SEQ ID NO: 3) (100 µM) | MMI-0400 (SEQ ID NO: 4) (100 µM) | MMI-0500 (SEQ ID NO: 7) (100 µM) |
|---|---|---|---|---|---|
| SGK2(h) | 103 | 119 | 56 | 98 | -1 |
| SGK3(h) | 95 | 58 | 10 | 8 | -3 |
| SIK(h) | 113 | 102 | 66 | 68 | 40 |
| Snk(h) | 94 | 109 | 114 | 131 | 122 |
| Src(1-530)(h) | 95 | 75 | 23 | 19 | 21 |
| Src(T341M)(h) | 98 | 56 | 70 | 76 | 59 |
| SRPK1(h) | 69 | 93 | 90 | 96 | 80 |
| SRPK2(h) | 92 | 100 | 106 | 97 | 80 |
| STK33(h) | 99 | 98 | 45 | 52 | 16 |
| Syk(h) | 45 | 36 | 24 | 9 | 5 |
| TAK1(h) | 116 | 124 | 122 | 177 | N/D |
| TAO1(h) | 99 | 105 | 82 | 73 | 24 |
| TAO2(h) | 95 | 93 | 70 | 74 | 15 |
| TAO3(h) | 45 | 102 | 77 | 67 | 12 |
| TBK1(h) | 106 | 98 | 37 | 39 | 16 |
| Tec(h) activated | 100 | 77 | 56 | 29 | 33 |
| Tie2(h) | 28 | 53 | 26 | 21 | 22 |
| Tie2(R849W)(h) | 102 | 89 | 117 | 108 | 106 |
| Tie2(Y897S)(h) | 99 | 85 | 83 | 87 | 80 |
| TLK2(h) | 113 | 129 | 114 | 151 | 133 |
| TrkA(h) | 74 | N/D | 25 | 17 | 24 |
| TrkB(h) | 4 | 7 | 5 | 8 | 12 |
| TSSK1(h) | 99 | 98 | 79 | 79 | 46 |
| TSSK2(h) | 107 | 91 | 98 | 94 | 92 |
| Txk(h) | 87 | 98 | 48 | 37 | 10 |
| ULK2(h) | 123 | 132 | 122 | 131 | 124 |
| ULK3(h) | 142 | 164 | 167 | 147 | 177 |
| WNK2(h) | 95 | 94 | 64 | 54 | 8 |
| WNK3(h) | 100 | 97 | 77 | 74 | 9 |
| VRK2(h) | 112 | 109 | 161 | 185 | 169 |
| Yes(h) | 49 | 93 | 67 | 14 | N/D |
| ZAP-70(h) | 79 | 58 | 75 | 33 | 1 |
| ZIPK(h) | 80 | 67 | 28 | 13 | 1 |

N/D: % activity could not be determined as the duplicates.
MMI-0100: YARAAARQARAKALARQLGVAA (SEQ ID NO: 1)
MMI-0200: YARAAARQARAKALNRQLGVA (SEQ ID NO: 19)
MMI-0300: FAKLAARLYRKALARQLGVAA (SEQ ID NO: 3)
MMI-0400: KAFAKLAARLYRKALARQLGVAA (SEQ ID NO: 4)
MMI-0500: HRRIKAWLKKIKALARQLGVAA (SEQ ID NO: 7)

Example 2. Formulation of MMI-0100 (YARAAARQARAKALARQLGVAA; SEQ ID NO: 1) and its Functional Equivalents According to some embodiments, MMI-0100 (YARAAARQARAKALARQLGVAA; SEQ ID NO: 1) and its functional equivalents are formulated as a lyophilized powder via spray drying, micronization (e.g., jet-milling), or as liquid formulation for nebulization.

Spray Drying

In some embodiments, spray drying is utilized for preparing MMI-0100 (YARAAARQARAKALARQLGVAA; SEQ ID NO: 1) and its functional equivalents in consideration of the following factors:

(a) proteins and peptides are prone to denaturation—that is, disruption to tertiary and sometimes secondary structures;

(b) the denaturation can be reversible or irreversible and can be caused by a variety of conditions such as increase in temperature, decrease in temperature, extremes of pH, addition of solvents, pressure, and shear denaturation (this applies to micronization);

(c) denatured proteins are less active and not therapeutic, sometimes completely inactive;

(d) spray drying is able to turn these amorphous, large molecules into discrete spherical particles with a specified particle size distribution, controlled by processing parameters; the spray dried particles can be very spherical, donut-shaped and are typically hollow, meaning that particles >5 µm can still be respirable but be resistant to clearance mechanisms in the lungs; and (e) Spray drying, with or without excipients, generally improves the stability of proteins.

A lyophilized formulation of MMI-0100 (YARAAARQARAKALARQLGVAA; SEQ ID NO: 1) and its functional equivalents is assessed for potential synergy with the spray drying process (e.g., matching of optimal moisture levels buffer concentrations/pH, excipient selection and the like) to ensure protection of peptide stability.

Initial spray drying runs target mutually agreed acceptance criteria with the aim of defining process parameters for the spray drying operation. For an inhalation product, particle size is considered an important criterion. For alveolar deposition in the region of interest (Type IIs), Mass Median Aerodynamic Diameters (MMADs) of 1-5 microns generally are accepted as being suitable for peripheral deposition in the alveolar spaces (Heyder, J. Proc Am Thorac Soc, 1(4):

315-320, 2004, incorporated by reference herein). Other studies have suggested that MMADs of 1-3 microns are a desirable starting target particle sizes for the spray drying process. Since the likely biospace target for MMI-0100 (YARAAARQARAKALARQLGVAA; SEQ ID NO: 1) is the alveolar region, a MMAD in the about 2 micron range is targeted initially to ensure deposition into the alveolar space.

Acceptance criteria include, but are not limited to, (1) particle size (i.e., $D_{90}$ of about 2 µm); (2) moisture levels (i.e., moisture less than 3% w/w); (3) powder density; and (4) surface appearance (spherical, rough, toroidal).

A process design experiment then is conducted to optimize spray drying process parameters, including, for example, but not limited to, (1) inlet pressure and drying temperature; (2) feedstock concentration and federate; and (3) peptide/excipient ratio (excipients are, for example, buffer salts and a monosaccharide)

Example 3. Production of Batches of MMI-0100 (YARAAARQARAKALARQLGVAA; SEQ ID NO: 1) for Continued Aerosol Performance Assessment 2-3 spray drying runs at the defined process parameters described above are performed to generate material for aerosol performance assessment.

Figure 1:
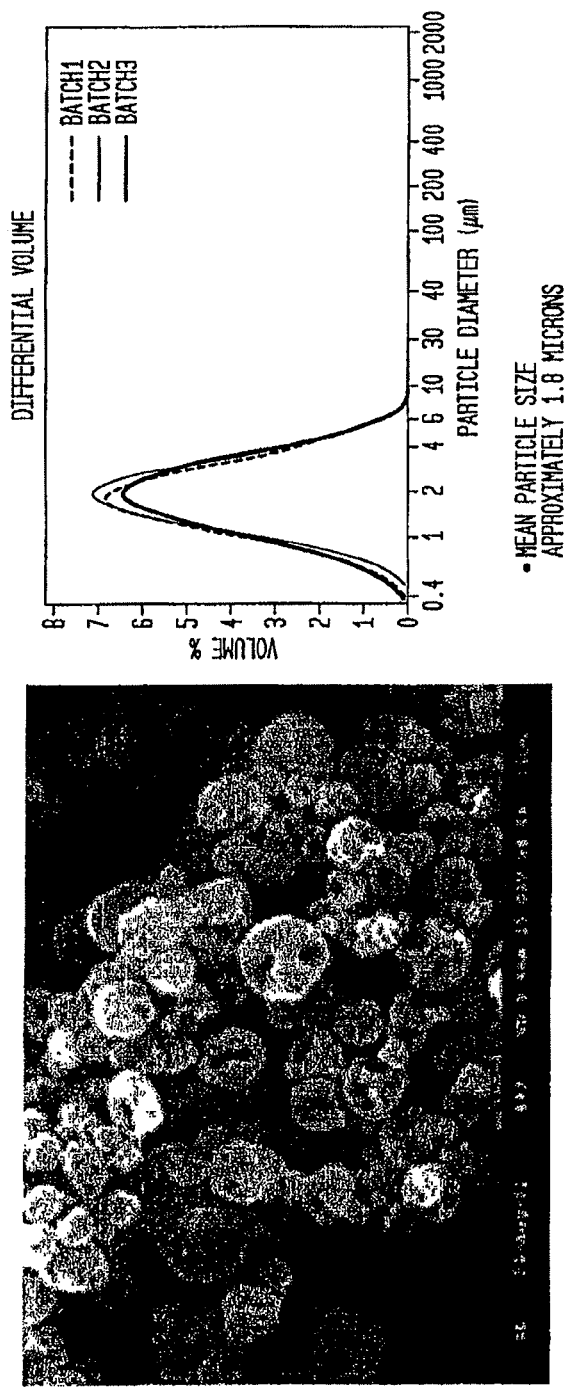
FIG. 1 shows delivery performance of neat spray-dried insulin.
Figure 2:
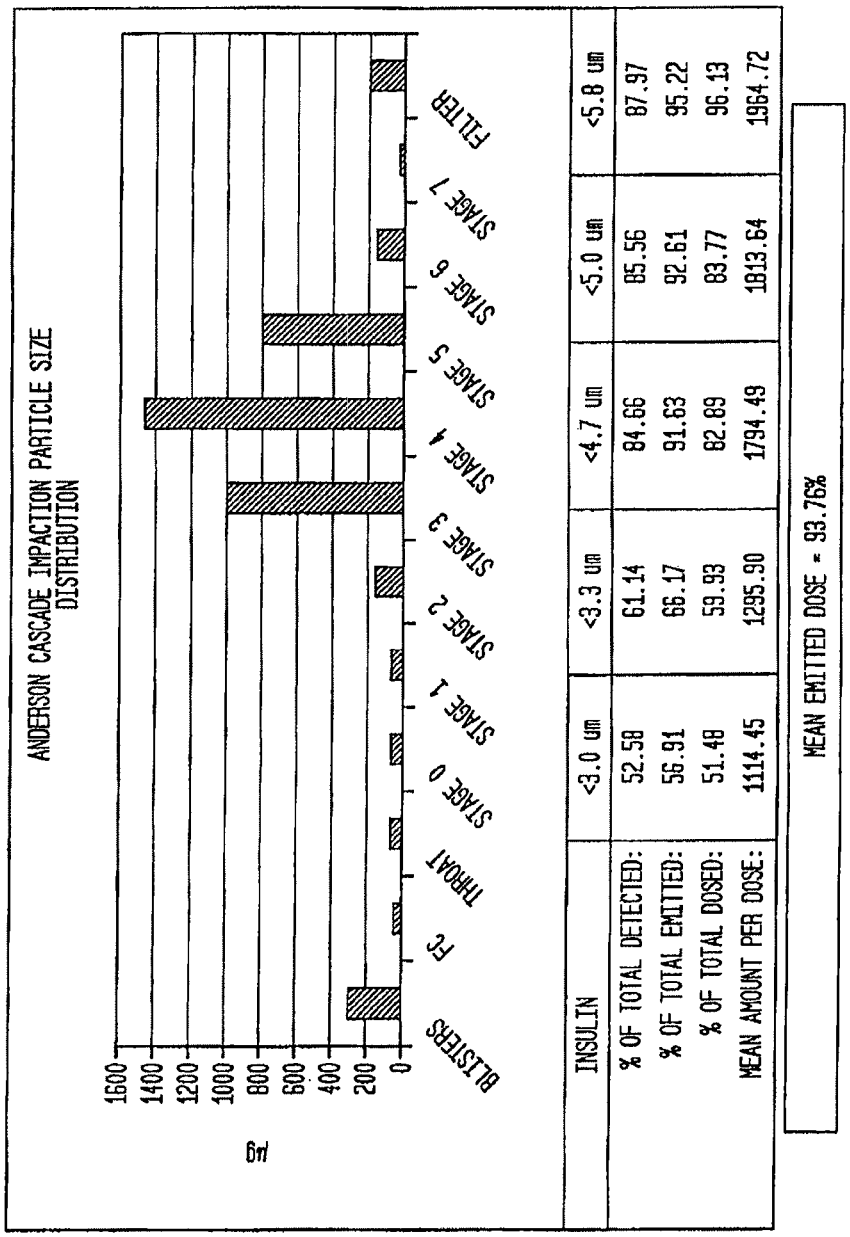
FIG. 2 shows particle size distribution of spray-dried insulin, which is determined by Anderson Cascade Impaction (ACI).

Spray-dried powders are well suited for delivery from an inhaler, for example, without limitation, a MicroDose inhaler. MicroDose routinely achieves both high emitted dose, and high fine particle fraction and dose with this formulation approach, both for neat as well as co-spray-dried blends. Exemplary aerosol performances for spray-dried insulin are shown in FIGS. 1 and 2.

Although dry micronization is a preferred powder production method for small molecules for pulmonary delivery, in contrast to spray-drying, it is a stressful method, which uses high shear forces. Because use of high shear forces may lead to fracturing of proteins and peptides, dry micronization is not routinely used for large molecules. In addition, if dose sizes are small, bulking agents are needed to improve the flowability and allow accurate measurement of the powders in filling operations. The primary excipient, and one of the only excipients approved for pulmonary delivery for this purpose is lactose, may need to be tested for chemical compatibility with MMI-0100 (YARAAARQARAKALARQLGVAA; SEQ ID NO: 1) or its functional eqivalents as lactose is incompatible with certain peptides.

The micronization process is fairly straightforward and well known in the art. Briefly, lyophilized dry powder of MMI-0100 (YARAAARQARAKALARQLGVAA; SEQ ID NO: 1) and its functional equivalents are run through milling stages until the prescribed target particle size distribution (i.e., MMAD, D10, D50, D90) is achieved. This neat micronized powder is tested for potency to ensure its activity post micronization, optimized for delivery from the inhaler, and its chemical and physical stability tested in the primary (heat sealed blister) packaging. The neat powder then is blended with a prioritized selection of approved pulmonary lactose grades to a target, tested for blend homogeneity, and run through the same inhaler optimization and stability testing.

MicroDose Dry Powder Inhaler (DPI)

Figure 3:
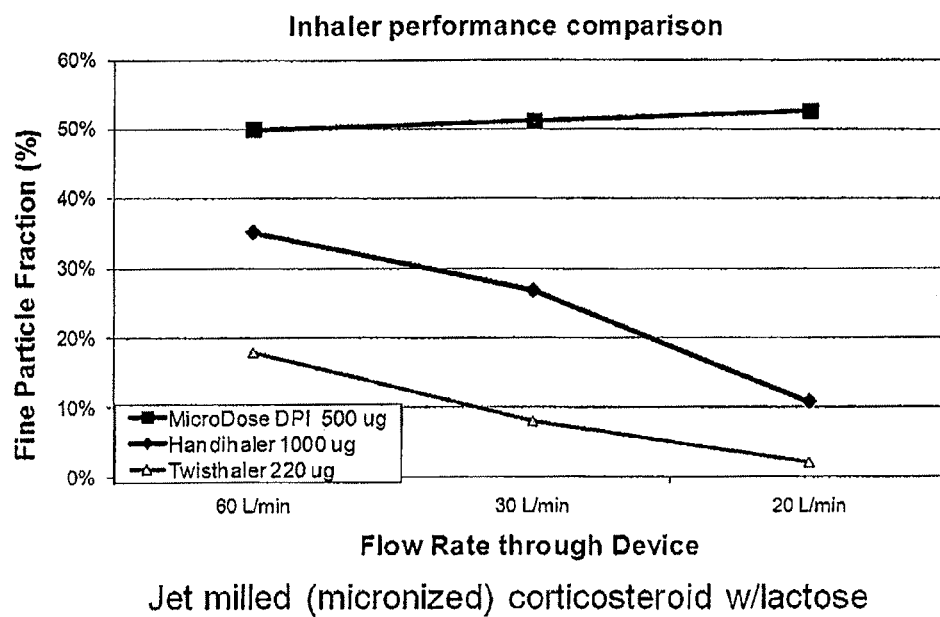
FIG. 3 shows efficiency and flow rate comparison of MicroDose Dry Powder Inhaler (DPI) vs. two marketed "passive" Dry Powder Inhalers (DPIs).
Figure 6:
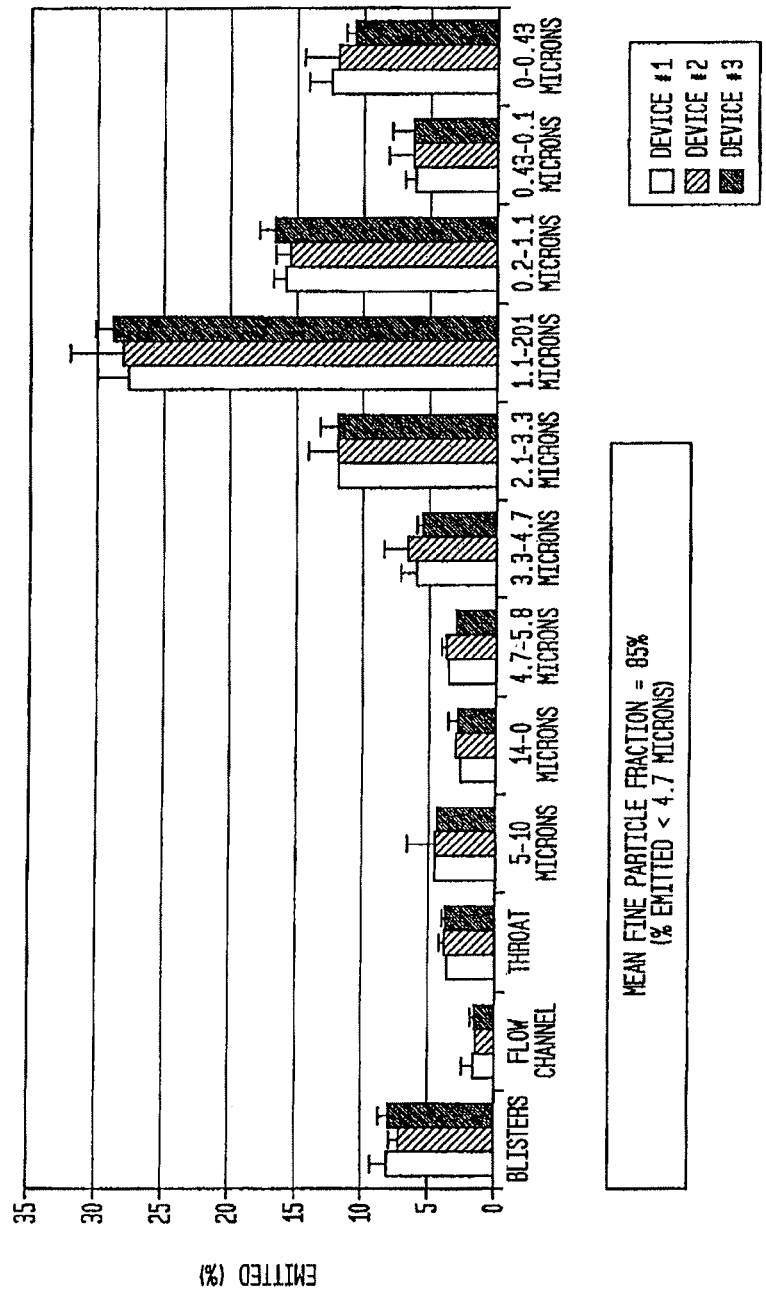
FIG. 6 shows particle size distribution of a spray-dried peptide (not insulin).
Figure 7:
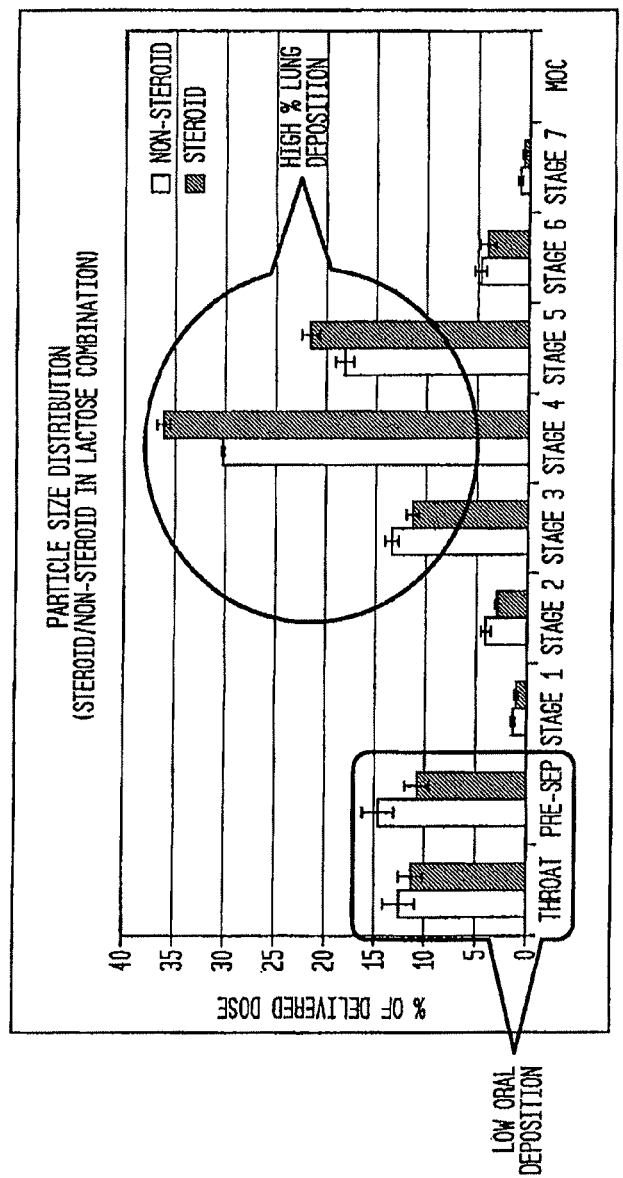
FIG. 7 shows particle size distribution of micronized/lactose blend combination, which is determined by Next Generation Impactor (NGI)
Figure 8:
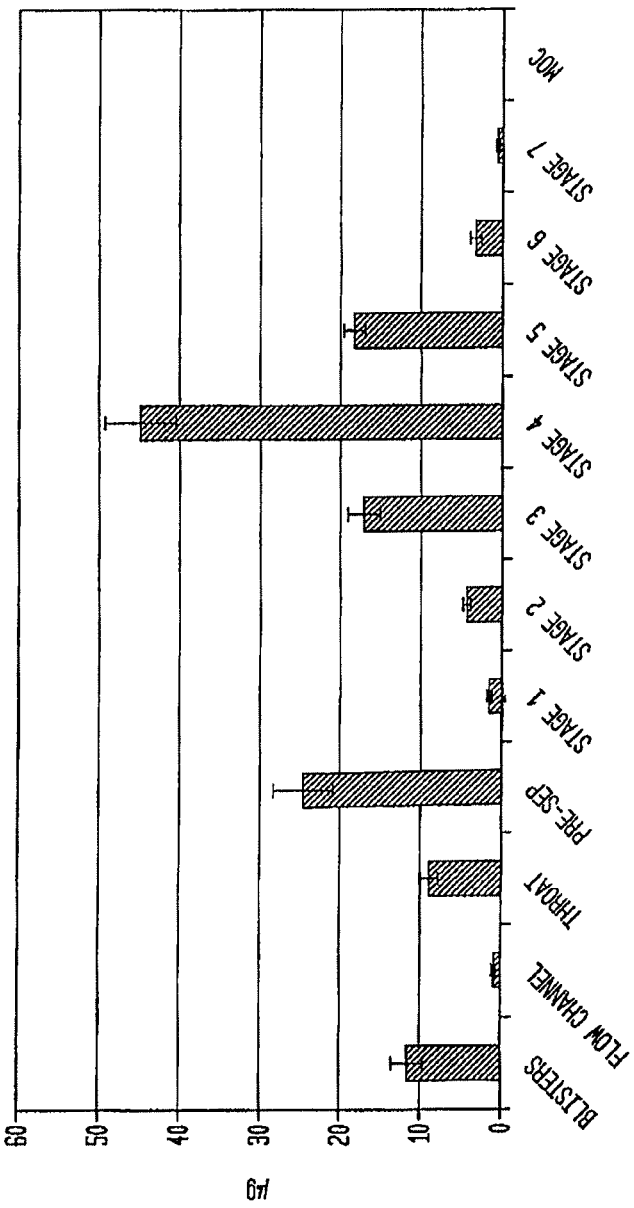
FIG. 8 shows delivery performance of micronized a small molecule (long-acting muscarinic agents (LAMA)/lactose blend).

According to some embodiment, MMI-0100 (YARAAARQARAKALARQLGVAA; SEQ ID NO: 1) and its functional equivalents can be administered using a dry powder inhaler (DPI). For example, the MicroDose dry powder inhaler (DPI) has an 'active' piezo driven aerosol generator that is breath actuated and achieves high efficiency of lung delivery independent of the patient's inhalation flow rate and volume. Unlike 'passive' DPIs that require a strong and forceful inhalation on the order of 40-60 liters per minute (LPM) flow for effective lung delivery, there is no breathing maneuver required for the MicroDose DPI, as it can deliver effectively over a very broad range of flow rates from as low as 10 LPM up to 90 LPM flow, with equivalent performance (see performance examples in FIGS. 3 and 4).

According to some other embodiments, MMI-0100 (YARAAARQARAKALARQLGVAA; SEQ ID NO: 1) and its functional equivalents can be administered using a tidal breathing application, such as a 'dry powder nebulizer' (DPN). The DPN delivers dry powder doses synchronized to inhalation tidal breathing with triggering as low as 2 litter per minute (LPM), expected peak flows of between 5 and 15 LPM and tidal volumes as low as 30 ml, which are much more challenging conditions than are expected with adult IPF patients. This new DPN has successfully completed its second clinical trial in adults, with completion of its first study in November, 2011. These results are accessible via internet on the world wide web (www) at the URL "clinicaltrials.gov/ct2/show/NCT01489306?spons=Microdose&rank=1."

The MicroDose electronic inhaler system is an extremely flexible formulation, can accurately and efficiently deliver both formulation modalities above with particularly high efficiency with spray dried drug products, and has shown this performance capability with over 30 small and large molecules. Spray-dried insulin in the primary packaging, for example, can last at least 18 months. Examples of delivery performance for both spray-dried peptides and micronized small molecules are shown in FIGS. 5-8.

As for the effect of the dry powder formulation on pulmonary membranes, e.g., sensitization, dry powder delivery, especially at low powder loads (<4-5 mg), is unlikely to affect pulmonary membranes or cause sensitization (cough, etc.) unless this is an intrinsic property of the active molecule (which we have not observed in animal studies). Excipients that have already been pulmonarily approved with excellent pulmonary biocompatibility are selected, and are present in very low quantities (i.e., low mg range). For instance, mannitol at low quantities is not likely to have an effect.

Liquid Nebulization

Alternatively, MMI-0100 (YARAAARQARAKALARQLGVAA; SEQ ID NO: 1) or its functional equivalents can be delivered via liquid nebulization. Previous preclinical studies have shown that MMI-0100 (YARAAARQARAKALARQLGVAA; SEQ ID NO: 1) can be delivered to rodents via an AeroGen® nebulizer system adapted for animal use.

In order to specifically address MMI-0100's (YARAAARQARAKALARQLGVAA; SEQ ID NO: 1) ability to be delivered to positively impact compromised lung, in the bleomycin animal model efficacy experiments, a solution of MMI-0100 (YARAAARQARAKALARQLGVAA; SEQ ID NO: 1) is effectively aerosolized. Local lung MMI-0100 (YARAAARQARAKALARQLGVAA; SEQ ID NO: 1) administration is achieved via a rodent nebulizer device designed and manufactured by Aerogen® (www.aerogen.com). The Aeroneb® Lab Micropump Nebulizer uses a high-efficiency aerosolization technology for use in preclinical aerosol research and inhalation studies, providing a valuable link between preclinical and clinical product development. The flow-rate is >0.3 ml/min, and is designed to deliver 2 mm-sized particles, with distribution into deepest alveoli. Efficacy of nebulized MMI-0100 (YARAAARQARAKALARQLGVAA; SEQ ID NO: 1) and cellular uptake throughout the lung has been demonstrated in the bleomycin mouse model of pulmonary fibrosis (see FIG. 16). Localized, clinically-relevant inhaled administration is as effective as conventional systemic injections in attenuating MK2 activation Example 4. The Level of Activated MK2 is Increased in Fibrotic Lesions of Patient Lungs with Idiopathic Pulmonary Fibrosis (IPF)

Mitogen-activated protein kinase (MAPK)-activated protein kinase 2 (MK2) is activated upon stress by p38MAPK-α and β. These two isoforms of p38MAPK bind to a basic docking motif in the carboxy terminus of MK2, which subsequently phosphorylate its regulatory sites. As a result of activation, MK2 is exported from the nucleus to the cytoplasm and co-transports active p38 MAPK to this compartment. MK2 stabilizes p38MAPK localization and is essential for differentiation, migration and cytokine production (Kotlyarov, A., Mol Cell Biol. 22(13): 4827-4835, 2002).

Figure 9:
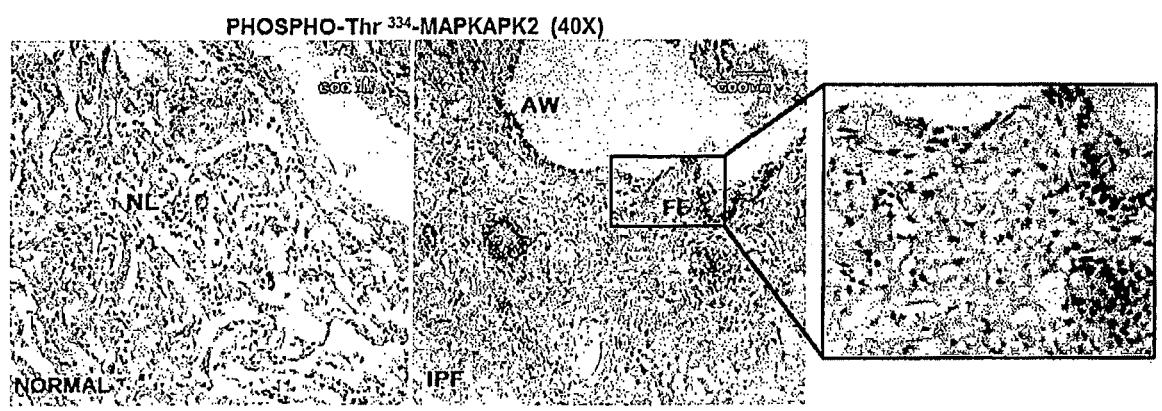
FIG. 9 shows immunohistochemical analysis of paraffin-embedded human idiopathic pulmonary fibrosis IPF lungs, showing nuclear localization of activated MK2 (i.e., Phospho-Thr$^{334}$-MAPKAPK2) at the fibroblastic focus. Normal lungs (left panel); IPF lung tissue biopsy section (right panel). Inset shows disruption of epithelial lining at the foci with cells staining positive (dark grey) for activated MK2. The abbreviations shown in FIG. 9 are as follows: NL (normal lung architecture with alveolar sacs); AW (air way); FF (fibroblastic foci from a lung tissue explants with IPF)

Therefore, in order to examine whether the p38MAPK-MK2 signaling pathway is activated in the lungs affected by IPF, lung sections obtained from normal and IPF patients were stained with a phospho-specific antibody against an activated form of MK2 (anti-phospho-Thr$^{334}$-MAP-KAPK2). Normal lung and IPF lung tissues were immunostained using DAB and nucleus was counterstained with Hematoxylin. As shown in FIG. 9, increased expression of activated MK2 was observed cells in the fibrotic foci from lung tissue explants derived from patients with IPF as compared with normal lung biopsy tissue (left). These results suggest that fibrosis formation in the lungs of IPF patients is characterized by aberrant activation of the p38MAPK-MK2 signaling pathway.

Example 5. Nebulized and Systemic Administration of MMI-0100 (YARAAARQARAKALARQLGVAA; SEQ ID NO: 1) Protects Against Bleomycin-Induced Lung Fibrosis in Mice One of the hallmarks of idiopathic pulmonary fibrosis (IPF) is the activation of mesenchymal cells and exuberant deposition of matrix, specifically collagen. The resultant accumulation of collagen in the lung can be measured both by histological and biochemical techniques, most notably via accumulation of hydroxyproline, which is almost totally derived from collagen in the lung and thus serves as a surrogate for whole lung collagen content (Umezawa H. et al., Cancer, 20(5):891-895, 1967).

Therefore, the therapeutic efficacy of the MMI-0100 peptide (YARAAARQARAKALARQLGVAA; SEQ ID NO: 1) on treating pulmonary fibrosis was assessed using a mouse model of bleomycin-induced pulmonary fibrosis by delivering the MMI-0100 (YARAAARQARAKALARQLGVAA; SEQ ID NO: 1) peptide systemically (intraperitoneal) or locally (via nebulized dosing) during prophylaxis or pre-fibrotic stage (i.e., drug administration beginning at day 7 post bleomycin injury; See FIG. 10) and by measuring the levels of collagen as indices of fibrosis in the bleomycin mouse.

Figure 10:
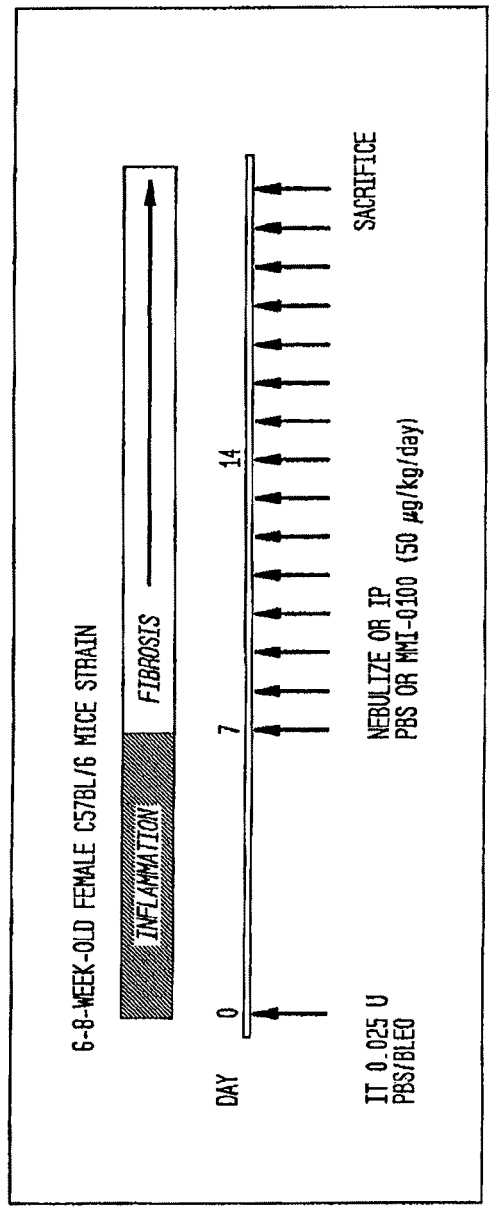
FIG. 10 shows a schematic diagram for testing ability of a compound to inhibit the development of fibrosis in the bleomycin mouse model of pulmonary fibrosis (Idiopathic Pulmonary Fibrosis (IPF) prevention model). Phosphate-buffered saline (PBS) or MMI-0100 (YARAAAR-QARAKALARQLGVAA (SEQ ID NO: 1)) is administered daily, either via nebulization or intraperitoneally, starting at day 7 post bleomycin delivery when inflammation subsides and fibrotic mechanisms are activated, until day 21 post bleomycin delivery when significant fibrosis is observed.

Briefly, fibrotic loci in the lungs of the mice were induced by delivering intratracheally about 0.025 U of bleomycin (dissolved in PBS) to C57BL/6 mice. In order to examine the efficacy of MMI-0100 (YARAAARQARAKALARQL-GVAA; SEQ ID NO: 1) in the treatment of the bleomycin-injured lungs in the prophylaxis/pre-fibrotic phase, a control (PBS) or MMI-0100 (YARAAARQARAKALARQL-GVAA; SEQ ID NO: 1) was administered daily, either intraperitoneally or via nebulization, starting at day 7 post bleomycin delivery (when inflammation subsides and fibrotic mechanisms are activated) until day 21 post bleomycin delivery (when significant fibrosis is observed) (FIG. 10). At 21 day post bleomycin delivery, lung tissues from the bleomycin mice treated with MMI-0100 (YARAAAR-QARAKALARQLGVAA; SEQ ID NO: 1) or a control (PBS), were isolated, fixed, embedded in paraffin, and sectioned for staining. Briefly, mice were sacrificed with a sodium pentobarbital injection (120 mg/kg) and the chest cavity was opened. The right mainstem bronchus was ligated and the right lung was removed. The trachea was cannulated and the left lung was perfused with 4% formaldehyde at 21 cm $H_2O$ pressure. The tissue blocks then were embedded in paraffin, and 4-mm sections were prepared, and stained with hematoxylin and eosin (H&E; for pathological examination) or Masson's Trichrome (for collagen staining)

Figure 11:
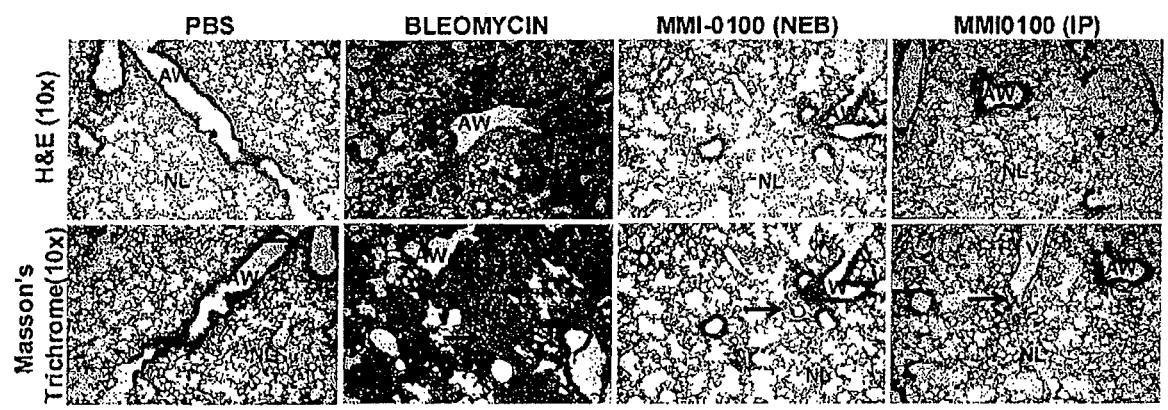
FIG. 11 shows that inhalation therapy and systemic administration of MMI-0100 (YARAAARQARAKALARQLGVAA; SEQ ID NO: 1) protects against bleomycin-induced lung fibrosis in mice. Upper panel: Hematoxylin and Eosin (H&E) staining of representative mouse lung tissues at day 21. Lower panel: Masson's blue trichrome staining of the same fields reveal extensive collagen deposition (arrows) with bleomycin injury. Abbreviations: AW: airway; NL: normal lung architecture; FF: fibrotic foci; V: vein.

As shown in FIG. 11, the lung sections from PBS-treated mice exhibited normal lung structures (NL) and airways (AW). In contrast, the lung sections from the bleomycin mice (at day 21) revealed narrowed airway (AW) structure with formation of fibrotic foci (FF) (upper panel; Hematoxylin & Eosin (H&E) staining) and increased accumulation of collagen (arrows in the lower panel; Masson's Trichrome staining) in lung tissues, which are reminiscence of those found in IPF patients. Administration of MMI-0100 (YARAAARQARAKALARQLGVAA; SEQ ID NO: 1), either via nebulization or intraperitoneally, however, significantly reduced development of fibrotic loci formation (upper panel, MMI-0100 (NEB) and MMI-0100 (IP)) and reduced collagen accumulation (lower panel, MMI-0100(NEB) and MMI-0100 (IP)) in the lungs of the bleomycin mice.

Figure 12:
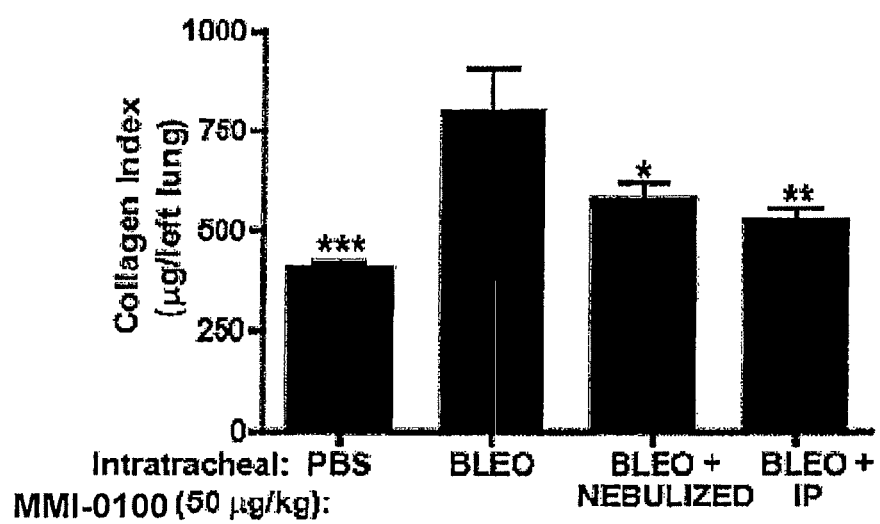
FIG. 12 shows that MMI-0100 (YARAAARQARAKALARQLGVAA; SEQ ID NO: 1) prevents significant collagen deposition due to bleomycin injury. Values represent means±SEM. n=5 animals per group. '*' $p<0.05$; '' $p<0.01$; '*' $p<0.001$. Collagen Index=constant factor for collagen 7.5× hydroxy proline concentrations.

Next, total collagen levels in the lungs of the bleomycin-injured mice (FIG. 12) were analyzed quantitatively by computing a constant conversion factor (7.5) for collagen from hydroxyproline concentrations (Neuman R. and Logan M, J Biol Chem., 186(2):549-56, 1950, incorporated by reference). As shown in FIG. 12, both nebulized (BLEO+NEBULIZED) and systemic (BLEO+IP) administration of MMI-0100 (YARAAARQARAKALARQLGVAA; SEQ ID NO: 1) during the post-inflammatory/pre-fibrotic stage significantly decreased collagen deposition compared to the bleomycin control.

Example 6. Dose-Response Data of MK2 Peptide Inhibitors in the Idiopathic Pulmonary Fibrosis Prevention Model Next, the effect of increasing doses of MK2 peptide inhibitors on collagen deposition was examined in vivo using the bleomycin mouse model of idiopathic pulmonary fibrosis (prevention model). Briefly, C57-BL/6 mice were subjected to bleomycin injury at day 0. Beginning at day 7 and continuing through day 21, mice were administered 25, 50 or 75 µg/kg of MMI-0100 (YARAAARQARAKALAR-QLGVAA; SEQ ID NO: 1) or MMI-0200 (YARAAAR-QARAKALNRQLGVA; SEQ ID NO: 19) daily via intraperitoneal (IP) injection. As shown in FIG. 13, Masson's blue trichrome staining revealed a decrease in collagen levels in the lung of the bleomycin injured mouse treated with MMI-0100 (YARAAARQARAKALARQLGVAA; SEQ ID NO: 1), suggesting that MMI-0100 (YARAAAR- QARAKALARQLGVAA; SEQ ID NO: 1) can protect fibrosis in the lungs due to bleomycin injury in a dose-dependent manner. These data suggest that MMI-0100 (YARAAAR-QARAKALARQLGVAA; SEQ ID NO: 1) retains its potential as a fibroprotective compound even at higher doses.

In contrast, treatment of the bleomycin injured mice with MMI-0200 (YARAAARQARAKALNRQLGVA; SEQ ID NO: 19) did not reduce, but rather increased the collagen deposition in the lung at the doses tested. This result, however, is consistent with a previous study involving MK2 knockout mice and MK2-/- mouse embryonic fibroblast (MEFs), in which all MK2 activity was ablated, which exhibited an aggravated fibrosis phenotype (Liu et al., Am J Respir Cell Mol Biol, 37: 507-517, 2007).

Without being limited by theory, these results suggest (1) that MK2 inhibitory peptides of the described invention may exhibit a spectrum of inhibitory activities against a specific group of kinases; (2) MMI-0100 (YARAAARQARAKA-LARQLGVAA; SEQ ID NO: 1) and MMI-0200 (YARAAARQARAKALNRQLGVA; SEQ ID NO: 19) may inhibit MK2 and other kinases differentially, which, depending on the dose applied, contributes to this spectrum of inhibitory activities; (3) that myofibroblast formation and/or migration might also be a part of the repair phase of fibrosis rather than of active damage; and (4) that a certain level of MK2 activity is, therefore, necessary for that process to occur (Liu et al., Am J Respir Cell Mol Biol, 37: 507-517, 2007).

In addition, the MK2 inhibitory peptides of the described invention were derived from the substrate binding site of MK2 downstream target HSPB1. Therefore, they can competitively inhibit the kinase activity of MK2 toward HSPB1. Without being limited by theory, the differential effects of MMI-0200 (YARAAARQARAKALNRQLGVA; SEQ ID NO: 19) on fibrosis may be attributed to its sequence differences, its homology to the HSPB1 biding sites, its differential inhibition of MK2 kinase activity toward a distinct target protein binding site, or a combination thereof.

Example 7. Administration of MMI-0100 (YARAAARQARAKALARQLGVAA; SEQ ID NO: 1) Effectively Blocks Systemic T-Cell Activation in Idiopathic Pulmonary Fibrosis Prevention Model Recent studies highlighted a key role for T lymphocytes in bleomycin-induced fibrosis (Wilson, M. et al., The Journal of Experimental Medicine, 207(3): 535-552, 2010). Therefore, in order to investigate the functional role of splenic (pan) T cells in the bleomycin injured mice treated with MMI-0100 (YARAAARQARAKALARQLGVAA; SEQ ID NO: 1), the autologous mixed lymphocyte reaction (MLR) was performed as described previously (Wilkes, D. et al., Journal of Leukocyte Biology, 64(5):578-586, 1998, incorporated by reference herein). Specifically, the ability of C57BL/6 purified antigen-presenting cells to induce proliferation in C57BL/6 T lymphocytes was examined in the assay.

C57-BL/6 mice were subjected to bleomycin injury at day 0. At day 7, the mice were administered 50 µg/kg/day MMI-0100 (YARAAARQARAKALARQLGVAA; SEQ ID NO: 1) daily by intraperitoneal (IP) injection or nebulizer (NEB) until day 21. Splenic T cells were isolated and cultured alone or in the presence of autologous antigen presenting cells (APCs from C57-BL/6 mice) or stimulated with antibodies against CD3 (α-CD3) for 48 h. The cells then were radiolabeled with triturated thymidine for 16 h and assessed for proliferation rates.

Figure 14:
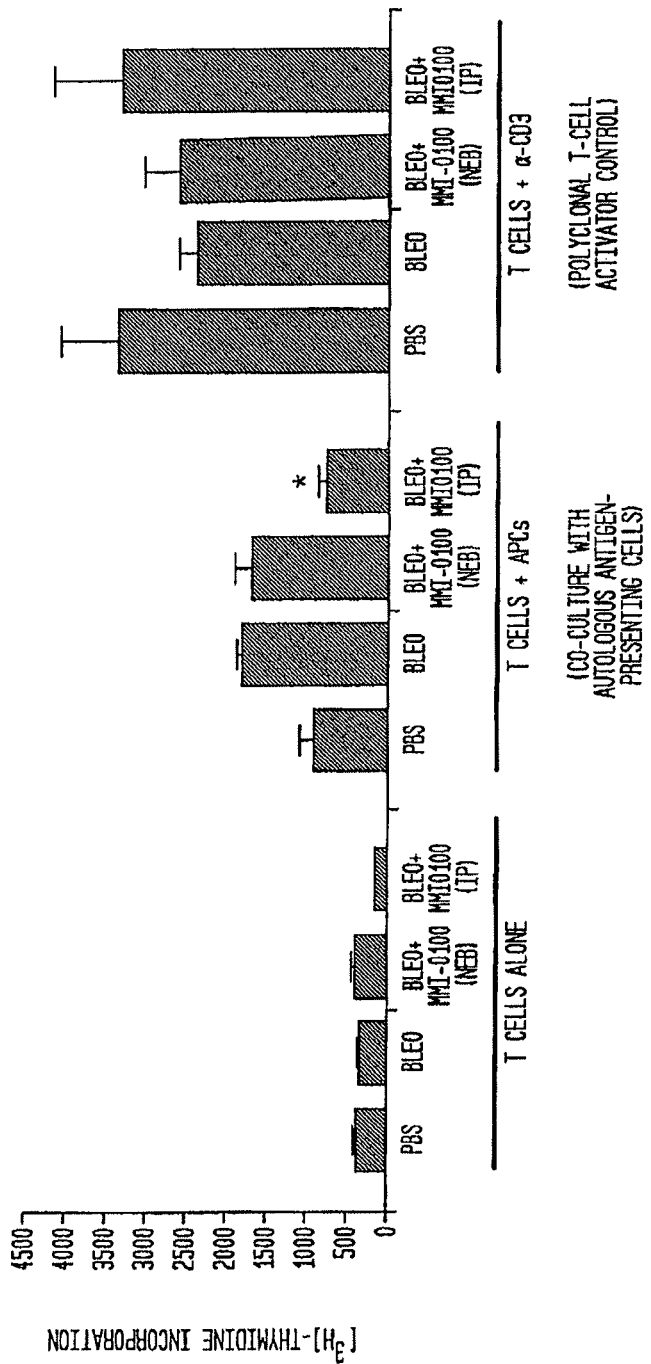
FIG. 14 shows that systemically-administered MMI-0100 (YARAAARQARAKALARQLGVAA; SEQ ID NO: 1) abrogates systemic T cell activation due to bleomycin injury. Values represent mean±SEM. 'p' value <0.01. n=4 animals/group. The abbreviations shown in FIG. 14 are as follows: (i) wild type mice treated with PBS (PBS); (ii) the bleomycin mice treated with PBS (BLEO); (iii) the bleomycin mice treated with nebulized MMI-0100 (YARAAARQARAKALARQLGVAA (SEQ ID NO: 1)) (BLEO+MMI-0100 (NEB)); and (iv) the bleomycin mice treated with intraperitoneal MMI-0100 (YARAAARQARAKALARQLGVAA (SEQ ID NO: 1)) (BLEO+MMI-0100 (IP)).

As shown in FIG. 14, T cells alone, regardless of treatment, exhibited very low proliferative capacity. However, when the T cells were co-cultured with autologous antigen presenting cells (i.e., APCs isolated from C57-BL/6 mice), the proliferative capacity was significantly higher for bleomycin-injured mice than for control mice. Interestingly, the proliferation of T cells from bleomycin treated mice seen in the presence of antigen presenting cells was significantly reduced by the systemic administration of MMI-0100 (YARAAARQARAKALARQLGVAA; SEQ ID NO: 1), but as expected, not by the inhaled mode. These data suggest the suppression of splenic T cell activation by MMI-0100 (YARAAARQARAKALARQLGVAA; SEQ ID NO: 1), and indicate that the peptide MK2 inhibitor is fibro-protective.

The viability of the T cells also was confirmed by stimulating the cells with antibodies against α-CD3, a polyclonal T cell activator. α-CD3 induced robust proliferation of the cells irrespective of the treatment group. The proliferative response to the polyclonal activator suggests that the MMI-0100 (YARAAARQARAKALARQLGVAA; SEQ ID NO: 1) peptide inhibitor does not affect the functional property of the splenic T cells, and that there is no toxicity with the administration of MMI-0100 (YARAAARQARAKALAR-QLGVAA; SEQ ID NO: 1) at this particular dose. In addition, the lack of splenic T cell response to nebulized MMI-0100 (YARAAARQARAKALARQLGVAA; SEQ ID NO: 1) suggests that little systemic distribution occurs with this mode of peptide delivery.

Figure 15:
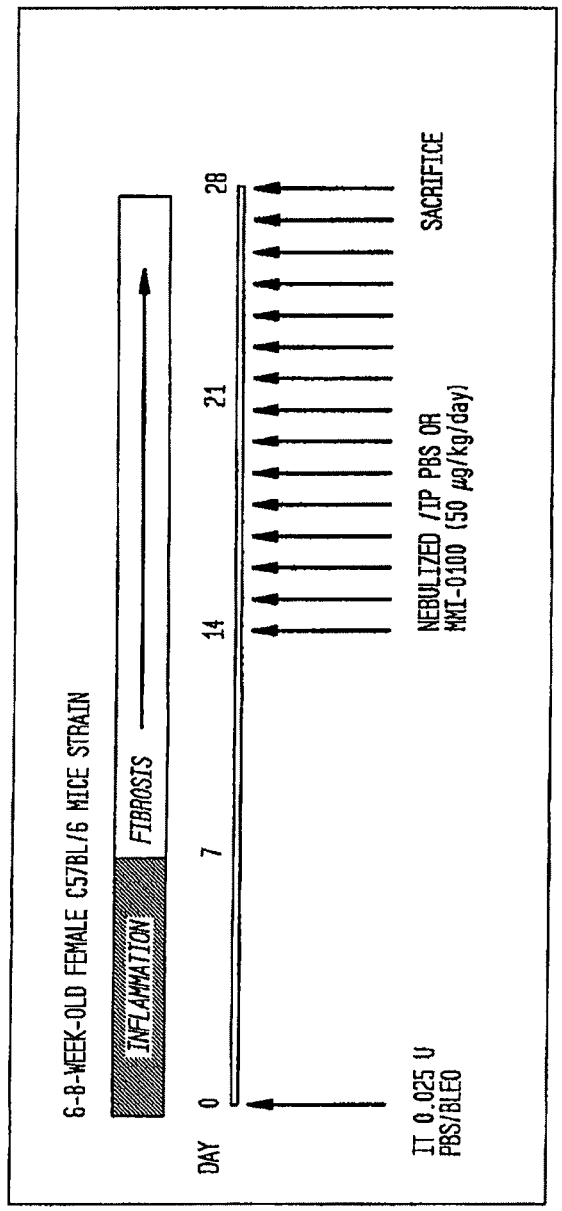
FIG. 15 shows a schematic diagram for testing ability of MMI-0100 (YARAAARQARAKALARQLGVAA; SEQ ID NO: 1) to abrogate fibrosis progression in the bleomycin model of idiopathic pulmonary fibrosis (IPF treatment model). PBS or MMI-0100 (YARAAARQARAKALARQLGVAA (SEQ ID NO: 1)) is administered via nebulization or intraperitoneally at the doses of 50 µg/kg daily starting at day 14 post bleomycin delivery until day 28 post bleomycin delivery.

Example 8. Systemic or Nebulized MMI-0100 (YARAAARQARAKALARQLGVAA; SEQ ID NO: 1) Treatment Protects Bleomycin Injured Lungs in the Post-Fibrotic Phase The classic bleomycin model, as depicted in FIG. 10, has been used widely in the literature in the pre-fibrotic stage to test efficacy of any intervention. Since both nebulized and systemic administration of the MMI-0100 (YARAAAR-QARAKALARQLGVAA; SEQ ID NO: 1) significantly protected the lung from bleomycin-induced fibrosis, the effect of systemic (intraperitoneal) or local (nebulized) administration of MMI-0100 (YARAAARQARAKALAR-QLGVAA; SEQ ID NO: 1) in the treatment of bleomycin injured lungs was examined further at the post-fibrotic stage, with drug intervention being begun at day 14, a time point when the lungs are significantly fibrosed (FIG. 15) (Pottier, N. et al., American Journal of Respiratory and Critical Care Medicine, 176(11): 1098-1107, 2007, incorporated by reference herein). The rescuing of scarred lungs that is shown in this model is clinically relevant, given that lungs of IPF patients already are scarred at the time of diagnosis.

More specifically, fibrotic loci in the lungs were induced by delivering intratracheally about 0.025 U of bleomycin (dissolved in PBS) to C57BL/6 mice. In order to examine the efficacy of MMI-0100 (YARAAARQARAKALARQL-GVAA; SEQ ID NO: 1) in the treatment of bleomycin-injured lungs in the post-fibrotic phase, PBS (control) or MMI-0100 (YARAAARQARAKALARQLGVAA; SEQ ID NO: 1) was administered to the mice either intraperitoneally or via nebulization daily starting at day 14 post bleomycin delivery until day 28 post bleomycin delivery. At 28 day post bleomycin delivery, the lung tissues of the bleomycin mice treated with MMI-0100 (YARAAARQARAKALARQL-GVAA; SEQ ID NO: 1) or a control (PBS), were isolated, fixed, embedded in paraffin, and sectioned for staining. Mice were sacrificed with a sodium pentobarbital injection (120 mg/kg) and the chest cavity was opened. The right mainstem bronchus was ligated and the right lung is removed. The trachea was cannulated and the left lung was perfused with 4% formaldehyde at 21 cm H$_2$O pressure. The tissue blocks then were embedded in paraffin, and 4-mm sections were prepared, and stained with hematoxylin and eosin (H&E; for pathological examination) or Masson's Trichrome (for collagen staining)

Figure 16:
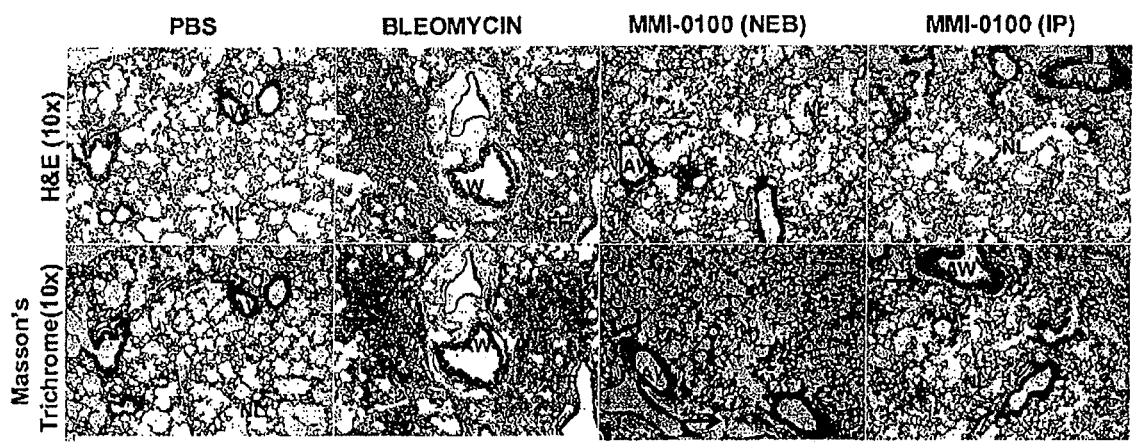
FIG. 16 shows that systemic (IP) or nebulized (NEB) administration of MMI-0100 (YARAAARQARAKALARQLGVAA; SEQ ID NO: 1) ameliorates bleomycin-induced lung fibrosis in mice. Upper panel: Hematoxylin and Eosin (H&E) staining; Lower panel: Masson's blue trichrome staining of the same fields. The abbreviations shown in FIG. 16 are as follows: PBS (wild type mice treated with PBS)

As shown in FIG. 16, regardless of the mode of drug administration, i.e., whether intraperitoneally delivered or locally applied to the lung, MMI-0100 (YARAAARQARAKALARQLGVAA; SEQ ID NO: 1) treatment "rescued" severely scarred lungs. Histological assessment was employed to examine lung architecture (Hematoxylin & Eosin (H&E) staining, top panel) and collagen distribution (Masson's blue trichrome staining, bottom panel). The histochemistry results show that while bleomycin-injured lungs are severely scarred, MMI-0100 (YARAAARQARAKALARQLGVAA; SEQ ID NO: 1)-treated mice have a clearer lung parenchyma.

Next, collagen deposition was determined quantitatively by using the standard hydroxyproline assay with whole left lung. Total collagen (soluble and insoluble) deposition was assessed by analyzing hydroxyproline concentrations in murine lungs day 28 post bleomycin injury. MMI-0100 (YARAAARQARAKALARQLGVAA (SEQ ID NO: 1)) was administered at the dose of 50 mg/kg/day by intraperitoneal injection (IP) or nebulizer (NEB) beginning at day 14 post bleomycin injury.

As shown in FIG. 17, MMI-0100 (YARAAARQARAKALARQLGVAA; SEQ ID NO: 1) treatment significantly arrested further progression of collagen deposition, as compared to baseline, at 28 days post-bleomycin injury and the onset of MMI-0100 (YARAAARQARAKALARQLGVAA; SEQ ID NO: 1) treatment. This is significant because while current literature shows effective prophylaxis in drug development, when IPF patients are diagnosed, there is pre-existing fibrosis. These results also suggest that MMI-0100 (YARAAARQARAKALARQLGVAA; SEQ ID NO: 1) has the potential to effectively halt or slow further progression of the disease and improve quality of life; and that the MMI-0100 (YARAAARQARAKALARQLGVAA; SEQ ID NO: 1) peptide, if used at a higher dose and/or for a longer treatment period, may result in even greater improvement in lung histology and physiology, and diminished fibrosis.

Example 9. Either Systemic or Local Administration of MMI-0100 (YARAAARQARAKALARQLGVAA; SEQ ID NO: 1) is Correlated with Reduced Activated MK2 in the Bleomycin Mouse Model of Idiopathic Pulmonary Fibrosis As discussed above, one of the principal targets of MMI-0100 (YARAAARQARAKALARQLGVAA; SEQ ID NO: 1) and its functional equivalents in the lung is MK2 kinase, which elicits inflammatory and fibrotic responses in the affected lungs. Therefore, in order to further validate the effects of MMI-0100 (YARAAARQARAKALARQLGVAA; SEQ ID NO: 1) in vivo, levels of activated MK2 (phospho-Thr$^{334}$-MAPKAPK2) were examined in untreated bleomycin injured mice as well as in MMI-0100 (YARAAARQARAKALARQLGVAA; SEQ ID NO: 1)-treated mice.

Briefly, C57-BL/6 mice were subjected to bleomycin injury at day 0. At day 14, the mice were administered 50 µg/kg of MMI-0100 (YARAAARQARAKALARQLGVAA; SEQ ID NO: 1) daily by intraperitoneal (IP) injection or nebulizer (NEB) until day 28 post bleomycin injury. Formalin-fixed lung tissue sections were immunostained against phospho-Thr$^{334}$ MK2. Control staining was with biotinylated secondary IgG antibody. Streptavidin-conjugated horseradish peroxidase was used with 3,3'-diaminobenzidene as substrate and nuclei was counterstained with hematoxylin. Whereas the bleomycin mice showed a visible increase in activated MK2 presence (dark nodules) if left untreated, most particularly in areas of significant collagen deposition, mice treated with MMI-0100 exhibited activated MK2 presence similar to normal tissue, with such distribution concentrated in peri-airway and blood vessel regions.

As shown in FIG. 18, regardless of the mode of delivery, i.e., either systemic or local administration, in contrast to the control, administration of nebulized or intraperitoneal MMI-0100 (YARAAARQARAKALARQLGVAA; SEQ ID NO: 1) was associated with decreased phospho-Thr$^{334}$-MAPKAPK2 staining (activated form of MK2) in the bleomycin mouse model.

Example 10. MMI-0100 (YARAAARQARAKALARQLGVAA; SEQ ID NO: 1) Downregulates Inflammatory Cytokines in Idiopathic Pulmonary Fibrosis Treatment Model One potential mechanism by which MMI-0100 (YARAAARQARAKALARQLGVAA; SEQ ID NO: 1) can inhibit fibrosis formation in the lung is by decreasing local concentrations of pro-inflammatory cytokines, and thereby deterring recruitment of monocytes and aberrant extracellular remodeling by macrophages in the lung (e.g., increase in collagen deposition, increase in cell adhesion and migration, decrease in matrix degradation). To explore this possibility, the ability of the MMI-0100 (YARAAARQARAKALARQLGVAA; SEQ ID NO: 1) peptide to inhibit production of pro-inflammatory cytokines was examined by measuring changes in interleukin-6 (IL-6) and Tumor Necrosis Factor-alpha (TNF-α) levels upon treatment with MMI-0100 (YARAAARQARAKALARQLGVAA; SEQ ID NO: 1) intraperitoneally or via nebulization.

Interleukin-6 (IL-6) is a multifunctional cytokine whose major actions include enhancement of immunoglobulin synthesis, activation of T cells, and modulation of acute-phase protein synthesis. Many different types of cells are known to produce IL-6, including monocytes, macrophages, endothelial cells, and fibroblasts, and expression of the IL-6 gene in these cells is regulated by a variety of inducers. Interleukin-1β (IL-1β) and tumor necrosis factor (TNF-α) are two key known inducers of IL-6 gene expression. Other inducers include activators of protein kinase C, calcium inophore A23187, and various agents causing elevation of intracellular cyclic AMP (cAMP) levels.

Tumor necrosis factor (TNF, also referred as TNF-α) is a cytokine involved in systemic inflammation and is a member of a group of cytokines that stimulate the acute phase reaction. Studies have shown that TNF-α induces expression of IL-6 via three distinct signaling pathways inside the cell, i.e., 1) NF-κB pathway 2) MAPK pathway, and 3) death signaling pathway.

As shown in FIG. 20, administration of either intraperitoneal (BLEO+MMI-0100 (IP)) or nebulized (BLEO+MMI-0100 (NEB)) MMI-0100 (YARAAARQARAKALARQLGVAA; SEQ ID NO: 1) significantly reduced the plasma level of both TNF-α (A, upper panel) and IL-6 (B, lower panel) in the bleomycin mouse model of idiopathic pulmonary fibrosis.

Example 11. Either Systemic or Local Administration of MMI-0100 (YARAAARQARAKALARQLGVAA; SEQ ID NO: 1) Effectively Blocks Myofibroblast Activation Accumulation in Murine Lung that is Significantly Scarred Due to Bleomycin-Injury The hallmark of idiopathic pulmonary fibrosis (IPF) is the accumulation of myofibroblasts at fibrotic lesions and expression of abundant alpha-smooth muscle actin (α-SMA), a marker for myofibroblast activation. Furthermore, activated myofibroblasts are in part responsible for rigidity of the lung parenchyma and aggravation of lung function.

Therefore, the expression level of α-SMA in bleomycin-injured lungs was assessed in the lungs of bleomycin-injured mice treated with MMI-0100 (YARAAARQARAKALARQLGVAA; SEQ ID NO: 1), either systemically (via intraperitoneal administration) or locally (via nebulization). As shown in FIG. 21, the level of α-SMA was significantly attenuated in MMI-0100 (YARAAARQARAKALARQLGVAA; SEQ ID NO: 1)-treated lungs compared to the level of α-SMA in untreated bleomycin-injured lungs.

Example 12. Dose Response Studies of MMI-0100 (YARAAARQARAKALARQLGVAA; SEQ ID NO: 1) in Modulating TGF-β1-Induced Myofibroblast Activation In Vitro The major hallmarks of idiopathic pulmonary fibrosis (IPF) are the presence of atypical and apoptotic epithelial cells, along with activated myofibroblasts that secrete exuberant amounts of matrix proteins including collagens, fibronectin and matrix metalloproteinases (Horowitz, J and Thannickal, V., *Treatments in Respiratory Medicine*, 5(5): 325-42, 2006). Under normal wound healing processes, a provisional matrix is formed by the myofibroblasts as a temporary scaffolding. Contraction of the provisional matrix results in subsequent re-epithelialization and eventual wound healing. However, when activated myofibroblasts are resistant to apoptosis, the resultant exuberant collagen deposition leads to stabilization of the matrix (Tomasek, J. et al., *Nature Reviews Molecular Cell Biology*, 3(5): 349-63, 2002). The end-result of unchecked myofibroblast proliferation, activation and resistance to apoptosis results in fibrotic lesions with stabilized matrix due to collagen deposition and thus eventual distortion of lung architecture (Yamashita, C. et al., *The American Journal of Pathology*, 179(4): 1733-45, 2011).

Therefore, since fibroblasts are the key cells involved in scar formation, the effect of MMI-0100 (YARAAARQARAKALARQLGVAA; SEQ ID NO: 1) on myofibroblast activation was assessed by examining the protein levels of α-smooth muscle actin (α-SMA) and fibronectin in cultured human fetal lung fibroblasts (IMR-90 cells) treated with TGF-β. As shown in FIGS. 22 and 23, MMI-0100 (YARAAARQARAKALARQLGVAA; SEQ ID NO: 1) effectively prevented myofibroblast activation induced by TGF-β in a dose-dependent manner, as shown by decreases in the levels of both α-smooth muscle actin (α-SMA) (FIG. 22) and fibronectin (FIG. 23).

In contrast, MMI-0200 (YARAAARQARAKALNRQLGVA; SEQ ID NO: 19) at the doses tested did not affect the TGF-β-mediated myofibroblast activation, as indicated by no changes in the protein level of myofibroblast activation markers α-smooth muscle actin (FIG. 21) and fibronectin (FIG. 23). Without being limited by theory, these results suggest (1) that MK2 inhibitory peptides of the described invention may exhibit a spectrum of inhibitory activities against a specific group of kinases; (2) that MMI-0100 (SEQ ID NO: 1) and MMI-0200 (SEQ ID NO: 19) may inhibit MK2 and other kinases differentially, which, depending on the dose applied, contributes to this spectrum of inhibitory activities; (3) that there might be compensatory pathways that regulate α-smooth muscle actin; (4) that myofibroblast formation and/or migration might also be a part of the repair phase of fibrosis rather than of active damage; and (5) that a certain level of MK2 activity is, therefore, necessary for that process to occur (Liu et al., Am J Respir Cell Mol Biol, 37: 507-517, 2007).

In addition, the MK2 inhibitory peptides of the described invention were derived from the substrate binding site of MK2 downstream target HSPB1. Therefore, they can competitively inhibit the kinase activity of MK2 toward HSPB1. Without being limited by theory, the differential effects of MMI-0200 (SEQ ID NO: 19) on fibrosis may be attributed to its sequence differences, its homology to the HSPB1 biding sites, and its differential inhibition of MK2 kinase activity toward a distinct target protein binding site.

Example 13. MMI-0100 Enhances Isoproterenol-Induced Airway Smooth Muscle Relaxation In Vitro Contractile activity in smooth muscle is determined primarily by the phosphorylation state of the myosin light chain. Calcium activated phosphorylation of the myosin light chain initiates smooth muscle contraction. The activator Ca2+ forms a complex with the acidic protein calmodulin, which in turn activates myosin light chain (MLC) kinase to phosphorylate the light chain of myosin.

In addition to the Ca2+-dependent activation of MLC kinase, the state of myosin light chain phosphorylation is further regulated by MLC phosphatase, which removes the high-energy phosphate from the light chain of myosin to promote smooth muscle relaxation. There are three subunits of MLC phosphatase: a 37-kDa catalytic subunit, a 20-kDa variable subunit, and a 110- to 130-kDa myosin-binding subunit. The myosin-binding subunit, when phosphorylated, inhibits the enzymatic activity of MLC phosphatase, allowing the light chain of myosin to remain phosphorylated, thereby promoting contraction. The small G protein RhoA and its downstream target Rho kinase play an important role in the regulation of MLC phosphatase activity. Rho kinase, a serine/threonine kinase, phosphorylates the myosin-binding subunit of MLC phosphatase, inhibiting its activity and thus promoting the phosphorylated state of the myosin light chain. Pharmacological inhibitors of Rho kinase, such as fasudil and Y-27632, block its activity by competing with the ATP-binding site on the enzyme. Rho kinase inhibition induces relaxation of isolated segments of smooth muscle contracted to many different agonists. In the intact animal, the pharmacological inhibitors of Rho kinase have been shown to cause relaxation of smooth muscle in arteries, resulting in a blood pressure-lowering effect. It is thought that receptors activate a heterotrimeric G protein that is coupled to RhoA/Rho kinase signaling via guanine nucleotide exchange factors (RhoGEFs). Because RhoGEFs facilitate activation of RhoA, they regulate the duration and intensity of signaling via heterotrimeric G protein receptor coupling. There are 70 RhoGEFs in the human genome, three of which have been identified in smooth muscle: PDZ-RhoGEF, LARG (leukemia-associated RhoGEF), and p115-RhoGEF.

Several recent studies suggest a role for additional regulators of MLC kinase and MLC phosphatase. Calmodulin-dependent protein kinase II promotes smooth muscle relaxation by decreasing the sensitivity of MLC kinase for Ca2+. Additionally, MLC phosphatase activity is stimulated by the 16-kDa protein telokin in phasic smooth muscle and is inhibited by a downstream mediator of DG/protein kinase C, CPI-17.

Smooth muscle relaxation occurs either as a result of removal of the contractile stimulus or by the direct action of a substance that stimulates inhibition of the contractile mechanism (e.g., atrial natriuretic factor is a vasodilator). The process of relaxation involves actin cytoskeletal regulation, a decreased intracellular Ca2+ concentration, Ca2+ sensitivity and increased MLC phosphatase activity.

Several mechanisms involving the sarcoplasmic reticulum and the plasma membrane are implicated in the removal of cytosolic Ca2+. Ca2+ uptake into the sarcoplasmic reticulum is dependent on ATP hydrolysis. A sarcoplasmic reticular Ca2+, Mg2+-ATPase, when phosphorylated, binds two Ca2+ ions, which then are translocated to the luminal side of the sarcoplasmic reticulum and released. Mg2+, which binds to the catalytic site of the ATPase, is necessary for the enzyme to mediate the reaction. The sarcoplasmic reticular Ca2+, Mg2+-ATPase is inhibited by several different pharmacological agents: vanadate, thapsigargin, and cyclopiazonic acid. Sarcoplasmic reticular Ca2+-binding proteins also contribute to decreased intracellular Ca2+ levels. Recent studies have identified calsequestrin and calreticulin as sarcoplasmic reticular Ca2+-binding proteins in smooth muscle.

Isometric and Isotonic Muscle Contraction

The term "isometric contraction" as used herein refers to a muscle contraction in which the muscle is activated, but it is held at a constant length instead of being allowed to lengthen or shorten. Therefore, the force generated during an isometric contraction becomes dependent on the length of the muscle while contracting. On the other hand, if the muscle is allowed to shorten, for example, if only one end of the muscle is fixed and the muscle shortens with a constant load, the contraction is called isotonic contraction.

In vitro, the isometric contraction of smooth muscle can be induced by applying a depolarizing solution, for example, concentrated potassium chloride solution, to the muscle to be examined. The high concentration of potassium depolarizes the muscle cell membrane and opens voltage-gated calcium channels, resulting in an influx of extracellular calcium and activation of contractile machinery.

The plasma membrane also contains Ca2+, Mg2+-ATPases, providing an additional mechanism for reducing the concentration of activator Ca2+ in the cell. This enzyme differs from the sarcoplasmic reticular protein in that it has an autoinhibitory domain that can be bound by calmodulin, causing stimulation of the plasma membrane Ca2+ pump.

Na+/Ca2+ exchangers also are located on the plasma membrane and aid in decreasing intracellular Ca2+. This low-affinity antiporter is closely coupled to intracellular Ca2+ levels and can be inhibited by amiloride and quinidine.

Inhibition of receptor-operated and voltage-operated Ca2+ channels located in the plasma membrane also can elicit relaxation. Channel antagonists such as dihydropyridine, phenylalkylamines, and benzothiazepines bind to distinct receptors on the channel protein and inhibit Ca2+ entry in smooth muscle.

MMI-0100 enhances ISO-Induced Relaxation of Porcine Airway Smooth Muscle. Porcine airway smooth muscle (PASM) rings were isolated from second generation bronchi, cartilage was peeled off and then hung in a muscle bath and equilibrated in Kreb's buffer for 3 hrs. Rings were contracted with $1.5 \times 10^{-7}$ M carbacholine (CCh, a carbamic acid choline ester)) and then relaxed with $10^{-7}$ M or $10^{-8}$ M of isoproterenol (ISO) before and after treatment with either buffer (untreated) or with 100 μM MMI-0100 for 1 hr and the force generated was measured. ISO is a β-adrenergic agonist that relaxes almost all varieties of some muscle when the tone is high, but its action is most pronounced on bronchial and gastrointestinal smooth muscle. It prevents or relieves bronchoconstruction. Its effect in asthma maybe due in part to an additional action to inhibit antigen-induced release of histamine and other mediators of inflammation; this action is shared by $β_2$-receptor-selective stimulants. Goodman & Gilman's The Pharmacological Basis of Therapeutics, Joel G. Hardman and Lee E. Limberd, Eds., $10^{th}$ Ed. McGraw-Hill, New York, 2001), page 228). Force was normalized to the weight and length of the tissue and converted to stress and relaxation induced was calculated.

FIG. 26 shows that MMI-0100 treatment enhanced ISO induced relaxation of PASM by 13% (panel B). An asterisk (*) indicates significance compared to untreated, p=0.011, n=3.

MMI-0100 enhances ISO-induced relaxation of human airway smooth muscle (HASM). Intact human airway tissues were either left untreated or were pre-treated with 200 μM MMI-0100 for 30 min. FIG. 27 shows that MMI-0100 enhances ISO-induced relaxation in intact human airway tissues in the muscle bath and reduced MK2 phosphorylation in intact human airway smooth muscle. (A) Representative tracings of force generation. Cumulative contractile responses to CCH (B) and % relaxation to ISO doses (C). n=4; p<0.05. Inset is an immunoblot showing MK2 phosphorylation level. HASM was hung in the muscle bath and frozen. MK2 phosphorylation was determined by SDS PAGE and immunoblotting. Thus, while MMI-0100 may not in and of itself cause relaxation of smooth muscle, it can potentiate agonist-induced relaxation of smooth muscle.

Model of MMI-100 in Asthma. FIG. 28 shows a proposed model of alleviation of asthma symptoms by MMI-0100. Without being limited by theory, as a utility for combinatorial therapy with β-agonists or corticosteroids, MMI-0100 will suppress MK2-mediated airway hyperreactivity (AHR), fibrosis and inflammation in asthma patients. MMI-0100 inhibits phosphorylation of actin cytoskeleton modulators such as HSP27 and LIM kinase, and mRNA stabilizing protein such as hnRNPAO.

Example 14. Efficacy of MMI-0100
(YARAAARQARAKALARQLGVAA; SEQ ID
NO: 1) in a Murine Asthma Model In Vivo Sensitization of mice: Pathogen free 8-10 week old female BALB/c mice will be obtained from Charles River Laboratories (Wilmington, Mass.). Mice will be acclimated for one week in an animal unit before experimentation. To sensitize, mice will be exposed to ovalbumin. During the fourth week, PBS or MMI-0100 peptide (3, 30, 100, 300 ng/kg) in 100 μl PBS will be administered via nebulization, nasal drip or intratracheal administration. Airway hyperresponsiveness to intravenous methacholine (MCh) will be determined for a given increasing dose of MCh the day after the last MCh challenge (day 36).

Determination of bronchoalveolar lavage (BAL) cytology and the effect on inflammation: Airway inflammation will be assessed by counting total BAL cells and staining total BAL cells for differential analysis. Cell free BAL fluid will be prepared by centrifugation (10 minutes at 1,500 rpm) and cytokine levels will be measured using a Multiplex mouse cytokine/chemokine assay kit (Millipore, Billerica, Mass.).

Airway remodeling: Airway remodeling will be determined by examining goblet cell hyperplasia, depositions of collagen III and α-smooth muscle actin expression around airways. Lung will be fixed and embedded in paraffin. Slides will be stained with Masson's Trichrome (Sigma-Aldrich, St. Louis, Mo.) and periodic acid-Schiff (PAS) stain (Millipore, Billerica, Mass.) to examine collagen deposition and airway mucus respectively. Hematoxylin (Sigma-Aldrich, St. Louis, Mo.) and eosin (Sigma-Aldrich, St. Louis, Mo.) staining will be performed to examine epithelium (epithelial and goblet cells) hypertrophy, airway smooth muscle (ASM) hypertrophy and hyperplasia, and immune cell infiltration. Staining for α-smooth muscle actin (R&D Systems, Minneapolis, Minn.) will also reveal the cell type responsible for subepithelial thickening.

Biodistribution and toxicity: Biodistribution of MMI-0100 peptides will be assayed using fluorescently tagged MMI-0100 peptides. Whole animal scanning will be performed using the Odyssey infrared imaging system (Li-cor Biosciences, Lincoln, Nebr.) and toxicity will be assayed by complete metabolic panel.

Determination of ex vivo responsiveness of isolated tracheal segments from house dust mite (HDM) sensitized mice: To directly measure the effect on ASM contractility, ASM rings will be isolated from control and asthmatic mice and contractile function will be measured ex vivo in a muscle bath. Physiologic function will also be determined using airway tissue from human donor lung tissue. The effect of MMI-0100 on albuterol induced relaxation will be determined.

While the described invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the described invention. All such modifications are intended to be within the scope of the claims appended hereto.

What is claimed is:

1. A method for treating asthma, comprising:
administering by inhalation to a subject in need thereof a pharmaceutical composition comprising a therapeutic amount of a polypeptide that is a functional equivalent of a polypeptide of the amino acid sequence YARAAARQARAKALARQLGVAA (SEQ ID NO: 1), wherein the functional equivalent polypeptide is made from a fusion between a first polypeptide that is a cell penetrating peptide (CPP) selected from the group consisting of a polypeptide of the amino acid sequence, FAKLAARLYR (SEQ ID NO: 16), KAFAKLAARLYR (SEQ ID NO: 17), and HRRIKAWLKKI (SEQ ID NO: 18), and a second polypeptide that is a therapeutic domain (TD) KALARQLGVAA (SEQ ID NO: 10), and a pharmaceutically acceptable carrier thereof,
wherein the asthma is a disease, condition or pathologic process whose progression is characterized by one or more of aberrant fibroblast proliferation and extracellular matrix deposition, producing constriction in an airway, airway remodeling, and airway obstruction, in lung tissue, and
wherein the therapeutic amount of the polypeptide is effective to reduce the constriction of small airway dimensions and airway obstruction, airway smooth muscle mass (ASM), disruption of surface epithelium, collagen deposition, thickening of basement membrane, or a combination thereof.

2. The method according to claim 1, wherein the functional equivalent of the polypeptide YARAAARQARAKALARQLGVAA (SEQ ID NO: 1) is of amino acid sequence FAKLAARLYRKALARQLGVAA (SEQ ID NO: 3).

3. The method according to claim 1, wherein the functional equivalent of the polypeptide YARAAARQARAKALARQLGVAA (SEQ ID NO: 1) is of amino acid sequence KAFAKLAARLYRKALARQLGVAA (SEQ ID NO: 4).

4. The method according to claim 1, wherein the functional equivalent of the polypeptide YARAAARQARAKALARQLGVAA (SEQ ID NO: 1) is of amino acid sequence HRRIKAWLKKIKALARQLGVAA (SEQ ID NO: 7).

5. The method according to claim 1, wherein the asthma is further characterized by an inflammation in the lung tissue.

6. The method according to claim 5, wherein the inflammation is acute or chronic inflammation.

7. The method according to claim 5, wherein the inflammation is mediated by at least one cytokine selected from the group consisting of Tumor Necrosis Factor-alpha (TNF-α), Interleukin-6 (IL-6), and Interleukin-1β (IL-1β).

8. The method according to claim 1, wherein the aberrant fibroblast proliferation and extracellular matrix deposition in the lung tissue is characterized by an aberrant activity of Mitogen-Activated Protein Kinase-Activated Protein Kinase 2 (MK2) in the lung tissue of the subject, compared to the activity of MK2 in the lung tissue of a normal healthy control subject.

9. The method according to claim 1, wherein the asthma is further characterized by at least one pathology selected from the group consisting of an aberrant deposition of an extracellular matrix protein in a pulmonary interstitium, an aberrant induction of myofibroblast differentiation and an aberrant promotion of attachment of myofibroblasts to an extracellular matrix, compared to a normal healthy control subject.

10. The method according to claim 1, wherein the asthma is associated with an allergic reaction, inhalation of environmental particulates, smoking, a bacterial infection, a viral infection, mechanical damage to a lung of the subject, an autoimmune disorder, a genetic disorder, or a combination thereof.

11. The method according to claim 1, wherein the therapeutic amount of the polypeptide is effective to enhance isoproterenol-induced relaxation of human airway smooth muscle.

12. The method according to claim 1, wherein the pharmaceutical composition further comprises at least one additional therapeutic agent.

13. The method according to claim 12, wherein the additional therapeutic agent is selected from the group consisting of a purified bovine Type V collagen, an IL-13 receptor antagonist, a protein tyrosine kinase inhibitor, an endothelial receptor antagonist, a dual endothelin receptor antagonist, a selective endothelin A receptor antagonist, a prostacyclin analog, an anti-connective tissue growth factor (CTGF) monoclonal antibody, an anti-lysyl oxidase-like 2 (LOXL2) monoclonal antibody, a c-Jun N-terminal kinase (JNK) inhibitor, pirfenidone, IFN-γ1b, a pan-neutralizing IgG4 human antibody against all three TGF-β isoforms, a TGF-β activation inhibitor, a recombinant human pentraxin-2 protein (rhPTX-2), a bispecific IL-4/IL-13 antibody, a humanized monoclonal antibody targeting integrin αvβ6, N-acetylcysteine, sildenafil, a tumor necrosis factor (TNF) antagonist, and a combination thereof.

14. The method according to claim 12, wherein the additional therapeutic agent is a glucocorticoid selected from the group consisting of prednisone, budesonide, mometasone furoate, fluticasone propionate, fluticasone furoate, and a combination thereof.

15. The method according to claim 12, wherein the additional therapeutic agent is a bronchodilator selected from the group consisting of a leukotriene modifier, an anticholinergic bronchodilator, a short-acting β2-agonist, a long-acting β2-agonist, and a combination thereof.

16. The method according to claim 12, wherein the additional therapeutic agent is an analgesic agent.

17. The method according to claim 12, wherein the additional therapeutic agent is an anti-infective agent.

18. The method according to claim 1, wherein the carrier is selected from the group consisting of a controlled release carrier, a delayed release carrier, a sustained release carrier, and a long-term release carrier.

19. The method according to claim 1, wherein the pharmaceutical composition is in a form of a dry powder.

20. The method according to claim 19, wherein the dry powder comprises microparticles with Mass Median Aerodynamic Diameter (MMAD) of 1 to 5 microns.

21. The method according to claim 1, wherein the pharmaceutical composition is administered via an inhalation device.

22. The method according to claim 21, wherein the inhalation device is a nebulizer.

23. The method according to claim 21, wherein the inhalation device is a metered-dose inhaler (MDI).

24. The method according to claim 21, wherein the inhalation device is a dry powder inhaler (DPI).

25. The method according to claim 21, wherein the inhalation device is a dry powder nebulizer.

* * * * *